US011820979B2

(12) United States Patent
Shriver et al.

(10) Patent No.: US 11,820,979 B2
(45) Date of Patent: Nov. 21, 2023

(54) BINDING POLYPEPTIDES AND METHODS OF MAKING THE SAME

(71) Applicant: VISTERRA, INC., Waltham, MA (US)

(72) Inventors: Zachary Shriver, Winchester, MA (US); Gregory Babcock, Marlborough, MA (US); Luke Robinson, Quincy, MA (US)

(73) Assignee: VISTERRA, INC., Waltham, MA (US)

( * ) Notice: Subject to any disclaimer, the term of this patent is extended or adjusted under 35 U.S.C. 154(b) by 605 days.

(21) Appl. No.: 15/852,718

(22) Filed: Dec. 22, 2017

(65) Prior Publication Data

US 2018/0201926 A1 Jul. 19, 2018

Related U.S. Application Data

(60) Provisional application No. 62/438,712, filed on Dec. 23, 2016.

(51) Int. Cl.
 *C12N 15/10* (2006.01)
 *C07K 16/18* (2006.01)
 *C07K 16/00* (2006.01)

(52) U.S. Cl.
 CPC .......... *C12N 15/1093* (2013.01); *C07K 16/00* (2013.01); *C07K 16/005* (2013.01); *C07K 16/18* (2013.01); *C07K 2317/10* (2013.01); *C07K 2317/56* (2013.01); *C07K 2317/622* (2013.01)

(58) Field of Classification Search
 CPC ............ C12N 15/1093; C07K 2317/10; C07K 2317/622; C07K 2317/56
 See application file for complete search history.

(56) References Cited

U.S. PATENT DOCUMENTS

| | | | |
|---|---|---|---|
| 6,143,527 A | 11/2000 | Pachuk et al. | |
| 8,691,730 B2 | 4/2014 | Vasquez et al. | |
| 8,877,688 B2 | 11/2014 | Vasquez et al. | |
| 9,090,674 B2 | 7/2015 | Reddy et al. | |
| 9,146,241 B2 | 9/2015 | Lavinder et al. | |
| 9,422,547 B1 | 8/2016 | Johnson et al. | |
| 9,738,699 B2 | 8/2017 | Johnson et al. | |
| 9,816,088 B2 | 11/2017 | Vigneault et al. | |
| 9,926,554 B2 | 3/2018 | Johnson et al. | |
| 9,926,555 B2 | 3/2018 | Johnson et al. | |
| 10,119,134 B2 | 11/2018 | Vigneault et al. | |
| 10,175,249 B2 | 1/2019 | Lavinder et al. | |
| 10,189,894 B2 | 1/2019 | Vasquez et al. | |
| 10,196,635 B2 | 2/2019 | Vasquez et al. | |
| 10,214,740 B2 | 2/2019 | Johnson et al. | |
| 10,392,614 B2 | 8/2019 | Vigneault et al. | |
| 10,392,663 B2 | 8/2019 | Emerson et al. | |
| 2002/0086330 A1 | 7/2002 | Rosen et al. | |
| 2006/0199191 A1 | 9/2006 | Obregon et al. | |
| 2007/0141048 A1* | 6/2007 | Oleksiewicz | ........ C07K 16/005 424/133.1 |
| 2008/0032399 A1 | 2/2008 | Harney et al. | |
| 2010/0056386 A1 | 3/2010 | Vasquez et al. | |
| 2011/0014659 A1 | 1/2011 | Balazs et al. | |
| 2011/0129855 A1* | 6/2011 | Pedersen | .................. A61P 43/00 435/7.21 |
| 2011/0275063 A1* | 11/2011 | Weitz | .................. G01N 33/5008 435/6.1 |
| 2011/0312505 A1 | 12/2011 | Reddy et al. | |
| 2012/0270748 A1* | 10/2012 | Chee | .................. C12N 15/1075 506/9 |
| 2013/0178370 A1 | 7/2013 | Lavinder et al. | |
| 2014/0057799 A1 | 2/2014 | Johnson et al. | |
| 2014/0127209 A1* | 5/2014 | Grabstein | ............... A61P 29/00 424/136.1 |
| 2014/0221250 A1 | 8/2014 | Vasquez et al. | |
| 2014/0243234 A1 | 8/2014 | Hayhurst | |
| 2014/0322716 A1 | 10/2014 | Robins | |
| 2014/0357500 A1 | 12/2014 | Vigneault et al. | |
| 2014/0364340 A1 | 12/2014 | Vasquez et al. | |
| 2015/0133317 A1 | 5/2015 | Robinson et al. | |
| 2015/0275296 A1 | 10/2015 | Klinger et al. | |
| 2015/0299786 A1 | 10/2015 | Robins | |
| 2015/0337369 A1 | 11/2015 | Davis et al. | |
| 2016/0024493 A1 | 1/2016 | Robins | |
| 2016/0032282 A1 | 2/2016 | Vigneault et al. | |
| 2016/0034639 A1 | 2/2016 | Reddy et al. | |
| 2016/0146830 A1 | 5/2016 | Lavinder et al. | |
| 2016/0244825 A1 | 8/2016 | Vigneault et al. | |
| 2016/0304956 A1 | 10/2016 | Robins | |
| 2016/0319348 A1 | 11/2016 | Georgiou et al. | |
| 2016/0362470 A1 | 12/2016 | Johnson et al. | |

(Continued)

FOREIGN PATENT DOCUMENTS

| | | |
|---|---|---|
| CN | 101370832 A | 2/2009 |
| EP | 2626433 A1 | 8/2013 |

(Continued)

OTHER PUBLICATIONS

Embleton, M. J., et al. "In-cell PCR From mRNA: Amplifying and Linking the Rearranged Immunoglobulin Heavy and Light Chain V-genes Within Single Cells." Nucleic acids research 20.15 (1992): 3831-3837. (Year: 1992).*

DeKosky et al., "In-depth determination and analysis of the human paired heavy- and light-chain antibody repertoire," Nature Medicine (2015) vol. 21, No. 1, pp. 86-91.

International Search Report and Written Opinion for International Application No. PCT/US2017/068204, dated Jun. 5, 2018.

(Continued)

*Primary Examiner* — Sahana S Kaup

(74) *Attorney, Agent, or Firm* — K&L Gates LLP

(57) ABSTRACT

Polypeptides, such as antibody molecules and TCR molecules, and methods of making the same, are disclosed. The polypeptides can be used to treat, prevent, and/or diagnose disorders.

32 Claims, 10 Drawing Sheets

Specification includes a Sequence Listing.

(56) References Cited

U.S. PATENT DOCUMENTS

| | | |
|---|---|---|
| 2016/0362681 A1 | 12/2016 | Johnson et al. |
| 2016/0362682 A1 | 12/2016 | Johnson et al. |
| 2016/0362683 A1 | 12/2016 | Johnson et al. |
| 2017/0044523 A1 | 2/2017 | Held et al. |
| 2017/0247683 A1 | 8/2017 | Johnson et al. |
| 2017/0247684 A1 | 8/2017 | Johnson et al. |
| 2017/0335391 A1 | 11/2017 | Emerson et al. |
| 2018/0127743 A1 | 5/2018 | Vigneault et al. |
| 2019/0203205 A1 | 7/2019 | Vasquez et al. |
| 2019/0225677 A1 | 7/2019 | Vasquez et al. |
| 2019/0256841 A1 | 8/2019 | Johnson et al. |
| 2019/0264198 A1 | 8/2019 | Vigneault et al. |

FOREIGN PATENT DOCUMENTS

| | | | | |
|---|---|---|---|---|
| WO | 2001062908 A2 | 8/2001 | | |
| WO | 2005/042774 A2 | 5/2005 | | |
| WO | 2008104184 A2 | 9/2008 | | |
| WO | 2009036379 A2 | 3/2009 | | |
| WO | 2009120922 A2 | 10/2009 | | |
| WO | 2010022738 A1 | 3/2010 | | |
| WO | 2010105256 A1 | 9/2010 | | |
| WO | 2011146514 A2 | 11/2011 | | |
| WO | 2013020087 A2 | 2/2013 | | |
| WO | 2013078455 A2 | 5/2013 | | |
| WO | 2013/092716 A1 | 6/2013 | | |
| WO | 2013092716 A1 | 6/2013 | | |
| WO | 2013/116698 A2 | 8/2013 | | |
| WO | 2013188831 A1 | 12/2013 | | |
| WO | WO-2013188872 A1 * | 12/2013 | ........... | C12Q 1/6806 |
| WO | 2014/043813 A1 | 3/2014 | | |
| WO | 2014144495 A1 | 9/2014 | | |
| WO | 2014145992 A1 | 9/2014 | | |
| WO | 2014/182197 A1 | 11/2014 | | |
| WO | WO-2015034928 A1 * | 3/2015 | ............. | C12N 15/11 |
| WO | 2015121434 A1 | 8/2015 | | |
| WO | 2015/176162 A1 | 11/2015 | | |
| WO | 2015166272 A2 | 11/2015 | | |
| WO | 2016044227 A1 | 3/2016 | | |
| WO | 2016069886 A1 | 5/2016 | | |
| WO | 2016/176322 A1 | 11/2016 | | |

OTHER PUBLICATIONS

Munson et al., "Identification of shared TCR sequences from T cells in human breast cancer using emulsion RT-PCR," PNAS (2016) vol. 113, No. 29, pp. 8272-8277.

Robertson et al., "Design and optimization of effector-activated ribozyme ligases," Nucleic Acids Research (2000) vol. 28, No. 8, pp. 1751-1759.

Turchaninova et al., "Pairing of T-cell receptor chains via emulsion PCR," Eur J Immunol (2013) vol. 43, pp. 2507-2515.

Search Report and Written Opinion issued in Singapore Patent Application No. 11201905649W dated Oct. 29, 2020, 12 pages.

D'Angelo, S. et al. "From deep sequencing to actual clones." Protein Engineering, Design & Selection: PEDS (2014) vol. 27, No. 10, pp. 301-307.

DeKosky, B. J. et al. "High-throughput sequencing of the paired human immunoglobulin heavy and light chain repertoire," Nature Biotechnology (2013) vol. 31, No. 2, pp. 166-169.

De Kok, S. et al. "Rapid and reliable DNA assembly via ligase cycling reaction," ACS Synthetic Biology (2014). vol. 3, No. 2, pp. 97-106.

Roth, T. L. et al. "A rapid and simple method for DNA engineering using cycled ligation assembly," PLOS ONE (2014) vol. 9, No. 9, e107329.

Kumaresan, P. et al. "High-throughput single copy DNA amplification and cell analysis in engineered nanoliter droplets," Analytical Chemistry (2008) vol. 80, No. 10, pp. 3522-3529.

Wang, X. et al. "Construction of Human Immunoglobulin Combinatorial Library and Screening of Phage Antibodies to Hepatitis B Surface Antigen," Act A Biochimica et Biophysica Sinica (1997) vol. 29, No. 2, pp. 183-191.

Howie, B. et al. "High-throughput pairing of T cell receptor α and β sequences." Science Translational Medicine vol. 7, No. 301 (2015): 1-11.

Robertson, M. P. & Ellington, A. D. "Design and optimization of effector-activated ribozyme ligases." Nucleic Acids Research vol. 28, No. 8 (2000): 1751-1759.

* cited by examiner

SEQUENCE LISTING

<160> NUMBER OF SEQ ID NOS: 32

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
chgatggggs tgtygttktr gc                                              22

<210> SEQ ID NO 2
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gtgcagcatc agccc                                                      15

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      primer -continued

<400> SEQUENCE: 3
gacatcaaga tgacccagtc tc                                                22

<210> SEQ ID NO 4
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
accagcagag ctctcacctg gtgcagcatc agccc                                  35

<210> SEQ ID NO 5
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ggaactaccg aaggcacagg tgaggtccag ctgcaacagt c                           41

<210> SEQ ID NO 6
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
acctgtgcct tcggtagttc caccagcaga gctctcacct g                           41

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ggcagtgggt ctgggacag                                                    19

<210> SEQ ID NO 8
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ggaactaccg aaggcacagg tgaggtgcac ctggtggagt ctggggg                     47

<210> SEQ ID NO 9
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ggatagtggg tgtaagtacc acgactacca atg    33

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tggatcgtta ctaatattcg c    21

<210> SEQ ID NO 11
<211> LENGTH: 63
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tggatcgtta ctaatattcg cggactcaga cacttccgtg cgacatcaag atgacccagt    60
ctc    63

<210> SEQ ID NO 12
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ggactcagac acttccgtgc gacatcaaga tgacccagtc tc    42

<210> SEQ ID NO 13
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
accagcagag ctctcacctg gtgcagcatc agccc    35

<210> SEQ ID NO 14
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gcaatccatc aacgtc    16

<210> SEQ ID NO 15
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 15
ggaactaccg aaggcacagg tgaggtccag ctgcaacagt c                          41

<210> SEQ ID NO 16
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
gcgaatatta gtaacgatcc aaaaaaaaaa aaaaaaaaa a                           41

<210> SEQ ID NO 17
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
gacgttgatg gattgcaaaa aaaaaaaaaa aaaaaa                               36

<210> SEQ ID NO 18
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
ctggacaggg atccakagtt ccaaaaaaaa aaaaaaaaa aaa                         43

<210> SEQ ID NO 19
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
gtgcagcatc agcccgaaaa aaaaaaaaaa aaaaaa                               36

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
tggatcgtta ctaatattcg c                                               21

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 21
tggatcgtta ctaatattcg c                                             21

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
tggatcgtta ctaatattcg c                                             21

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
tgacccagtc tccatcttca                                               20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
tgttgttttg gctgaggaga                                               20

<210> SEQ ID NO 25
<211> LENGTH: 60
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(5)
<223> OTHER INFORMATION: This region may encompass 3-5 residues
<220> FEATURE:
<221> NAME/KEY: MISC_FEATURE
<222> LOCATION: (7)..(11)
<223> OTHER INFORMATION: This region may encompass 3-5 residues
<220> FEATURE:
<221> NAME/KEY: MISC_FEATURE
<222> LOCATION: (13)..(17)
<223> OTHER INFORMATION: This region may encompass 3-5 residues
<220> FEATURE:
<221> NAME/KEY: MISC_FEATURE
<222> LOCATION: (19)..(23)
<223> OTHER INFORMATION: This region may encompass 3-5 residues
<220> FEATURE:
<221> NAME/KEY: MISC_FEATURE
<222> LOCATION: (25)..(29)
<223> OTHER INFORMATION: This region may encompass 3-5 residues
<220> FEATURE:
<221> NAME/KEY: MISC_FEATURE
<222> LOCATION: (31)..(35)
<223> OTHER INFORMATION: This region may encompass 3-5 residues
<220> FEATURE:
<221> NAME/KEY: MISC_FEATURE
<222> LOCATION: (37)..(41)
<223> OTHER INFORMATION: This region may encompass 3-5 residues
```

```
<220> FEATURE:
<221> NAME/KEY: MISC_FEATURE
<222> LOCATION: (43)..(47)
<223> OTHER INFORMATION: This region may encompass 3-5 residues
<220> FEATURE:
<221> NAME/KEY: MISC_FEATURE
<222> LOCATION: (49)..(53)
<223> OTHER INFORMATION: This region may encompass 3-5 residues
<220> FEATURE:
<221> NAME/KEY: MISC_FEATURE
<222> LOCATION: (55)..(59)
<223> OTHER INFORMATION: This region may encompass 3-5 residues
<220> FEATURE:
<221> NAME/KEY: MISC_FEATURE
<222> LOCATION: (1)..(60)
<223> OTHER INFORMATION: This sequence may encompass 1-10 "(Gly)m-Ser"
      repeating units, wherein m is 3-5
<220> FEATURE:
<223> OTHER INFORMATION: See specification as filed for detailed
      description of substitutions and preferred embodiments

<400> SEQUENCE: 25

Gly Gly Gly Gly Gly Ser Gly Gly Gly Gly Ser Gly Gly Gly Gly
1               5                   10                  15

Gly Ser Gly Gly Gly Gly Ser Gly Gly Gly Gly Gly Ser Gly Gly
            20                  25                  30

Gly Gly Gly Ser Gly Gly Gly Gly Gly Ser Gly Gly Gly Gly Ser
        35                  40                  45

Gly Gly Gly Gly Gly Ser Gly Gly Gly Gly Ser
    50                  55                  60

<210> SEQ ID NO 26
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(50)
<223> OTHER INFORMATION: This sequence may encompass 1-10 "Gly Gly Gly
      Gly Ser" repeating units
<220> FEATURE:
<223> OTHER INFORMATION: See specification as filed for detailed
      description of substitutions and preferred embodiments

<400> SEQUENCE: 26

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser
    50

<210> SEQ ID NO 27
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ggactcagac acttccgtgc gacatcaaga tgacccagtc tc                    42
```

```
<210> SEQ ID NO 28
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
cgtgacacat gtggttcaag tacggchgat ggggstgtyg ttktrgc                47

<210> SEQ ID NO 29
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
ggactcagac acttccgtgc attgtgctga cgcaaactgt ta                     42

<210> SEQ ID NO 30
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
gaatattagt aacgatccag gactcggacc gacatcaaga tgacccagtc tc          52

<210> SEQ ID NO 31
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
gaatattagt aacgatccag gactcggacc attgtgctga cgcaaactgt ta          52

<210> SEQ ID NO 32
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(25)
<223> OTHER INFORMATION: This sequence may encompass 1-5 "Gly Gly Gly
      Gly Ser" repeating units
<220> FEATURE:
<223> OTHER INFORMATION: See specification as filed for detailed
      description of substitutions and preferred embodiments

<400> SEQUENCE: 32

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25
```

BINDING POLYPEPTIDES AND METHODS OF MAKING THE SAME

CROSS REFERENCE TO RELATED APPLICATIONS

This application claims the benefit of U.S. Provisional Application No. 62/438,712, filed Dec. 23, 2016. The contents of the aforesaid application are hereby incorporated by reference in their entirety.

SEQUENCE LISTING

The instant application contains a Sequence Listing which has been submitted electronically in ASCII format and is hereby incorporated by reference in its entirety. Said ASCII copy, created on Feb. 16, 2018, is named P2029-701510 SL.txt and is 10,248 bytes in size.

BACKGROUND

Monoclonal antibody therapies are a class of immunotherapies that involve monoclonal antibodies (mAbs) that are capable of specifically interacting with disease-relevant biological molecules. In recent years, the disease areas that therapeutic antibodies can target have significantly expanded, and a number of monoclonal antibodies and antibody-derivative products have been approved for therapeutic use in the United States and many other countries. Monoclonal antibody therapies are currently used or investigated for treating various diseases or conditions, including, for example, infectious diseases, cancer, immune diseases, organ transplantation, cardiovascular diseases, and metabolic diseases.

Given the ability of monoclonal antibodies and antibody-derivative products in modulating various biological functions, the need exists for developing new approaches for generation of antibodies suitable for treating, preventing, and diagnosing disorders.

SUMMARY

This disclosure provides, at least in part, binding polypeptides (e.g., antibody molecules or T-cell receptor (TCR) molecules) that comprise one or more of the structural or functional properties disclosed herein. In an embodiment, libraries of the binding polypeptides, methods for making the polypeptides or libraries, nucleic acid molecules encoding the binding polypeptides, expression vectors, host cells, compositions (e.g., pharmaceutical compositions), kits, and containers, are also provided. The polypeptides (e.g., antibody molecules or TCR molecules) disclosed herein can be used (alone or in combination with other agents or therapeutic modalities) to treat, prevent and/or diagnose disorders, such as disorders and conditions disclosed herein.

In an aspect, the disclosure features a method of making a nucleic acid sequence comprising a sequence that encodes a heavy chain element (HC element) of an antibody heavy chain variable region (HCVR) and a light chain element (LC element) of an antibody light chain variable region (LCVR), and wherein the HCVR and LCVR are matched, the method comprising:

a) acquiring an isolated production reaction site, e.g., a production micro-chamber, comprising:

i) a heavy chain (HC) strand, wherein the HC strand is a strand of a heavy chain double-stranded cDNA (HC ds cDNA) comprising a segment that encodes an HC element of the HCVR from a cell, e.g., a heavy chain variable region sequence (HCVRS); and ii) a light chain (LC) strand, wherein the LC strand is a strand of a light chain double-stranded cDNA (LC ds cDNA) comprising a segment that encodes an LC element of the LCVR from the cell, e.g., a light chain variable region sequence (LCVRS), and b) covalent linking, e.g., ligation, of an HC strand to an LC strand, wherein the isolated production reaction site, e.g., a production micro-chamber, does not include a nucleic acid encoding an HCVR or an LCVR from a cell other than the cell (e.g., a different cell, e.g., a different B cell), thereby making a nucleic acid sequence comprising a sequence that encodes an HC element of an HCVR and a LC element of an LCVR, wherein the HCVR and LCVR are matched.

In an embodiment, the HC element comprises, or consists of, an HCVRS, or a functional fragment thereof (e.g., an antigen binding fragment thereof). In an embodiment, the LC element comprises, or consists of, an LCVRS, or a functional fragment thereof (e.g., an antigen binding fragment thereof).

In an embodiment, the HC ds cDNA comprises a segment that encodes an HCVRS. In an embodiment, the LC ds cDNA comprises a segment that encodes an LCVRS. In an embodiment, the HC ds cDNA comprises a segment that encodes an HCVRS, and the LC ds cDNA comprises a segment that encodes an LCVRS.

In an embodiment, the cell is an immune cell, e.g., a B cell, e.g., a human B cell. In an embodiment, the cell is a mammalian cell or an avian cell.

In an embodiment, the nucleic acid sequence is configured such that, when expressed, the HC element and the LC element (e.g., the HCVRS and the LCVRS) form a functional antigen binding molecule, e.g., an scFv, an Fab, or an scFab. In an embodiment, the antigen binding molecule, e.g., an scFv, is functional in vitro, ex vivo, or in vivo, e.g., as determined by a method or assay described herein.

In an embodiment, acquiring an isolated production reaction site, e.g., a production micro-chamber, comprises:

a) acquiring a capture substrate bound to: (i) a first double-stranded cDNA (ds cDNA) comprising a strand that is complementary to a first mRNA that encodes an HCVR from a cell; and (ii) a second ds cDNA comprising a strand complementary to a second mRNA encoding an LCVR from the cell (the cDNA loaded capture substrate), and b) maintaining the isolated production reaction site, e.g., the production micro-chamber, under conditions that allow amplification of the first and second ds cDNAs, to produce: a plurality of HC ds cDNAs comprising a segment that encodes an HC element of the HCVR from the cell, e.g., an HCVRS; and a plurality of LC ds cDNAs comprising a segment that encodes an LC element of the LCVR from the cell, e.g., an LCVRS.

In an embodiment, the HC ds cDNA is identical, or substantially identical, to the first ds cDNA. For example, the sense strand of the HC ds cDNA is at least 80%, 85%, 90%, 95%, 98%, 99%, or 100% identical to, or differs by no more than 1, 2, 5, 10, 15, 20, 25, 30, 35, 40, 45, or 50 nucleotides from, the sense strand of the first ds cDNA, and/or the antisense strand of the HC ds cDNA is at least 80%, 85%, 90%, 95%, 98%, 99%, or 100% identical to, or differs by no more than 1, 2, 5, 10, 15, 20, 25, 30, 35, 40, 45, or 50 nucleotides from, the antisense strand of the first ds cDNA.

In an embodiment, the LC ds cDNA is identical, or substantially identical, to the second ds cDNA. For example, the sense strand of the LC ds cDNA is at least 80%, 85%, 90%, 95%, 98%, 99%, or 100% identical to, or differs by no more than 1, 2, 5, 10, 15, 20, 25, 30, 35, 40, 45, or 50 nucleotides from, the sense strand of the second ds cDNA, and/or the antisense strand of the LC ds cDNA is at least 80%, 85%, 90%, 95%, 98%, 99%, or 100% identical to, or differs by no more than 1, 2, 5, 10, 15, 20, 25, 30, 35, 40, 45, or 50 nucleotides from, the antisense strand of the second ds cDNA.

In an embodiment, the HC strand is a sense strand. In an embodiment, the LC strand is a sense strand. In an embodiment, the HC strand is an antisense strand. In an embodiment, the LC strand is an antisense strand. In an embodiment, both the HC strand and the LC strand are sense strands. In an embodiment, both the HC strand and the LC strand are antisense strands.

In an embodiment, the capture substrate comprises a bead, e.g., a magnetic bead. In an embodiment, the capture substrate comprises a moiety (e.g., an oligonucleotide) which binds to cDNA, e.g., (i) a moiety which binds to the HC strand; (ii) a moiety which binds to the LC strand; or (iii) both (i) and (ii). In an embodiment, the moiety which binds to the HC strand is different from the moiety which binds to the LC strand, e.g., to facilitate creating conditions favorable to capturing similar levels of each DNA molecule type. In an embodiment, the moiety which binds to the HC strand is identical to the moiety which binds to the LC strand.

In an embodiment, the first mRNA and the second mRNA are disposed on an mRNA loaded capture substrate.

In an embodiment, the isolated production reaction site, e.g., the production micro-chamber, comprises: a reagent mixture suitable for producing, from the first and second mRNAs (e.g., after the first and second mRNAs are released from the mRNA loaded capture substrate into a solution), a first ds cDNA comprising a segment that encodes an HC element of the HCVR of the cell, e.g., an HCVRS, and a second ds cDNA comprising a segment that encodes an LC element of the LCVR of the cell, e.g., an LCVRS.

In an embodiment, the isolated production reaction site, e.g., production micro-chamber, comprises primers that mediate the production of the first ds cDNA. In an embodiment, the isolated production reaction site, e.g., production micro-chamber, comprises primers that mediate the production of the second ds cDNA.

In an embodiment, a cDNA strand that is complementary to a first mRNA that encodes an HCVR from a cell is made by reverse transcription of the first mRNA. In an embodiment, a cDNA strand that is complementary to a second mRNA that encodes an LCVR from a cell is made by reverse transcription of the second mRNA.

In an embodiment, the reverse transcription takes place in the isolated production reaction site, e.g., a production-micro chamber. In an embodiment, the reverse transcription takes place in an isolated cell reaction site, e.g., a cell isolation micro-chamber. In an embodiment, the reverse transcription takes place outside the isolated production reaction site, e.g., a production micro-chamber, or outside an isolated cell reaction site, e.g., a cell isolation micro-chamber. In an embodiment, the reverse transcription takes place outside the isolated production reaction site, e.g., a production-micro chamber, and outside an isolated cell reaction site, e.g., a cell isolation micro-chamber. In an embodiment, the reverse transcription takes place outside an isolated reaction site, e.g., outside a micro-chamber.

In an embodiment, the amplification comprises 30 or fewer cycles, e.g., 20 or fewer cycles, e.g., 15 or fewer, 14 or fewer, 13 or fewer, 12 or fewer, 11 or fewer, 10 or fewer, 9 or fewer, 8 or fewer, 7 or fewer, 6 or fewer, or 5 or fewer cycles.

In an embodiment, the reverse transcription and/or amplification uses one or more primers, e.g., comprising a sequence specific for an HCVRS and/or an LCVRS.

In an embodiment, the reverse transcription and/or amplification comprises using two or more primers that mediate the production of the HC ds cDNA, wherein at least one primer comprises a nucleotide modification, and wherein at least one primer does not comprise a nucleotide modification. In an embodiment, the amplification comprises using two or more primers that mediate the production of the LC ds cDNA, wherein at least one primer comprises a nucleotide modification, and wherein at least one primer does not comprise a nucleotide modification.

In an embodiment, at least one primer comprises a nucleotide modification, e.g., which reduces, e.g., inhibits, DNA synthesis, e.g., by a DNA polymerase. In an embodiment, at least one primer does not comprise a nucleotide modification, e.g., which reduces, e.g., inhibits, DNA synthesis, e.g., by a DNA polymerase.

In an embodiment, the nucleotide modification inhibits a DNA polymerase from extending the DNA. Without wishing to be bound by theory, it is believed that in an embodiment, any chemical entity that reduces (e.g., blocks) DNA polymerase extension can be used in accordance with the methods described herein.

In an embodiment, the nucleotide modification is an insertion of a spacer to the primer, e.g., between two adjacent nucleotides in the primer. In an embodiment, the spacer is a flexible spacer. In an embodiment, the spacer is a carbon spacer (e.g., —(CH2)n-, wherein n=3, 4, 5, 6, 7, 8, 9, 10, or more), two or more (e.g., three, four, five, six, seven, eight, nine, ten, or more) abasic nucleotides, or a polyethylene glycol (PEG) spacer. In an embodiment, the spacer is a PEG spacer. In an embodiment, the nucleotide modification is 2'-O-methyl, 2'-OH, 2'-NH$_2$, or uracil, e.g., to a ribose.

In an embodiment, the nucleotide modification is located internally or at the 3' end of the primer. In an embodiment, at least one primer comprises (i) a first member; (ii) a second member; and optionally (iii) a third member, e.g., comprising a nucleotide modification described herein, e.g., located between (i) and (ii).

In an embodiment, the first member is capable of annealing with the second member. In an embodiment, the first member is capable of annealing with the second member in the same primer, e.g., through intra-molecular hybridization, e.g., to form a hairpin structure comprising a duplex region of 4, 5, 6, 7, 8, 9, 10, 11, 12, 13, 14, 15, 16, 17, 18, 19, 20, more basepairs. In another embodiment, the first member is capable of annealing hybridizing with the second member in a different primer, e.g., through inter-molecular hybridization, e.g., to form a double-stranded structure comprising a duplex region of 4, 5, 6, 7, 8, 9, 10, 11, 12, 13, 14, 15, 16, 17, 18, 19, 20, more basepairs. Without wishing to be bound by theory, it is believed that in an embodiment, there are at least two secondary structures that the modified primers can form and facilitate reduction (e.g., prevention) of competition to substrate (e.g., bead) capture. For example, the secondary structure can be a hairpin-like structure formed by intra-molecular hybridization (within the same primer), or the secondary structure can be a duplex structure formed by inter-molecular hybridization (between two different primers).

In an embodiment, the first member comprises a sequence that is complementary to the sequence of an oligonucleotide attached to the capture substrate. In an embodiment, the second member comprises (e.g., from 5' to 3') one, two, or all of: (i) a sequence that is complementary to at least a portion of the first member; (ii) a universal priming sequence (e.g., for PCR amplification or next-generation sequencing); and (iii) a sequence complementary to a target sequence, e.g., an HCVRS and/or an LCVRS. In an embodiment, the universal priming sequence is identical, or substantially identical, to the sequence that is complementary to at least a portion of the first member. In another embodiment, the universal priming sequence is different from the sequence that is complementary to at least a portion of the first member. In an embodiment, the second member comprises a sequence for homologous recombination (e.g., in a yeast or mammalian cell).

In an embodiment, at least one primer comprises a sequence encoding at least a portion of a linker sequence, or a complementary sequence thereof. In an embodiment, primer that comprises a sequence encoding at least a portion of a linker sequence, or a complementary sequence thereof, is phosphorylated, e.g., 5' phosphorylated. Without wishing to be bound by theory, it is believed that in an embodiment, any sequence with the general properties of flexibility (e.g., facilitated by glycine) and hydrophilicity can work effectively in accordance with the methods described herein. Exemplary linkers can generally have overrepresentation of one or more of Gly, Ser, Thr, or Ala and underrepresentation of hydrophobic residues, e.g., one or more of Trp, Tyr, Phe, Cys, Met, Leu, or Ile. The length of the primer may vary, e.g., 3-50 amino acid residues (e.g., 5-45, 10-40, 15-35, 20-30, 10-20, 10-30, 20-40, or 30-40 amino acid residues). In an embodiment, the linker sequence comprises, or consists of, ((Gly)m-Ser))n, where m=3, 4, 5, or more and n=1, 2, 3, 4, 5, 6, 7, 8, 9, 10, or more (SEQ ID NO: 25). In an embodiment, the linker sequence comprises, or consists of, (Gly-Gly-Gly-Gly-Ser)n, where n=1, 2, 3, 4, 5, 6, 7, 8, 9, 10, or more (SEQ ID NO: 26).

In an embodiment, the primer is a primer described herein, e.g., in Examples.

In an embodiment, the reverse transcription, the amplification, or both, occurs in a solution in the isolated production reaction site, e.g., production micro-chamber. In an embodiment, the reverse transcription, the amplification, or both, does not occur on the substrate (e.g., bead). For example, the reverse transcription, the amplification, or both, can occur on in a solution within a droplet.

In an embodiment, the HC ds cDNA comprises a 5' overhang, e.g., a 5' overhang that is capable of hybridizing to an oligonucleotide attached to a capture substrate. In an embodiment, the HC ds cDNA comprises a blunt end, e.g., a blunt end comprising a 5' phosphate. In an embodiment, the LC ds cDNA comprises a 5' overhang, e.g., a 5' overhang that is capable of hybridizing to an oligonucleotide attached to a capture substrate. In an embodiment, the LC ds cDNA comprises a blunt end, e.g., a blunt end comprising a 5' phosphate. In an embodiment, the HC ds cDNA and the LC ds cDNA comprise sticky ends, e.g., both have 5' overhangs.

In an embodiment, the HC strand and the LC strand are covalently linked, e.g., ligated, to produce a single stranded nucleic acid sequence, wherein the HC and LC strands are both sense strands or both antisense strands. In an embodiment, a denatured HC strand of the HC ds cDNA to a denatured LC strand of the LC ds cDNA are covalently linked, e.g., ligated, wherein the HC and LC strands are both sense strands or both antisense strands. In an embodiment, the HC strand is present in the HC ds cDNA and the LC strand is present in the LC ds cDNA, and wherein the HC ds cDNA and the LC ds cDNA are covalently linked, e.g., ligated, e.g., to produce a double stranded nucleic acid sequence.

In an embodiment, the covalent linking, e.g., ligation, occurs in the isolated production reaction site. In an embodiment, the isolated production reaction site, e.g., a production micro-chamber, or the isolated linkage reaction site, e.g., a linkage micro-chamber, comprises a reagent that is capable of covalently linking, e.g., ligating, the HC and LC strands or the HC and LC ds cDNAs. In an embodiment, the isolated production reaction site, e.g., a production micro-chamber comprises an enzyme that covalently couples the HC and LC strands or the HC and LC ds cDNAs. In an embodiment, the enzyme is a ligase, e.g., a thermal stable ligase. In an embodiment, the covalent linking comprises ligase thermocycling.

In an embodiment, the covalent linking, e.g., ligation, occurs in a site different from the isolated production reaction site, e.g., occurs in an isolated linkage reaction site, e.g., a linkage micro-chamber. In an embodiment, the HC strand and the LC strand are transferred from the isolated production site to the isolated linkage reaction site, e.g., a linkage micro-chamber, and the covalent linking occurs in the isolated linkage reaction site, e.g., a linkage micro-chamber. In an embodiment, the isolated linkage reaction site, e.g., a linkage micro-chamber, comprises a reagent that is capable of covalently linking, e.g., ligating, the HC and LC strands or the HC and LC ds cDNAs. In an embodiment, the isolated linkage reaction site, e.g., a linkage micro-chamber, comprises an enzyme that covalently couples the HC and LC strands or the HC and LC ds cDNAs. In an embodiment, the enzyme is a ligase, e.g., a thermal stable ligase. In an embodiment, the covalent linking comprises ligase thermocycling.

In an embodiment, the covalent linking, e.g., ligation, comprises: (a) heating the isolated linkage reaction site, e.g., the linkage micro-chamber, under conditions (e.g., at 95° C.) that allow denaturation of the HC strand and the LC strand; (b) cooling the isolated linkage reaction site, e.g., the linkage micro-chamber, under conditions (e.g., at 50-65° C.) that allow hybridization of the splint oligonucleotide to the HC strand and the LC strand; (c) maintaining the isolated linkage reaction site, e.g., the linkage micro-chamber, under conditions (e.g., at 45-65° C.) that allow ligation of the HC strand and the LC strand (e.g., formation of phosphodiester bond between the HC strand and the LC strand); and (d) repeating steps (a), (b), and (c) sequentially for 2, 5, 10, 15, 20, 25, 30, 35, 40, 45, 50, or more cycles.

In an embodiment, the HC strand and the LC strand are covalently linked, e.g., ligated, in the presence of a splint oligonucleotide. In an embodiment, the splint oligonucleotide is hybridized to a sequence comprising the junction of the HC strand and the LC strand, or a sequence complementary thereof, and forms a duplexed region at the site of ligation. In an embodiment, the splint oligonucleotide comprises a modification (e.g., an $NH_2$ group) that inhibits DNA synthesis, e.g., by a DNA polymerase. In an embodiment, the modification is at the 3' end of the splint oligonucleotide.

In an embodiment, a strand complimentary to the covalently linked, e.g., ligated, HC and LC strands is produced by amplification.

In an embodiment, the method, e.g., the step of covalent linkage, does not include a step of overlap extension polymerase chain reaction (OE-PCR), also known as splicing by overlap extension or splicing by overhang extension (SOE) PCR.

In an embodiment, the method further comprises, prior to acquiring the isolated production reaction site, e.g., a production micro-chamber, acquiring an mRNA loaded capture substrate.

In an embodiment, acquiring the mRNA loaded capture substrate comprising: a) acquiring an isolated cell reaction site, e.g., a cell isolation micro-chamber, comprising: i) a cell; and ii) a capture substrate capable of binding a first mRNA encoding an HCVR from the cell and a second mRNA encoding an LCVR from the cell; and b) maintaining the isolated cell reaction site, e.g., the cell isolation micro-chamber, under conditions that allow lysis of the cell and binding of the capture substrate with the first mRNA and the second mRNA to form the mRNA loaded capture substrate, wherein the isolated cell reaction site, e.g., cell isolation micro-chamber, does not include a nucleic acid encoding an HCVR or an LCVR from a cell other than the cell (e.g., a different cell).

In an embodiment, the isolated cell reaction site, e.g., cell isolation micro-chamber, comprises a lysing reagent, e.g., a detergent. In an embodiment, the cell is lysed by heat or an enzyme. In an embodiment, the capture substrate comprises a moiety (e.g., an oligonucleotide) which binds mRNA, e.g., an oligo(dT).

In an embodiment, the method further comprises releasing the mRNA loaded capture substrate from the isolated cell reaction site, e.g., the cell isolation micro-chamber. In an embodiment, the releasing step is performed in the presence of a poly(dA) or poly(dT) oligonucleotide, e.g., to reduce cross-binding of non-captured mRNA.

In an embodiment, the mRNA loaded capture substrate is transferred from the isolated cell reaction site, e.g., the cell isolation micro-chamber, to the isolated production reaction site, e.g., the production micro-chamber.

In an embodiment, the method further comprises releasing the nucleic acid sequence from the isolated production reaction site, e.g., the production micro-chamber. In an embodiment, the method further comprises amplifying the nucleic acid sequence. In an embodiment, amplification of the nucleic acid sequence occurs outside the isolated production reaction site, e.g., the production micro-chamber, e.g., after the nucleic acid is released from the isolated production reaction site, e.g., the production micro-chamber. In an embodiment, amplification of the nucleic acid sequence occurs at the isolated production reaction site, e.g., the production micro-chamber.

In an embodiment, the method further comprises sequencing all or a portion of the nucleic acid sequence.

In an embodiment, the method further comprises inserting all or a portion of nucleic acid sequence into a vector. In an embodiment, the vector supplies an additional HC element or LC element not included in the nucleic acid sequence. In an embodiment, the vector supplies an HC CDR1, an HC CDR2, or both. In an embodiment, the method further comprises expressing the vector.

In an embodiment, the method further comprises expressing the nucleic acid sequence to produce a polypeptide comprising a segment that encodes an HC element of the HCVR, e.g., an HCVRS, and a segment that encodes an LC element of the LCVR, e.g., an LCVRS. In an embodiment, the LC element is N-terminal to the HC element in the polypeptide. In an embodiment, the HC element is C-terminal to the LC element in the polypeptide.

In an embodiment, the method further comprises contacting the polypeptide with an antigen. In an embodiment, the method further comprises determining if the polypeptide binds the antigen, in vitro, ex vivo, or in vivo, e.g., by a method or assay described herein.

In an aspect, the disclosure features a method of making a nucleic acid sequence comprising a sequence that encodes a heavy chain element (HC element) of an antibody heavy chain variable region (HCVR) and a light chain element (LC element) of an antibody light chain variable region (LCVR), and wherein the HCVR and LCVR are matched, comprising:

a) acquiring an isolated cell reaction site (e.g., an isolated cell reaction site described herein), e.g., a cell isolation micro-chamber, comprising: i) a cell (e.g., a cell described herein); and ii) a capture substrate (e.g., a capture substrate described herein) capable of binding a first mRNA encoding an HCVR from the cell and a second mRNA encoding an LCVR from the cell;

b) maintaining the isolated cell reaction site, e.g., the cell isolation micro-chamber, under conditions that allow lysis of the cell and binding of the capture substrate with the first mRNA and the second mRNA to form an mRNA loaded capture substrate, wherein the isolated cell reaction site, e.g., cell isolation micro-chamber, does not include a nucleic acid encoding an HCVR or an LCVR from a cell other than the cell (e.g., a different cell);

c) contacting the mRNA loaded capture substrate with a reaction mixture, e.g., a reaction mixture comprising reverse transcriptase, that uses the loaded mRNA as a template to make cDNA (this can occur, e.g., in the isolated cell reaction site, in an isolated production reaction site, or in neither, e.g., not in an isolated reaction site);

d) acquiring an isolated production reaction site (e.g., an isolated production reaction site described herein), e.g., a production micro-chamber, comprising: i) a heavy chain (HC) strand, wherein the HC strand is a strand of a heavy chain double-stranded cDNA (HC ds cDNA) comprising a segment that encodes an HC element of the HCVR from the cell, e.g., a heavy chain variable region sequence (HCVRS); and ii) a light chain (LC) strand, wherein the LC strand is a strand of a light chain double-stranded cDNA (LC ds cDNA) comprising a segment that encodes an LC element of the LCVR from the cell, e.g., a light chain variable region sequence (LCVRS), wherein the isolated production reaction site, e.g., a production micro-chamber, does not include a nucleic acid encoding an LCVR or an HCVR from a cell other than the cell (e.g., a different cell); and e) covalent linking, e.g., ligation, of the HC strand to the LC strand.

In an embodiment, one or more (e.g., two, three, four, or all) of the steps a)-e) are performed in accordance with a method described herein. In an embodiment, each of the steps a)-e) is performed in accordance with a method described herein.

In an aspect, the disclosure features a method of making a nucleic acid sequence comprising a sequence that encodes a heavy chain element (HC element) of an antibody heavy chain variable region (HCVR) and a light chain element (LC element) of an antibody light chain variable region (LCVR), and wherein the HCVR and LCVR are matched, comprising:

a) acquiring an isolated cell reaction site (e.g., an isolated cell reaction site described herein), e.g., a cell isolation micro-chamber, comprising: i) a cell (e.g., a cell described herein); and ii) a capture substrate (e.g., a capture substrate described herein) capable of binding a first mRNA encoding an HCVR from the cell and a second mRNA encoding an LCVR from the cell;

b) maintaining the isolated cell reaction site, e.g., the cell isolation micro-chamber, under conditions that allow lysis of the cell and binding of the capture substrate with the first mRNA and the second mRNA to form the mRNA loaded capture substrate, wherein the isolated cell reaction site, e.g., cell isolation micro-chamber, does not include a nucleic acid encoding an HCVR or an LCVR from a cell other than the cell (e.g., a different cell);

c) acquiring an isolated production reaction site (e.g., an isolated production reaction site described herein), e.g., a production micro-chamber, comprises: contacting the mRNA loaded capture substrate with a reaction mixture, e.g., a reaction mixture comprising reverse transcriptase, that uses the loaded mRNA as a template, to produce: a first double-stranded cDNA (ds cDNA) comprising a strand that is complementary to a first mRNA that encodes an HCVR from a cell; and a second ds cDNA comprising a strand complementary to a second mRNA encoding an LCVR from the cell (the cDNA loaded capture substrate);

wherein the isolated production reaction site, e.g., a production micro-chamber, does not include a nucleic acid encoding an LCVR or an HCVR from a cell other than the cell (e.g., a different cell).

d) maintaining the isolated production reaction site, e.g., the production micro-chamber, under conditions that allow amplification of the first and second ds cDNAs, to produce: a plurality of HC ds cDNAs comprising a segment that encodes an HC element of the HCVR from the cell, e.g., an HCVRS; and a plurality of LC ds cDNAs comprising a segment that encodes an LC element of the LCVR from the cell, e.g., an LCVRS;

e) acquiring an isolated linkage reaction site (e.g., an isolated linkage reaction site described herein), e.g., a linkage micro-chamber, comprising: covalent linking, e.g., ligation, of a strand of the HC ds cDNA (HC strand) to a strand of the LC ds cDNA (LC strand), wherein the HC and LC strands are both sense strands or antisense strands; and f) amplifying the covalently linked, e.g., ligated, HC and LC strands.

In an embodiment, one or more (e.g., two, three, four, five, or all) of the steps a)-f) are performed in accordance with a method described herein. In an embodiment, each of the steps a)-f) is performed in accordance with a method described herein.

In an aspect, the disclosure features a method of making a library comprising a plurality of unique members, the method comprising:

making the plurality of members, wherein each of the members comprises a sequence that encodes a heavy chain element (HC element) of a heavy chain variable region (HCVR) and a light chain element (LC element) of a light chain variable region (LCVR), and wherein the HCVR and LCVR are matched, made by a method described herein, wherein each unique nucleic acid sequence of the plurality comprises an HC element and an LC element from a different unique cell (e.g., a cell described herein), thereby making a library comprising a plurality of unique members.

In an embodiment, the plurality of unique members comprises at least $10^4$, $10^5$, $10^6$, $10^7$, $10^8$, or $10^9$ unique members. In an embodiment, the plurality of unique members comprises $10^4$ to $10^9$, $10^4$ to $10^8$, $10^4$ to $10^7$, $10^4$ to $10^6$, $10^4$ to $10^5$, $10^8$ to $10^9$, $10^7$ to $10^9$, $10^6$ to $10^9$, $10^5$ to $10^9$, $10^5$ to $10^8$, $10^6$ to $10^7$, $10^4$ to $10^5$, $10^5$ to $10^6$, $10^6$ to $10^7$, $10^7$ to $10^8$, or $10^8$ to $10^9$ unique members. In an embodiment, at least 80%, 85%, 90%, 95%, 96%, 97%, 98%, 99%, or 100%, of the members in the library are unique members (which encode matched HC element and LC element sequences). In an embodiment, less than 20%, 15%, 10%, 5%, 4%, 3%, 2%, or 1%, of the members in the library are unique members (which encode matched HC element and LC element sequences).

In an aspect, the disclosure features a library comprising a plurality of unique members, wherein, i) each unique member of the plurality comprises a segment that encodes an HC element, e.g., an HCVRS, and a segment that encodes an LC element, e.g., an LCVRS, wherein the HC element and the LC element in each unique member is matched;

ii) each unique member of the plurality comprises a segment that encodes an HC element, e.g., an HCVRS, and a segment that encodes an LC element, e.g., an LCVRS, from a different unique cell; and iii) the library comprises one or more (e.g., two, three, four, or all) of the following properties:
   a) the library is made by a method described herein;
   b) the plurality of unique members comprises at least $10^4$, $10^5$, $10^6$, $10^7$, $10^8$, or $10^9$ unique nucleic acid sequences;
   c) the plurality of unique members comprises $10^4$ to $10^9$, $10^4$ to $10^8$, $10^4$ to $10^7$, $10^4$ to $10^6$, $10^4$ to $10^5$, $10^8$ to $10^9$, $10^7$ to $10^9$, $10^6$ to $10^9$, $10^5$ to $10^9$, $10^5$ to $10^8$, $10^6$ to $10^7$, $10^4$ to $10^5$, $10^5$ to $10^6$, $10^6$ to $10^7$, $10^7$ to $10^8$, or $10^8$ to $10^9$ unique members;
   d) at least 80%, 85%, 90%, 95%, 96%, 97%, 98%, 99%, or 100%, of the members in the library are unique members (which encode matched HC element and LC element sequences); or
   e) less than 20%, 15%, 10%, 5%, 4%, 3%, 2%, or 1%, of the members in the library are unique members (which encode matched HC element and LC element sequences).

In an embodiment, each unique member of the plurality is configured such that, when expressed, the HC element, e.g., the HCVRS, and the LC element, e.g., the LCVRS, form a functional antigen binding molecule, e.g., an scFv, an Fab, or an scFab.

In an embodiment, the library is a display library. In an embodiment, each of the members of the plurality further encodes a polypeptide that results in display of the member on the surface of a display entity. In an embodiment, the library is a phage display library. In an embodiment, the library is a yeast display library. In an embodiment, the library is a mammalian display library.

In an aspect, the disclosure features a method of making a binding polypeptide (e.g., a polypeptide comprising an HC element and an LC element), the method comprising: a) acquiring a library described herein, e.g., by a method described herein; and b) expressing a polypeptide encoded by a unique nucleic acid of the library.

In an embodiment, the method further comprises contacting the polypeptide with an antigen. In an embodiment, the method further comprises retrieving (e.g., isolating or purifying) the nucleic acid that encodes a polypeptide that binds the antigen.

In an aspect, the disclosure features an isolated production reaction site, e.g., a production micro-chamber, which is an isolated production reaction site described herein (e.g., comprising a nucleic acid encoding an HCVR and a nucleic acid encoding a LCVR, wherein the HCVR and the LCVR are matched).

In an embodiment, the isolated production reaction site, e.g., a production micro-chamber, does not include a nucleic acid encoding an HCVR or an LCVR from a different cell.

In an embodiment, the isolated production reaction site, e.g., a production micro-chamber, comprises one, two, or all of: (i) one or more primers specific to V gene sequences of the HC and LC; (ii) one or more primers specific to overhangs introduced onto the HC and LC cDNAs; or (iii) one or more primers comprising a first member, a second member, and a third member comprising a nucleotide modification (e.g., a spacer) located between the first and second members, wherein the first member is capable of annealing with the second member of the same primer or a different primer, e.g., forming a structure comprising a duplex region of 4, 5, 6, 7, 8, 9, 10, 11, 12, 13, 14, 15, 16, 17, 18, 19, 20, more basepairs.

In an embodiment, the isolated production reaction site, e.g., a production micro-chamber, does not comprise a reagent that can covalently link nucleic acids, e.g., a ligase, e.g., a thermostable ligase. In another embodiment, the isolated production reaction site, e.g., a production micro-chamber, comprises a reagent that can covalently link nucleic acids, e.g., a ligase, e.g., a thermostable ligase.

In an aspect, the disclosure features a self-annealing oligonucleotide comprising a first member, a second member, and third member comprising a nucleotide modification (e.g., a spacer) located between the first and second members, wherein the first member is capable of annealing with the second member of the same oligonucleotide (e.g., for a method of making a nucleic acid sequence comprising a sequence that encodes an HC element of an HCVR and a LC element of an LCVR, wherein the HCVR and LCVR are matched).

In an embodiment, the first and second members are capable of forming a hairpin structure comprising a duplex region of 4, 5, 6, 7, 8, 9, 10, 11, 12, 13, 14, 15, 16, 17, 18, 19, 20, more basepairs. In an embodiment, the first member is 5-40 nucleotides, e.g., 5-10, 5-20, 5-30, 30-40, 20-40, 10-30, 10-30, or 15-25 nucleotides, in length. In an embodiment, the second member is 5-40 nucleotides, e.g., 5-10, 5-20, 5-30, 30-40, 20-40, 10-30, 10-30, or 15-25 nucleotides, in length.

In an embodiment, the spacer is a spacer described herein, e.g., a flexible spacer or a PEG spacer.

In an embodiment, the first member comprises a sequence that is complementary to the sequence of an oligonucleotide attached to a capture substrate.

In an embodiment, the second member comprises (e.g., from 5' to 3') one, two, or all of: (i) a sequence that is complementary to at least a portion of the first member; (ii) a universal priming sequence (e.g., for PCR amplification or next-generation sequencing); and (iii) a sequence complementary to a target sequence, e.g., an HCVRS and/or an LCVRS. In an embodiment, the universal priming sequence is identical, or substantially identical, to the sequence that is complementary to at least a portion of the first member. In another embodiment, the universal priming sequence is different from the sequence that is complementary to at least a portion of the first member. In an embodiment, the second member comprises a sequence for homologous recombination (e.g., in a yeast or mammalian cell).

In an aspect, the disclosure features an isolated linkage reaction site, e.g., a linkage micro-chamber, which is an isolated linkage reaction site described herein (e.g., comprising a nucleic acid encoding an HCVR and a nucleic acid encoding a LCVR, wherein the HCVR and the LCVR are matched).

In an embodiment, the isolated linkage reaction site, e.g., a linkage micro-chamber, does not include a nucleic acid encoding an HCVR or an LCVR from a different cell.

In an embodiment, the isolated linkage reaction site, e.g., a linkage micro-chamber, comprises a splint oligonucleotide (e.g., a splint oligonucleotide described herein) that is capable of hybridizing to a sequence comprising the junction of the HC strand and the LC strand, or a sequence complementary thereof, to form a duplexed region at the site of ligation.

In an embodiment, the isolated linkage reaction site, e.g., a linkage micro-chamber, comprises a reagent that can covalently link nucleic acids, e.g., a ligase, e.g., a thermostable ligase.

In an aspect, the disclosure features a method of making a nucleic acid sequence comprising a sequence that encodes an α chain element (AC element) of a TCR α chain variable region (ACVR) and a β chain element (BC element) of a TCR β chain variable region (BCVR), and wherein the ACVR and the BCVR are matched, the method comprising:

a) acquiring an isolated production reaction site, e.g., a production micro-chamber, comprising:

i) an α chain (AC) strand, wherein the AC strand is a strand of an α chain double-stranded cDNA (AC ds cDNA) comprising a segment that encodes an AC element of the ACVR from a cell, e.g., an α chain variable region sequence (ACVRS); and ii) a β chain (BC) strand, wherein the BC strand is a strand of a β chain ds cDNA (BC ds cDNA) comprising a segment that encodes a BC element of the BCVR from the cell, e.g., a β chain variable region sequence (BCVRS), and b) covalent linking, e.g., ligation, of the first strand to the second strand, wherein the isolated production reaction site, e.g., a production micro-chamber, does not include a nucleic acid encoding an ACVR or a BCVR from a cell other than the cell (e.g., a different cell, e.g., a different T cell), thereby making a nucleic acid sequence comprising a sequence that encodes an AC element of an ACVR and a BC element of a BCVR, wherein the ACVR and the BCVR are matched.

In an embodiment, the AC element comprises, or consists of, an ACVRS, or a functional fragment thereof (e.g., an antigen binding fragment thereof). In an embodiment, the BC element comprises, or consists of, a BCVRS, or a functional fragment thereof (e.g., an antigen binding fragment thereof).

In an embodiment, the AC ds cDNA comprises a segment that encodes an ACVRS. In an embodiment, the BC ds cDNA comprises a segment that encodes a BCVRS. In an embodiment, the AC ds cDNA comprises a segment that encodes an ACVRS, and the BC ds cDNA comprises a segment that encodes a BCVRS.

In an embodiment, the cell is an immune cell, e.g., a T cell, e.g., a human T cell. In an embodiment, the cell is a mammalian cell or an avian cell.

In an embodiment, the nucleic acid sequence is configured such that, when expressed, the AC element and the BC element (e.g., the ACVRS and the BCVRS) form a functional antigen binding molecule, e.g., a single chain or a complex of a TCR α chain and a β chain. In an embodiment, the antigen binding molecule, e.g., a TCR α chain and/or a β chain, is functional in vitro, ex vivo, or in vivo, e.g., as determined by a method or assay described herein.

In an embodiment, acquiring an isolated production reaction site, e.g., a production micro-chamber, comprises:

a) acquiring a capture substrate bound to: (i) a first double-stranded cDNA (ds cDNA) comprising a strand that is complementary to a first mRNA that encodes an ACVR from a cell; and (ii) a second ds cDNA comprising a strand complementary to a second mRNA encoding a BCVR from the cell (the cDNA loaded capture substrate), and b) maintaining the isolated production reaction site, e.g., the production micro-chamber, under conditions that allow amplification of the first and second ds cDNAs, to produce: a plurality of AC ds cDNAs comprising a segment that encodes an AC element of the ACVR from the cell, e.g., an ACVRS; and a plurality of BC ds cDNAs comprising a segment that encodes a BC element of the BCVR from the cell, e.g., a BCVRS.

In an embodiment, the AC ds cDNA is identical, or substantially identical, to the first ds cDNA. For example, the sense strand of the AC ds cDNA is at least 80%, 85%, 90%, 95%, 98%, 99%, or 100% identical to, or differs by no more than 1, 2, 5, 10, 15, 20, 25, 30, 35, 40, 45, or 50 nucleotides from, the sense strand of the first ds cDNA, and/or the antisense strand of the AC ds cDNA is at least 80%, 85%, 90%, 95%, 98%, 99%, or 100% identical to, or differs by no more than 1, 2, 5, 10, 15, 20, 25, 30, 35, 40, 45, or 50 nucleotides from, the antisense strand of the first ds cDNA.

In an embodiment, the BC ds cDNA is identical, or substantially identical, to the second ds cDNA. For example, the sense strand of the BC ds cDNA is at least 80%, 85%, 90%, 95%, 98%, 99%, or 100% identical to, or differs by no more than 1, 2, 5, 10, 15, 20, 25, 30, 35, 40, 45, or 50 nucleotides from, the sense strand of the second ds cDNA, and/or the antisense strand of the BC ds cDNA is at least 80%, 85%, 90%, 95%, 98%, 99%, or 100% identical to, or differs by no more than 1, 2, 5, 10, 15, 20, 25, 30, 35, 40, 45, or 50 nucleotides from, the antisense strand of the second ds cDNA.

In an embodiment, the AC strand is a sense strand. In an embodiment, the BC strand is a sense strand. In an embodiment, the AC strand is an antisense strand. In an embodiment, the BC strand is an antisense strand. In an embodiment, both the AC strand and the BC strand are sense strands. In an embodiment, both the AC strand and the BC strand are antisense strands.

In an embodiment, the capture substrate comprises a bead, e.g., a magnetic bead. In an embodiment, the capture substrate comprises a moiety (e.g., an oligonucleotide) which binds to cDNA, e.g., (i) a moiety which binds to the AC strand; (ii) a moiety which binds to the BC strand; or (iii) both (i) and (ii). In an embodiment, the moiety which binds to the AC strand is different from the moiety which binds to the BC strand, e.g., to facilitate creating conditions favorable to capturing similar levels of each DNA molecule type. In an embodiment, the moiety which binds to the AC strand is identical to the moiety which binds to the BC strand.

In an embodiment, the first mRNA and the second mRNA are disposed on an mRNA loaded capture substrate.

In an embodiment, the isolated production reaction site, e.g., the production micro-chamber, comprises: a reagent mixture suitable for producing, from the first and second mRNAs (e.g., after the first and second mRNAs are released from the loaded mRNA capture substrate into a solution), a first cDNA comprising a segment that encodes an AC element of the ACVR of the cell, e.g., an ACVRS, and a second cDNA comprising a segment that encodes a BC element of the BCVR of the cell, e.g., a BCVRS.

In an embodiment, the isolated production reaction site, e.g., production micro-chamber, comprises primers that mediate the production of the first ds cDNA. In an embodiment, the isolated production reaction site, e.g., production micro-chamber, comprises primers that mediate the production of the second ds cDNA.

In an embodiment, a cDNA strand that is complementary to a first mRNA that encodes an ACVR from a cell is made by reverse transcription of the first mRNA. In an embodiment, a cDNA strand that is complementary to a second mRNA that encodes a BCVR from a cell is made by reverse transcription of the second mRNA.

In an embodiment, the reverse transcription takes place in the isolated production reaction site, e.g., a production-micro chamber. In an embodiment, the reverse transcription takes place in an isolated cell reaction site, e.g., a cell isolation micro-chamber. In an embodiment, the reverse transcription takes place outside the isolated production reaction site, e.g., a production micro-chamber, or outside an isolated cell reaction site, e.g., a cell isolation micro-chamber. In an embodiment, the reverse transcription takes place outside the isolated production reaction site, e.g., a production-micro chamber, and outside an isolated cell reaction site, e.g., a cell isolation micro-chamber. In an embodiment, the reverse transcription takes place outside an isolated reaction site, e.g., outside a micro-chamber.

In an embodiment, the amplification comprises 20 or fewer cycles, e.g., 15 or fewer, 14 or fewer, 13 or fewer, 12 or fewer, 11 or fewer, 10 or fewer, 9 or fewer, 8 or fewer, 7 or fewer, 6 or fewer, or 5 or fewer cycles.

In an embodiment, the reverse transcription and/or amplification uses one or more primers, e.g., comprising a sequence specific for an ACVRS and/or a BCVRs.

In an embodiment, the reverse transcription and/or amplification comprises using two or more primers that mediate the production of the AC ds cDNA, wherein at least one primer comprises a nucleotide modification, and wherein at least one primer does not comprise a nucleotide modification. In an embodiment, the amplification comprises using two or more primers that mediate the production of the BC ds cDNA, wherein at least one primer comprises a nucleotide modification, and wherein at least one primer does not comprise a nucleotide modification.

In an embodiment, at least one primer comprises a nucleotide modification, e.g., which reduces, e.g., inhibits, DNA synthesis, e.g., by a DNA polymerase. In an embodiment, at least one primer does not comprise a nucleotide modification, e.g., which reduces, e.g., inhibits, DNA synthesis, e.g., by a DNA polymerase.

In an embodiment, the nucleotide modification inhibits a DNA polymerase from extending the DNA. Without wishing to be bound by theory, it is believed that in an embodiment, any chemical entity that reduces (e.g., blocks) DNA polymerase extension can be used in accordance with the methods described herein.

In an embodiment, the nucleotide modification is an insertion of a spacer to the primer, e.g., between two adjacent nucleotides in the primer. In an embodiment, the spacer is a flexible spacer. In an embodiment, the spacer is a carbon spacer (e.g., —(CH2)n-, wherein n=3, 4, 5, 6, 7, 8, 9, 10, or more), two or more (e.g., three, four, five, six, seven, eight, nine, ten, or more) abasic nucleotides, or a polyethylene glycol (PEG) spacer. In an embodiment, the spacer is a PEG spacer. In an embodiment, the nucleotide modification is 2'-O-methyl, 2'-OH, 2'-NH$_2$, or uracil, e.g., to a ribose.

In an embodiment, the nucleotide modification is located internally or at the 3' end of the primer. In an embodiment, at least one primer comprises (i) a first member; (ii) a second member; and optionally (iii) a third member, e.g., comprising a nucleotide modification described herein, e.g., located between (i) and (ii).

In an embodiment, the first member is capable of annealing with the second member. In an embodiment, the first member is capable of annealing with the second member in the same primer, e.g., through intra-molecular hybridization, e.g., to form a hairpin structure comprising a duplex region of 4, 5, 6, 7, 8, 9, 10, 11, 12, 13, 14, 15, 16, 17, 18, 19, 20, more basepairs. In another embodiment, the first member is capable of annealing hybridizing with the second member in a different primer, e.g., through inter-molecular hybridization, e.g., to form a double-stranded structure comprising a duplex region of 4, 5, 6, 7, 8, 9, 10, 11, 12, 13, 14, 15, 16, 17, 18, 19, 20, more basepairs. Without wishing to be bound by theory, it is believed that in an embodiment, there are at least two secondary structures that the modified primers can form and facilitate reduction (e.g., prevention) of competition to substrate (e.g., bead) capture. For example, the secondary structure can be a hairpin-like structure formed by intra-molecular hybridization (within the same primer), or the secondary structure can be a duplex structure formed by inter-molecular hybridization (between two different primers).

In an embodiment, the first member comprises a sequence that is complementary to the sequence of an oligonucleotide attached to the capture substrate. In an embodiment, the second member comprises (e.g., from 5' to 3') one, two, or all of: (i) a sequence that is complementary to at least a portion of the first member; (ii) a universal priming sequence (e.g., for PCR amplification or next-generation sequencing); and (iii) a sequence complementary to a target sequence, e.g., an ACVRS and/or a BCVRS. In an embodiment, the universal priming sequence is identical, or substantially identical, to the sequence that is complementary to at least a portion of the first member. In another embodiment, the universal priming sequence is different from the sequence that is complementary to at least a portion of the first member. In an embodiment, the second member comprises a sequence for homologous recombination (e.g., in a yeast or mammalian cell).

In an embodiment, at least one primer comprises a sequence encoding at least a portion of a linker sequence, or a complementary sequence thereof. In an embodiment, the primer that comprises a sequence encoding at least a portion of a linker sequence, or a complementary sequence thereof, is phosphorylated, e.g., 5' phosphorylated. Without wishing to be bound by theory, it is believed that in an embodiment, any sequence with the general properties of flexibility (e.g., facilitated by glycine) and hydrophilicity can work effectively in accordance with the methods described herein. Exemplary linkers can generally have overrepresentation of one or more of Gly, Ser, Thr, or Ala and underrepresentation of hydrophobic residues, e.g., one or more of Trp, Tyr, Phe, Cys, Met, Leu, or Ile. The length of the primer may vary, e.g., 3-50 amino acid residues (e.g., 5-45, 10-40, 15-35, 20-30, 10-20, 10-30, 20-40, or 30-40 amino acid residues). In an embodiment, the linker sequence comprises, or consists of, ((Gly)m-Ser))n, where m=3, 4, 5, or more and n=1, 2, 3, 4, 5, 6, 7, 8, 9, 10, or more (SEQ ID NO: 25). In an embodiment, the linker sequence comprises, or consists of, (Gly-Gly-Gly-Gly-Ser)n, where n=1, 2, 3, 4, 5, 6, 7, 8, 9, 10, or more (SEQ ID NO: 26).

In an embodiment, the primer is a primer described herein, e.g., in Examples.

In an embodiment, the reverse transcription, the amplification, or both, occurs in a solution in the isolated production reaction site, e.g., production micro-chamber. In an embodiment, the reverse transcription, the amplification, or both, does not occur on the substrate (e.g., bead). For example, the reverse transcription, the amplification, or both, can occur on in a solution within a droplet.

In an embodiment, the AC ds cDNA comprises a 5' overhang, e.g., a 5' overhang that is capable of hybridizing to an oligonucleotide attached to a capture substrate. In an embodiment, the AC ds cDNA comprises a blunt end, e.g., a blunt end comprising a 5' phosphate. In an embodiment, the BC ds cDNA comprises a 5' overhang, e.g., a 5' overhang that is capable of hybridizing to an oligonucleotide attached to a capture substrate. In an embodiment, the BC ds cDNA comprises a blunt end, e.g., a blunt end comprising a 5' phosphate. In an embodiment, the AC ds cDNA and the BC ds cDNA comprise sticky ends, e.g., both have 5' overhangs.

In an embodiment, the AC strand and the BC strand are covalently linked, e.g., ligated, to produce a single stranded nucleic acid sequence, wherein the AC and BC strands are both sense strands or both antisense strands. In an embodiment, a denatured AC strand of the AC ds cDNA to a denatured BC strand of the BC ds cDNA are covalently linked, e.g., ligated, wherein the AC and BC strands are both sense strands or both antisense strands. In an embodiment, the AC strand is present in the AC ds cDNA and the BC strand is present in the BC ds cDNA, and wherein the AC ds cDNA and the BC ds cDNA are covalently linked, e.g., ligated, e.g., to produce a double stranded nucleic acid sequence.

In an embodiment, the covalent linking, e.g., ligation, occurs in the isolated production reaction site. In an embodiment, the isolated production reaction site, e.g., a production micro-chamber, or the isolated linkage reaction site, e.g., a linkage micro-chamber, comprises a reagent that is capable of covalently linking, e.g., ligating, the AC and BC strands or the AC and BC ds cDNAs. In an embodiment, the isolated production reaction site, e.g., a production micro-chamber comprises an enzyme that covalently couples the AC and BC strands or the AC and BC ds cDNAs. In an embodiment, the enzyme is a ligase, e.g., a thermal stable ligase. In an embodiment, the covalent linking comprises ligase thermocycling.

In an embodiment, the covalent linking, e.g., ligation, occurs in a site different from the isolated production reaction site, e.g., occurs in an isolated linkage reaction site, e.g., a linkage micro-chamber. In an embodiment, the AC strand and the BC strand are transferred from the isolated production site to the isolated linkage reaction site, e.g., a linkage micro-chamber, and the covalent linking occurs in the isolated linkage reaction site, e.g., a linkage micro-chamber. In an embodiment, the isolated linkage reaction site, e.g., a linkage micro-chamber, comprises a reagent that is capable of covalently linking, e.g., ligating, the AC and BC strands or the AC and BC ds cDNAs. In an embodiment, the isolated linkage reaction site, e.g., a linkage micro-chamber, comprises an enzyme that covalently couples the AC and BC strands or the AC and BC ds cDNAs. In an embodiment, the enzyme is a ligase, e.g., a thermal stable ligase. In an embodiment, the covalent linking comprises ligase thermocycling.

In an embodiment, the covalent linking, e.g., ligation, comprises: (a) heating the isolated linkage reaction site, e.g., the linkage micro-chamber, under conditions (e.g., at 95° C.) that allow denaturation of the AC strand and the BC strand; (b) cooling the isolated linkage reaction site, e.g., the linkage micro-chamber, under conditions (e.g., at 50-65° C.) that allow hybridization of the splint oligonucleotide to the AC strand and the BC strand; (c) maintaining the isolated linkage reaction site, e.g., the linkage micro-chamber, under conditions (e.g., at 45-65° C.) that allow ligation of the AC strand and the BC strand (e.g., formation of phosphodiester bond between the AC strand and the BC strand); and (d) repeating steps (a), (b), and (c) sequentially for 2, 5, 10, 15, 20, 25, 30, 35, 40, 45, 50, or more cycles.

In an embodiment, the AC strand and the BC strand are covalently linked, e.g., ligated, in the presence of a splint oligonucleotide. In an embodiment, the splint oligonucleotide is hybridized to a sequence comprising the junction of the AC strand and the BC strand, or a sequence complementary thereof, and forms a duplexed region at the site of ligation. In an embodiment, the splint oligonucleotide comprises a modification (e.g., an NH$_2$ group) that inhibits DNA synthesis, e.g., by a DNA polymerase. In an embodiment, the modification is at the 3' end of the splint oligonucleotide.

In an embodiment, a strand complimentary to the covalently linked, e.g., ligated, AC and BC strands is produced by amplification.

In an embodiment, the method, e.g., the step of covalent linkage, does not include a step of overlap extension polymerase chain reaction (OE-PCR), also known as splicing by overlap extension or splicing by overhang extension (SOE) PCR.

In an embodiment, the method further comprises, prior to acquiring the isolated production reaction site, e.g., a production micro-chamber, acquiring an mRNA loaded capture substrate.

In an embodiment, acquiring the mRNA loaded capture substrate comprising: a) acquiring an isolated cell reaction site, e.g., a cell isolation micro-chamber, comprising: i) a cell; and ii) a capture substrate capable of binding a first mRNA encoding an ACVR from the cell and a second mRNA encoding a BCVR from the cell; and b) maintaining the isolated cell reaction site, e.g., the cell isolation micro-chamber, under conditions that allow lysis of the cell and binding of the capture substrate with the first mRNA and the second mRNA to form the mRNA loaded capture substrate, wherein the isolated cell reaction site, e.g., cell isolation micro-chamber, does not include a nucleic acid encoding an ACVR or a BCVR from a cell other than the cell (e.g., a different cell).

In an embodiment, the isolated cell reaction site, e.g., cell isolation micro-chamber, comprises a lysing reagent, e.g., a detergent. In an embodiment, the cell is lysed by heat or an enzyme. In an embodiment, the capture substrate comprises a moiety (e.g., an oligonucleotide) which binds mRNA, e.g., an oligo(dT).

In an embodiment, the method further comprises releasing the mRNA loaded capture substrate from the isolated cell reaction site, e.g., the cell isolation micro-chamber. In an embodiment, the releasing step is performed in the presence of a poly(dA) or poly(dT) oligonucleotide, e.g., to reduce cross-binding of non-captured mRNA.

In an embodiment, the mRNA loaded capture substrate is transferred from the isolated cell reaction site, e.g., the cell isolation micro-chamber, to the isolated production reaction site, e.g., the production micro-chamber.

In an embodiment, the method further comprises releasing the nucleic acid sequence from the isolated production reaction site, e.g., the production micro-chamber. In an embodiment, the method further comprises amplifying the nucleic acid sequence. In an embodiment, amplification of the nucleic acid sequence occurs outside the isolated production reaction site, e.g., the production micro-chamber, e.g., after the nucleic acid is released from the isolated production reaction site, e.g., the production micro-chamber. In an embodiment, amplification of the nucleic acid sequence occurs at the isolated production reaction site, e.g., the production micro-chamber.

In an embodiment, the method further comprises sequencing all or a portion of the nucleic acid sequence.

In an embodiment, the method further comprises inserting all or a portion of nucleic acid sequence into a vector. In an embodiment, the vector supplies an additional AC element or BC element not included in the nucleic acid sequence. In an embodiment, the method further comprises expressing the vector.

In an embodiment, the method further comprises expressing the nucleic acid sequence to produce a polypeptide comprising a segment that encodes an AC element of the ACVR, e.g., an ACVRS, and a segment that encodes a BC element of the BCVR, e.g., a BCVRS. In an embodiment, the BC element is N-terminal to the AC element in the polypeptide. In an embodiment, the AC element is C-terminal to the BC element in the polypeptide.

In an embodiment, the method further comprises contacting the polypeptide with an antigen. In an embodiment, the method further comprises determining if the polypeptide binds the antigen, in vitro, ex vivo, or in vivo, e.g., by a method or assay described herein.

In an embodiment, the disclosure features a method of making a nucleic acid sequence comprising a sequence that encodes a TCR α chain element (AC element) of TCR α chain variable region (ACVR) and a TCR β chain element (BC element) of a TCR β chain variable region (BCVR), and wherein the ACVR and BCVR are matched, comprising:

a) acquiring an isolated cell reaction site (e.g., an isolated cell reaction site described herein), e.g., a cell isolation micro-chamber, comprising: i) a cell (e.g., a cell described herein); and ii) a capture substrate (e.g., a capture substrate described herein) capable of binding a first mRNA encoding an ACVR from the cell and a second mRNA encoding a BCVR from the cell;

b) maintaining the isolated cell reaction site, e.g., the cell isolation micro-chamber, under conditions that allow lysis of the cell and binding of the capture substrate with the first mRNA and the second mRNA to form an mRNA loaded capture substrate, wherein the isolated cell reaction site, e.g., cell isolation micro-chamber, does not include a nucleic acid encoding an ACVR or a BCVR from a cell other than the cell (e.g., a different cell);

c) contacting the mRNA loaded capture substrate with a reaction mixture, e.g., a reaction mixture comprising reverse transcriptase, that uses the loaded mRNA as a template to make cDNA (this can occur, e.g., in the isolated cell reaction site, in an isolated production reaction site, or in neither, e.g., not in an isolated reaction site);

d) acquiring an isolated production reaction site (e.g., an isolated production reaction site described herein), e.g., a production micro-chamber, comprising: i) a TCR α chain (AC) strand, wherein the AC strand is a strand of a TCR α chain double-stranded cDNA (AC ds cDNA) comprising a segment that encodes an AC element of the ACVR from the cell, e.g., a TCR α chain variable region sequence (ACVRS); and ii) a TCR β chain (BC) strand, wherein the BC strand is a strand of a TCR β chain double-stranded cDNA (BC ds cDNA) comprising a segment that encodes a BC element of the BCVR from the cell, e.g., a TCR β chain variable region sequence (BCVRS), wherein the isolated production reaction site, e.g., a production micro-chamber, does not include a nucleic acid encoding an ACVR or a BCVR from a cell other than the cell (e.g., a different cell); and e) covalent linking, e.g., ligation, of the AC strand to the BC strand.

In an embodiment, one or more (e.g., two, three, four, or all) of the steps a)-e) are performed in accordance with a method described herein. In an embodiment, each of the steps a)-e) is performed in accordance with a method described herein.

In an aspect, the disclosure features a method of making a nucleic acid sequence comprising a sequence that encodes a TCR α chain element (AC element) of a TCR α chain variable region (ACVR) and a TCR β chain element (BC element) of a TCR β chain variable region (BCVR), and wherein the ACVR and BCVR are matched, comprising:

a) acquiring an isolated cell reaction site (e.g., an isolated cell reaction site described herein), e.g., a cell isolation micro-chamber, comprising: i) a cell (e.g., a cell described herein); and ii) a capture substrate (e.g., a capture substrate described herein) capable of binding a first mRNA encoding an ACVR from the cell and a second mRNA encoding a BCVR from the cell;

b) maintaining the isolated cell reaction site, e.g., the cell isolation micro-chamber, under conditions that allow lysis of the cell and binding of the capture substrate with the first mRNA and the second mRNA to form the mRNA loaded capture substrate, wherein the isolated cell reaction site, e.g., cell isolation micro-chamber, does not include a nucleic acid encoding an ACVR or a BCVR from a cell other than the cell (e.g., a different cell);

c) acquiring an isolated production reaction site (e.g., an isolated production reaction site described herein), e.g., a production micro-chamber, comprises: contacting the mRNA loaded capture substrate with a reaction mixture, e.g., a reaction mixture comprising reverse transcriptase, that uses the loaded mRNA as a template, to produce: a first double-stranded cDNA (ds cDNA) comprising a strand that is complementary to a first mRNA that encodes an ACVR from a cell; and a second ds cDNA comprising a strand complementary to a second mRNA encoding a BCVR from the cell (the cDNA loaded capture substrate);

wherein the isolated production reaction site, e.g., a production micro-chamber, does not include a nucleic acid encoding an ACVR or a BCVR from a cell other than the cell (e.g., a different cell).

d) maintaining the isolated production reaction site, e.g., the production micro-chamber, under conditions that allow amplification of the first and second ds cDNAs, to produce: a plurality of AC ds cDNAs comprising a segment that encodes an AC element of the ACVR from the cell, e.g., an ACVRS; and a plurality of BC ds cDNAs comprising a segment that encodes a BC element of the BCVR from the cell, e.g., a BCVRS;

e) acquiring an isolated linkage reaction site (e.g., an isolated linkage reaction site described herein), e.g., a linkage micro-chamber, comprising: covalent linking, e.g., ligation, of a strand of the AC ds cDNA (AC strand) to a strand of the BC ds cDNA (BC strand), wherein the AC and BC strands are both sense strands or antisense strands; and f) amplifying the covalently linked, e.g., ligated, AC and BC strands.

In an embodiment, one or more (e.g., two, three, four, five, or all) of the steps a)-f) are performed in accordance with a method described herein. In an embodiment, each of the steps a)-f) is performed in accordance with a method described herein.

In an aspect, the disclosure features a method of making a library comprising a plurality of unique members, the method comprising:

making the plurality of members, wherein each of the members comprises a sequence that encodes a TCR α chain element (AC element) of a TCR α chain variable region (ACVR) and a TCR β chain element (BC element) of a TCR β chain variable region (BCVR), and wherein the ACVR and BCVR are matched, made by a method described herein, wherein each unique nucleic acid sequence of the plurality comprises an AC element and a BC element from a different unique cell (e.g., a cell described herein), thereby making a library comprising a plurality of unique members.

In an embodiment, the plurality of unique members comprises at least $10^4$, $10^5$, $10^6$, $10^7$, $10^8$, or $10^9$ unique members. In an embodiment, the plurality of unique members comprises $10^4$ to $10^9$, $10^4$ to $10^8$, $10^4$ to $10^7$, $10^4$ to $10^6$, $10^4$ to $10^5$, $10^8$ to $10^9$, $10^7$ to $10^9$, $10^6$ to $10^9$, $10^5$ to $10^9$, $10^5$ to $10^8$, $10^6$ to $10^7$, $10^4$ to $10^5$, $10^5$ to $10^6$, $10^6$ to $10^7$, $10^7$ to $10^8$, or $10^8$ to $10^9$ unique members. In an embodiment, at least 80%, 85%, 90%, 95%, 96%, 97%, 98%, 99%, or 100%, of the members in the library are unique members (which encode matched AC element and BC element sequences). In an embodiment, less than 20%, 15%, 10%, 5%, 4%, 3%, 2%, or 1%, of the members in the library are unique members (which encode matched AC element and BC element sequences).

In an aspect, the disclosure features a library comprising a plurality of unique members, wherein, i) each unique member of the plurality comprises a segment that encodes an AC element, e.g., an ACVRS, and a segment that encodes a BC element, e.g., a BCVRS, wherein the AC element and the BC element in each unique member is matched;

ii) each unique member of the plurality comprises a segment that encodes an AC element, e.g., an ACVRS, and a segment that encodes a BC element, e.g., a BCVRS, from a different unique cell; and iii) the library comprises one or more (e.g., two, three, four, or all) of the following properties:

a) the library is made by a method described herein;

b) the plurality of unique members comprises at least $10^4$, $10^5$, $10^6$, $10^7$, $10^8$, or $10^9$ unique nucleic acid sequences;

c) the plurality of unique members comprises $10^4$ to $10^9$, $10^4$ to $10^8$, $10^4$ to $10^7$, $10^4$ to $10^6$, $10^4$ to $10^5$, $10^8$ to $10^9$, $10^7$ to $10^9$, $10^6$ to $10^9$, $10^5$ to $10^9$, $10^5$ to $10^8$, $10^6$ to $10^7$, $10^4$ to $10^5$, $10^5$ to $10^6$, $10^6$ to $10^7$, $10^7$ to $10^8$, or $10^8$ to $10^9$ unique members;

d) at least 80%, 85%, 90%, 95%, 96%, 97%, 98%, 99%, or 100%, of the members in the library are unique members (which encode matched AC element and BC element sequences); or e) less than 20%, 15%, 10%, 5%, 4%, 3%, 2%, or 1%, of the members in the library are unique members (which encode matched AC element and BC element sequences).

In an embodiment, each unique member of the plurality is configured such that, when expressed, the AC element, e.g., the ACVRS, and the BC element, e.g., the BCVRS, form a functional antigen binding molecule, e.g., a single chain or a complex of a TCR α chain and a β chain.

In an embodiment, the library is a display library. In an embodiment, each of the members of the plurality further encodes a polypeptide that results in display of the member on the surface of a display entity. In an embodiment, the library is a phage display library. In an embodiment, the library is a yeast display library. In an embodiment, the library is a mammalian display library.

In an aspect, the disclosure features a method of making a binding polypeptide (e.g., a polypeptide comprising an AC element and a BC element), the method comprising: a) acquiring a library described herein, e.g., by a method described herein; and b) expressing a polypeptide encoded by a unique nucleic acid of the library.

In an embodiment, the method further comprises contacting the polypeptide with an antigen. In an embodiment, the method further comprises retrieving (e.g., isolating or purifying) the nucleic acid that encodes a polypeptide that binds the antigen.

In an aspect, the disclosure features an isolated production reaction site, e.g., a production micro-chamber, which is an isolated production reaction site described herein (e.g., comprising a nucleic acid encoding an ACVR and a nucleic acid encoding a BCVR, wherein the ACVR and the BCVR are matched).

In an embodiment, the isolated production reaction site, e.g., a production micro-chamber, does not include a nucleic acid encoding an ACVR or a BCVR from a different cell.

In an embodiment, the isolated production reaction site, e.g., a production micro-chamber, comprises one, two, or all of: (i) one or more primers specific to V gene sequences of the AC and BC; (ii) one or more primers specific to overhangs introduced onto the AC and BC cDNAs; or (iii) one or more primers comprising a first member, a second member, and a third member comprising a nucleotide modification (e.g., a spacer) located between the first and second members, wherein the first member is capable of annealing with the second member of the same primer or a different primer, e.g., forming a structure comprising a duplex region of 4, 5, 6, 7, 8, 9, 10, 11, 12, 13, 14, 15, 16, 17, 18, 19, 20, more basepairs.

In an embodiment, the isolated production reaction site, e.g., a production micro-chamber, does not comprise a reagent that can covalently link nucleic acids, e.g., a ligase, e.g., a thermostable ligase. In another embodiment, the isolated production reaction site, e.g., a production micro-chamber, comprises a reagent that can covalently link nucleic acids, e.g., a ligase, e.g., a thermostable ligase.

In an aspect, the disclosure features a self-annealing oligonucleotide comprising a first member, a second member, and third member comprising a nucleotide modification (e.g., a spacer) located between the first and second members, wherein the first member is capable of annealing with the second member of the same oligonucleotide (e.g., for a method of making a nucleic acid sequence comprising a sequence that encodes an AC element of an ACVR and a BC element of a BCVR, wherein the ACVR and BCVR are matched).

In an embodiment, the first and second members are capable of forming a hairpin structure comprising a duplex region of 4, 5, 6, 7, 8, 9, 10, 11, 12, 13, 14, 15, 16, 17, 18, 19, 20, more basepairs. In an embodiment, the first member is 5-40 nucleotides, e.g., 5-10, 5-20, 5-30, 30-40, 20-40, 10-30, 10-30, or 15-25 nucleotides, in length. In an embodiment, the second member is 5-40 nucleotides, e.g., 5-10, 5-20, 5-30, 30-40, 20-40, 10-30, 10-30, or 15-25 nucleotides, in length.

In an embodiment, the spacer is a spacer described herein, e.g., a flexible spacer or a PEG spacer.

In an embodiment, the first member comprises a sequence that is complementary to the sequence of an oligonucleotide attached to a capture substrate.

In an embodiment, the second member comprises (e.g., from 5' to 3') one, two, or all of: (i) a sequence that is complementary to at least a portion of the first member; (ii) a universal priming sequence (e.g., for PCR amplification or next-generation sequencing); and (iii) a sequence complementary to a target sequence, e.g., an ACVRS and/or a BCVRS. In an embodiment, the universal priming sequence is identical, or substantially identical, to the sequence that is complementary to at least a portion of the first member. In another embodiment, the universal priming sequence is different from the sequence that is complementary to at least a portion of the first member. In an embodiment, the second member comprises a sequence for homologous recombination (e.g., in a yeast or mammalian cell).

In an aspect, the disclosure features an isolated linkage reaction site, e.g., a linkage micro-chamber, which is an isolated linkage reaction site described herein (e.g., comprising a nucleic acid encoding an ACVR and a nucleic acid encoding a BCVR, wherein the ACVR and the BCVR are matched).

In an embodiment, the isolated linkage reaction site, e.g., a linkage micro-chamber, does not include a nucleic acid encoding an ACVR or a BCVR from a different cell.

In an embodiment, the isolated linkage reaction site, e.g., a linkage micro-chamber, comprises a splint oligonucleotide (e.g., a splint oligonucleotide described herein) that is capable of hybridizing to a sequence comprising the junction of the AC strand and the BC strand, or a sequence complementary thereof, to form a duplexed region at the site of ligation.

In an embodiment, the isolated linkage reaction site, e.g., a linkage micro-chamber, comprises a reagent that can covalently link nucleic acids, e.g., a ligase, e.g., a thermostable ligase.

In an aspect, the disclosure features a method of making a nucleic acid sequence comprising a sequence that encodes a γ chain element (GC element) of a TCR γ chain variable region (GCVR) and a δ chain element (DC element) of a TCR δ chain variable region (DCVR), and wherein the GCVR and the DCVR are matched, the method comprising:

a) acquiring an isolated production reaction site, e.g., a production micro-chamber, comprising:

i) an γ chain (GC) strand, wherein the GC strand is a strand of an γ chain double-stranded cDNA (GC ds cDNA) comprising a segment that encodes a GC element of the GCVR from a cell, e.g., an γ chain variable region sequence (GCVRS); and ii) a δ chain (DC) strand, wherein the DC strand is a strand of a δ chain ds cDNA (DC ds cDNA) comprising a segment that encodes a DC element of the DCVR from the cell, e.g., a δ chain variable region sequence (DCVRS), and b) covalent linking, e.g., ligation, of the first strand to the second strand, wherein the isolated production reaction site, e.g., a production micro-chamber, does not include a nucleic acid encoding a GCVR or a DCVR from a cell other than the cell (e.g., a different cell, e.g., a different T cell), thereby making a nucleic acid sequence comprising a sequence that encodes a GC element of a GCVR and a DC element of a DCVR, wherein the GCVR and the DCVR are matched.

In an embodiment, the GC element comprises, or consists of, a GCVRS, or a functional fragment thereof (e.g., an antigen binding fragment thereof). In an embodiment, the DC element comprises, or consists of, a DCVRS, or a functional fragment thereof (e.g., an antigen binding fragment thereof).

In an embodiment, the GC ds cDNA comprises a segment that encodes a GCVRS. In an embodiment, the DC ds cDNA comprises a segment that encodes a DCVRS. In an embodiment, the GC ds cDNA comprises a segment that encodes a GCVRS, and the DC ds cDNA comprises a segment that encodes a DCVRS.

In an embodiment, the cell is an immune cell, e.g., a T cell, e.g., a human T cell. In an embodiment, the cell is a mammalian cell or an avian cell.

In an embodiment, the nucleic acid sequence is configured such that, when expressed, the GC element and the DC element (e.g., the GCVRS and the DCVRS) form a functional antigen binding molecule, e.g., a single chain or a complex of a TCR γ chain and a δ chain. In an embodiment, the antigen binding molecule, e.g., a TCR γ chain and/or a δ chain, is functional in vitro, ex vivo, or in vivo, e.g., as determined by a method or assay described herein.

In an embodiment, acquiring an isolated production reaction site, e.g., a production micro-chamber, comprises:

a) acquiring a capture substrate bound to: (i) a first double-stranded cDNA (ds cDNA) comprising a strand that is complementary to a first mRNA that encodes a GCVR from a cell; and (ii) a second ds cDNA comprising a strand complementary to a second mRNA encoding a DCVR from the cell (the cDNA loaded capture substrate), and b) maintaining the isolated production reaction site, e.g., the production micro-chamber, under conditions that allow amplification of the first and second ds cDNAs, to produce: a plurality of GC ds cDNAs comprising a segment that encodes a GC element of the GCVR from the cell, e.g., a GCVRS; and a plurality of DC ds cDNAs comprising a segment that encodes a DC element of the DCVR from the cell, e.g., a DCVRS.

In an embodiment, the GC ds cDNA is identical, or substantially identical, to the first ds cDNA. For example, the sense strand of the GC ds cDNA is at least 80%, 85%, 90%, 95%, 98%, 99%, or 100% identical to, or differs by no more than 1, 2, 5, 10, 15, 20, 25, 30, 35, 40, 45, or 50 nucleotides from, the sense strand of the first ds cDNA, and/or the antisense strand of the GC ds cDNA is at least 80%, 85%, 90%, 95%, 98%, 99%, or 100% identical to, or differs by no more than 1, 2, 5, 10, 15, 20, 25, 30, 35, 40, 45, or 50 nucleotides from, the antisense strand of the first ds cDNA.

In an embodiment, the DC ds cDNA is identical, or substantially identical, to the second ds cDNA. For example, the sense strand of the DC ds cDNA is at least 80%, 85%, 90%, 95%, 98%, 99%, or 100% identical to, or differs by no more than 1, 2, 5, 10, 15, 20, 25, 30, 35, 40, 45, or 50 nucleotides from, the sense strand of the second ds cDNA, and/or the antisense strand of the DC ds cDNA is at least 80%, 85%, 90%, 95%, 98%, 99%, or 100% identical to, or differs by no more than 1, 2, 5, 10, 15, 20, 25, 30, 35, 40, 45, or 50 nucleotides from, the antisense strand of the second ds cDNA.

In an embodiment, the GC strand is a sense strand. In an embodiment, the DC strand is a sense strand. In an embodiment, the GC strand is an antisense strand. In an embodiment, the DC strand is an antisense strand. In an embodiment, both the GC strand and the DC strand are sense strands. In an embodiment, both the GC strand and the DC strand are antisense strands.

In an embodiment, the capture substrate comprises a bead, e.g., a magnetic bead. In an embodiment, the capture substrate comprises a moiety (e.g., an oligonucleotide) which binds to cDNA, e.g., (i) a moiety which binds to the GC strand; (ii) a moiety which binds to the DC strand; or (iii) both (i) and (ii). In an embodiment, the moiety which binds to the GC strand is different from the moiety which binds to the DC strand, e.g., to facilitate creating conditions favorable to capturing similar levels of each DNA molecule type. In an embodiment, the moiety which binds to the GC strand is identical to the moiety which binds to the DC strand.

In an embodiment, the first mRNA and the second mRNA are disposed on an mRNA loaded capture substrate.

In an embodiment, the isolated production reaction site, e.g., the production micro-chamber, comprises: a reagent mixture suitable for producing, from the first and second mRNAs (e.g., after the first and second mRNAs are released from the mRNA loaded capture substrate into a solution), a first cDNA comprising a segment that encodes a GC element of the GCVR of the cell, e.g., a GCVRS, and a second cDNA comprising a segment that encodes a DC element of the DCVR of the cell, e.g., a DCVRS.

In an embodiment, the isolated production reaction site, e.g., production micro-chamber, comprises primers that mediate the production of the first ds cDNA. In an embodiment, the isolated production reaction site, e.g., production micro-chamber, comprises primers that mediate the production of the second ds cDNA.

In an embodiment, a cDNA strand that is complementary to a first mRNA that encodes a GCVR from a cell is made by reverse transcription of the first mRNA. In an embodiment, a cDNA strand that is complementary to a second mRNA that encodes a DCVR from a cell is made by reverse transcription of the second mRNA.

In an embodiment, the reverse transcription takes place in the isolated production reaction site, e.g., a production-micro chamber. In an embodiment, the reverse transcription takes place in an isolated cell reaction site, e.g., a cell isolation micro-chamber. In an embodiment, the reverse transcription takes place outside the isolated production reaction site, e.g., a production micro-chamber, or outside an isolated cell reaction site, e.g., a cell isolation micro-chamber. In an embodiment, the reverse transcription takes place outside the isolated production reaction site, e.g., a production-micro chamber, and outside an isolated cell reaction site, e.g., a cell isolation micro-chamber. In an embodiment, the reverse transcription takes place outside an isolated reaction site, e.g., outside a micro-chamber.

In an embodiment, the amplification comprises 20 or fewer cycles, e.g., 15 or fewer, 14 or fewer, 13 or fewer, 12 or fewer, 11 or fewer, 10 or fewer, 9 or fewer, 8 or fewer, 7 or fewer, 6 or fewer, or 5 or fewer cycles.

In an embodiment, the reverse transcription and/or amplification uses one or more primers, e.g., comprising a sequence specific for a GCVRS and/or a DCVRS.

In an embodiment, the reverse transcription and/or amplification comprises using two or more primers that mediate the production of the GC ds cDNA, wherein at least one primer comprises a nucleotide modification, and wherein at least one primer does not comprise a nucleotide modification. In an embodiment, the amplification comprises using two or more primers that mediate the production of the DC ds cDNA, wherein at least one primer comprises a nucleotide modification, and wherein at least one primer does not comprise a nucleotide modification.

In an embodiment, at least one primer comprises a nucleotide modification, e.g., which reduces, e.g., inhibits, DNA synthesis, e.g., by a DNA polymerase. In an embodiment, at least one primer does not comprise a nucleotide modification, e.g., which reduces, e.g., inhibits, DNA synthesis, e.g., by a DNA polymerase.

In an embodiment, the nucleotide modification inhibits a DNA polymerase from extending the DNA. Without wishing to be bound by theory, it is believed that in an embodiment, any chemical entity that reduces (e.g., blocks) DNA polymerase extension can be used in accordance with the methods described herein.

In an embodiment, the nucleotide modification is an insertion of a spacer to the primer, e.g., between two adjacent nucleotides in the primer. In an embodiment, the spacer is a flexible spacer. In an embodiment, the spacer is a carbon spacer (e.g., —(CH2)n-, wherein n=3, 4, 5, 6, 7, 8, 9, 10, or more), two or more (e.g., three, four, five, six, seven, eight, nine, ten, or more) abasic nucleotides, or a polyethylene glycol (PEG) spacer. In an embodiment, the spacer is a PEG spacer. In an embodiment, the nucleotide modification is 2'-O-methyl, 2'-OH, 2'-NH$_2$, or uracil, e.g., to a ribose.

In an embodiment, the nucleotide modification is located internally or at the 3' end of the primer. In an embodiment, at least one primer comprises (i) a first member; (ii) a second member; and optionally (iii) a third member, e.g., comprising a nucleotide modification described herein, e.g., located between (i) and (ii).

In an embodiment, the first member is capable of annealing with the second member. In an embodiment, the first member is capable of annealing with the second member in the same primer, e.g., through intra-molecular hybridization, e.g., to form a hairpin structure comprising a duplex region of 4, 5, 6, 7, 8, 9, 10, 11, 12, 13, 14, 15, 16, 17, 18, 19, 20, more basepairs. In another embodiment, the first member is capable of annealing hybridizing with the second member in a different primer, e.g., through inter-molecular hybridization, e.g., to form a double-stranded structure comprising a duplex region of 4, 5, 6, 7, 8, 9, 10, 11, 12, 13, 14, 15, 16, 17, 18, 19, 20, more basepairs. Without wishing to be bound by theory, it is believed that in an embodiment, there are at least two secondary structures that the modified primers can form and facilitate reduction (e.g., prevention) of competition to substrate (e.g., bead) capture. For example, the secondary structure can be a hairpin-like structure formed by intra-molecular hybridization (within the same primer), or the secondary structure can be a duplex structure formed by inter-molecular hybridization (between two different primers).

In an embodiment, the first member comprises a sequence that is complementary to the sequence of an oligonucleotide attached to the capture substrate. In an embodiment, the second member comprises (e.g., from 5' to 3') one, two, or all of: (i) a sequence that is complementary to at least a portion of the first member; (ii) a universal priming sequence (e.g., for PCR amplification or next-generation sequencing); and (iii) a sequence complementary to a target sequence, e.g., a GCVRS and/or a DCVRS. In an embodiment, the universal priming sequence is identical, or substantially identical, to the sequence that is complementary to at least a portion of the first member. In another embodiment, the universal priming sequence is different from the sequence that is complementary to at least a portion of the first member. In an embodiment, the second member comprises a sequence for homologous recombination (e.g., in a yeast or mammalian cell).

In an embodiment, at least one primer comprises a sequence encoding at least a portion of a linker sequence, or a complementary sequence thereof. In an embodiment, the primer that comprises a sequence encoding at least a portion of a linker sequence, or a complementary sequence thereof, is phosphorylated, e.g., 5' phosphorylated. Without wishing to be bound by theory, it is believed that in an embodiment, any sequence with the general properties of flexibility (e.g., facilitated by glycine) and hydrophilicity can work effectively in accordance with the methods described herein. Exemplary linkers can generally have overrepresentation of one or more of Gly, Ser, Thr, or Ala and underrepresentation of hydrophobic residues, e.g., one or more of Trp, Tyr, Phe, Cys, Met, Leu, or Ile. The length of the primer may vary, e.g., 3-50 amino acid residues (e.g., 5-45, 10-40, 15-35, 20-30, 10-20, 10-30, 20-40, or 30-40 amino acid residues). In an embodiment, the linker sequence comprises, or consists of, ((Gly)m-Ser))n, where m=3, 4, 5, or more and n=1, 2, 3, 4, 5, 6, 7, 8, 9, 10, or more (SEO ID NO: 25). In an embodiment, the linker sequence comprises, or consists of, (Gly-Gly-Gly-Gly-Ser)n, where n=1, 2, 3, 4, 5, 6, 7, 8, 9, 10, or more (SEO ID NO: 26).

In an embodiment, the primer is a primer described herein, e.g., in Examples.

In an embodiment, the reverse transcription, the amplification, or both, occurs in a solution in the isolated production reaction site, e.g., production micro-chamber. In an embodiment, the reverse transcription, the amplification, or both, does not occur on the substrate (e.g., bead). For example, the reverse transcription, the amplification, or both, can occur on in a solution within a droplet.

In an embodiment, the GC ds cDNA comprises a 5' overhang, e.g., a 5' overhang that is capable of hybridizing to an oligonucleotide attached to a capture substrate. In an embodiment, the GC ds cDNA comprises a blunt end, e.g., a blunt end comprising a 5' phosphate. In an embodiment, the DC ds cDNA comprises a 5' overhang, e.g., a 5' overhang that is capable of hybridizing to an oligonucleotide attached to a capture substrate. In an embodiment, the DC ds cDNA comprises a blunt end, e.g., a blunt end comprising a 5' phosphate. In an embodiment, the GC ds cDNA and the DC ds cDNA comprise sticky ends, e.g., both have 5' overhangs.

In an embodiment, the GC strand and the DC strand are covalently linked, e.g., ligated, to produce a single stranded nucleic acid sequence, wherein the GC and DC strands are both sense strands or both antisense strands. In an embodiment, a denatured GC strand of the GC ds cDNA to a denatured DC strand of the DC ds cDNA are covalently linked, e.g., ligated, wherein the GC and DC strands are both sense strands or both antisense strands. In an embodiment, the GC strand is present in the GC ds cDNA and the DC strand is present in the DC ds cDNA, and wherein the GC ds cDNA and the DC ds cDNA are covalently linked, e.g., ligated, e.g., to produce a double stranded nucleic acid sequence.

In an embodiment, the covalent linking, e.g., ligation, occurs in the isolated production reaction site. In an embodiment, the isolated production reaction site, e.g., a production micro-chamber, or the isolated linkage reaction site, e.g., a linkage micro-chamber, comprises a reagent that is capable of covalently linking, e.g., ligating, the GC and DC strands or the GC and DC ds cDNAs. In an embodiment, the isolated production reaction site, e.g., a production micro-chamber comprises an enzyme that covalently couples the GC and DC strands or the GC and DC ds cDNAs. In an embodiment, the enzyme is a ligase, e.g., a thermal stable ligase. In an embodiment, the covalent linking comprises ligase thermocycling.

In an embodiment, the covalent linking, e.g., ligation, occurs in a site different from the isolated production reaction site, e.g., occurs in an isolated linkage reaction site, e.g., a linkage micro-chamber. In an embodiment, the GC strand and the DC strand are transferred from the isolated production site to the isolated linkage reaction site, e.g., a linkage micro-chamber, and the covalent linking occurs in the isolated linkage reaction site, e.g., a linkage micro-chamber. In an embodiment, the isolated linkage reaction site, e.g., a linkage micro-chamber, comprises a reagent that is capable of covalently linking, e.g., ligating, the GC and DC strands or the GC and DC ds cDNAs. In an embodiment, the isolated linkage reaction site, e.g., a linkage micro-chamber, comprises an enzyme that covalently couples the GC and DC strands or the GC and DC ds cDNAs. In an embodiment, the enzyme is a ligase, e.g., a thermal stable ligase. In an embodiment, the covalent linking comprises ligase thermocycling.

In an embodiment, the covalent linking, e.g., ligation, comprises: (a) heating the isolated linkage reaction site, e.g., the linkage micro-chamber, under conditions (e.g., at 95° C.) that allow denaturation of the GC strand and the DC strand; (b) cooling the isolated linkage reaction site, e.g., the linkage micro-chamber, under conditions (e.g., at 50-65° C.) that allow hybridization of the splint oligonucleotide to the GC strand and the DC strand; (c) maintaining the isolated linkage reaction site, e.g., the linkage micro-chamber, under conditions (e.g., at 45-65° C.) that allow ligation of the GC strand and the DC strand (e.g., formation of phosphodiester bond between the GC strand and the DC strand); and (d) repeating steps (a), (b), and (c) sequentially for 2, 5, 10, 15, 20, 25, 30, 35, 40, 45, 50, or more cycles.

In an embodiment, the GC strand and the DC strand are covalently linked, e.g., ligated, in the presence of a splint oligonucleotide. In an embodiment, the splint oligonucleotide is hybridized to a sequence comprising the junction of the GC strand and the DC strand, or a sequence complementary thereof, and forms a duplexed region at the site of ligation. In an embodiment, the splint oligonucleotide comprises a modification (e.g., an $NH_2$ group) that inhibits DNA synthesis, e.g., by a DNA polymerase. In an embodiment, the modification is at the 3' end of the splint oligonucleotide.

In an embodiment, a strand complimentary to the covalently linked, e.g., ligated, GC and DC strands is produced by amplification.

In an embodiment, the method, e.g., the step of covalent linkage, does not include a step of overlap extension polymerase chain reaction (OE-PCR), also known as splicing by overlap extension or splicing by overhang extension (SOE) PCR.

In an embodiment, the method further comprises, prior to acquiring the isolated production reaction site, e.g., a production micro-chamber, acquiring an mRNA loaded capture substrate.

In an embodiment, acquiring the mRNA loaded capture substrate comprising: a) acquiring an isolated cell reaction site, e.g., a cell isolation micro-chamber, comprising: i) a cell; and ii) a capture substrate capable of binding a first mRNA encoding a GCVR from the cell and a second mRNA encoding a DCVR from the cell; and b) maintaining the isolated cell reaction site, e.g., the cell isolation micro-chamber, under conditions that allow lysis of the cell and binding of the capture substrate with the first mRNA and the second mRNA to form the mRNA loaded capture substrate, wherein the isolated cell reaction site, e.g., cell isolation micro-chamber, does not include a nucleic acid encoding a GCVR or a DCVR from a cell other than the cell (e.g., a different cell).

In an embodiment, the isolated cell reaction site, e.g., cell isolation micro-chamber, comprises a lysing reagent, e.g., a detergent. In an embodiment, the cell is lysed by heat or an enzyme. In an embodiment, the capture substrate comprises a moiety (e.g., an oligonucleotide) which binds mRNA, e.g., an oligo(dT).

In an embodiment, the method further comprises releasing the mRNA loaded capture substrate from the isolated cell reaction site, e.g., the cell isolation micro-chamber. In an embodiment, the releasing step is performed in the presence of a poly(dA) or poly(dT) oligonucleotide, e.g., to reduce cross-binding of non-captured mRNA.

In an embodiment, the mRNA loaded capture substrate is transferred from the isolated cell reaction site, e.g., the cell isolation micro-chamber, to the isolated production reaction site, e.g., the production micro-chamber.

In an embodiment, the method further comprises releasing the nucleic acid sequence from the isolated production reaction site, e.g., the production micro-chamber. In an embodiment, the method further comprises amplifying the nucleic acid sequence. In an embodiment, amplification of the nucleic acid sequence occurs outside the isolated production reaction site, e.g., the production micro-chamber, e.g., after the nucleic acid is released from the isolated production reaction site, e.g., the production micro-chamber. In an embodiment, amplification of the nucleic acid sequence occurs at the isolated production reaction site, e.g., the production micro-chamber.

In an embodiment, the method further comprises sequencing all or a portion of the nucleic acid sequence.

In an embodiment, the method further comprises inserting all or a portion of nucleic acid sequence into a vector. In an embodiment, the vector supplies an additional GC element or DC element not included in the nucleic acid sequence. In an embodiment, the method further comprises expressing the vector.

In an embodiment, the method further comprises expressing the nucleic acid sequence to produce a polypeptide comprising a segment that encodes a GC element of the GCVR, e.g., a GCVRS, and a segment that encodes a DC element of the DCVR, e.g., a DCVRS. In an embodiment, the DC element is N-terminal to the GC element in the polypeptide. In an embodiment, the GC element is C-terminal to the DC element in the polypeptide.

In an embodiment, the method further comprises contacting the polypeptide with an antigen. In an embodiment, the method further comprises determining if the polypeptide binds the antigen, in vitro, ex vivo, or in vivo, e.g., by a method or assay described herein.

In an embodiment, the disclosure features a method of making a nucleic acid sequence comprising a sequence that encodes a TCR γ chain element (GC element) of TCR γ chain variable region (GCVR) and a TCR δ chain element (DC element) of a TCR δ chain variable region (DCVR), and wherein the GCVR and DCVR are matched, comprising:

a) acquiring an isolated cell reaction site (e.g., an isolated cell reaction site described herein), e.g., a cell isolation micro-chamber, comprising: i) a cell (e.g., a cell described herein); and ii) a capture substrate (e.g., a capture substrate described herein) capable of binding a first mRNA encoding a GCVR from the cell and a second mRNA encoding a DCVR from the cell;

b) maintaining the isolated cell reaction site, e.g., the cell isolation micro-chamber, under conditions that allow lysis of the cell and binding of the capture substrate with the first mRNA and the second mRNA to form an mRNA loaded capture substrate, wherein the isolated cell reaction site, e.g., cell isolation micro-chamber, does not include a nucleic acid encoding a GCVR or a DCVR from a cell other than the cell (e.g., a different cell);

c) contacting the mRNA loaded capture substrate with a reaction mixture, e.g., a reaction mixture comprising reverse transcriptase, that uses the loaded mRNA as a template to make cDNA (this can occur, e.g., in the isolated cell reaction site, in an isolated production reaction site, or in neither, e.g., not in an isolated reaction site);

d) acquiring an isolated production reaction site (e.g., an isolated production reaction site described herein), e.g., a production micro-chamber, comprising: i) a TCR γ chain (GC) strand, wherein the GC strand is a strand of a TCR γ chain double-stranded cDNA (GC ds cDNA) comprising a segment that encodes a GC element of the GCVR from the cell, e.g., a TCR γ chain variable region sequence (GCVRS); and ii) a TCR δ chain (DC) strand, wherein the DC strand is a strand of a TCR δ chain double-stranded cDNA (DC ds cDNA) comprising a segment that encodes a DC element of the DCVR from the cell, e.g., a TCR δ chain variable region sequence (DCVRS), wherein the isolated production reaction site, e.g., a production micro-chamber, does not include a nucleic acid encoding a GCVR or a DCVR from a cell other than the cell (e.g., a different cell); and e) covalent linking, e.g., ligation, of the GC strand to the DC strand.

In an embodiment, one or more (e.g., two, three, four, or all) of the steps a)-e) are performed in accordance with a method described herein. In an embodiment, each of the steps a)-e) is performed in accordance with a method described herein.

In an aspect, the disclosure features a method of making a nucleic acid sequence comprising a sequence that encodes a TCR γ chain element (GC element) of a TCR γ chain variable region (GCVR) and a TCR δ chain element (DC element) of a TCR δ chain variable region (DCVR), and wherein the GCVR and DCVR are matched, comprising:

a) acquiring an isolated cell reaction site (e.g., an isolated cell reaction site described herein), e.g., a cell isolation micro-chamber, comprising: i) a cell (e.g., a cell described herein); and ii) a capture substrate (e.g., a capture substrate described herein) capable of binding a first mRNA encoding a GCVR from the cell and a second mRNA encoding a DCVR from the cell;

b) maintaining the isolated cell reaction site, e.g., the cell isolation micro-chamber, under conditions that allow lysis of the cell and binding of the capture substrate with the first mRNA and the second mRNA to form the mRNA loaded capture substrate, wherein the isolated cell reaction site, e.g., cell isolation micro-chamber, does not include a nucleic acid encoding a GCVR or a DCVR from a cell other than the cell (e.g., a different cell);

c) acquiring an isolated production reaction site (e.g., an isolated production reaction site described herein), e.g., a production micro-chamber, comprises: contacting the mRNA loaded capture substrate with a reaction mixture, e.g., a reaction mixture comprising reverse transcriptase, that uses the loaded mRNA as a template, to produce: a first double-stranded cDNA (ds cDNA) comprising a strand that is complementary to a first mRNA that encodes a GCVR from a cell; and a second ds cDNA comprising a strand complementary to a second mRNA encoding a DCVR from the cell (the cDNA loaded capture substrate);

wherein the isolated production reaction site, e.g., a production micro-chamber, does not include a nucleic acid encoding a GCVR or a DCVR from a cell other than the cell (e.g., a different cell).

d) maintaining the isolated production reaction site, e.g., the production micro-chamber, under conditions that allow amplification of the first and second ds cDNAs, to produce: a plurality of GC ds cDNAs comprising a segment that encodes a GC element of the GCVR from the cell, e.g., a GCVRS; and a plurality of DC ds cDNAs comprising a segment that encodes a DC element of the DCVR from the cell, e.g., a DCVRS;

e) acquiring an isolated linkage reaction site (e.g., an isolated linkage reaction site described herein), e.g., a linkage micro-chamber, comprising: covalent linking, e.g., ligation, of a strand of the GC ds cDNA (GC strand) to a strand of the DC ds cDNA (DC strand), wherein the GC and DC strands are both sense strands or antisense strands; and f) amplifying the covalently linked, e.g., ligated, GC and DC strands.

In an embodiment, one or more (e.g., two, three, four, five, or all) of the steps a)-f) are performed in accordance with a method described herein. In an embodiment, each of the steps a)-f) is performed in accordance with a method described herein.

In an aspect, the disclosure features a method of making a library comprising a plurality of unique members, the method comprising:

making the plurality of members, wherein each of the members comprises a sequence that encodes a TCR γ chain element (GC element) of a TCR γ chain variable region (GCVR) and a TCR δ chain element (DC element) of a TCR δ chain variable region (DCVR), and wherein the GCVR and DCVR are matched, made by a method described herein, wherein each unique nucleic acid sequence of the plurality comprises a GC element and a DC element from a different unique cell (e.g., a cell described herein), thereby making a library comprising a plurality of unique members.

In an embodiment, the plurality of unique members comprises at least $10^4$, $10^5$, $10^6$, $10^7$, $10^8$, or $10^9$ unique members. In an embodiment, the plurality of unique members comprises $10^4$ to $10^9$, $10^4$ to $10^8$, $10^4$ to $10^7$, $10^4$ to $10^6$, $10^4$ to $10^5$, $10^8$ to $10^9$, $10^7$ to $10^9$, $10^6$ to $10^9$, $10^5$ to $10^9$, $10^5$ to $10^8$, $10^6$ to $10^7$, $10^4$ to $10^5$, $10^5$ to $10^6$, $10^6$ to $10^7$, $10^7$ to $10^8$, or $10^8$ to $10^9$ unique members. In an embodiment, at least 80%, 85%, 90%, 95%, 96%, 97%, 98%, 99%, or 100%, of the members in the library are unique members (which encode matched GC element and DC element sequences). In an embodiment, less than 20%, 15%, 10%, 5%, 4%, 3%, 2%, or 1%, of the members in the library are unique members (which encode matched GC element and DC element sequences).

In an aspect, the disclosure features a library comprising a plurality of unique members, wherein, i) each unique member of the plurality comprises a segment that encodes a GC element, e.g., a GCVRS, and a segment that encodes a DC element, e.g., a DCVRS, wherein the GC element and the DC element in each unique member is matched;

ii) each unique member of the plurality comprises a segment that encodes an GC element, e.g., a GCVRS, and a segment that encodes a DC element, e.g., a DCVRS, from a different unique cell; and iii) the library comprises one or more of the following properties:

a) the library is made by a method described herein;

b) the plurality of unique members comprises at least $10^4$, $10^5$, $10^6$, $10^7$, $10^8$, or $10^9$ unique nucleic acid sequences;

c) the plurality of unique members comprises $10^4$ to $10^9$, $10^4$ to $10^8$, $10^4$ to $10^7$, $10^4$ to $10^6$, $10^4$ to $10^5$, $10^8$ to $10^9$, $10^7$ to $10^9$, $10^6$ to $10^9$, $10^5$ to $10^9$, $10^5$ to $10^8$, $10^6$ to $10^7$, $10^4$ to $10^5$, $10^5$ to $10^6$, $10^6$ to $10^7$, $10^7$ to $10^8$, or $10^8$ to $10^9$ unique members;

d) at least 80%, 85%, 90%, 95%, 96%, 97%, 98%, 99%, or 100%, of the members in the library are unique members (which encode matched GC element and DC element sequences); or e) less than 20%, 15%, 10%, 5%, 4%, 3%, 2%, or 1%, of the members in the library are unique members (which encode matched GC element and DC element sequences).

In an embodiment, each unique member of the plurality is configured such that, when expressed, the GC element, e.g., the GCVRS, and the DC element, e.g., the DCVRS, form a functional antigen binding molecule, e.g., a single chain or a complex of a TCR γ chain and a δ chain.

In an embodiment, the library is a display library. In an embodiment, each of the members of the plurality further encodes a polypeptide that results in display of the member on the surface of a display entity. In an embodiment, the library is a phage display library. In an embodiment, the library is a yeast display library. In an embodiment, the library is a mammalian display library.

In an aspect, the disclosure features a method of making a binding polypeptide (e.g., a polypeptide comprising a GC element and a DC element), the method comprising: a) acquiring a library described herein, e.g., by a method described herein; and b) expressing a polypeptide encoded by a unique nucleic acid of the library.

In an embodiment, the method further comprises contacting the polypeptide with an antigen. In an embodiment, the method further comprises retrieving (e.g., isolating or purifying) the nucleic acid that encodes a polypeptide that binds the antigen.

In an aspect, the disclosure features an isolated production reaction site, e.g., a production micro-chamber, which is an isolated production reaction site described herein (e.g., comprising a nucleic acid encoding a GCVR and a nucleic acid encoding a DCVR, wherein the GCVR and the DCVR are matched).

In an embodiment, the isolated production reaction site, e.g., a production micro-chamber, does not include a nucleic acid encoding a GCVR or a DCVR from a different cell.

In an embodiment, the isolated production reaction site, e.g., a production micro-chamber, comprises one, two, or all of: (i) one or more primers specific to V gene sequences of the GC and DC; (ii) one or more primers specific to overhangs introduced onto the GC and DC cDNAs; or (iii) one or more primers comprising a first member, a second member, and a third member comprising a nucleotide modification (e.g., a spacer) located between the first and second members, wherein the first member is capable of annealing with the second member of the same primer or a different primer, e.g., forming a structure comprising a duplex region of 4, 5, 6, 7, 8, 9, 10, 11, 12, 13, 14, 15, 16, 17, 18, 19, 20, more basepairs.

In an embodiment, the isolated production reaction site, e.g., a production micro-chamber, does not comprise a reagent that can covalently link nucleic acids, e.g., a ligase, e.g., a thermostable ligase. In another embodiment, the isolated production reaction site, e.g., a production micro-chamber, comprises a reagent that can covalently link nucleic acids, e.g., a ligase, e.g., a thermostable ligase.

In an aspect, the disclosure features a self-annealing oligonucleotide comprising a first member, a second member, and third member comprising a nucleotide modification (e.g., a spacer) located between the first and second members, wherein the first member is capable of annealing with the second member of the same oligonucleotide (e.g., for a method of making a nucleic acid sequence comprising a sequence that encodes a GC element of a GCVR and a DC element of a DCVR, wherein the GCVR and DCVR are matched).

In an embodiment, the first and second members are capable of forming a hairpin structure comprising a duplex region of 4, 5, 6, 7, 8, 9, 10, 11, 12, 13, 14, 15, 16, 17, 18, 19, 20, more basepairs. In an embodiment, the first member is 5-40 nucleotides, e.g., 5-10, 5-20, 5-30, 30-40, 20-40, 10-30, 10-30, or 15-25 nucleotides, in length. In an embodiment, the second member is 5-40 nucleotides, e.g., 5-10, 5-20, 5-30, 30-40, 20-40, 10-30, 10-30, or 15-25 nucleotides, in length.

In an embodiment, the spacer is a spacer described herein, e.g., a flexible spacer or a PEG spacer.

In an embodiment, the first member comprises a sequence that is complementary to the sequence of an oligonucleotide attached to a capture substrate.

In an embodiment, the second member comprises (e.g., from 5' to 3') one, two, or all of: (i) a sequence that is complementary to at least a portion of the first member; (ii) a universal priming sequence (e.g., for PCR amplification or next-generation sequencing); and (iii) a sequence complementary to a target sequence, e.g., a GCVRS and/or a DCVRS. In an embodiment, the universal priming sequence is identical, or substantially identical, to the sequence that is complementary to at least a portion of the first member. In another embodiment, the universal priming sequence is different from the sequence that is complementary to at least a portion of the first member. In an embodiment, the second member comprises a sequence for homologous recombination (e.g., in a yeast or mammalian cell).

In an aspect, the disclosure features an isolated linkage reaction site, e.g., a linkage micro-chamber, which is an isolated linkage reaction site described herein (e.g., comprising a nucleic acid encoding a GCVR and a nucleic acid encoding a DCVR, wherein the GCVR and the DCVR are matched).

In an embodiment, the isolated linkage reaction site, e.g., a linkage micro-chamber, does not include a nucleic acid encoding a GCVR or a DCVR from a different cell.

In an embodiment, the isolated linkage reaction site, e.g., a linkage micro-chamber, comprises a splint oligonucleotide (e.g., a splint oligonucleotide described herein) that is capable of hybridizing to a sequence comprising the junction of the GC strand and the DC strand, or a sequence complementary thereof, to form a duplexed region at the site of ligation.

In an embodiment, the isolated linkage reaction site, e.g., a linkage micro-chamber, comprises a reagent that can covalently link nucleic acids, e.g., a ligase, e.g., a thermostable ligase.

BRIEF DESCRIPTION OF THE DRAWINGS

In FIG. 2A, a cell (e.g., an immune cell, such as a B cell) is lysed and mRNAs encoding an HCVR and a matched LCVR are captured on a bead. In FIG. 2B, captured mRNAs are converted to cDNA by reverse transcription followed by amplification by DNA polymerase (PCR) to create cDNA beads comprising matched pairs of HCVR and LCVR cDNAs. A self-annealing primer (e.g., a primer comprising a first member and a second member capable of hybridizing to the first member, with the first and second members separated by a spacer, e.g., a PEG spacer, and further comprising a sequence capable of hybridizing to an HCVR or LCVR sequence) can be used for the reverse transcription reaction and/or DNA polymerase amplification. In FIG. 2C, matched LCVR and HCVR cDNA products can be fused using a ligase cycling reaction, in which matched pairs of LCVRs and HCVRs are brought together using a splint oligo comprising sequences capable of hybridizing to an end of each of the LCVR or HCVR sequences (e.g., the 3' terminus of the LCVR and the 5' terminus of the HCVR). In FIG. 2D, the fused LCVR/HCVR product can be amplified, e.g., by PCR.

In FIG. 4A, denaturing PAGE of ligase cycling products showed that ligase-containing reactions yielded the linked VH+VL products for each of 4G2 and 9E10, as well as the individual VH and VL polynucleotides. The linked VH+VL products were not detected in reactions lacking ligase. In FIG. 4B, agarose gel electrophoresis of bulk PCR re-amplification products showed that native pairing was retained for when VH-VL linked polynucleotides for 4G2 and 9E10 were mixed in the PCR reaction.

In FIG. 5A, a series of forward PCR primer designs were tested for their capacity to capture PCR product, including (1) a VL primer comprising a spacer and with 5' sequence complementary to oligo on bead and 3' sequence that is complementary to VL template sequence, (2) a VL primer lacking a spacer and with 5' sequence complementary to oligo on bead and 3' sequence that is complementary to VL template sequence, (3) a VL primer lacking 5' sequence complementary to oligo on bead and 3' sequence that is complementary to VL template sequence, and (4) a VH primer with similar design as in (1) but with 3'-end having sequence complementary to VH template (for DNA polymerase extension). In FIG. 5B, the VL primer comprising a spacer was used for efficient and specific PCR capture of VL oligo, VH oligo, and VH+VL oligo. Of the remaining primers, only the VH primer was capable of capturing any of the oligos (specifically, the VH oligo and VH+VL oligo).

DETAILED DESCRIPTION

Figure 1:
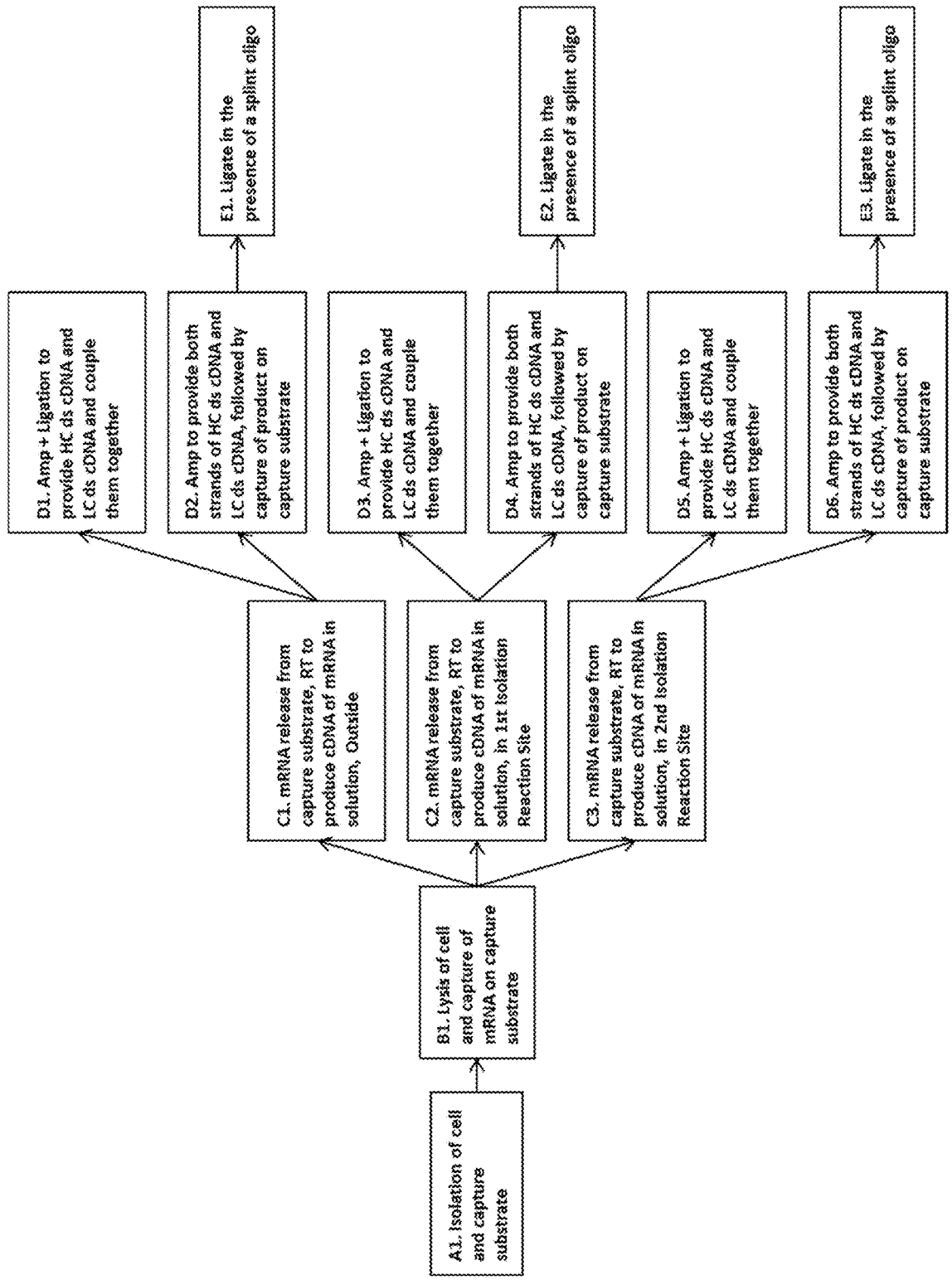
FIG. 1 depicts a number of ways of making nucleic acid sequence comprising a sequence that encodes a heavy chain element (HC element) of an antibody heavy chain variable region (HCVR) and a light chain element (LC element) of an antibody light chain variable region (LCVR), and wherein the HCVR and LCVR are matched. The A1, B1 and C2 boxes indicate steps occurring in an isolated reaction site, particularly, in an isolated cell reaction site. The C3, D1, D2, D3, D4, D5 and D6 boxes indicate steps occurring in an isolated reaction site, particularly, in an isolated production reaction site. The E1, E2 and E3 boxes indicate steps occurring in an isolated reaction site, particularly, in an isolated linkage reaction site. The C1 box indicates steps that need not occur in an isolated reaction site. As is discussed in the text, the isolated reaction sites are free of nucleic acid that would result in a mismatched HC and LC element.
Figure 2A:
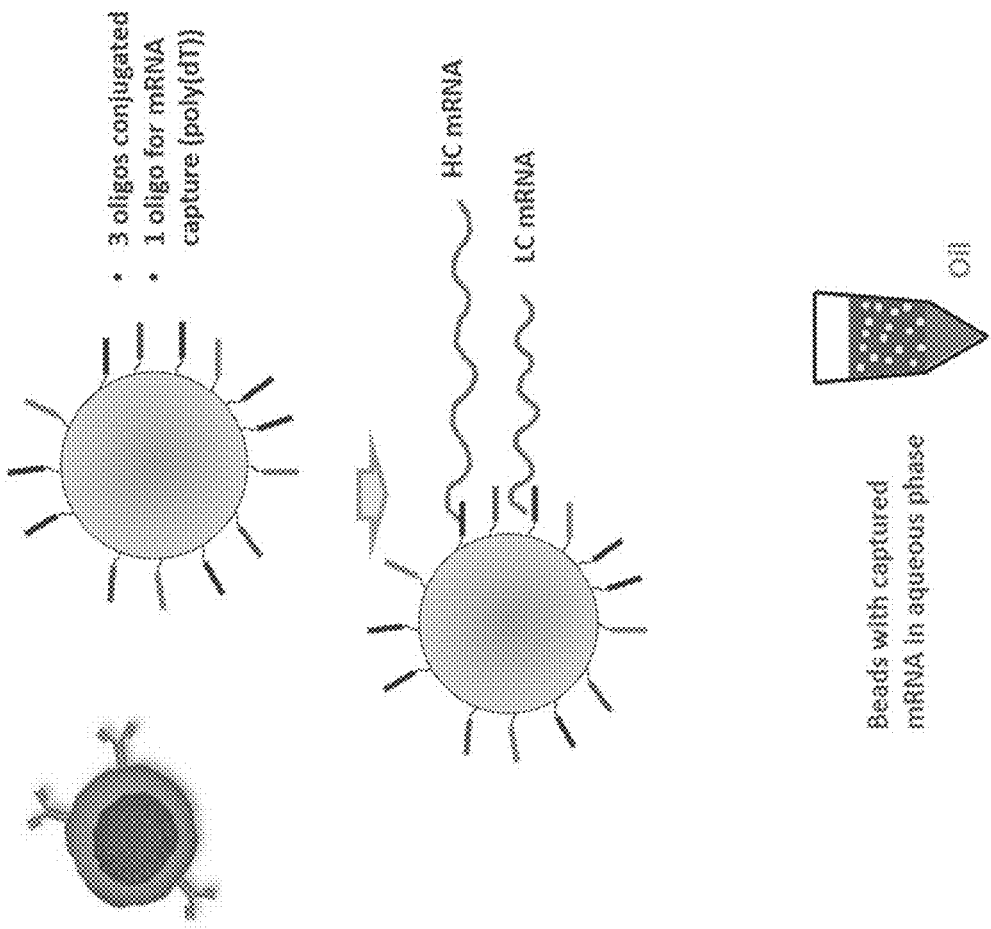
FIGS. 2A-2D are a series of diagrams showing an exemplary method of making a nucleic acid comprising a sequence that encodes a heavy chain element (HC element) of an antibody heavy chain variable region (HCVR) and a light chain element (LC element) of an antibody light chain variable region (LCVR), and wherein the HCVR and LCVR are matched.
Figure 2B:
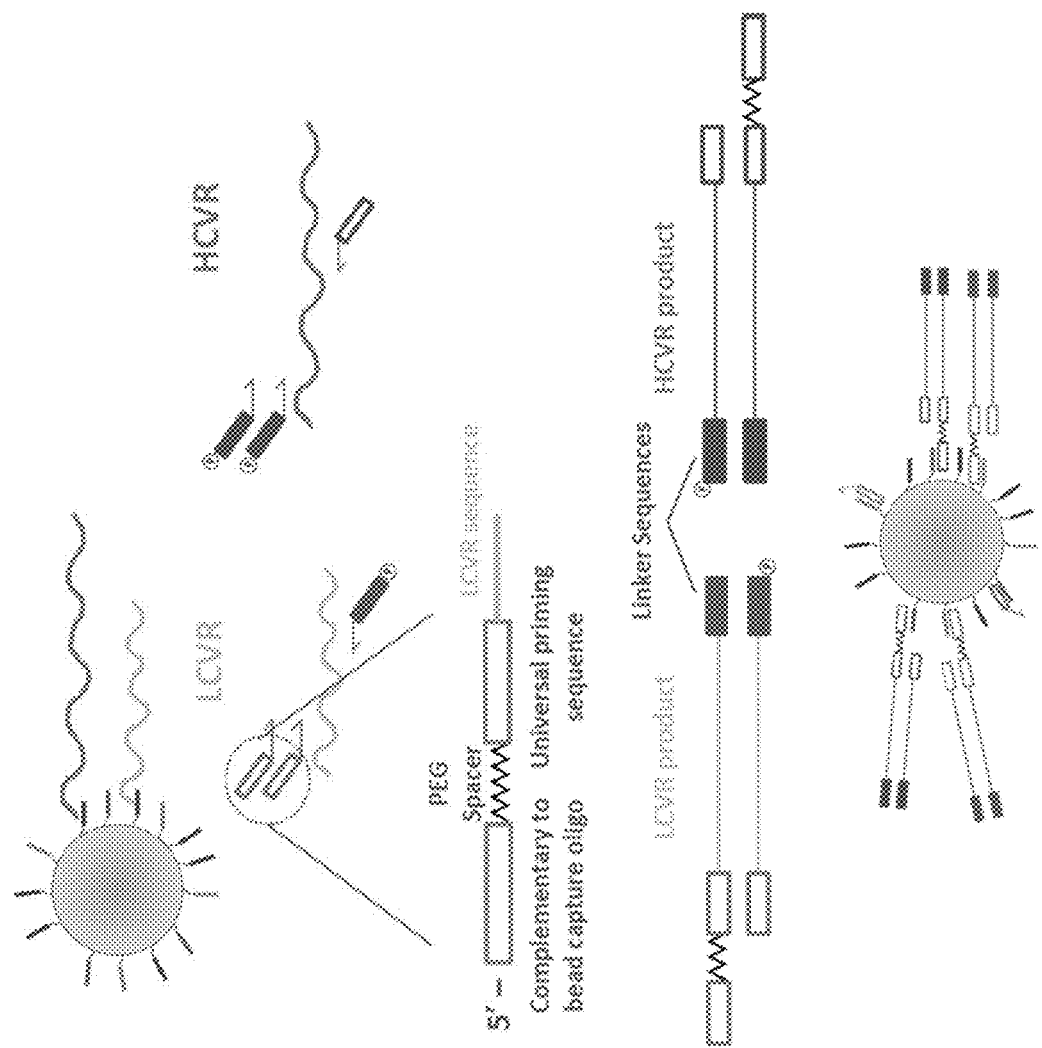
Figure 2C:
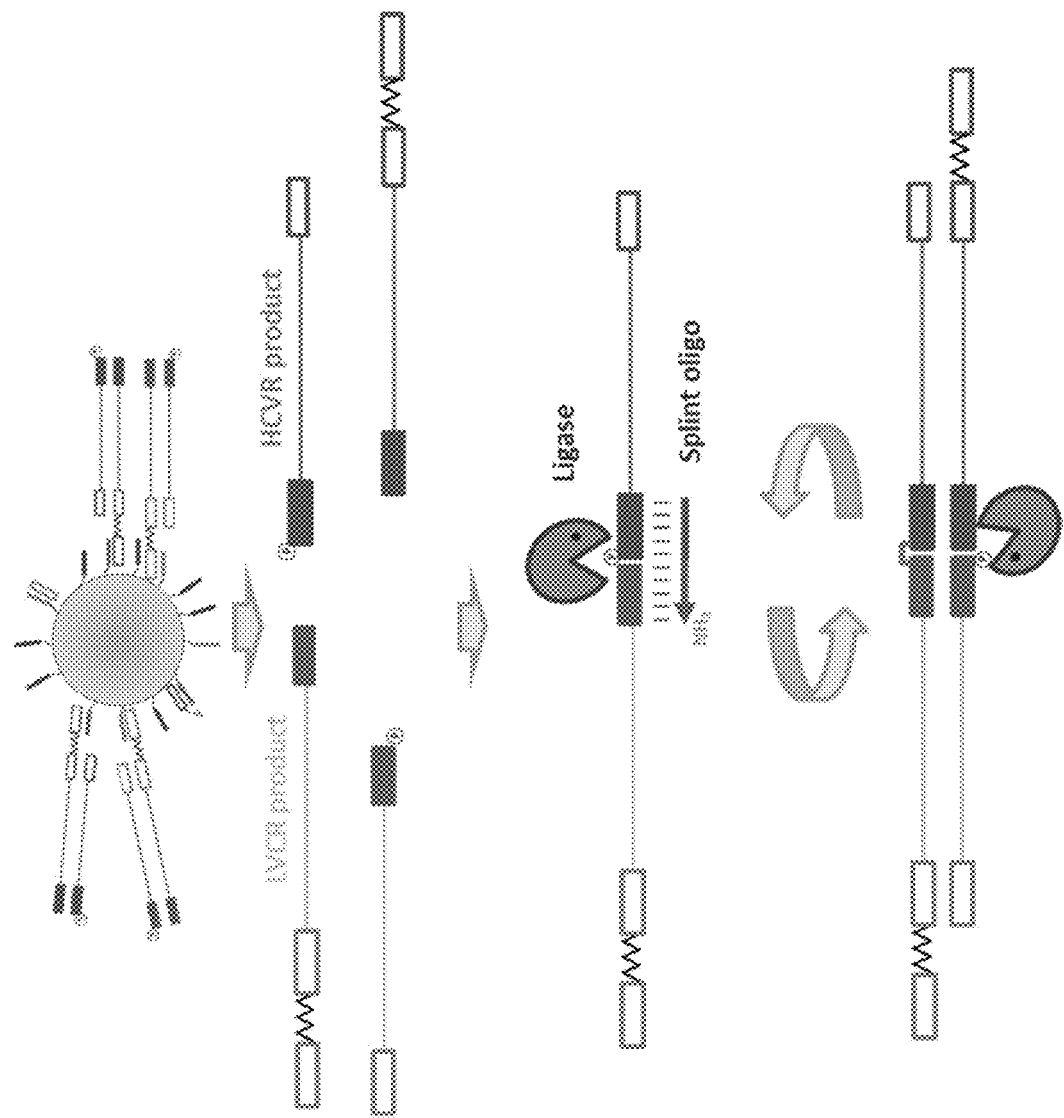
Figure 2D:
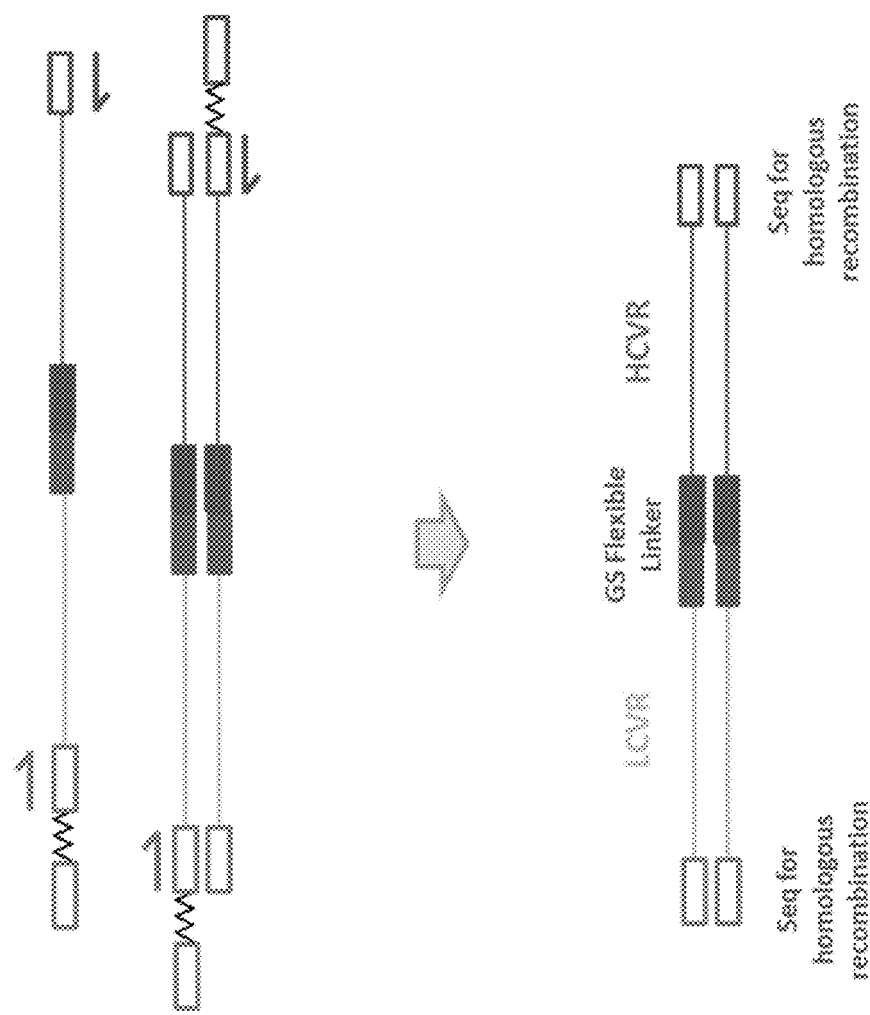

Disclosed herein are polypeptides (e.g., antibody molecules or T cell receptor molecules) that bind to a target molecule or cell, e.g., a human protein or cell, with high affinity and specificity. In an embodiment, the polypeptide is a binding polypeptide. In an embodiment, the binding polypeptide is an antibody molecule. In an embodiment, the binding polypeptide is a TCR molecule (e.g., a soluble TCR molecule). In an embodiment, libraries of the polypeptides, methods for making the polypeptides or libraries, nucleic acid molecules encoding the polypeptides, expression vectors, host cells, and compositions (e.g., pharmaceutical compositions), kits, containers, are also provided. The methods described herein are useful for making or selecting functional polypeptides that contain two or more chains that are naturally matched or paired. The polypeptides (e.g., antibody molecules or T cell receptor molecules) disclosed herein can be used (alone or in combination with other agents or therapeutic modalities) to treat, prevent and/or diagnose disorders, such as disorders and conditions disclosed herein.

Without wishing to be bound by theory, it is believed that the methods described herein can facilitate, e.g., high-throughput phenotypic (e.g., binding) screening of millions of B-cell/plasma cell antibodies, and antibody discovery from B-cells derived from different species, including, but not limited to, human, mouse, rat, rabbit, or chicken. For example, the only requirement can be knowledge of primers to appropriately amplify VH and VL sequences from that species.

Since the workflow described herein is amenable to use in any species, it can significantly improve ability to discover diverse binding polypeptides (e.g., antibodies) to target antigens (post immunization/vaccination), as each species develops different types of binding polypeptides (e.g., antibodies) to an antigen. Immune tolerance issues (e.g., to a target epitope) can be better overcome by using a species which lacks the target antigen or has significant amino acid differences to the target antigen, e.g., chicken has reduced tolerance to human antigens/epitopes than human or mouse does to human antigens/epitopes.

The methods described herein can facilitate making a 'phenotypic copy' of an antibody repertoire in yeast, which are rugged and can be regrown. This facilitates rigorous and repeated testing of the antibody repertoire, unlike when using primary B-cells, which are sensitive, do no survive long in vitro, and cannot survive rigorous antibody/BCR binding characterizations.

Other methods to generate natively paired VH-VL sequences in droplets can use splicing by overlap extension with DNA polymerase (PCR) to link the DNA, which may have limitations with specificity and can result in heterogeneous products of divergent sizes due to imprecise linking. The ligation methods described here do not suffer from such issues.

Additionally, droplet methods using splicing by overlap extension PCR suffer from an inherent limitation in which any PCR products not fused within drops have the potential to become fused during non-drop PCR amplification due to the common appended sequence between VH and VL. Fusion occurring outside of drops leads to non-native pairing, as chains are not compartmentalized. For the exemplary ligation workflow described herein, there is no need to add common sequence to VH and VL, and therefore this issue is precluded from occurring.

Such PCR amplification can lead to significantly biased representation of divergent sequences, as some sequences amplify more efficiently than others, which can lead to dramatic differences after the exponential amplification which occurs in PCR. The workflow described herein reduces this issue by having PCR products captured onto a bead. For example, if a cell's VH and VL sequences are amplified very well or poorly, a similar amount of product will be captured onto the bead. Thereby, there is a more even representation of antibody sequences in the final library, relative to methods that omit this step and perform linking by splicing by overlap extension PCR.

Definitions

An "HC variable region," as that term is used herein, refers to a polypeptide comprising heavy chain CDRs 1, 2 and 3 and heavy chain FW regions 1, 2, 3, and 4.

An "LC variable region," as that term is used herein, refers to a polypeptide comprising light chain CDRs 1, 2 and 3 and light chain FW regions 1, 2, 3, and 4.

A "heavy chain variable region sequence," or "HCVRS," as that term is used herein, refers to a polypeptide comprising sufficient sequence from heavy chain CDRs and sufficient sequence from heavy chain FW regions, to allow binding of antigen. In embodiments the HCVRS can assemble with a light chain variable region, and, e.g., bind antigen. In an embodiment, a HCVRS comprises sufficient sequence from heavy chain CDRs 1, 2, and 3, and sufficient sequence from heavy chain FW regions, e.g., heavy chain FW regions 1, 2, 3, and 4, to allow binding of antigen. In an embodiment, a HCVRS comprises heavy chain CDRs 1, 2, and 3, and sufficient sequence from heavy chain FW regions, e.g., heavy chain FW regions 1, 2, 3, and 4, to complex with a light chain variable region and to allow binding of antigen.

A "light chain variable region sequence," or "LCVRS," as that term is used herein, refers to a polypeptide comprising sufficient sequence from light chain CDRs and sufficient sequence from light chain FW regions, to allow binding of antigen. In embodiments the LCVRS can assemble with a heavy chain variable region, and, e.g., bind antigen. In an embodiment, a LCVRS comprises sufficient sequence from light chain CDRs 1, 2, and 3, and sufficient sequence from light chain FW regions, e.g., light chain FW regions 1, 2, 3, and 4, to allow binding of antigen. In an embodiment, a LCVRS comprises light chain CDRs 1, 2, and 3, and sufficient sequence from light chain FW regions, e.g., light chain FW regions 1, 2, 3, and 4, to complex with a heavy chain variable region and to allow binding of antigen.

"Element" of an LC or HC variable region, as that term is used herein, refers to a sequence that encodes at least one amino acid. In an embodiment, an element comprises a CDR. In an embodiment an element comprises a FW region. In an embodiment, and element comprises a CDR and a FW region. In an embodiment an element comprises a HCVRS or a LCVRS. In an embodiment, the element comprises at least 10, 20, 30, 40, 50, 60, 70, 80, 90, or 100 amino acid residues.

A "micro-chamber," as that term is used herein, refers to a compartment that is dimensioned, e.g., is sufficiently small, such that upon formation it contains a single cell, or the content from a single cell. In an embodiment, the micro-chamber has a volume of that is 10 to 10,000 times greater of a cell that it contains. In an embodiment, the micro-chamber has a volume of 20 pL. In an embodiment, the micro-chamber has a maximum dimension of 100 nL. In an embodiment the micro-chamber comprises a droplet of liquid. In embodiment, the micro-chamber comprises a droplet of a first liquid disposed in an immiscible media, e.g., a gas or second liquid. In an embodiment, the micro-chamber comprises a droplet of a first liquid, e.g., a lysis buffer or a PCR reaction buffer, formed by dispersing the first liquid in an immiscible second liquid, e.g., a fluorinated oil. In an embodiment, the micro-chamber comprises a substrate and a substance other than the substrate, e.g., a solution. In an embodiment, the droplet comprises a substrate (e.g., a capture substrate, e.g., a bead) and a substance other than the substrate, e.g., a solution.

"Acquiring," as that term is used herein, refers to possession of provision of an entity, e.g., a physical entity or data. Acquiring a physical entity includes making or manufacturing a physical entity (directly acquiring) as well as receiving a physical entity from another party or source (indirectly acquiring). Acquiring a data or a value includes generating the data or value (directly acquiring) as well as receiving the data or value from another party or source (indirectly acquiring).

"Matched," as that term is used herein in connection with a heavy chain variable region and a light chain variable region, means they are from the same cell. With respect to an element of a light chain variable region and an element of a heavy chain variable region it means that the light chain variable region and the heavy chain variable region from which the elements are derived are from the same cell.

An "isolated reaction site," as that term is used here, refers to a site, e.g., a location on a substrate, a micro chamber, or a well on a substrate, which allows for sufficient separation between a first loaded capture substrate and a second loaded capture substrate, or generally, from HC or LC (or a chain or β chain, or γ chain or δ chain) encoding nucleic acid of another cell, such that the first loaded capture substrate is not contaminated with nucleic acid encoding a HC or LC (or α chain or β chain, or γ chain or δ chain) from another cell. In an embodiment an isolated reaction site provides sufficient separation between a first mRNA loaded capture substrate and a second mRNA loaded capture substrate, or generally, from LC or HC encoding nucleic acid of another cell, that the first loaded mRNA capture substrate is not contaminated with nucleic acid, e.g., mRNA, encoding an HC or LC (or α chain or β chain, or γ chain or δ chain) from another cell. In an embodiment an isolated reaction site provides sufficient separation between a first cDNA loaded capture substrate and a second cDNA loaded capture substrate, or generally, from HC or LC (or α chain or β chain, or γ chain or δ chain) encoding nucleic acid of another cell, that the first loaded cDNA capture substrate is not contaminated with nucleic acid, e.g., cDNA, encoding a HC or LC (or α chain or β chain, or γ chain or δ chain) from another cell. Separation can be provided, e.g., by sufficient distance between isolated reaction sites on a substrate; by configuring the isolated reaction sites such that they are not in fluid connection, or by formation of an immiscible barrier between a volume or chamber and the environment. In an embodiment, the isolated reaction site comprises a substrate and a substance other than the substrate, e.g., a solution.

"Complimentary," as that term is used herein, refers to sequences which can form Watson-Crick pairing. When a first sequence is complementary with a second sequence it can be complementary to the entire second sequence or to less than all of the second sequence.

A "display entity," as that term is used herein, refers to an entity, e.g., a phage or cell, e.g., a yeast cell, which includes a gene that encodes a polypeptide.

An "AC variable region," as that term is used herein, refers to a polypeptide comprising TCR α chain CDRs 1, 2 and 3 and α chain FW regions 1, 2, 3, and 4.

A "BC variable region," as that term is used herein, refers to a polypeptide comprising β chain CDRs 1, 2 and 3 and β chain FW regions 1, 2, 3, and 4.

A "GC variable region," as that term is used herein, refers to a polypeptide comprising TCR γ chain CDRs 1, 2 and 3 and γ chain FW regions 1, 2, 3, and 4.

A "DC variable region," as that term is used herein, refers to a polypeptide comprising δ chain CDRs 1, 2 and 3 and δ chain FW regions 1, 2, 3, and 4.

An "α chain variable region sequence," or "ACVRS," as that term is used herein, refers to a polypeptide comprising sufficient sequence from α chain CDRs and sufficient sequence from α chain FW regions, to allow binding of antigen. In embodiments the ACVRS can assemble with a β chain variable region, and, e.g., bind antigen. In an embodiment, a ACVRS comprises sufficient sequence from α chain CDRs 1, 2, and 3, and sufficient sequence from α chain FW regions, e.g., α chain FW regions 1, 2, 3, and 4, to allow binding of antigen. In an embodiment, an ACVRS comprises α chain CDRs 1, 2, and 3, and sufficient sequence from α chain FW regions, e.g., α chain FW regions 1, 2, 3, and 4, to complex with a β chain variable region and to allow binding of antigen.

A "β chain variable region sequence," or "BCVRS," as that term is used herein, refers to a polypeptide comprising sufficient sequence from β chain CDRs and sufficient sequence from β chain FW regions, to allow binding of antigen. In embodiments the BCVRS can assemble with an α chain variable region, and, e.g., bind antigen. In an embodiment, a BCVRS comprises sufficient sequence from β chain CDRs 1, 2, and 3, and sufficient sequence from β chain FW regions, e.g., β chain FW regions 1, 2, 3, and 4, to allow binding of antigen. In an embodiment, a BCVRS comprises β chain CDRs 1, 2, and 3, and sufficient sequence from β chain FW regions, e.g., β chain FW regions 1, 2, 3, and 4, to complex with an α chain variable region and to allow binding of antigen.

A "γ chain variable region sequence," or "GCVRS," as that term is used herein, refers to a polypeptide comprising sufficient sequence from γ chain CDRs and sufficient sequence from γ chain FW regions, to allow binding of antigen. In embodiments the GCVRS can assemble with a δ chain variable region, and, e.g., bind antigen. In an embodiment, a GCVRS comprises sufficient sequence from γ chain CDRs 1, 2, and 3, and sufficient sequence from γ chain FW regions, e.g., γ chain FW regions 1, 2, 3, and 4, to allow binding of antigen. In an embodiment, a GCVRS comprises γ chain CDRs 1, 2, and 3, and sufficient sequence from γ chain FW regions, e.g., γ chain FW regions 1, 2, 3, and 4, to complex with a δ chain variable region and to allow binding of antigen.

A "δ chain variable region sequence," or "DCVRS," as that term is used herein, refers to a polypeptide comprising sufficient sequence from δ chain CDRs and sufficient sequence from δ chain FW regions, to allow binding of antigen. In embodiments the DCVRS can assemble with a γ chain variable region, and, e.g., bind antigen. In an embodiment, a DCVRS comprises sufficient sequence from δ chain CDRs 1, 2, and 3, and sufficient sequence from δ chain FW regions, e.g., δ chain FW regions 1, 2, 3, and 4, to allow binding of antigen. In an embodiment, a DCVRS comprises δ chain CDRs 1, 2, and 3, and sufficient sequence from δ chain FW regions, e.g., δ chain FW regions 1, 2, 3, and 4, to complex with an α chain variable region and to allow binding of antigen.

"Element" of an α chain or β chain variable region, as that term is used herein, refers to a sequence that encodes at least one amino acid. In an embodiment, an element comprises a CDR. In an embodiment an element comprises a FW region. In an embodiment, and element comprises a CDR and a FW region. In an embodiment an element comprises an ACVRS or a BCVRS. In an embodiment, the element comprises at least 10, 20, 30, 40, 50, 60, 70, 80, 90, or 100 amino acid residues.

"Element" of a γ chain or δ chain variable region, as that term is used herein, refers to a sequence that encodes at least one amino acid. In an embodiment, an element comprises a CDR. In an embodiment an element comprises a FW region. In an embodiment, and element comprises a CDR and a FW region. In an embodiment an element comprises a GCVRS or a DCVRS. In an embodiment, the element comprises at least 10, 20, 30, 40, 50, 60, 70, 80, 90, or 100 amino acid residues.

"Matched," as that term is used herein in connection with an α chain variable region and a β chain variable region, means they are from the same cell. With respect to an element of an α chain variable region and an element of a β chain variable region it means that the α chain variable region and the β chain variable region from which the elements are derived are from the same cell.

"Matched," as that term is used herein in connection with a γ chain variable region and a δ chain variable region, means they are from the same cell. With respect to an element of a γ chain variable region and an element of a δ chain variable region it means that the γ chain variable region and the γ chain variable region from which the elements are derived are from the same cell.

As used herein, the articles "a" and "an" refer to one or to more than one (e.g., to at least one) of the grammatical object of the article.

The term "or" is used herein to mean, and is used interchangeably with, the term "and/or", unless context clearly indicates otherwise.

"About" and "approximately" shall generally mean an acceptable degree of error for the quantity measured given the nature or precision of the measurements. Exemplary degrees of error are within 20 percent (%), typically, within 10%, and more typically, within 5% of a given value or range of values.

The compositions and methods disclosed herein encompass polypeptides and nucleic acids having the sequences specified, or sequences substantially identical or similar thereto, e.g., sequences at least 85%, 90%, 95% identical or higher to the sequence specified.

In the context of an amino acid sequence, the term "substantially identical" is used herein to refer to a first amino acid that contains a sufficient or minimum number of amino acid residues that are i) identical to, or ii) conservative substitutions of aligned amino acid residues in a second amino acid sequence such that the first and second amino acid sequences can have a common structural domain and/or common functional activity. For example, amino acid sequences that contain a common structural domain having at least about 85%, 90%, 91%, 92%, 93%, 94%, 95%, 96%, 97%, 98% or 99% identity to a reference sequence, e.g., a sequence provided herein.

In the context of nucleotide sequence, the term "substantially identical" is used herein to refer to a first nucleic acid sequence that contains a sufficient or minimum number of nucleotides that are identical to aligned nucleotides in a second nucleic acid sequence such that the first and second nucleotide sequences encode a polypeptide having common functional activity, or encode a common structural polypeptide domain or a common functional polypeptide activity. For example, nucleotide sequences having at least about 85%, 90%, 91%, 92%, 93%, 94%, 95%, 96%, 97%, 98% or 99% identity to a reference sequence, e.g., a sequence provided herein.

The term "functional variant" refers polypeptides that have a substantially identical amino acid sequence to the naturally-occurring sequence, or are encoded by a substantially identical nucleotide sequence, and are capable of having one or more activities of the naturally-occurring sequence.

Calculations of homology or sequence identity between sequences (the terms are used interchangeably herein) are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a typical embodiment, the length of a reference sequence aligned for comparison purposes is at least 30%, e.g., at least 40%, 50%, 60%, e.g., at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position.

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In some embodiments, the percent identity between two amino acid sequences is determined using the Needleman and Wunsch ((1970) *J. Mol. Biol.* 48:444-453) algorithm which has been incorporated into the GAP program in the GCG software package (available at www.gcg.com), using either a Blossum 62 matrix or a PAM250 matrix, and a gap weight of 16, 14, 12, 10, 8, 6, or 4 and a length weight of 1, 2, 3, 4, 5, or 6. In certain embodiments, the percent identity between two nucleotide sequences is determined using the GAP program in the GCG software package (available at www.gcg.com), using a NWSgapdna.CMP matrix and a gap weight of 40, 50, 60, 70, or 80 and a length weight of 1, 2, 3, 4, 5, or 6. One suitable set of parameters (and the one that should be used unless otherwise specified) are a Blossum 62 scoring matrix with a gap penalty of 12, a gap extend penalty of 4, and a frameshift gap penalty of 5. The percent identity between two amino acid or nucleotide sequences can be determined using the algorithm of E. Meyers and W. Miller ((1989) CABIOS, 4:11-17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215: 403-10. BLAST nucleotide searches can be performed with the NBLAST program, score=100, wordlength=12 to obtain nucleotide sequences homologous to a nucleic acid as described herein. BLAST protein searches can be performed with the XBLAST program, score=50, wordlength=3 to obtain amino acid sequences homologous to protein molecules described herein. To obtain gapped alignments for comparison purposes, Gapped BLAST can be utilized as described in Altschul et al., (1997) *Nucleic Acids Res.* 25:3389-3402. When utilizing BLAST and gapped BLAST programs, the default parameters of the respective programs (e.g., XBLAST and NBLAST) can be used. See www.ncbi.nlm.nih.gov.

As used herein, the term "hybridizes under low stringency, medium stringency, high stringency, or very high stringency conditions" describes conditions for hybridization and washing. Guidance for performing hybridization reactions can be found in *Current Protocols in Molecular Biology*, John Wiley & Sons, N.Y. (1989), 6.3.1-6.3.6, which is incorporated by reference. Aqueous and nonaqueous methods are described in that reference and either can be used. Specific hybridization conditions referred to herein are as follows: 1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and preferably 4) very high stringency hybridization conditions are 0.5M sodium phosphate, 7% SDS at 65° C., followed by one or more washes at 0.2×SSC, 1% SDS at 65° C. Very high stringency conditions 4) are suitable conditions and the ones that should be used unless otherwise specified.

It is understood that the molecules described herein may have additional conservative or non-essential amino acid substitutions, which do not have a substantial effect on their functions.

The term "amino acid" is intended to embrace all molecules, whether natural or synthetic, which include both an amino functionality and an acid functionality and capable of being included in a polymer of naturally-occurring amino acids. Exemplary amino acids include naturally-occurring amino acids; analogs, derivatives and congeners thereof; amino acid analogs having variant side chains; and all stereoisomers of any of any of the foregoing. As used herein the term "amino acid" includes both the D- or L-optical isomers and peptidomimetics.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

The terms "polypeptide," "peptide" and "protein" (if single chain) are used interchangeably herein to refer to polymers of amino acids of any length. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component. The polypeptide can be isolated from natural sources, can be a produced by recombinant techniques from a eukaryotic or prokaryotic host, or can be a product of synthetic procedures. In an embodiment, the polypeptide is an antibody molecule. In another embodiment, the polypeptide is a TCR molecule, e.g., soluble TCR molecule.

The terms "nucleic acid," "nucleic acid sequence," "nucleotide sequence," or "polynucleotide sequence," and "polynucleotide" are used interchangeably. They refer to a polymeric form of nucleotides of any length, either deoxyribonucleotides or ribonucleotides, or analogs thereof. The polynucleotide may be either single-stranded or double-stranded, and if single-stranded may be the coding strand or non-coding (antisense) strand. A polynucleotide may comprise modified nucleotides, such as methylated nucleotides and nucleotide analogs. The sequence of nucleotides may be interrupted by non-nucleotide components. A polynucleotide may be further modified after polymerization, such as by conjugation with a labeling component. The nucleic acid may be a recombinant polynucleotide, or a polynucleotide of genomic, cDNA, semisynthetic, or synthetic origin which either does not occur in nature or is linked to another polynucleotide in a non-natural arrangement.

The term "isolated," as used herein, refers to material that is removed from its original or native environment (e.g., the natural environment if it is naturally occurring). For example, a naturally-occurring polynucleotide or polypeptide present in a living animal is not isolated, but the same polynucleotide or polypeptide, separated by human intervention from some or all of the co-existing materials in the natural system, is isolated. Such polynucleotides could be part of a vector and/or such polynucleotides or polypeptides could be part of a composition, and still be isolated in that such vector or composition is not part of the environment in which it is found in nature.

As used herein, the term "treat," e.g., a disorder described herein, means that a subject (e.g., a human) who has a disorder, e.g., a disorder described herein, and/or experiences a symptom of a disorder, e.g., a disorder described herein, will, in an embodiment, suffer less a severe symptom and/or recover faster when an antibody molecule is administered than if the antibody molecule were never administered. Treatment can, e.g., partially or completely, alleviate, ameliorate, relieve, inhibit, or reduce the severity of, and/or reduce incidence, and optionally, delay onset of, one or more manifestations of the effects or symptoms, features, and/or causes of the disorder. In an embodiment, treatment is of a subject who does not exhibit certain signs of the disorder, and/or of a subject who exhibits only early signs of the disorder. In an embodiment, treatment is of a subject who exhibits one or more established signs of a disorder. In an embodiment, treatment is of a subject diagnosed as suffering from a disorder.

As used herein, the term "prevent," a disorder, means that a subject (e.g., a human) is less likely to have the disorder, if the subject receives a polypeptide (e.g., antibody molecule).

Various aspects of the compositions and methods herein are described in further detail below. Additional definitions are set out throughout the specification.

Libraries of Binding Polypeptides

Disclosed herein are libraries (e.g., display libraries) of binding polypeptides, e.g., antibody molecules or T cell receptor molecules, and methods of making libraries of binding polypeptides, e.g., antibody molecules or T cell receptor molecules.

In an embodiment, a method described herein links two DNA fragments, such as sequences encoding an antibody heavy chain variable region (or a portion thereof) and an antibody light chain variable region (or a portion thereof), a TCR α chain (or a portion thereof) and a TCR β chain (or a portion thereof), or a TCR γ chain (or a portion thereof) and a TCR δ chain (or a portion thereof), using a ligase-mediated approach.

For example, antibodies are composed of two types of polypeptide chains, light chain and heavy chain, each of which are translated from separate mRNA molecules. In order to copy a functional unit of a particular antibody (or B cell receptor) from a B cell, knowledge of the particular heavy chain and its cognate light chain must be maintained. This is typically performed using methods in which individual clones are in wells of microwell plates, which keeps clones segregated and the result heavy and light chain sequences thus are known to be paired. Such cloning processes scale well to B cell numbers compatible with 96- or 384-well plates. However, B cell repertoires in humans and animals can range from about $10^6$-$10^{11}$ B cells, many of which are different clones (i.e., different BCRs or antibodies). Thus, there is a need to be able to, in an efficient manner, make copies of millions to billions of B cells which (1) retains native pairing of chains and (2) allows for functional interrogation of such a large number of unique clones. Such a method can facilitate making a renewable copy of an antibody repertoire which can be functionally interrogated by a variety of methods.

In an embodiment, a method described herein uses one or more (e.g., two, three, or all) of the following: (1) miniaturized compartmentalization of individual cells (e.g., B cells or T cells) in droplets (pL to nL volume drops), (2) lysing and PCR amplifying two chains (e.g., antibody VH and VL, TCR α and β chains, or TCR γ and δ chains), (3) specifically linking the two chains, such that native chain pairing is retained and that a thermostable ligase catalyzes the linking, and (4) amplifying the linked DNA in a manner that allows for high throughput phenotypic interrogation of clones by a surface display technology, such as yeast or phage display.

The methods described herein can result in a nucleic acid sequence, when expressed, encodes a functional polypeptide, e.g., a functional antigen binding polypeptide. For example, the HC element and the LC element (or the AC element and the BC element, or the GC element and the DC element) are not configured in a head-to-head or tail-to-tail orientation. In an embodiment, the HC element and the LC element (or the AC element and the BC element, or the GC element and the DC element) are configured in a head-to-tail orientation. For example, the C-terminus of the LC element (or LCVRS) is linked, directly or indirectly, with the N-terminus of the HC element (or HCVRS), or the C-terminus of the HC element (or HCVRS) is linked, directly or indirectly, with the C-terminus of the LC element (or LCVRS).

Exemplary Workflow

Cells (e.g., immune cells, e.g., B cells or T cells) are encapsulated individually into drops. In the drops, the cells are lysed and mRNA is captured onto beads, which contain oligonucleotides to hybridize to mRNA. The beads facilitate maintaining native pairing information (e.g., the native pairing between two chains, e.g., a heavy chain and a light chain in a single B cell; an α chain and a β chain in a single T cell; or a γ chain and a δ chain in a single T cell). Next, the mRNA is reversed transcribed to cDNA by a reverse transcriptase (RT). The reverse transcription can be performed within the lysis drops, outside of drops, or in the subsequent drop (TCR' drop). Beads having captured mRNA or cDNA are recovered from the initial drops. The beads are then encapsulated into new drops, wherein the nucleic acids are amplified, either by RT-PCR (when mRNA is template) or PCR (when cDNA is template). The cDNAs encoding the two chains are amplified in drops. The amplified products are captured back onto beads by specific complementary nucleic acid hybridization. The beads having captured products are recovered from drops and subsequently encapsulated into new drops. The amplified product encoding one chain (e.g., VH) is linked with the amplification product encoding the other chain (e.g., VL) in drops using a thermostable ligase. In an approach ("linking cohesive products"), cohesive (or "sticky-end") PCR products are generated, and covalent ligation of hybridized cohesive PCR products are performed by a thermostable ligase. In another approach ("ligase cycling reaction"), no cohesive PCR products are produced. Rather, in drops, DNA is linked together through use of a thermostable ligase and a splint (or bridging) oligonucleotide. While not wishing to be bound by theory, it is believed that in an embodiment, the methods described herein reduce or preclude the possibility of unintended fusing caused by overlap extension PCR methods (Turchaninova et al. *Eur J Immunol*. 2013; 43(9): 2507-2515). The ligated products, representing natively paired chains, are further amplified to generate sufficient material to create a display library, such as in yeast or phage. The amplified product, encoding natively paired chains (e.g., antibody heavy chain and light chain, TCR α chain and β chain, or TCR γ chain and δ chain) in a format such as an scFv, scFab, Fab, or full-length IgG, are introduced to an appropriate expression or display vehicle, such as yeast or phage display. The constructed library, e.g., having >$10^4$ and up to $10^9$ or larger members, can be rapidly interrogated for desired binding and/or other phenotypic properties, using established methods.

Generation of Cohesive PCR Products that are Suitable Substrates for Ligase

In an embodiment, amplification (e.g., PCR) products with cohesive ends that are suitable substrates for ligase are generated. Without wishing to be bound by theory, it is believed that in an embodiment, DNA polymerase extension can be prematurely terminated at a defined location, e.g., through use of a chemically modified (e.g., lesioned) nucleotide or base, or other alterations to the primer used for amplification. These chemically modified nucleotides or bases (or other primer alterations) are subsequently incorporated into one strand of the amplification product. As the DNA polymerase reads through the template strand which contains the modified nucleotide, it prematurely stops extension at (or near) the modified nucleotide, as it is not able to read through. This early polymerase termination due to the modification can lead to production of an amplification product with a cohesive end. The amplification product can hybridize (or anneal) efficiently with another amplification product having a complementary cohesive end, which can be produced in an analogous matter. For example, a PCR product encoding one chain (e.g., VH) and a PCR product encoding another chain (e.g., VL), each having a complementary cohesive end, can hybridize (or anneal) to each other with high efficiency. Next, a thermostable ligase, present in the droplet with the DNA polymerase (e.g., throughout thermocycling), catalyzes ligation (covalent linkage) of the hybridized (or annealed) DNA molecules.

In an embodiment, the native paring information is maintained during amplification and ligation. In an embodiment, both amplification and ligation occur in the same drop, e.g., without breaking the drop. In an embodiment, the ligase retains at least 50%, e.g., at least 60%, 70%, 80%, 85%, 90%, 95%, or 99% activity, at 95° C. or more (e.g., 96° C. or more, 97° C. or more, or 98° C. or more), during one or more (e.g., 2, 3, 4, 5, 6, 7, 8, 9, 10, 15, 20, 25, or more) thermocycles. In an embodiment, the ligase retains at least 50%, e.g., at least 60%, 70%, 80%, 85%, 90%, 95%, or 99% activity, at 95° C. or more (e.g., 96° C. or more, 97° C. or more, or 98° C. or more), for at least 5 minutes (e.g., at least 10 minutes, 15 minutes, 20 minutes, 25 minutes, 30 minutes, 45 minutes, or 60 minutes). In an embodiment, the ligase retains at least 50%, e.g., at least 60%, 70%, 80%, 85%, 90%, 95%, or 99% activity, at 95° C. or more (e.g., 96° C. or more, 97° C. or more, or 98° C. or more), in a buffer condition that allows for DNA polymerase activity.

In an embodiment, the modification inhibits or blocks DNA polymerase activity and remains a substrate for ligation. In an embodiment, the modification does not inhibit or prevent binding of the amplification product to a ligase. In an embodiment, the modification does not inhibit or prevent formation of a phosphodiester bond. In an embodiment, the modification does not comprise a large bulky chemical group. Exemplary modifications include, but are not limited to, a ribose 2'-C ($2^{nd}$ carbon) modification (e.g., OH (i.e., a ribonucleotide, not a deoxyribonucleotide), O-methyl (O—$CH_3$), or amine ($NH_2$)); a ribose 4'-C ($4^{th}$ carbon) modification; a base modification (e.g., a non-native base, a uracil, or others); an abasic site (e.g., an AP site or apyrimidine/apurine); or a staggered primer (e.g., different length overhang). In an embodiment, the modification comprises a uracil and a DNA polymerase that is inhibited by uracil (e.g., an archaeal DNA polymerase) is used for amplification.

Exemplary steps for performing a cohesive-end PCR-ligation experiment in drops are illustrated below.

Cell Encapsulation

Cells can be encapsulated individually into droplets. In an embodiment, the cell is an immune cell. In an embodiment, the cell is a B cell. In an embodiment, the cell is a T cell. In an embodiment, the cell is an antibody-producing cell. In an embodiment, the cell is an isolated cell or purified cell. In an embodiment, the cell is obtained from a subject, e.g., a human, mouse, rabbit, rat, goat, sheep, or chicken.

In an embodiment, the volume of the droplet is from 10 pL to 100 nL, e.g., from 10 pL to 100 pL, from 10 pL to 1000 pL, from 10 pL to 10 nL, from 10 nL to 100 nL, from 1000 pL to 100 nL, from 100 pL to 100 nL, from 100 pL to 10 nL, from 100 pL to 1000 pL, from 1000 pL to 10 nL, or from 100 pL to 1000 pL. In an embodiment, the volume of the droplet is from 100 pL to 1000 pL. In an embodiment, the droplet is a water-in-oil droplet. In an embodiment, the droplet is present in a carrier (e.g., oil) phase, e.g., a carrier phase comprising 3M™ HFE-7500 with about 1% fluorosurfactant (RAN Biotechnologies).

The droplets can be formed, e.g., using a microfluidic chip (e.g., 2R 100 μm from Dolomite) with the flow of fluid phase controlled by a syringe or pressure pump. In an embodiment, the aqueous phase of the droplet comprises a buffer, a reagent that aids cell lysis, and a bead. In an embodiment, the buffer comprises Tris at pH 7.5. In an embodiment, the reagent that aids cell lysis comprises a detergent. Exemplary detergents that can be used to aid cell lysis include, but are not limited to, Tween-20, Triton X, IGEPAL, or sodium lauroyl sarcosinate (Sarkosyl). In an embodiment, the bead is a magnetic bead. In an embodiment, the bead comprises, is coupled to, an oligonucleotide (e.g., a primer), e.g., to anneal to an mRNA (e.g., an mRNA encoding a heavy chain or a light chain).

In an embodiment, the droplet contains no more than one cell after encapsulation. In an embodiment, the droplet contains a plurality of beads. In an embodiment, a plurality of beads are obtained, and at least 80%, e.g., at least 85%, 90%, 95%, 98%, 99%, or 100%, of the plurality contains no more than one cell per droplet. In an embodiment, a plurality of beads are obtained, and at least 80%, e.g., at least 85%, 90%, 95%, 98%, 99%, or 100%, of the plurality contains at least one bead per droplet. Typically, the occupancy of drops is no more than one cell per droplet, and at least one bead per droplet.

Cell Lysis

After encapsulation, the droplets can be incubated to facilitate cell lysis. In an embodiment, an emulsion (e.g., containing coalesce different solution phases) is heated, e.g., to reduce mRNA secondary structures so that it can be more efficiently captured onto the bead and/or to improved lysis efficiency in the presence of a detergent (e.g., Tween20). In an embodiment, the emulsion is incubated at a temperature between 40° C. and 80° C., e.g., between 40° C. and 60° C., 50° C. and 70° C., or 60° C. and 80° C., e.g., at 40° C., 50° C., 60° C., 70° C., or 80° C. In an embodiment, the emulsion is incubated for 5 to 60 minutes, e.g., 10 to 45 minutes, 15 to 30 minutes, 5 to 30 minutes, or 30 to 50 minutes. In an embodiment, the cell is lysed by heat. In an embodiment, the cell is lysed by an enzyme. Typically, after the cell is lysed, mRNA is released and is captured on a bead by annealing to the oligonucleotides on the bead.

Bead Recovery

Emulsions (e.g., containing coalesce different solution phases) can be broken using a drop destabilizing reagent, e.g., perfluorooctanol (PFO). In an embodiment, the bead-containing aqueous phase is recovered. In an embodiment, the bead is a magnetic bead, and is isolated using magnet. In an embodiment, the bead is washed and resuspended in a buffer (e.g., Tris, pH 7.5).

Reverse Transcription

Reverse transcription can be performed using standard methods. In an embodiment, the reverse transcription is performed in a non-emulsion reaction. In an embodiment, the reverse transcription is performed in an emulsion reaction. In an embodiment, the bead with captured mRNA is resuspended in a buffer-enzyme mix (e.g., Superscript II RT) and incubated at 35° C. to 45° C. (e.g., at 40° C.) for 10 to 60 minutes (e.g., 15 minutes) to facilitate reverse transcription. In an embodiment, the oligonucleotide coupled to the bead is used as a primer for the synthesis of the first strand cDNA. In an embodiment, the bead is washed with a buffer (e.g., Tris, pH 7.5) after reverse transcription.

Bead Encapsulation Beads can be encapsulated individually into droplets. In an embodiment, the volume of the droplet is from 5 pL to 500 pL, e.g., from 5 pL to 400 pL, from 5 pL to 300 pL, from 5 pL to 200 pL, from 5 pL to 100 pL, from 5 pL to 50 pL, from 5 pL to 25 pL, from 400 pL to 500 pL, from 300 pL to 500 pL, from 200 pL to 500 pL, from 100 pL to 500 pL, from 50 pL to 500 pL, from 25 pL to 500 pL, from 10 pL to 500 pL, from 10 pL to 400 pL, from 25 pL to 300 pL, from 50 pL to 200 pL, or from 10 pL to 50 pL. In an embodiment, the volume of the droplet is from 10 pL to 50 pL.

In an embodiment, the droplet is a water-in-oil droplet. In an embodiment, the droplet is present in a carrier (e.g., oil) phase, e.g., a carrier phase comprising 3M™ HFE-7500 with about 1% fluorosurfactant (RAN Biotechnologies).

In an embodiment, the droplet contains one bead after encapsulation. In an embodiment, a plurality of beads are obtained, and at least 80%, e.g., at least 85%, 90%, 95%, 98%, 99%, or 100%, of the plurality contains no more than one bead per droplet.

PCR-Ligation Reaction

In an embodiment, a PCR-ligation reaction is performed. In an embodiment, the PCR-ligation reaction generates a ligated product (e.g., a double-stranded DNA) that comprises a nucleotide sequence that encodes an antibody heavy chain variable region (or a portion thereof) and an antibody light chain variable region (or a portion thereof). In an embodiment, the PCR-ligation reaction generates a ligated product (e.g., a double-stranded DNA) that comprises a nucleotide sequence that encodes a TCR α chain (or a portion thereof) and a TCR β chain (or a portion thereof). In an embodiment, the PCR-ligation reaction generates a ligated product (e.g., a double-stranded DNA) that comprises a nucleotide sequence that encodes a TCR γ chain (or a portion thereof) and a TCR δ chain (or a portion thereof). In an embodiment, the PCR-ligation reaction is performed in a droplet comprising a bead that is coupled with cDNA, a DNA polymerase, oligonucleotides (e.g., for amplification of the cDNA), a ligase (e.g., a thermostable ligase), and a buffer.

Exemplary DNA polymerases that can be used in the reaction include, but are not limited to, Phusion® High-Fidelity DNA Polymerase (NEB), Q5® High-Fidelity DNA Polymerase (NEB), Pfu DNA polymerase, KAPA DNA polymerase, Vent® DNA polymerase, or Taq DNA polymerase.

In an embodiment, the ligated product contains an scFv, a Fab, or scFab cassette. In an embodiment, the cassette (e.g., scFv cassette) is constructed as VL-Linker-VH. Without wishing to be bound by theory, it is believed that in an embodiment, the order can be switched to VH-Linker-VL, with no significant impact on expression or function. In an embodiment, the cassette (e.g., scFv) cassette is constructed as VH-Linker-VL. In an embodiment, the cassette comprises a constant region sequence (e.g., a CH1 domain and/or a CL domain), e.g., VH-CH1 coupled with VL-CL.

Similarly, the ligated product can contain a cassette constructed as α chain-Linker-β chain or β chain-Linker-α chain, or γ chain-Linker-δ chain or δ chain-Linker-γ chain.

In an embodiment, the reverse primer for the VL sequence contains one, two, or all of the following: (a) an overhang sequence encoding a linker sequence (b) at least one modified nucleotide (e.g., 3 consecutive nucleotides with 2'-O-methyl modification), e.g., in the overhang; or (c) a 5'-phosphate. In an embodiment, the forward primer for the VH sequence contains one, two, or all of the following: (a) an overhang sequence encoding a linker sequence (b) at least one modified nucleotide (e.g., 3 consecutive nucleotides with 2'-O-methyl modification), e.g., in the overhang; or (c) a 5'-phosphate.

In an embodiment, the reverse primer for the VH sequence contains one, two, or all of the following: (a) an overhang sequence encoding a linker sequence (b) at least one modified nucleotide (e.g., 3 consecutive nucleotides with 2'-O-methyl modification), e.g., in the overhang; or (c) a 5'-phosphate. In an embodiment, the forward primer for the VL sequence contains one, two, or all of the following: (a) an overhang sequence encoding a linker sequence (b) at least one modified nucleotide (e.g., 3 consecutive nucleotides with 2'-O-methyl modification), e.g., in the overhang; or (c) a 5'-phosphate.

Similarly, in an embodiment, the reverse primer for the α chain (or γ chain) sequence contains one, two, or all of the following: (a) an overhang sequence encoding a linker sequence (b) at least one modified nucleotide (e.g., 3 consecutive nucleotides with 2'-O-methyl modification), e.g., in the overhang; or (c) a 5'-phosphate. In an embodiment, the forward primer for the β chain (or δ chain) sequence contains one, two, or all of the following: (a) an overhang sequence encoding a linker sequence (b) at least one modified nucleotide (e.g., 3 consecutive nucleotides with 2'-O-methyl modification), e.g., in the overhang; or (c) a 5'-phosphate.

Similarly, in an embodiment, the reverse primer for the β chain (or δ chain) sequence contains one, two, or all of the following: (a) an overhang sequence encoding a linker sequence (b) at least one modified nucleotide (e.g., 3 consecutive nucleotides with 2'-O-methyl modification), e.g., in the overhang; or (c) a 5'-phosphate. In an embodiment, the forward primer for the α chain (or γ chain) sequence contains one, two, or all of the following: (a) an overhang sequence encoding a linker sequence (b) at least one modified nucleotide (e.g., 3 consecutive nucleotides with 2'-O-methyl modification), e.g., in the overhang; or (c) a 5'-phosphate.

Exemplary ligases (e.g., thermostable ligases) that can be used in the reaction include, but are not limited to, Taq DNA ligase, Pfu DNA ligase, Ampligase® thermostable DNA ligase, Tsc DNA ligase, Rma DNA ligase, Tfi DNA ligase, or Tth DNA ligase.

In an embodiment, the buffer supports both DNA polymerase and ligase enzymatic activities.

In an embodiment, the thermocycling is performed with emulsion (e.g., in a PCR tube). In an embodiment, the thermocycling is performed using the following conditions: initial denaturation at 95-98° C. for 30 seconds to 2 minutes; 10-30 cycles of: denaturation at 95-98° C. for 10-30 seconds, primer annealing at 50-60° C. for 10-30 seconds, polymerase extension at 72° C. for 30 seconds, and cohesive product annealing and ligation at 45-55° C. for 3 minutes. The reaction can be hold at 4° C.

Recovery of Aqueous Portion

Emulsions (e.g., containing coalesce different solution phases) can be broken using a drop destabilizing reagent, e.g., perfluorooctanol (PFO). In an embodiment, the aqueous portion (e.g., containing linked product, and optionally, non-linked product) is recovered. In an embodiment, the bead is discarded.

Purification of Linked Product

Linked product (e.g., representing natively linked VL-linker-VH) can be purified from non-linked products (e.g., non-linked VH and VL). The ligated products are separated from non-ligated products by size separation. For example, denaturing PAGE (polyacrylamide gel electrophoresis) or denaturing HPLC-SEC can be used. The linked product (~800-900 bp) is isolated from non-linked product (~350-500 bp). For denaturing PAGE purification, the ligated band is cut out from the gel and an elecro-elution is performed to extract DNA from gel slice (Bio-Rad Electro-Elutor).

Amplification of Purified Linked Product

The purified linked product can be amplified, e.g., by PCR. For example, the purified linked product is amplified by PCR using a DNA polymerase (e.g., Taq polymerase) under conditions that can moderately read through DNA containing modified nucleotides.

The final PCR product can be introduced to yeast using standard methods (e.g., electroporation with expression vector) to create a natively paired library derived from biological sources.

Ligase Cycling

In an embodiment, the different chains (e.g., VH and VL) are not amplified in a manner which incorporates DNA sequence common to both chains, which would facilitate annealing of sticky-end products directly to each other. In an embodiment, a bridging (or splint) oligonucleotide is included after the amplification of cDNA but in the presence of a thermostable ligase. The bridging oligonucleotide can facilitate bringing the two chains immediately adjacent to each other such that they become a substrate of ligase. Ligase, in turn, catalyzes a covalent bond formation between chains of DNA. Since this mechanism does not lead to incorporation of sequence common to both chains in each chain (e.g., overhang DNA with common sequence in both VH and VL), there is no opportunity for splicing by overlap extension PCR.

The steps of this approach are generally the same as above except beginning at the emulsion PCR step. PCR amplification of cDNA can be performed in drops. Primers can add overhang sequences, but there is generally no common sequence to both chains (e.g., VL and VH) that is added (unlike the above strategy). The bead in the drop, through its conjugated oligonucleotides, becomes filled or saturated with dsDNA products of the two chains (e.g., VH and VL), each with specific overhang sequence. Drops are broken, and any PCR product not linked or annealed to beads is washed away. Beads containing dsDNA of two chains (e.g., VH and VL) are encapsulated into new drops in the presence of a thermostable ligase and a splint oligonucleotide. In this emulsion format, thermocycling is performed, which facilitates formation of the 3-DNA piece complex. This complex is a substrate for ligase, which catalyzes covalent bond formation, linking the two chains. In an embodiment, thermocycling aids conversion of all 'top strand' DNA to linked product, until one substrate becomes limiting. In another embodiment, both strands become ligated. For example, once the 'top strand' is ligated, it can serve as the 'splint' for the opposing strand, which ligase will recognize as a substrate. Without wishing to be bound by theory, it is believed that, this facet specifically makes the reaction efficient, that is, initial ligated product can serve as more templates (splints) to generate even more additional ligated product. Drops are broken, and the ligated products are amplified by standard PCR means.

Exemplary steps for performing a ligase cycling experiment are illustrated below.

Cell Encapsulation

Cells can be encapsulated individually into droplets. In an embodiment, the cell is an immune cell. In an embodiment, the cell is a B cell. In an embodiment, the cell is a T cell. In an embodiment, the cell is an antibody-producing cell. In an embodiment, the cell is an isolated cell or purified cell. In an embodiment, the cell is obtained from a subject, e.g., a human, mouse, rabbit, rat, goat, sheep, or chicken.

In an embodiment, the volume of the droplet is from 10 pL to 100 nL, e.g., from 10 pL to 100 pL, from 10 pL to 1000 pL, from 10 pL to 10 nL, from 10 nL to 100 nL, from 1000 pL to 100 nL, from 100 pL to 100 nL, from 100 pL to 10 nL, from 100 pL to 1000 pL, from 1000 pL to 10 nL, or from 100 pL to 1000 pL. In an embodiment, the volume of the droplet is from 100 pL to 1000 pL.

In an embodiment, the droplet is a water-in-oil droplet. In an embodiment, the droplet is present in a carrier (e.g., oil) phase, e.g., a carrier phase comprising 3M™ HFE-7500 with about 1% fluorosurfactant (RAN Biotechnologies).

The droplets can be formed, e.g., using a microfluidic chip (e.g., 2R 100 μm from Dolomite) with the flow of fluid phase controlled by a syringe or pressure pump. In an embodiment, the aqueous phase of the droplet comprises a buffer, a reagent that aids cell lysis, and a bead. In an embodiment, the buffer comprises Tris at pH 7.5. In an embodiment, the reagent that aids cell lysis comprises a detergent. Exemplary detergents that can be used to aid cell lysis include, but are not limited to, Tween-20, Triton X, IGEPAL, or sodium lauroyl sarcosinate (Sarkosyl). In an embodiment, the bead is a magnetic bead. In an embodiment, the bead comprises, is coupled to, an oligonucleotide (e.g., a primer), e.g., to anneal to an mRNA (e.g., an mRNA encoding a heavy chain or a light chain).

In an embodiment, the droplet contains no more than one cell after encapsulation. In an embodiment, the droplet contains a plurality of beads. In an embodiment, a plurality of beads are obtained, and at least 80%, e.g., at least 85%, 90%, 95%, 98%, 99%, or 100%, of the plurality contains no more than one cell per droplet. In an embodiment, a plurality of beads are obtained, and at least 80%, e.g., at least 85%, 90%, 95%, 98%, 99%, or 100%, of the plurality contains at least one bead per droplet. Typically, the occupancy of drops is no more than one cell per droplet, and at least one bead per droplet.

Cell Lysis

After encapsulation, the droplets can be incubated to facilitate cell lysis. In an embodiment, an emulsion (e.g., containing coalesce different solution phases) is heated to improved lysis efficiency in the presence of a detergent (e.g., Tween20). In an embodiment, the emulsion is incubated at a temperature between 40° C. and 80° C., e.g., between 40° C. and 60° C., 50° C. and 70° C., or 60° C. and 80° C., e.g., at 40° C., 50° C., 60° C., 70° C., or 80° C. In an embodiment, the emulsion is incubated for 5 to 60 minutes, e.g., 10 to 45 minutes, 15 to 30 minutes, 5 to 30 minutes, or 30 to 50 minutes. In an embodiment, the cell is lysed by heat. In an embodiment, the cell is lysed by an enzyme. Typically, after the cell is lysed, mRNA is released and is captured on a bead by annealing to the oligonucleotides on the bead.

Bead Recovery

Emulsions (e.g., containing coalesce different solution phases) can be broken using a drop destabilizing reagent, e.g., perfluorooctanol (PFO). In an embodiment, the bead-containing aqueous phase is recovered. In an embodiment, the bead is a magnetic bead, and is isolated using magnet. In an embodiment, the bead is washed and resuspended in a buffer (e.g., Tris, pH 7.5). In an embodiment, the bead is kept cold to reduce dissociation of mRNA from the bead.

Reverse Transcription

Reverse transcription can be performed using standard methods. In an embodiment, the reverse transcription is performed in a non-emulsion reaction. In an embodiment, the reverse transcription is performed in an emulsion reaction. In a typical embodiment, the reverse transcription step is performed within the PCR drop. For example, mRNA-beads are encapsulated into drops with both reverse transcriptase and DNA polymerase to facilitate cDNA formation and dsDNA amplification. In an embodiment, the bead with captured mRNA is resuspended in a buffer-enzyme mix (e.g., Superscript II RT) and incubated at 35° C. to 45° C. (e.g., at 40° C.) for 10 to 60 minutes (e.g., 15 minutes) to facilitate reverse transcription. In an embodiment, the oligonucleotide coupled to the bead is used as a primer for the synthesis of the first strand cDNA. In an embodiment, the bead is washed with a buffer (e.g., Tris, pH 7.5) after reverse transcription.

Bead Encapsulation for PCR

Beads can be encapsulated individually into droplets. In an embodiment, the volume of the droplet is from 5 pL to 500 pL, e.g., from 5 pL to 400 pL, from 5 pL to 300 pL, from 5 pL to 200 pL, from 5 pL to 100 pL, from 5 pL to 50 pL, from 5 pL to 25 pL, from 400 pL to 500 pL, from 300 pL to 500 pL, from 200 pL to 500 pL, from 100 pL to 500 pL, from 50 pL to 500 pL, from 25 pL to 500 pL, from 10 pL to 500 pL, from 10 pL to 400 pL, from 25 pL to 300 pL, from 50 pL to 200 pL, or from 10 pL to 50 pL. In an embodiment, the volume of the droplet is from 10 pL to 50 pL.

In an embodiment, the droplet is a water-in-oil droplet. In an embodiment, the droplet is present in a carrier (e.g., oil) phase, e.g., a carrier phase comprising 3M™ HFE-7500 with about 1% fluorosurfactant (RAN Biotechnologies).

In an embodiment, the droplet contains one bead after encapsulation. In an embodiment, a plurality of beads are obtained, and at least 80%, e.g., at least 85%, 90%, 95%, 98%, 99%, or 100%, of the plurality contains no more than one bead per droplet.

PCR Reaction

In an embodiment, a PCR reaction is performed. In an embodiment, the PCR reaction is performed in a droplet comprising a bead that is coupled with cDNA, a DNA polymerase, oligonucleotides (e.g., for amplification of the cDNA), and a buffer.

Exemplary DNA polymerases that can be used in the reaction include, but are not limited to, Phusion® High-Fidelity DNA Polymerase (NEB), Q5® High-Fidelity DNA Polymerase (NEB), Pfu DNA polymerase, KAPA DNA polymerase, Vent® DNA polymerase, or Taq DNA polymerase.

In an embodiment, the PCR product contains an scFv cassette. In an embodiment, the scFv cassette is constructed as VL-Linker-VH. Without wishing to be bound by theory, it is believed that in an embodiment, the order can be switched to VH-Linker-VL, with no significant impact on expression or function. In an embodiment, the scFv cassette is constructed as VH-Linker-VL.

Similarly, the PCR product can contain a cassette constructed as α chain-Linker-β chain or β chain-Linker-α chain, or γ chain-Linker-δ chain or δ chain-Linker-γ chain.

In an embodiment, a primer for a target variable region sequence described herein can contain (e.g., from 5' to 3'): a first sequence that is complementary to the sequence of an oligonucleotide attached to a capture substrate, a spacer (e.g., a spacer described herein, e.g., a PEG spacer), a sequence that is complementary to at least a portion of the first sequence, a universal priming sequence, and a sequence complementary to the target variable region sequence.

In an embodiment, the reverse primer for the VL sequence contains one, two, or all of the following: (a) an overhang sequence encoding a linker sequence (b) at least one modified nucleotide (e.g., 3 consecutive nucleotides with 2'-O-methyl modification), e.g., in the overhang; or (c) a 5'-phosphate. In an embodiment, the forward primer for the VH sequence contains one, two, or all of the following: (a) an overhang sequence encoding a linker sequence (b) at least one modified nucleotide (e.g., 3 consecutive nucleotides with 2'-O-methyl modification), e.g., in the overhang; or (c) a 5'-phosphate.

In an embodiment, the reverse primer for the VH sequence contains one, two, or all of the following: (a) an overhang sequence encoding a linker sequence (b) at least one modified nucleotide (e.g., 3 consecutive nucleotides with 2'-O-methyl modification), e.g., in the overhang; or (c) a 5'-phosphate. In an embodiment, the forward primer for the VL sequence contains one, two, or all of the following: (a) an overhang sequence encoding a linker sequence (b) at least one modified nucleotide (e.g., 3 consecutive nucleotides with 2'-O-methyl modification), e.g., in the overhang; or (c) a 5'-phosphate.

Similarly, in an embodiment, the reverse primer for the α chain (or γ chain) sequence contains one, two, or all of the following: (a) an overhang sequence encoding a linker sequence (b) at least one modified nucleotide (e.g., 3 consecutive nucleotides with 2'-O-methyl modification), e.g., in the overhang; or (c) a 5'-phosphate. In an embodiment, the forward primer for the β chain (or δ chain) sequence contains one, two, or all of the following: (a) an overhang sequence encoding a linker sequence (b) at least one modified nucleotide (e.g., 3 consecutive nucleotides with 2'-O-methyl modification), e.g., in the overhang; or (c) a 5'-phosphate.

Similarly, in an embodiment, the reverse primer for the β chain (or δ chain) sequence contains one, two, or all of the following: (a) an overhang sequence encoding a linker sequence (b) at least one modified nucleotide (e.g., 3 consecutive nucleotides with 2'-O-methyl modification), e.g., in the overhang; or (c) a 5'-phosphate. In an embodiment, the forward primer for the α chain (or γ chain) sequence contains one, two, or all of the following: (a) an overhang sequence encoding a linker sequence (b) at least one modified nucleotide (e.g., 3 consecutive nucleotides with 2'-O-methyl modification), e.g., in the overhang; or (c) a 5'-phosphate.

In an embodiment, the thermocycling is performed with emulsion (e.g., in a PCR tube). In an embodiment, the thermocycling is performed using the following conditions: initial denaturation at 95-98° C. for 30 seconds to 2 minutes; 10-30 cycles of: denaturation at 95-98° C. for 10-30 seconds, primer annealing at 50-60° C. for 10-30 seconds, and polymerase extension at 72° C. for 30 seconds. In an embodiment, the reaction undergoes a slow cooling to facilitate capture of PCR products onto beads. The reaction can be hold at 4° C.

Bead Recovery

Emulsions (e.g., containing coalesce different solution phases) can be broken using a drop destabilizing reagent, e.g., perfluorooctanol (PFO). In an embodiment, the bead-containing aqueous phase is recovered. In an embodiment, the bead is a magnetic bead, and is isolated using magnet. In an embodiment, the bead is washed and resuspended in a buffer (e.g., Tris, pH 7.5).

Bead Encapsulation for Ligase Cycling

Beads can be encapsulated individually into droplets. In an embodiment, the volume of the droplet is from 5 pL to 500 pL, e.g., from 5 pL to 400 pL, from 5 pL to 300 pL, from 5 pL to 200 pL, from 5 pL to 100 pL, from 5 pL to 50 pL, from 5 pL to 25 pL, from 400 pL to 500 pL, from 300 pL to 500 pL, from 200 pL to 500 pL, from 100 pL to 500 pL, from 50 pL to 500 pL, from 25 pL to 500 pL, from 10 pL to 500 pL, from 10 pL to 400 pL, from 25 pL to 300 pL, from 50 pL to 200 pL, or from 10 pL to 50 pL. In an embodiment, the volume of the droplet is from 10 pL to 50 pL.

In an embodiment, the droplet is a water-in-oil droplet. In an embodiment, the droplet is present in a carrier (e.g., oil) phase, e.g., a carrier phase comprising 3M™ HFE-7500 with about 1% fluorosurfactant (RAN Biotechnologies).

In an embodiment, the droplet contains one bead after encapsulation. In an embodiment, a plurality of beads are obtained, and at least 80%, e.g., at least 85%, 90%, 95%, 98%, 99%, or 100%, of the plurality contains no more than one bead per droplet.

Ligase Cycling Reaction

In an embodiment, a ligase cycling reaction is performed. In an embodiment, the ligase cycling reaction is performed in a droplet comprising a bead that is coupled with PCR product, a Splint oligonucleotide (e.g., complementary and anneals to 3' terminus of one strand (e.g., "top" VL strand) and 5' terminus of another strand (e.g., "top" VH strand)), a thermostable ligase, and one or more reaction components that supports ligase enzymatic activity (e.g., NAD).

Exemplary ligases (e.g., thermostable ligases) that can be used in the reaction include, but are not limited to, Taq DNA ligase, Pfu DNA ligase, Ampligase® thermostable DNA ligase, Tsc DNA ligase, Rma DNA ligase, Tfi DNA ligase, or Tth DNA ligase.

In an embodiment, the thermocycling is performed with emulsion (e.g., in a PCR tube). In an embodiment, the thermocycling is performed using the following conditions: 3-15 cycles of: denaturation at 90-95° C. for 30 seconds, and annealing and ligation at 50-60° C. for 1-3 minutes. The reaction can be hold at 4° C.

Recovery of Aqueous Portion

Emulsions (e.g., containing coalesce different solution phases) can be broken using a drop destabilizing reagent, e.g., perfluorooctanol (PFO). In an embodiment, the aqueous portion (e.g., containing linked product, and optionally, non-linked product) is recovered. In an embodiment, the bead is discarded.

Purification of Linked Product

Linked product (e.g., representing natively linked VL-linker-VH) can be purified from non-linked products (e.g., non-linked VH and VL). The ligated products are separated from non-ligated products by size separation. For example, denaturing PAGE (polyacrylamide gel electrophoresis), denaturing HPLC-SEC, agarose gel electrophoresis or AMPure XP beads can be used. The linked product (~800-900 bp) is isolated from non-linked product (~350-500 bp). For denaturing PAGE purification, the ligated band is cut out from the gel and an elecro-elution is performed to extract DNA from gel slice (Bio-Rad Electro-Elutor).

Amplification of Purified Linked Product

The purified linked product can be amplified, e.g., by PCR. For example, the purified linked product is amplified by PCR using a DNA polymerase (e.g., Taq polymerase) under standard conditions with oligonucleotides that anneal the outer termini of the ligated product.

The final PCR product can be introduced to yeast or mammalian cells using standard methods (e.g., electroporation with expression vector) to create a natively paired library derived from biological sources.

Exemplary steps in a method of making a nucleic acid comprising a sequence that encodes a heavy chain element (HC element) of an antibody heavy chain variable region (HCVR) and a light chain element (LC element) of an antibody light chain variable region (LCVR), and wherein the HCVR and LCVR are matched, are illustrated in FIGS. 2A-2D.

Additional Exemplary Methods

In an aspect, the disclosure features a method of making a nucleic acid sequence comprising a sequence that encodes a heavy chain element (HC element) of an antibody heavy chain variable region (HCVR) and a light chain element (LC element) of an antibody light chain variable region (LCVR), and wherein the HCVR and LCVR are matched, the method comprising carrying out the following steps from FIG. 1: A1, B1, C1, and D1, thereby making a nucleic acid sequence comprising a sequence that encodes an HC element of an HCVR and a LC element of an LCVR, wherein the HCVR and LCVR are matched.

In an aspect, the disclosure features a method of making a nucleic acid sequence comprising a sequence that encodes a heavy chain element (HC element) of an antibody heavy chain variable region (HCVR) and a light chain element (LC element) of an antibody light chain variable region (LCVR), and wherein the HCVR and LCVR are matched, the method comprising carrying out the following steps from FIG. 1: A1, B1, C1, D2, and E1, thereby making a nucleic acid sequence comprising a sequence that encodes an HC element of an HCVR and a LC element of an LCVR, wherein the HCVR and LCVR are matched.

In an aspect, the disclosure features a method of making a nucleic acid sequence comprising a sequence that encodes a heavy chain element (HC element) of an antibody heavy chain variable region (HCVR) and a light chain element (LC element) of an antibody light chain variable region (LCVR), and wherein the HCVR and LCVR are matched, the method comprising carrying out the following steps from FIG. 1: A1, B1, C2, and D3, thereby making a nucleic acid sequence comprising a sequence that encodes an HC element of an HCVR and a LC element of an LCVR, wherein the HCVR and LCVR are matched.

In an aspect, the disclosure features a method of making a nucleic acid sequence comprising a sequence that encodes a heavy chain element (HC element) of an antibody heavy chain variable region (HCVR) and a light chain element (LC element) of an antibody light chain variable region (LCVR), and wherein the HCVR and LCVR are matched, the method comprising carrying out the following steps from FIG. 1: A1, B1, C2, D4 and E2, thereby making a nucleic acid sequence comprising a sequence that encodes an HC element of an HCVR and a LC element of an LCVR, wherein the HCVR and LCVR are matched.

In an aspect, the disclosure features a method of making a nucleic acid sequence comprising a sequence that encodes a heavy chain element (HC element) of an antibody heavy chain variable region (HCVR) and a light chain element (LC element) of an antibody light chain variable region (LCVR), and wherein the HCVR and LCVR are matched, the method comprising carrying out the following steps from FIG. 1: A1, B1, C3, and D5, thereby making a nucleic acid sequence comprising a sequence that encodes an HC element of an HCVR and a LC element of an LCVR, wherein the HCVR and LCVR are matched.

In an aspect, the disclosure features a method of making a nucleic acid sequence comprising a sequence that encodes a heavy chain element (HC element) of an antibody heavy chain variable region (HCVR) and a light chain element (LC element) of an antibody light chain variable region (LCVR), and wherein the HCVR and LCVR are matched, the method comprising carrying out the following steps from FIG. 1: A1, B1, C3, D6 and E3, thereby making a nucleic acid sequence comprising a sequence that encodes an HC element of an HCVR and a LC element of an LCVR, wherein the HCVR and LCVR are matched.

In the aforesaid exemplary methods, the cDNA is typically not captured on the substrate (e.g., bead) in this workflow concept. For example, mRNA dissociates from the substrate (e.g., bead), then cDNA is made in solution in the isolated reaction site (e.g., micro-chamber), e.g., in the drop, and then PCR product is made from cDNA as template in solution in the isolated reaction site (e.g., micro-chamber), e.g., in drop. In an embodiment, the method includes an RT-PCR reaction, where both enzymatic steps occur in solution in drop. In the aforesaid exemplary methods, the amplified products are typically captured onto the substrate (e.g., bead), which can facilitate transitioning the paired products into the next isolated reaction site (e.g., micro-chamber), e.g., the next drop.

Antibody Molecules

Disclosed herein are antibody molecules and libraries of antibody molecules. In an embodiment, the antibody molecule or library of antibody molecules are made by a method described herein.

As used herein, the term "antibody molecule" refers to a protein, e.g., an immunoglobulin chain or a fragment thereof, comprising at least one immunoglobulin variable domain sequence. The term "antibody molecule" includes, for example, full-length, mature antibodies and antigen-binding fragments of an antibody. For example, an antibody molecule can include a heavy (H) chain variable domain sequence (abbreviated herein as VH), and a light (L) chain variable domain sequence (abbreviated herein as VL). In another example, an antibody molecule includes two heavy (H) chain variable domain sequences and two light (L) chain variable domain sequence, thereby forming two antigen binding sites, such as Fab, Fab', F(ab')2, Fc, Fd, Fd', Fv, single chain antibodies (scFv for example), single variable domain antibodies, diabodies (Dab) (bivalent and bispecific), and chimeric (e.g., humanized) antibodies, which may be produced by the modification of whole antibodies or those synthesized de novo using recombinant DNA technologies. These functional antibody fragments retain the ability to selectively bind with their respective antigen or receptor. Antibodies and antibody fragments can be from any class of antibodies including, but not limited to, IgG, IgA, IgM, IgD, and IgE, and from any subclass (e.g., IgG1, IgG2, IgG3, and IgG4) of antibodies. The antibody molecules can be monoclonal or polyclonal. The antibody molecule can also be a human, humanized, CDR-grafted, or in vitro generated antibody. The antibody molecule can have a heavy chain constant region chosen from, e.g., IgG1, IgG2, IgG3, or IgG4. The antibody molecule can also have a light chain chosen from, e.g., kappa or lambda. The term "immunoglobulin" (Ig) is used interchangeably with the term "antibody" herein.

Examples of antigen-binding fragments include: (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a diabody (dAb) fragment, which consists of a VH domain; (vi) a camelid or camelized variable domain; (vii) a single chain Fv (scFv), see e.g., Bird et al. (1988) *Science* 242:423-426; and Huston et al. (1988) *Proc. Natl. Acad. Sci. USA* 85:5879-5883); (viii) a single domain antibody. These antibody fragments may be obtained using any suitable method, including several conventional techniques known to those with skill in the art, and the fragments can be screened for utility in the same manner as are intact antibodies.

The term "antibody" includes intact molecules as well as functional fragments thereof. Constant regions of the antibodies can be altered, e.g., mutated, to modify the properties of the antibody (e.g., to increase or decrease one or more of: Fc receptor binding, antibody glycosylation, the number of cysteine residues, effector cell function, or complement function).

The antibody molecule can be a single chain antibody. A single-chain antibody (scFV) may be engineered (see, for example, Colcher, D. et al. (1999) *Ann N Y Acad Sci* 880:263-80; and Reiter, Y. (1996) *Clin Cancer Res* 2:245-52). The single chain antibody can be dimerized or multimerized to generate multivalent antibodies having specificities for different epitopes of the same target protein.

The antibody molecules disclosed herein can also be single domain antibodies. Single domain antibodies can include antibodies whose complementary determining regions are part of a single domain polypeptide. Examples include, but are not limited to, heavy chain antibodies, antibodies naturally devoid of light chains, single domain antibodies derived from conventional 4-chain antibodies, engineered antibodies and single domain scaffolds other than those derived from antibodies. Single domain antibodies may be any of the art, or any future single domain antibodies. Single domain antibodies may be derived from any species including, but not limited to mouse, human, camel, llama, fish, shark, goat, rabbit, and bovine. According to some aspects, a single domain antibody is a naturally occurring single domain antibody known as heavy chain antibody devoid of light chains. Such single domain antibodies are disclosed in WO 94/04678, for example. For clarity reasons, this variable domain derived from a heavy chain antibody naturally devoid of light chain is known herein as a VHH or nanobody to distinguish it from the conventional VH of four chain immunoglobulins. Such a VHH molecule can be derived from antibodies raised in Camelidae species, for example in camel, llama, dromedary, alpaca and guanaco. Other species besides Camelidae may produce heavy chain antibodies naturally devoid of light chain; such VHHs are also contemplated.

The VH and VL regions can be subdivided into regions of hypervariability, termed "complementarity determining regions" (CDR), interspersed with regions that are more conserved, termed "framework regions" (FR or FW). The terms "complementarity determining region," and "CDR," as used herein refer to the sequences of amino acids within antibody variable regions which confer antigen specificity and binding affinity. As used herein, the terms "framework," "FW" and "FR" are used interchangeably.

The extent of the framework region and CDRs has been precisely defined by a number of methods (see, Kabat, E. A., et al. (1991) Sequences of Proteins of Immunological Interest, Fifth Edition, U.S. Department of Health and Human Services, NIH Publication No. 91-3242; Chothia, C. et al. (1987) *J. Mol. Biol.* 196:901-917; and the AbM definition used by Oxford Molecular's AbM antibody modeling software. See, generally, e.g., Protein Sequence and Structure Analysis of Antibody Variable Domains. In: Antibody Engineering Lab Manual (Ed.: Duebel, S. and Kontermann, R., Springer-Verlag, Heidelberg). In an embodiment, the following definitions are used: AbM definition of CDR1 of the heavy chain variable domain and Kabat definitions for the other CDRs. In an embodiment, Kabat definitions are used for all CDRs. In addition, embodiments described with respect to Kabat or AbM CDRs may also be implemented using Chothia hypervariable loops. Each VH and VL typically includes three CDRs and four FRs, arranged from amino-terminus to carboxy-terminus in the following order: FR1, CDR1, FR2, CDR2, FR3, CDR3, and FR4.

As used herein, an "immunoglobulin variable domain sequence" refers to an amino acid sequence which can form the structure of an immunoglobulin variable domain. For example, the sequence may include all or part of the amino acid sequence of a naturally-occurring variable domain. For example, the sequence may or may not include one, two, or more N- or C-terminal amino acids, or may include other alterations that are compatible with formation of the protein structure.

The term "antigen-binding region" refers to the part of an antibody molecule that comprises determinants that form an interface that binds to an antigen, or an epitope thereof. With respect to proteins (or protein mimetics), the antigen-binding region typically includes one or more loops (of at least, e.g., four amino acids or amino acid mimics) that form an interface that binds to the antigen. Typically, the antigen-binding region of an antibody molecule includes at least one or two CDRs and/or hypervariable loops, or more typically at least three, four, five or six CDRs and/or hypervariable loops.

The terms "compete" or "cross-compete" are used interchangeably herein to refer to the ability of an antibody molecule to interfere with binding of another antibody molecule, to a target. The interference with binding can be direct or indirect (e.g., through an allosteric modulation of the antibody molecule or the target). The extent to which an antibody molecule is able to interfere with the binding of another antibody molecule to the target, and therefore whether it can be said to compete, can be determined using a competition binding assay, for example, a FACS assay, an ELISA or BIACORE assay. In an embodiment, a competition binding assay is a quantitative competition assay. In an embodiment, a first antibody molecule is said to compete for binding to the target with a second antibody molecule when the binding of the first antibody molecule to the target is reduced by 10% or more, e.g., 20% or more, 30% or more, 40% or more, 50% or more, 55% or more, 60% or more, 65% or more, 70% or more, 75% or more, 80% or more, 85% or more, 90% or more, 95% or more, 98% or more, 99% or more in a competition binding assay (e.g., a competition assay described herein).

The terms "monoclonal antibody" or "monoclonal antibody composition" as used herein refer to a preparation of antibody molecules of single molecular composition. A monoclonal antibody composition displays a single binding specificity and affinity for a particular epitope. A monoclonal antibody can be made by hybridoma technology or by methods that do not use hybridoma technology (e.g., recombinant methods).

An "effectively human" protein is a protein that does not evoke a neutralizing antibody response, e.g., the human anti-murine antibody (HAMA) response. HAMA can be problematic in a number of circumstances, e.g., if the antibody molecule is administered repeatedly, e.g., in treatment of a chronic or recurrent disease condition. A HAMA response can make repeated antibody administration potentially ineffective because of an increased antibody clearance from the serum (see, e.g., Saleh et al., Cancer Immunol. Immunother. 32:180-190 (1990)) and also because of potential allergic reactions (see, e.g., LoBuglio et al., Hybridoma, 5:5117-5123 (1986)).

The antibody molecule can be a polyclonal or a monoclonal antibody. In some embodiments, the antibody can be recombinantly produced, e.g., produced by any suitable phage display or combinatorial methods.

Various phage display and combinatorial methods for generating antibodies are known in the art (as described in, e.g., Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) Bio/Technology 9:1370-1372; Hay et al. (1992) Hum Antibod Hybridomas 3:81-85; Huse et al. (1989) Science 246:1275-1281; Griffths et al. (1993) EMBO J 12:725-734; Hawkins et al. (1992) J Mol Biol 226:889-896; Clackson et al. (1991) Nature 352:624-628; Gram et al. (1992) PNAS 89:3576-3580; Garrad et al. (1991) Bio/Technology 9:1373-1377; Hoogenboom et al. (1991) Nuc Acid Res 19:4133-4137; and Barbas et al. (1991) PNAS 88:7978-7982, the contents of all of which are incorporated by reference herein).

In an embodiment, the antibody molecule is a fully human antibody (e.g., an antibody made in a mouse which has been genetically engineered to produce an antibody from a human immunoglobulin sequence), or a non-human antibody, e.g., a rodent (mouse or rat), goat, primate (e.g., monkey), camel antibody. In an embodiment, the non-human antibody is a rodent (mouse or rat antibody). Methods of producing rodent antibodies are known in the art.

Human monoclonal antibodies can be generated using transgenic mice carrying the human immunoglobulin genes rather than the mouse system. Splenocytes from these transgenic mice immunized with the antigen of interest are used to produce hybridomas that secrete human mAbs with specific affinities for epitopes from a human protein (see e.g., Wood et al. International Application WO 91/00906, Kucherlapati et al. PCT publication WO 91/10741; Lonberg et al. International Application WO 92/03918; Kay et al. International Application 92/03917; Lonberg, N. et al. 1994 Nature 368:856-859; Green, L. L. et al. 1994 Nature Genet. 7:13-21; Morrison, S. L. et al. 1994 Proc. Natl. Acad. Sci. USA 81:6851-6855; Bruggeman et al. 1993 Year Immunol 7:33-40; Tuaillon et al. 1993 PNAS 90:3720-3724; Bruggeman et al. 1991 Eur J Immunol 21:1323-1326).

An antibody can be one in which the variable region, or a portion thereof, e.g., the CDRs, are generated in a non-human organism, e.g., a rat or mouse. Chimeric, CDR-grafted, and humanized antibodies are within the invention. Antibodies generated in a non-human organism, e.g., a rat or mouse, and then modified, e.g., in the variable framework or constant region, to decrease antigenicity in a human are within the invention.

Chimeric antibodies can be produced by any suitable recombinant DNA technique. Several are known in the art (see Robinson et al., International Patent Publication PCT/US86/02269; Akira, et al., European Patent Application 184,187; Taniguchi, M., European Patent Application 171,496; Morrison et al., European Patent Application 173,494; Neuberger et al., International Application WO 86/01533; Cabilly et al. U.S. Pat. No. 4,816,567; Cabilly et al., European Patent Application 125,023; Better et al. (1988 Science 240:1041-1043); Liu et al. (1987) PNAS 84:3439-3443; Liu et al., 1987, J. Immunol. 139:3521-3526; Sun et al. (1987) PNAS 84:214-218; Nishimura et al., 1987, Canc. Res. 47:999-1005; Wood et al. (1985) Nature 314:446-449; and Shaw et al., 1988, J. Natl Cancer Inst. 80:1553-1559).

A humanized or CDR-grafted antibody will have at least one or two but generally all three recipient CDRs (of heavy and or light immunoglobulin chains) replaced with a donor CDR. The antibody may be replaced with at least a portion of a non-human CDR or only some of the CDRs may be replaced with non-human CDRs. It is only necessary to replace the number of CDRs required for binding of the humanized antibody to an antigen. In an embodiment, the donor will be a rodent antibody, e.g., a rat or mouse antibody, and the recipient will be a human framework or a human consensus framework. Typically, the immunoglobulin providing the CDRs is called the "donor" and the immunoglobulin providing the framework is called the "acceptor." In some embodiments, the donor immunoglobulin is a non-human (e.g., rodent). The acceptor framework is typically a naturally-occurring (e.g., a human) framework or a consensus framework, or a sequence about 85% or higher, e.g., 90%, 95%, 99% or higher identical thereto.

As used herein, the term "consensus sequence" refers to the sequence formed from the most frequently occurring amino acids (or nucleotides) in a family of related sequences (See e.g., Winnaker, From Genes to Clones (Verlagsgesellschaft, Weinheim, Germany 1987). In a family of proteins, each position in the consensus sequence is occupied by the amino acid occurring most frequently at that position in the family. If two amino acids occur equally frequently, either can be included in the consensus sequence. A "consensus framework" refers to the framework region in the consensus immunoglobulin sequence.

An antibody can be humanized by any suitable method, and several such methods known in the art (see e.g., Morrison, S. L., 1985, Science 229:1202-1207, by Oi et al., 1986, BioTechniques 4:214, and by Queen et al. U.S. Pat. Nos. 5,585,089, 5,693,761 and 5,693,762, the contents of all of which are hereby incorporated by reference).

Humanized or CDR-grafted antibodies can be produced by CDR-grafting or CDR substitution, wherein one, two, or all CDRs of an immunoglobulin chain can be replaced. See e.g., U.S. Pat. No. 5,225,539; Jones et al. 1986 Nature 321:552-525; Verhoeyan et al. 1988 Science 239:1534; Beidler et al. 1988 J. Immunol. 141:4053-4060; Winter U.S. Pat. No. 5,225,539, the contents of all of which are hereby expressly incorporated by reference. Winter describes a CDR-grafting method which may be used to prepare humanized antibodies (UK Patent Application GB 2188638A, filed on Mar. 26, 1987; Winter U.S. Pat. No. 5,225,539), the contents of which is expressly incorporated by reference.

Also provided are humanized antibodies in which specific amino acids have been substituted, deleted or added. Criteria for selecting amino acids from the donor are described in, e.g., U.S. Pat. No. 5,585,089, e.g., columns 12-16 of U.S. Pat. No. 5,585,089, the contents of which are hereby incorporated by reference. Other techniques for humanizing antibodies are described in Padlan et al. EP 519596 A1, published on Dec. 23, 1992.

In an embodiment, the antibody molecule has a heavy chain constant region chosen from, e.g., the heavy chain constant regions of IgG1, IgG2 (e.g., IgG2a), IgG3, IgG4, IgM, IgA1, IgA2, IgD, and IgE; particularly, chosen from, e.g., the (e.g., human) heavy chain constant regions of IgG1, IgG2, IgG3, and IgG4. In another embodiment, the antibody molecule has a light chain constant region chosen from, e.g., the (e.g., human) light chain constant regions of kappa or lambda. The constant region can be altered, e.g., mutated, to modify the properties of the antibody molecule (e.g., to increase or decrease one or more of: Fc receptor binding, antibody glycosylation, the number of cysteine residues, effector cell function, and/or complement function). In an embodiment, the antibody molecule has effector function and can fix complement. In another embodiment, the antibody molecule does not recruit effector cells or fix complement. In certain embodiments, the antibody molecule has reduced or no ability to bind an Fc receptor. For example, it may be an isotype or subtype, fragment or other mutant, which does not support binding to an Fc receptor, e.g., it has a mutagenized or deleted Fc receptor binding region.

In an embodiment, a constant region of the antibody molecule is altered. Methods for altering an antibody constant region are known in the art. Antibody molecules with altered function, e.g. altered affinity for an effector ligand, such as FcR on a cell, or the C1 component of complement can be produced by replacing at least one amino acid residue in the constant portion of the antibody with a different residue (see e.g., EP 388,151 A1, U.S. Pat. Nos. 5,624,821 and 5,648,260, the contents of all of which are hereby incorporated by reference) Amino acid mutations which stabilize antibody structure, such as S228P (EU nomenclature, S241P in Kabat nomenclature) in human IgG4 are also contemplated. Similar type of alterations could be described which if applied to the murine, or other species immunoglobulin would reduce or eliminate these functions.

In an embodiment, the only amino acids in the antibody molecule are canonical amino acids. In an embodiment, the antibody molecule comprises naturally-occurring amino acids; analogs, derivatives and congeners thereof; amino acid analogs having variant side chains; and/or all stereoisomers of any of any of the foregoing. The antibody molecule may comprise the D- or L-optical isomers of amino acids and peptidomimetics.

A polypeptide of an antibody molecule described herein may be linear or branched, it may comprise modified amino acids, and it may be interrupted by non-amino acids. The antibody molecule may also be modified; for example, by disulfide bond formation, glycosylation, lipidation, acetylation, phosphorylation, or any other manipulation, such as conjugation with a labeling component. The polypeptide can be isolated from natural sources, can be a produced by recombinant techniques from a eukaryotic or prokaryotic host, or can be a product of synthetic procedures.

The antibody molecule described herein can be used alone in unconjugated form, or can be bound to a substance, e.g., a toxin or moiety (e.g., a therapeutic drug; a compound emitting radiation; molecules of plant, fungal, or bacterial origin; or a biological protein (e.g., a protein toxin) or particle (e.g., a recombinant viral particle, e.g., via a viral coat protein). For example, the antibody molecule can be coupled to a radioactive isotope such as an $\alpha$-, $\beta$-, or $\gamma$-emitter, or a $\beta$- and $\gamma$-emitter.

An antibody molecule can be derivatized or linked to another functional molecule (e.g., another peptide or protein). As used herein, a "derivatized" antibody molecule is one that has been modified. Methods of derivatization include but are not limited to the addition of a fluorescent moiety, a radionucleotide, a toxin, an enzyme or an affinity ligand such as biotin. Accordingly, the antibody molecules are intended to include derivatized and otherwise modified forms of the antibodies described herein, including immunoadhesion molecules. For example, an antibody molecule can be functionally linked (by chemical coupling, genetic fusion, noncovalent association or otherwise) to one or more other molecular entities, such as another antibody (e.g., a bispecific antibody or a diabody), a detectable agent, a toxin, a pharmaceutical agent, and/or a protein or peptide that can mediate association of the antibody or antibody portion with another molecule (such as a streptavidin core region or a polyhistidine tag).

Some types of derivatized antibody molecule are produced by crosslinking two or more antibodies (of the same type or of different types, e.g., to create bispecific antibodies). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill.

Useful detectable agents with which an antibody molecule may be derivatized (or labeled) to include fluorescent compounds, various enzymes, prosthetic groups, luminescent materials, bioluminescent materials, fluorescent emitting metal atoms, e.g., europium (Eu), and other anthanides, and radioactive materials (described below). Exemplary fluorescent detectable agents include fluorescein, fluorescein isothiocyanate, rhodamine, 5dimethylamine-1-napthalenesulfonyl chloride, phycoerythrin and the like. An antibody may also be derivatized with detectable enzymes, such as alkaline phosphatase, horseradish peroxidase, $\beta$-galactosidase, acetylcholinesterase, glucose oxidase and the like. When an antibody is derivatized with a detectable enzyme, it is detected by adding additional reagents that the enzyme uses to produce a detectable reaction product. For example, when the detectable agent horseradish peroxidase is present, the addition of hydrogen peroxide and diaminobenzidine leads to a colored reaction product, which is detectable. An antibody molecule may also be derivatized with a prosthetic group (e.g., streptavidin/biotin and avidin/biotin). For example, an antibody may be derivatized with biotin, and detected through indirect measurement of avidin or streptavidin binding. Examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of bioluminescent materials include luciferase, luciferin, and aequorin.

Labeled antibody molecules can be used, for example, diagnostically and/or experimentally in a number of contexts, including (i) to isolate a predetermined antigen by standard techniques, such as affinity chromatography or immunoprecipitation; (ii) to detect a predetermined antigen (e.g., in a cellular lysate or cell supernatant) in order to evaluate the abundance and pattern of expression of the protein; (iii) to monitor protein levels in tissue as part of a clinical testing procedure, e.g., to determine the efficacy of a given treatment regimen.

An antibody molecule may be conjugated to another molecular entity, typically a label or a therapeutic (e.g., antimicrobial (e.g., antibacterial or bactericidal), immunomodulatory, immunostimularoty, cytotoxic, or cytostatic) agent or moiety. Radioactive isotopes can be used in diagnostic or therapeutic applications. Radioactive isotopes that can be coupled to the antibody molecules include, but are not limited to α-, β-, or γ-emitters, or β- and γ-emitters. Such radioactive isotopes include, but are not limited to iodine ($^{131}$I or $^{125}$I), yttrium ($^{90}$Y), lutetium ($^{177}$Lu), actinium ($^{225}$Ac), praseodymium, astatine ($^{211}$At), rhenium ($^{186}$Re), bismuth ($^{212}$Bi or $^{213}$Bi), indium ($^{111}$In), technetium ($^{99m}$Tc), phosphorus ($^{32}$P), rhodium ($^{188}$Rh), sulfur ($^{35}$S), carbon ($^{14}$C), tritium ($^{3}$H), chromium ($^{51}$Cr), chlorine ($^{36}$Cl), cobalt ($^{57}$Co or $^{58}$Co), iron ($^{59}$Fe), selenium ($^{75}$Se), or gallium ($^{67}$Ga). Radioisotopes useful as therapeutic agents include yttrium ($^{90}$Y), lutetium ($^{177}$Lu), actinium ($^{225}$Ac), praseodymium, astatine ($^{211}$At), rhenium ($^{186}$Re), bismuth ($^{212}$Bi or $^{213}$Bi), and rhodium ($^{188}$Rh). Radioisotopes useful as labels, e.g., for use in diagnostics, include iodine ($^{131}$I or $^{125}$I), indium ($^{111}$In), technetium ($^{99m}$Tc), phosphorus ($^{32}$P), carbon ($^{14}$C), and tritium ($^{3}$H), or one or more of the therapeutic isotopes listed above.

The present disclosure provides radiolabeled antibody molecules and methods of labeling the same. In an embodiment, a method of labeling an antibody molecule is disclosed. The method includes contacting an antibody molecule, with a chelating agent, to thereby produce a conjugated antibody. The conjugated antibody is radiolabeled with a radioisotope, e.g., $^{111}$Indium, $^{90}$Yttrium and $^{177}$Lutetium, to thereby produce a labeled antibody molecule.

In some aspects, this disclosure provides a method of making an antibody molecule disclosed herein. The method includes: providing an antigen, or a fragment thereof; obtaining an antibody molecule that specifically binds to the antigen; evaluating efficacy of the antibody molecule in modulating activity of the antigen and/or organism expressing the antigen. The method can further include administering the antibody molecule, including a derivative thereof (e.g., a humanized antibody molecule) to a subject, e.g., a human.

This disclosure provides an isolated nucleic acid molecule encoding the above antibody molecule, vectors and host cells thereof. The nucleic acid molecule includes, but is not limited to, RNA, genomic DNA and cDNA.

Other Binding Polypeptides

The disclosures herein are not intended to be limited to antibody molecules. The methods described herein are broadly applicable to any binding polypeptides that have two or more chains (e.g., having at least two paired or matched chains).

In an embodiment, the binding molecule comprises an X chain variable region and a Y chain variable region. For example, in any of the aspects, embodiments, and definitions herein, an antibody heavy chain (or variable region) can be replaced with an X chain (or variable region), and an antibody light chain (or variable region) can be replaced with a Y chain (or variable region).

In an aspect, the disclosure features a method of making a nucleic acid sequence comprising a sequence that encodes an X chain element (XC element) of an antibody heavy chain variable region (XCVR) and a Y chain element (YC element) of an antibody light chain variable region (YCVR), and wherein the XCVR and YCVR are matched, the method comprising:

a) acquiring an isolated production reaction site, e.g., a production micro-chamber, comprising:

i) an X chain (XC) strand, wherein the XC strand is a strand of an X chain double-stranded cDNA (XC ds cDNA) comprising a segment that encodes an XC element of the XCVR from a cell, e.g., an X chain variable region sequence (XCVRS); and ii) a Y chain (YC) strand, wherein the YC strand is a strand of a Y chain double-stranded cDNA (YC ds cDNA) comprising a segment that encodes a YC element of the YCVR from the cell, e.g., a Y chain variable region sequence (YCVRS), and b) covalent linking, e.g., ligation, of an XC strand to a YC strand, wherein the isolated production reaction site, e.g., a production micro-chamber, does not include a nucleic acid encoding a YCVR or an XCVR from a cell other than the cell (e.g., a different cell), thereby making a nucleic acid sequence comprising a sequence that encodes an XC element of an XCVR and a YC element of a YCVR, wherein the XCVR and YCVR are matched.

"Matched," as that term is used herein in connection with an X chain variable region and a Y chain variable region, means they are from the same cell. In an embodiment, the X chain variable region and the Y chain variable region can form a multimeric protein or a part of a multimeric protein. With respect to an element of an X chain variable region and an element of a Y chain variable region it means that the X chain variable region and the Y chain variable region from which the elements are derived are from the same cell.

An "X chain variable region sequence," or "XCVRS," as that term is used herein, refers to a polypeptide comprising sufficient sequence to allow binding of another polypeptide (e.g., an antigen). In embodiments the XCVRS can assemble with a Y chain variable region, and, e.g., bind antigen. A "Y chain variable region sequence," or "YCVRS," as that term is used herein, refers to a polypeptide comprising sufficient sequence to allow binding of another polypeptide (e.g., an antigen). In embodiments the YCVRS can assemble with an X chain variable region, and, e.g., bind antigen.

"Element" of an XC or YC variable region, as that term is used herein, refers to a sequence that encodes at least one amino acid. In an embodiment, an element comprises a CDR. In an embodiment an element comprises a FW region.

In an embodiment, the XC element comprises, or consists of, an XCVRS. In an embodiment, the YC element comprises, or consists of, a YCVRS.

In an embodiment, the XC ds cDNA comprises a segment that encodes an XCVRS. In an embodiment, the YC ds cDNA comprises a segment that encodes a YCVRS. In an embodiment, the XC ds cDNA comprises a segment that encodes an XCVRS, and the YC ds cDNA comprises a segment that encodes a YCVRS.

In an embodiment, the cell is an immune cell, e.g., a B cell, e.g., a human B cell. In an embodiment, the cell is a mammalian cell or an avian cell.

In an embodiment, the nucleic acid sequence is configured such that, when expressed, the XC element and the YC element (e.g., the XCVRS and the YCVRS) form a functional antigen binding molecule, e.g., a single chain or a complex of an XC and a YC. In an embodiment, the antigen binding molecule is functional in vitro, ex vivo, or in vivo, e.g., as determined by a method or assay described herein.

In an embodiment, acquiring an isolated production reaction site, e.g., a production micro-chamber, comprises:

a) acquiring a capture substrate bound to: (i) a first double-stranded cDNA (ds cDNA) comprising a strand that is complementary to a first mRNA that encodes an XCVR from a cell; and (ii) a second ds cDNA comprising a strand complementary to a second mRNA encoding a YCVR from the cell (the cDNA loaded capture substrate), and b) maintaining the isolated production reaction site, e.g., the production micro-chamber, under conditions that allow amplification of the first and second ds cDNAs, to produce: a plurality of XC ds cDNAs comprising a segment that encodes an XC element of the XCVR from the cell, e.g., an XCVRS; and a plurality of YC ds cDNAs comprising a segment that encodes a YC element of the YCVR from the cell, e.g., a YCVRS.

In an embodiment, the XC ds cDNA is identical, or substantially identical, to the first ds cDNA. For example, the sense strand of the XC ds cDNA is at least 80%, 85%, 90%, 95%, 98%, 99%, or 100% identical to, or differs by no more than 1, 2, 5, 10, 15, 20, 25, 30, 35, 40, 45, or 50 nucleotides from, the sense strand of the first ds cDNA, and/or the antisense strand of the XC ds cDNA is at least 80%, 85%, 90%, 95%, 98%, 99%, or 100% identical to, or differs by no more than 1, 2, 5, 10, 15, 20, 25, 30, 35, 40, 45, or 50 nucleotides from, the antisense strand of the first ds cDNA.

In an embodiment, the YC ds cDNA is identical, or substantially identical, to the second ds cDNA. For example, the sense strand of the YC ds cDNA is at least 80%, 85%, 90%, 95%, 98%, 99%, or 100% identical to, or differs by no more than 1, 2, 5, 10, 15, 20, 25, 30, 35, 40, 45, or 50 nucleotides from, the sense strand of the second ds cDNA, and/or the antisense strand of the YC ds cDNA is at least 80%, 85%, 90%, 95%, 98%, 99%, or 100% identical to, or differs by no more than 1, 2, 5, 10, 15, 20, 25, 30, 35, 40, 45, or 50 nucleotides from, the antisense strand of the second ds cDNA.

In an embodiment, the XC strand is a sense strand. In an embodiment, the YC strand is a sense strand. In an embodiment, the XC strand is an antisense strand. In an embodiment, the YC strand is an antisense strand. In an embodiment, both the XC strand and the YC strand are sense strands. In an embodiment, both the XC strand and the YC strand are antisense strands.

In an embodiment, the capture substrate comprises a bead, e.g., a magnetic bead. In an embodiment, the capture substrate comprises a moiety (e.g., an oligonucleotide) which binds to cDNA, e.g., (i) a moiety which binds to the XC strand; (ii) a moiety which binds to the YC strand; or (iii) both (i) and (ii). In an embodiment, the moiety which binds to the XC strand is different from the moiety which binds to the YC strand, e.g., to facilitate creating conditions favorable to capturing similar levels of each DNA molecule type. In an embodiment, the moiety which binds to the XC strand is identical to the moiety which binds to the YC strand.

In an embodiment, the first mRNA and the second mRNA are disposed on an mRNA loaded capture substrate.

In an embodiment, the isolated production reaction site, e.g., the production micro-chamber, comprises: a reagent mixture suitable for producing, from the first and second mRNAs (e.g., after the first and second mRNAs are released from the mRNA loaded capture substrate into a solution), a first cDNA comprising a segment that encodes an XC element of the XCVR of the cell, e.g., an XCVRS, and a second cDNA comprising a segment that encodes a YC element of the YCVR of the cell, e.g., a YCVRS.

In an embodiment, the isolated production reaction site, e.g., production micro-chamber, comprises primers that mediate the production of the first ds cDNA. In an embodiment, the isolated production reaction site, e.g., production micro-chamber, comprises primers that mediate the production of the second ds cDNA.

In an embodiment, a cDNA strand that is complementary to a first mRNA that encodes an XCVR from a cell is made by reverse transcription of the first mRNA. In an embodiment, a cDNA strand that is complementary to a second mRNA that encodes a YCVR from a cell is made by reverse transcription of the second mRNA.

In an embodiment, the reverse transcription takes place in the isolated production reaction site, e.g., a production-micro chamber. In an embodiment, the reverse transcription takes place in an isolated cell reaction site, e.g., a cell isolation micro-chamber. In an embodiment, the reverse transcription takes place outside the isolated production reaction site, e.g., a production micro-chamber, or outside an isolated cell reaction site, e.g., a cell isolation micro-chamber. In an embodiment, the reverse transcription takes place outside the isolated production reaction site, e.g., a production-micro chamber, and outside an isolated cell reaction site, e.g., a cell isolation micro-chamber. In an embodiment, the reverse transcription takes place outside an isolated reaction site, e.g., outside a micro-chamber.

In an embodiment, the amplification comprises 30 or fewer cycles, e.g., 20 or fewer cycles, e.g., 15 or fewer, 14 or fewer, 13 or fewer, 12 or fewer, 11 or fewer, 10 or fewer, 9 or fewer, 8 or fewer, 7 or fewer, 6 or fewer, or 5 or fewer cycles.

In an embodiment, the reverse transcription and/or amplification uses one or more primers, e.g., comprising a sequence specific for an XCVRS and/or a YCVRS.

In an embodiment, the reverse transcription and/or amplification comprises using two or more primers that mediate the production of the XC ds cDNA, wherein at least one primer comprises a nucleotide modification, and wherein at least one primer does not comprise a nucleotide modification. In an embodiment, the amplification comprises using two or more primers that mediate the production of the YC ds cDNA, wherein at least one primer comprises a nucleotide modification, and wherein at least one primer does not comprise a nucleotide modification.

In an embodiment, at least one primer comprises a nucleotide modification, e.g., which reduces, e.g., inhibits, DNA synthesis, e.g., by a DNA polymerase. In an embodiment, at least one primer does not comprise a nucleotide modification, e.g., which reduces, e.g., inhibits, DNA synthesis, e.g., by a DNA polymerase.

In an embodiment, the nucleotide modification inhibits a DNA polymerase from extending the DNA. Without wishing to be bound by theory, it is believed that in an embodiment any chemical entity that reduces (e.g., blocks) DNA polymerase extension can be used in accordance with the methods described herein.

In an embodiment, the nucleotide modification is an insertion of a spacer to the primer, e.g., between two adjacent nucleotides in the primer. In an embodiment, the spacer is a flexible spacer. In an embodiment, the spacer is a carbon spacer (e.g., —(CH2)n-, wherein n=3, 4, 5, 6, 7, 8, 9, 10, or more), two or more (e.g., three, four, five, six, seven, eight, nine, ten, or more) abasic nucleotides, or a polyethylene glycol (PEG) spacer. In an embodiment, the spacer is a PEG spacer. In an embodiment, the nucleotide modification is 2'-O-methyl, 2'-OH, 2'-NH$_2$, or uracil, e.g., to a ribose. In an embodiment, the nucleotide modification is located internally or at the 3' end of the primer. In an embodiment, at least one primer comprises (i) a first member; (ii) a second member; and optionally (iii) a third member, e.g., comprising a nucleotide modification described herein, e.g., located between (i) and (ii).

In an embodiment, the first member is capable of annealing with the second member. In an embodiment, the first member is capable of annealing with the second member in the same primer, e.g., through intra-molecular hybridization, e.g., to form a hairpin structure comprising a duplex region of 4, 5, 6, 7, 8, 9, 10, 11, 12, 13, 14, 15, 16, 17, 18, 19, 20, more basepairs. In another embodiment, the first member is capable of annealing hybridizing with the second member in a different primer, e.g., through inter-molecular hybridization, e.g., to form a double-stranded structure comprising a duplex region of 4, 5, 6, 7, 8, 9, 10, 11, 12, 13, 14, 15, 16, 17, 18, 19, 20, more basepairs. Without wishing to be bound by theory, it is believed that in an embodiment, there are at least two secondary structures that the modified primers can form and facilitate reduction (e.g., prevention) of competition to substrate (e.g., bead) capture. For example, the secondary structure can be a hairpin-like structure formed by intra-molecular hybridization (within the same primer), or the secondary structure can be a duplex structure formed by inter-molecular hybridization (between two different primers).

In an embodiment, the first member comprises a sequence that is complementary to the sequence of an oligonucleotide attached to the capture substrate. In an embodiment, the second member comprises (e.g., from 5' to 3') one, two, or all of: (i) a sequence that is complementary to at least a portion of the first member; (ii) a universal priming sequence (e.g., for PCR amplification or next-generation sequencing); and (iii) a sequence complementary to a target sequence, e.g., an XCVRS and/or a YCVRS. In an embodiment, the universal priming sequence is identical, or substantially identical, to the sequence that is complementary to at least a portion of the first member. In another embodiment, the universal priming sequence is different from the sequence that is complementary to at least a portion of the first member. In an embodiment, the second member comprises a sequence for homologous recombination (e.g., in a yeast or mammalian cell).

In an embodiment, at least one primer comprises a sequence encoding at least a portion of a linker sequence, or a complementary sequence thereof. In an embodiment, the primer that comprises a sequence encoding at least a portion of a linker sequence, or a complementary sequence thereof, is phosphorylated, e.g., 5' phosphorylated. Without wishing to be bound by theory, it is believed that in an embodiment, any sequence with the general properties of flexibility (e.g., facilitated by glycine) and hydrophilicity can work effectively in accordance with the methods described herein. Exemplary linkers can generally have overrepresentation of one or more of Gly, Ser, Thr, or Ala and underrepresentation of hydrophobic residues, e.g., one or more of Trp, Tyr, Phe, Cys, Met, Leu, or Ile. The length of the primer may vary, e.g., 3-50 amino acid residues (e.g., 5-45, 10-40, 15-35, 20-30, 10-20, 10-30, 20-40, or 30-40 amino acid residues). In an embodiment, the linker sequence comprises, or consists of, ((Gly)m-Ser))n, where m=3, 4, 5, or more and n=1, 2, 3, 4, 5, 6, 7, 8, 9, 10, or more (SEQ ID NO: 25). In an embodiment, the linker sequence comprises, or consists of, (Gly-Gly-Gly-Gly-Ser)n, where n=1, 2, 3, 4, 5, 6, 7, 8, 9, 10, or more (SEQ ID NO: 26)

In an embodiment, the primer is a primer described herein, e.g., in Examples.

In an embodiment, the reverse transcription, the amplification, or both, occurs in a solution in the isolated production reaction site, e.g., production micro-chamber. In an embodiment, the reverse transcription, the amplification, or both, does not occur on the substrate (e.g., bead). For example, the reverse transcription, the amplification, or both, can occur on in a solution within a droplet.

In an embodiment, the XC ds cDNA comprises a 5' overhang, e.g., a 5' overhang that is capable of hybridizing to an oligonucleotide attached to a capture substrate. In an embodiment, the XC ds cDNA comprises a blunt end, e.g., a blunt end comprising a 5' phosphate. In an embodiment, the YC ds cDNA comprises a 5' overhang, e.g., a 5' overhang that is capable of hybridizing to an oligonucleotide attached to a capture substrate. In an embodiment, the YC ds cDNA comprises a blunt end, e.g., a blunt end comprising a 5' phosphate. In an embodiment, the XC ds cDNA and the YC ds cDNA comprise sticky ends, e.g., both have 5' overhangs.

In an embodiment, the XC strand and the YC strand are covalently linked, e.g., ligated, to produce a single stranded nucleic acid sequence, wherein the XC and YC strands are both sense strands or both antisense strands. In an embodiment, a denatured XC strand of the XC ds cDNA to a denatured YC strand of the YC ds cDNA are covalently linked, e.g., ligated, wherein the XC and YC strands are both sense strands or both antisense strands. In an embodiment, the XC strand is present in the XC ds cDNA and the YC strand is present in the YC ds cDNA, and wherein the XC ds cDNA and the YC ds cDNA are covalently linked, e.g., ligated, e.g., to produce a double stranded nucleic acid sequence.

In an embodiment, the covalent linking, e.g., ligation, occurs in the isolated production reaction site. In an embodiment, the isolated production reaction site, e.g., a production micro-chamber, or the isolated linkage reaction site, e.g., a linkage micro-chamber, comprises a reagent that is capable of covalently linking, e.g., ligating, the XC and YC strands or the XC and YC ds cDNAs. In an embodiment, the isolated production reaction site, e.g., a production micro-chamber comprises an enzyme that covalently couples the XC and YC strands or the XC and YC ds cDNAs. In an embodiment, the enzyme is a ligase, e.g., a thermal stable ligase. In an embodiment, the covalent linking comprises ligase thermocycling.

In an embodiment, the covalent linking, e.g., ligation, occurs in a site different from the isolated production reaction site, e.g., occurs in an isolated linkage reaction site, e.g., a linkage micro-chamber. In an embodiment, the XC strand and the YC strand are transferred from the isolated production site to the isolated linkage reaction site, e.g., a linkage micro-chamber, and the covalent linking occurs in the isolated linkage reaction site, e.g., a linkage micro-chamber. In an embodiment, the isolated linkage reaction site, e.g., a linkage micro-chamber, comprises a reagent that is capable of covalently linking, e.g., ligating, the XC and YC strands or the XC and YC ds cDNAs. In an embodiment, the isolated linkage reaction site, e.g., a linkage micro-chamber, comprises an enzyme that covalently couples the XC and YC strands or the XC and YC ds cDNAs. In an embodiment, the enzyme is a ligase, e.g., a thermal stable ligase. In an embodiment, the covalent linking comprises ligase thermocycling.

In an embodiment, the covalent linking, e.g., ligation, comprises: (a) heating the isolated linkage reaction site, e.g., the linkage micro-chamber, under conditions (e.g., at 95° C.) that allow denaturation of the XC strand and the YC strand; (b) cooling the isolated linkage reaction site, e.g., the linkage micro-chamber, under conditions (e.g., at 50-65° C.) that allow hybridization of the splint oligonucleotide to the XC strand and the YC strand; (c) maintaining the isolated linkage reaction site, e.g., the linkage micro-chamber, under conditions (e.g., at 45-65° C.) that allow ligation of the XC strand and the YC strand (e.g., formation of phosphodiester bond between the XC strand and the YC strand); and (d) repeating steps (a), (b), and (c) sequentially for 2, 5, 10, 15, 20, 25, 30, 35, 40, 45, 50, or more cycles.

In an embodiment, the XC strand and the YC strand are covalently linked, e.g., ligated, in the presence of a splint oligonucleotide. In an embodiment, the splint oligonucleotide is hybridized to a sequence comprising the junction of the XC strand and the YC strand, or a sequence complementary thereof, and forms a duplexed region at the site of ligation. In an embodiment, the splint oligonucleotide comprises a modification (e.g., an $NH_2$ group) that inhibits DNA synthesis, e.g., by a DNA polymerase. In an embodiment, the modification is at the 3' end of the splint oligonucleotide. In an embodiment, a strand complimentary to the covalently linked, e.g., ligated, XC and YC strands is produced by amplification.

In an embodiment, the method, e.g., the step of covalent linkage, does not include a step of overlap extension polymerase chain reaction (OE-PCR), also known as splicing by overlap extension or splicing by overhang extension (SOE) PCR.

In an embodiment, the method further comprises, prior to acquiring the isolated production reaction site, e.g., a production micro-chamber, acquiring an mRNA loaded capture substrate.

In an embodiment, acquiring the mRNA loaded capture substrate comprising: a) acquiring an isolated cell reaction site, e.g., a cell isolation micro-chamber, comprising: i) a cell; and ii) a capture substrate capable of binding a first mRNA encoding an XCVR from the cell and a second mRNA encoding a YCVR from the cell; and b) maintaining the isolated cell reaction site, e.g., the cell isolation micro-chamber, under conditions that allow lysis of the cell and binding of the capture substrate with the first mRNA and the second mRNA to form the mRNA loaded capture substrate, wherein the isolated cell reaction site, e.g., cell isolation micro-chamber, does not include a nucleic acid encoding an XCVR or a YCVR from a cell other than the cell (e.g., a different cell).

In an embodiment, the isolated cell reaction site, e.g., cell isolation micro-chamber, comprises a lysing reagent, e.g., a detergent. In an embodiment, the cell is lysed by heat or an enzyme. In an embodiment, the capture substrate comprises a moiety (e.g., an oligonucleotide) which binds mRNA, e.g., an oligo(dT).

In an embodiment, the method further comprises releasing the mRNA loaded capture substrate from the isolated cell reaction site, e.g., the cell isolation micro-chamber. In an embodiment, the releasing step is performed in the presence of a poly(dA) or poly(dT) oligonucleotide, e.g., to reduce cross-binding of non-captured mRNA.

In an embodiment, the mRNA loaded capture substrate is transferred from the isolated cell reaction site, e.g., the cell isolation micro-chamber, to the isolated production reaction site, e.g., the production micro-chamber.

In an embodiment, the method further comprises releasing the nucleic acid sequence from the isolated production reaction site, e.g., the production micro-chamber. In an embodiment, the method further comprises amplifying the nucleic acid sequence. In an embodiment, amplification of the nucleic acid sequence occurs outside the isolated production reaction site, e.g., the production micro-chamber, e.g., after the nucleic acid is released from the isolated production reaction site, e.g., the production micro-chamber. In an embodiment, amplification of the nucleic acid sequence occurs at the isolated production reaction site, e.g., the production micro-chamber.

In an embodiment, the method further comprises sequencing all or a portion of the nucleic acid sequence.

In an embodiment, the method further comprises inserting all or a portion of nucleic acid sequence into a vector. In an embodiment, the vector supplies an additional XC element or YC element not included in the nucleic acid sequence. In an embodiment, the vector supplies an XC CDR1, an XC CDR2, or both. In an embodiment, the method further comprises expressing the vector.

In an embodiment, the method further comprises expressing the nucleic acid sequence to produce a polypeptide comprising a segment that encodes an XC element of the XCVR, e.g., an XCVRS, and a segment that encodes a YC element of the YCVR, e.g., a YCVRS. In an embodiment, the YC element is N-terminal to the XC element in the polypeptide. In an embodiment, the XC element is C-terminal to the YC element in the polypeptide.

In an embodiment, the method further comprises contacting the polypeptide with an antigen. In an embodiment, the method further comprises determining if the polypeptide binds the antigen, in vitro, ex vivo, or in vivo, e.g., by a method or assay described herein.

In an aspect, the disclosure features a method of making a nucleic acid sequence comprising a sequence that encodes an X chain element (XC element) of an antibody heavy chain variable region (XCVR) and a Y chain element (YC element) of an antibody light chain variable region (YCVR), and wherein the XCVR and YCVR are matched, comprising:

a) acquiring an isolated cell reaction site (e.g., an isolated cell reaction site described herein), e.g., a cell isolation micro-chamber, comprising: i) a cell (e.g., a cell described herein); and ii) a capture substrate (e.g., a capture substrate described herein) capable of binding a first mRNA encoding an XCVR from the cell and a second mRNA encoding a YCVR from the cell;

b) maintaining the isolated cell reaction site, e.g., the cell isolation micro-chamber, under conditions that allow lysis of the cell and binding of the capture substrate with the first mRNA and the second mRNA to form an mRNA loaded capture substrate, wherein the isolated cell reaction site, e.g., cell isolation micro-chamber, does not include a nucleic acid encoding an XCVR or a YCVR from a cell other than the cell (e.g., a different cell);

c) contacting the mRNA loaded capture substrate with a reaction mixture, e.g., a reaction mixture comprising reverse transcriptase, that uses the loaded mRNA as a template to make cDNA (this can occur, e.g., in the isolated cell reaction site, in an isolated production reaction site, or in neither, e.g., not in an isolated reaction site);

d) acquiring an isolated production reaction site (e.g., an isolated production reaction site described herein), e.g., a production micro-chamber, comprising: i) an X chain (XC) strand, wherein the XC strand is a strand of an X chain double-stranded cDNA (XC ds cDNA) comprising a segment that encodes an XC element of the XCVR from the cell, e.g., an X chain variable region sequence (XCVRS); and ii) a Y chain (YC) strand, wherein the YC strand is a strand of a Y chain double-stranded cDNA (YC ds cDNA)

comprising a segment that encodes a YC element of the YCVR from the cell, e.g., a Y chain variable region sequence (YCVRS), wherein the isolated production reaction site, e.g., a production micro-chamber, does not include a nucleic acid encoding a YCVR or an XCVR from a cell other than the cell (e.g., a different cell); and e) covalent linking, e.g., ligation, of the XC strand to the YC strand.

In an embodiment, one or more (e.g., two, three, four, or all) of the steps a)-e) are performed in accordance with a method described herein. In an embodiment, each of the steps a)-e) is performed in accordance with a method described herein.

In an aspect, the disclosure features a method of making a nucleic acid sequence comprising a sequence that encodes an X chain element (XC element) of an antibody heavy chain variable region (XCVR) and a Y chain element (YC element) of an antibody light chain variable region (YCVR), and wherein the XCVR and YCVR are matched, comprising:

a) acquiring an isolated cell reaction site (e.g., an isolated cell reaction site described herein), e.g., a cell isolation micro-chamber, comprising: i) a cell (e.g., a cell described herein); and ii) a capture substrate (e.g., a capture substrate described herein) capable of binding a first mRNA encoding an XCVR from the cell and a second mRNA encoding a YCVR from the cell;

b) maintaining the isolated cell reaction site, e.g., the cell isolation micro-chamber, under conditions that allow lysis of the cell and binding of the capture substrate with the first mRNA and the second mRNA to form the mRNA loaded capture substrate, wherein the isolated cell reaction site, e.g., cell isolation micro-chamber, does not include a nucleic acid encoding an XCVR or a YCVR from a cell other than the cell (e.g., a different cell);

c) acquiring an isolated production reaction site (e.g., an isolated production reaction site described herein), e.g., a production micro-chamber, comprises: contacting the mRNA loaded capture substrate with a reaction mixture, e.g., a reaction mixture comprising reverse transcriptase, that uses the loaded mRNA as a template, to produce: a first double-stranded cDNA (ds cDNA) comprising a strand that is complementary to a first mRNA that encodes an XCVR from a cell; and a second ds cDNA comprising a strand complementary to a second mRNA encoding a YCVR from the cell (the cDNA loaded capture substrate);

wherein the isolated production reaction site, e.g., a production micro-chamber, does not include a nucleic acid encoding a YCVR or an XCVR from a cell other than the cell (e.g., a different cell).

d) maintaining the isolated production reaction site, e.g., the production micro-chamber, under conditions that allow amplification of the first and second ds cDNAs, to produce: a plurality of XC ds cDNAs comprising a segment that encodes an XC element of the XCVR from the cell, e.g., an XCVRS; and a plurality of YC ds cDNAs comprising a segment that encodes a YC element of the YCVR from the cell, e.g., a YCVRS;

e) acquiring an isolated linkage reaction site (e.g., an isolated linkage reaction site described herein), e.g., a linkage micro-chamber, comprising: covalent linking, e.g., ligation, of a strand of the XC ds cDNA (XC strand) to a strand of the YC ds cDNA (YC strand), wherein the XC and YC strands are both sense strands or antisense strands; and f) amplifying the covalently linked, e.g., ligated, XC and YC strands.

In an embodiment, one or more (e.g., two, three, four, five, or all) of the steps a)-f) are performed in accordance with a method described herein. In an embodiment, each of the steps a)-f) is performed in accordance with a method described herein.

In an aspect, the disclosure features a method of making a library comprising a plurality of unique members, the method comprising:

making the plurality of members, wherein each of the members comprises a sequence that encodes an X chain element (XC element) of an X chain variable region (XCVR) and a Y chain element (YC element) of a Y chain variable region (YCVR), and wherein the XCVR and YCVR are matched, made by a method described herein, wherein each unique nucleic acid sequence of the plurality comprises an XC element and a YC element from a different unique cell (e.g., a cell described herein), thereby making a library comprising a plurality of unique members.

In an embodiment, the plurality of unique members comprises at least $10^4$, $10^5$, $10^6$, $10^7$, $10^8$, or $10^9$ unique members. In an embodiment, the plurality of unique members comprises $10^4$ to $10^9$, $10^4$ to $10^8$, $10^4$ to $10^7$, $10^4$ to $10^6$, $10^4$ to $10^5$, $10^8$ to $10^9$, $10^7$ to $10^9$, $10^6$ to $10^9$, $10^5$ to $10^9$, $10^5$ to $10^8$, $10^6$ to $10^7$, $10^4$ to $10^5$, $10^5$ to $10^6$, $10^6$ to $10^7$, $10^7$ to $10^8$, or $10^8$ to $10^9$ unique members. In an embodiment, at least 80%, 85%, 90%, 95%, 96%, 97%, 98%, 99%, or 100%, of the members in the library are unique members (which encode matched XC element and YC elements sequences). In an embodiment, less than 20%, 15%, 10%, 5%, 4%, 3%, 2%, or 1%, of the members in the library are unique members (which encode matched XC element and YC elements sequences).

In an aspect, the disclosure features a library comprising a plurality of unique members, wherein, i) each unique member of the plurality comprises a segment that encodes an XC element, e.g., an XCVRS, and a segment that encodes a YC element, e.g., a YCVRS, wherein the XC element and the YC element in each unique member is matched;

ii) each unique member of the plurality comprises a segment that encodes an XC element, e.g., an XCVRS, and a segment that encodes a YC element, e.g., a YCVRS, from a different unique cell; and iii) the library comprises one or more (e.g., two, three, four, or all) of the following properties:

a) the library is made by a method described herein;
b) the plurality of unique members comprises at least $10^4$, $10^5$, $10^6$, $10^7$, $10^8$, or $10^9$ unique nucleic acid sequences;
c) the plurality of unique members comprises $10^4$ to $10^9$, $10^4$ to $10^8$, $10^4$ to $10^7$, $10^4$ to $10^6$, $10^4$ to $10^5$, $10^8$ to $10^9$, $10^7$ to $10^9$, $10^6$ to $10^9$, $10^5$ to $10^9$, $10^5$ to $10^8$, $10^6$ to $10^7$, $10^4$ to $10^5$, $10^5$ to $10^6$, $10^6$ to $10^7$, $10^7$ to $10^8$, or $10^8$ to $10^9$ unique members;
d) at least 80%, 85%, 90%, 95%, 96%, 97%, 98%, 99%, or 100%, of the members in the library are unique members (which encode matched XC element and YC elements sequences); or
e) less than 20%, 15%, 10%, 5%, 4%, 3%, 2%, or 1%, of the members in the library are unique members (which encode matched XC element and YC elements sequences).

In an embodiment, each unique member of the plurality is configured such that, when expressed, the XC element, e.g., the XCVRS, and the YC element, e.g., the YCVRS, form a functional antigen binding molecule, e.g., an scFv.

In an embodiment, the library is a display library. In an embodiment, each of the members of the plurality further encodes a polypeptide that results in display of the member on the surface of a display entity. In an embodiment, the library is a phage display library. In an embodiment, the library is a yeast display library. In an embodiment, the library is a mammalian display library.

In an aspect, the disclosure features a method of making a binding polypeptide (e.g., a polypeptide comprising an XC element and a YC element), the method comprising: a) acquiring a library described herein, e.g., by a method described herein; and b) expressing a polypeptide encoded by a unique nucleic acid of the library.

In an embodiment, the method further comprises contacting the polypeptide with an antigen. In an embodiment, the method further comprises retrieving (e.g., isolating or purifying) the nucleic acid that encodes a polypeptide that binds the antigen.

In an aspect, the disclosure features an isolated production reaction site, e.g., a production micro-chamber, which is an isolated production reaction site described herein (e.g., comprising a nucleic acid encoding an XCVR and a nucleic acid encoding a YCVR, wherein the XCVR and the YCVR are matched).

In an embodiment, the isolated production reaction site, e.g., a production micro-chamber, does not include a nucleic acid encoding an XCVR or a YCVR from a different cell.

In an embodiment, the isolated production reaction site, e.g., a production micro-chamber, comprises one, two, or all of: (i) one or more primers specific to V gene sequences of the XC and YC; (ii) one or more primers specific to overhangs introduced onto the XC and YC cDNAs; or (iii) one or more primers comprising a first member, a second member, and a third member comprising a nucleotide modification (e.g., a spacer) located between the first and second members, wherein the first member is capable of annealing with the second member of the same primer or a different primer, e.g., forming a structure comprising a duplex region of 4, 5, 6, 7, 8, 9, 10, 11, 12, 13, 14, 15, 16, 17, 18, 19, 20, more basepairs.

In an embodiment, the isolated production reaction site, e.g., a production micro-chamber, does not comprise a reagent that can covalently link nucleic acids, e.g., a ligase, e.g., a thermostable ligase. In another embodiment, the isolated production reaction site, e.g., a production micro-chamber, comprises a reagent that can covalently link nucleic acids, e.g., a ligase, e.g., a thermostable ligase.

In an aspect, the disclosure features a self-annealing oligonucleotide comprising a first member, a second member, and third member comprising a nucleotide modification (e.g., a spacer) located between the first and second members, wherein the first member is capable of annealing with the second member of the same oligonucleotide (e.g., for a method of making a nucleic acid sequence comprising a sequence that encodes an XC element of an XCVR and a YC element of a YCVR, wherein the XCVR and YCVR are matched).

In an embodiment, the first and second members are capable of forming a hairpin structure comprising a duplex region of 4, 5, 6, 7, 8, 9, 10, 11, 12, 13, 14, 15, 16, 17, 18, 19, 20, more basepairs. In an embodiment, the first member is 5-40 nucleotides, e.g., 5-10, 5-20, 5-30, 30-40, 20-40, 10-30, 10-30, or 15-25 nucleotides, in length. In an embodiment, the second member is 5-40 nucleotides, e.g., 5-10, 5-20, 5-30, 30-40, 20-40, 10-30, 10-30, or 15-25 nucleotides, in length.

In an embodiment, the spacer is a spacer described herein, e.g., a flexible spacer or a PEG spacer.

In an embodiment, the first member comprises a sequence that is complementary to the sequence of an oligonucleotide attached to a capture substrate.

In an embodiment, the second member comprises (e.g., from 5' to 3') one, two, or all of: (i) a sequence that is complementary to at least a portion of the first member; (ii) a universal priming sequence (e.g., for PCR amplification or next-generation sequencing); and (iii) a sequence complementary to a target sequence, e.g., an XCVRS and/or a YCVRS. In an embodiment, the universal priming sequence is identical, or substantially identical, to the sequence that is complementary to at least a portion of the first member. In another embodiment, the universal priming sequence is different from the sequence that is complementary to at least a portion of the first member. In an embodiment, the second member comprises a sequence for homologous recombination (e.g., in a yeast or mammalian cell).

In an aspect, the disclosure features an isolated linkage reaction site, e.g., a linkage micro-chamber, which is an isolated linkage reaction site described herein (e.g., comprising a nucleic acid encoding an XCVR and a nucleic acid encoding a YCVR, wherein the XCVR and the YCVR are matched).

In an embodiment, the isolated linkage reaction site, e.g., a linkage micro-chamber, does not include a nucleic acid encoding an XCVR or a YCVR from a different cell.

In an embodiment, the isolated linkage reaction site, e.g., a linkage micro-chamber, comprises a splint oligonucleotide (e.g., a splint oligonucleotide described herein) that is capable of hybridizing to a sequence comprising the junction of the XC strand and the YC strand, or a sequence complementary thereof, to form a duplexed region at the site of ligation.

In an embodiment, the isolated linkage reaction site, e.g., a linkage micro-chamber, comprises a reagent that can covalently link nucleic acids, e.g., a ligase, e.g., a thermostable ligase.

T-Cell Receptor Molecules

The disclosures herein are not intended to be limited to antibody molecules. In an embodiment, the binding molecule is a TCR molecule, e.g., a soluble TCR molecule. In an embodiment, the binding molecule comprises a TCR α chain variable region and a TCR β chain variable region. In an embodiment, the binding molecule comprises a TCR γ chain variable region and a TCR δ chain variable region. For example, in any of the aspects, embodiments, and definitions herein, an antibody heavy chain (or variable region) can be replaced with a TCR α chain (or variable region), and an antibody light chain (or variable region) can be replaced with a TCR β chain (or variable region); or an antibody heavy chain (or variable region) can be replaced with a TCR γ chain (or variable region), and an antibody light chain (or variable region) can be replaced with a TCR δ chain (or variable region).

Disclosed herein are T-cell receptor (TCR) molecules and libraries of TCR molecules. In an embodiment, the TCR molecule or library of TCR molecules are made by a method described herein.

As used herein, the term "TCR molecule," also known as "T-cell receptor molecule" or "T cell receptor molecule," refers to a protein, e.g., a TCR chain or a fragment thereof, comprising at least one TCR variable domain sequence. The term "TCR molecule" includes, for example, full-length, mature TCRs and antigen-binding fragments of a TCR. For example, a TCR molecule can include an α chain variable domain sequence and a β chain variable domain sequence. In another example, a TCR molecule can include a γ chain variable domain sequence and a δ chain variable domain sequence. In an embodiment, the TCR molecule is a soluble TCR molecule.

T-cell receptors can be found on the surface of T cells and are responsible for recognizing fragments of antigen as peptides bound to major histocompatibility complex (MHC) molecules. A TCR typically include two different protein chains. In humans, in about 95% of T cells the TCR include an alpha (α) chain and a beta (β) chain (encoded by TRA and TRB, respectively), whereas in about 5% of T cells the TCR include gamma and delta (γ/δ) chains (encoded by TRG and TRD, respectively). This ratio can change during ontogeny and in diseased states (such as leukemia). When the TCR engages with antigenic peptide and MHC (peptide/MHC), the T lymphocyte is activated through signal transduction, e.g., a series of biochemical events mediated by associated enzymes, co-receptors, specialized adaptor molecules, and activated or released transcription factors.

For example, the naturally-occurring TCR is typically a disulfide-linked membrane-anchored heterodimeric protein including, e.g., the highly variable alpha (α) and beta (β) chains expressed as part of a complex with the invariant CD3 chain molecules. T cells expressing this receptor are sometimes referred to as α:β (or αβ) T cells, though a minority of T cells express an alternate receptor, formed by variable gamma (γ) and delta (δ) chains, sometimes referred as γδ T cells.

Each chain of TCR can include two extracellular domains: a variable (V) region and a constant (C) region. The constant region is proximal to the cell membrane, followed by a transmembrane region and a short cytoplasmic tail, while the variable region can bind to the peptide/MHC complex.

The variable domain of the TCR α chain or β chain each can have three hypervariable or complementarity determining regions (CDRs). There can also be an additional area of hypervariability on the β chain (HV4), which typically does not contact antigen and is not considered a CDR. The residues in these variable domains are located in two regions of the TCR, at the interface of the α and β chains and in the β-chain framework region that is in proximity to the CD3 signal-transduction complex. Without wishing to be bound by theory, it is believed that in an embodiment, CDR3 is the main CDR responsible for recognizing processed antigen. CDR1 of the alpha chain can interact with the N-terminal part of the antigenic peptide, and CDR1 of the β chain can interact with the C-terminal part of the peptide. CDR2 may recognize the MHC. CDR4 of the β chain is generally not thought to participate in antigen recognition, but may interact with superantigens.

The constant domain of the TCR include, e.g., short connecting sequences, which form a link between the two chains, e.g., through disulfide bonds.

The generation of TCR diversity arises mainly from genetic recombination of the DNA encoded segments in individual somatic T cells by somatic V(D)J recombination. Each recombined TCR may possess unique antigen specificity, determined by the structure of the antigen-binding site, e.g., formed by the α and β chains in case of αβ T cells or γ and δ chains on case of γδ T cells. For example, the TCR α and γ chains can be generated by VJ recombination, and the β and δ chains can be generated by VDJ recombination. The intersection of these specific regions (e.g., V and J for α or γ chain; V, D, and J for β or δ chain) corresponds to the CDR3 region that is typically important for peptide/MHC recognition.

The TCR receptor can form a complex of variable TCR chains (e.g., α and β chains with three dimeric signaling modules CD3δ/ε, CD3γ/ε and CD247 ζ/ζ or ζ/η). T cell can express clonal TCRs which recognize specific peptide/MHC complex during physical contact between T cell and antigen-presenting cell-APC (MHC class II) or any other cell type (MHC class I). The signal from the T-cell complex can be enhanced by simultaneous binding of the MHC molecules by a specific co-receptor. For example, on helper T cells and regulatory T cells, the co-receptor is CD4 that is specific for MHC class II, and on cytotoxic T cells, the co-receptor is CD8 that is specific for MHC class I.

The term "TCR" includes intact molecules as well as functional fragments thereof. TCR fragments may be obtained using any suitable method, including several conventional techniques known to those with skill in the art, and the fragments can be screened for utility in the same manner as are intact TCRs. Constant regions of the TCRs can be altered, e.g., mutated, to modify the properties of the TCR.

The TCR molecule can be a single chain TCR. The single chain TCR can be dimerized or multimerized to generate multivalent TCRs having specificities for different epitopes of the same target protein.

The TCR molecules disclosed herein can also be single domain TCRs. Single domain TCRs can include TCRs whose complementary determining regions are part of a single domain polypeptide. Examples include, but are not limited to, α, β, γ, or δ chain TCRs, TCRs naturally devoid of a α, β, γ, or δ chain, single domain TCRs derived from conventional two-chain TCRs, engineered TCRs and single domain scaffolds other than those derived from TCRs. Single domain TCRs may be any of the art, or any future single domain TCRs. Single domain TCRs may be derived from any species including, but not limited to mouse, human, camel, llama, fish, shark, goat, rabbit, and bovine.

The variable regions can be subdivided into regions of hypervariability, termed "complementarity determining regions" (CDR), interspersed with regions that are more conserved, termed "framework regions" (FR or FW). The terms "complementarity determining region," and "CDR," as used herein in the context of TCR molecules refer to the sequences of amino acids within TCR variable regions which confer antigen specificity and binding affinity. As used herein, the terms "framework," "FW" and "FR" are used interchangeably.

As used herein, a "TCR variable domain sequence" refers to an amino acid sequence which can form the structure of a TCR variable domain. For example, the sequence may include all or part of the amino acid sequence of a naturally-occurring variable domain. For example, the sequence may or may not include one, two, or more N- or C-terminal amino acids, or may include other alterations that are compatible with formation of the protein structure.

The term "antigen-binding region" refers to the part of a TCR molecule that comprises determinants that form an interface that binds to an antigen, or an epitope thereof. With respect to proteins (or protein mimetics), the antigen-binding region typically includes one or more loops (of at least, e.g., four amino acids or amino acid mimics) that form an interface that binds to the antigen. Typically, the antigen-binding region of a TCR molecule includes at least one or two CDRs and/or hypervariable loops, or more typically at least three, four, five or six CDRs and/or hypervariable loops.

The terms "compete" or "cross-compete" are used interchangeably herein to refer to the ability of a TCR molecule to interfere with binding of another TCR molecule, to a target. The interference with binding can be direct or indirect (e.g., through an allosteric modulation of the TCR molecule or the target). The extent to which an antibody molecule is able to interfere with the binding of another TCR molecule to the target, and therefore whether it can be said to compete, can be determined using a competition binding assay, for example, a FACS assay, an ELISA or BIACORE assay. In an embodiment, a competition binding assay is a quantitative competition assay. In an embodiment, a first TCR molecule is said to compete for binding to the target with a second TCR molecule when the binding of the first antibody molecule to the target is reduced by 10% or more, e.g., 20% or more, 30% or more, 40% or more, 50% or more, 55% or more, 60% or more, 65% or more, 70% or more, 75% or more, 80% or more, 85% or more, 90% or more, 95% or more, 98% or more, 99% or more in a competition binding assay (e.g., a competition assay described herein).

The TCR molecule can be a polyclonal or a monoclonal. In some embodiments, the TCR can be recombinantly produced, e.g., produced by any suitable phage display or combinatorial methods. Phage display and combinatorial methods are known in the art.

In an embodiment, the TCR molecule is a fully human TCR (e.g., a TCR made in a mouse which has been genetically engineered to produce a TCR from a human TCR sequence), or a non-human TCR, e.g., a rodent (mouse or rat), goat, primate (e.g., monkey), camel TCR. In an embodiment, the non-human TCR is a rodent (mouse or rat TCR). For example, Human TCRs can be generated using transgenic mice carrying the human TCR genes rather than the mouse system.

A TCR can be one in which the variable region, or a portion thereof, e.g., the CDRs, are generated in a non-human organism, e.g., a rat or mouse. Chimeric, CDR-grafted, and humanized TCRs are within the invention. TCRs generated in a non-human organism, e.g., a rat or mouse, and then modified, e.g., in the variable framework or constant region, to decrease antigenicity in a human are within the invention.

Chimeric TCRs can be produced by any suitable recombinant DNA technique.

A humanized or CDR-grafted TCR will have at least one or two but generally all three recipient CDRs (of TCR chains) replaced with a donor CDR. The TCR may be replaced with at least a portion of a non-human CDR or only some of the CDRs may be replaced with non-human CDRs. It is only necessary to replace the number of CDRs required for binding of the humanized TCR to an antigen. In an embodiment, the donor will be a rodent TCR, e.g., a rat or mouse TCR, and the recipient will be a human framework or a human consensus framework. Typically, the TCR providing the CDRs is called the "donor" and the TCR providing the framework is called the "acceptor." In some embodiments, the donor TCR is a non-human (e.g., rodent). The acceptor framework is typically a naturally-occurring (e.g., a human) framework or a consensus framework, or a sequence about 85% or higher, e.g., 90%, 95%, 99% or higher identical thereto.

As used herein, the term "consensus sequence" refers to the sequence formed from the most frequently occurring amino acids (or nucleotides) in a family of related sequences (See e.g., Winnaker, From Genes to Clones (Verlagsgesellschaft, Weinheim, Germany 1987). In a family of proteins, each position in the consensus sequence is occupied by the amino acid occurring most frequently at that position in the family. If two amino acids occur equally frequently, either can be included in the consensus sequence. A "consensus framework" refers to the framework region in the consensus TCR sequence.

A TCR can be humanized by any suitable method. Humanized or CDR-grafted TCR s can be produced by CDR-grafting or CDR substitution, wherein one, two, or all CDRs of an immunoglobulin chain can be replaced. Also provided are humanized TCRs in which specific amino acids have been substituted, deleted or added.

In an embodiment, the TCR molecule has a constant region. The constant region can be altered, e.g., mutated, to modify a property of the TCR molecule. In an embodiment, a constant region of the TCR molecule is altered. Methods for altering a constant region are known in the art.

In an embodiment, the only amino acids in the TCR molecule are canonical amino acids. In an embodiment, the TCR molecule comprises naturally-occurring amino acids; analogs, derivatives and congeners thereof; amino acid analogs having variant side chains; and/or all stereoisomers of any of any of the foregoing. The TCR molecule may comprise the D- or L-optical isomers of amino acids and peptidomimetics.

A polypeptide of a TCR molecule described herein may be linear or branched, it may comprise modified amino acids, and it may be interrupted by non-amino acids. The TCR molecule may also be modified; for example, by disulfide bond formation, glycosylation, lipidation, acetylation, phosphorylation, or any other manipulation, such as conjugation with a labeling component. The polypeptide can be isolated from natural sources, can be a produced by recombinant techniques from a eukaryotic or prokaryotic host, or can be a product of synthetic procedures.

The TCR molecule described herein can be used alone in unconjugated form, or can be bound to a substance, e.g., a toxin or moiety (e.g., a therapeutic drug; a compound emitting radiation; molecules of plant, fungal, or bacterial origin; or a biological protein (e.g., a protein toxin) or particle (e.g., a recombinant viral particle, e.g., via a viral coat protein). For example, the TCR molecule can be coupled to a radioactive isotope such as an $\alpha$-, $\beta$-, or $\gamma$-emitter, or a $\beta$- and $\gamma$-emitter.

A TCR molecule can be derivatized or linked to another functional molecule (e.g., another peptide or protein). As used herein, a "derivatized" TCR molecule is one that has been modified. Methods of derivatization include but are not limited to the addition of a fluorescent moiety, a radionucleotide, a toxin, an enzyme or an affinity ligand such as biotin. Accordingly, the TCR molecules are intended to include derivatized and otherwise modified forms of the antibodies described herein, including immunoadhesion molecules. For example, a TCR molecule can be functionally linked (by chemical coupling, genetic fusion, noncovalent association or otherwise) to one or more other molecular entities, such as another TCR (e.g., a bispecific TCR), a detectable agent, a toxin, a pharmaceutical agent, and/or a protein or peptide that can mediate association of the TCR or TCR portion with another molecule (such as a streptavidin core region or a polyhistidine tag).

Some types of derivatized TCR molecule are produced by crosslinking two or more TCRs (of the same type or of different types, e.g., to create bispecific TCRs). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill.

Useful detectable agents with which a TCR molecule may be derivatized (or labeled) to include fluorescent compounds, various enzymes, prosthetic groups, luminescent materials, bioluminescent materials, fluorescent emitting metal atoms, e.g., europium (Eu), and other anthanides, and radioactive materials (described below). Exemplary fluorescent detectable agents include fluorescein, fluorescein isothiocyanate, rhodamine, 5dimethylamine-1-napthalenesulfonyl chloride, phycoerythrin and the like. A TCR may also be derivatized with detectable enzymes, such as alkaline phosphatase, horseradish peroxidase, β-galactosidase, acetylcholinesterase, glucose oxidase and the like. When a TCR is derivatized with a detectable enzyme, it is detected by adding additional reagents that the enzyme uses to produce a detectable reaction product. For example, when the detectable agent horseradish peroxidase is present, the addition of hydrogen peroxide and diaminobenzidine leads to a colored reaction product, which is detectable. A TCR molecule may also be derivatized with a prosthetic group (e.g., streptavidin/biotin and avidin/biotin). For example, a TCR may be derivatized with biotin, and detected through indirect measurement of avidin or streptavidin binding. Examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of bioluminescent materials include luciferase, luciferin, and aequorin.

Labeled TCR molecules can be used, for example, diagnostically and/or experimentally in a number of contexts, including (i) to isolate a predetermined antigen by standard techniques, such as affinity chromatography or immunoprecipitation; (ii) to detect a predetermined antigen (e.g., in a cellular lysate or cell supernatant) in order to evaluate the abundance and pattern of expression of the protein; (iii) to monitor protein levels in tissue as part of a clinical testing procedure, e.g., to determine the efficacy of a given treatment regimen.

A TCR molecule may be conjugated to another molecular entity, typically a label or a therapeutic (e.g., antimicrobial (e.g., antibacterial or bactericidal), immunomodulatory, immunostimularoty, cytotoxic, or cytostatic) agent or moiety. Radioactive isotopes can be used in diagnostic or therapeutic applications. Radioactive isotopes that can be coupled to the antibody molecules include, but are not limited to α-, β-, or γ-emitters, or β- and γ-emitters. Such radioactive isotopes include, but are not limited to iodine ($^{131}$I or $^{125}$I), yttrium ($^{90}$Y), lutetium ($^{177}$Lu), actinium ($^{225}$Ac), praseodymium, astatine ($^{211}$At), rhenium ($^{186}$Re), bismuth ($^{212}$Bi or $^{213}$Bi), indium ($^{111}$In), technetium ($^{99}$mTc), phosphorus ($^{32}$P), rhodium ($^{188}$Rh), sulfur ($^{35}$S), carbon ($^{14}$C), tritium ($^{3}$H), chromium ($^{51}$Cr), chlorine ($^{36}$Cl), cobalt ($^{57}$Co or $^{58}$Co), iron ($^{59}$Fe), selenium ($^{75}$Se), or gallium ($^{67}$Ga). Radioisotopes useful as therapeutic agents include yttrium ($^{90}$Y), lutetium ($^{177}$Lu), actinium ($^{225}$Ac), praseodymium, astatine ($^{211}$At), rhenium ($^{186}$Re), bismuth ($^{212}$Bi or $^{213}$Bi), and rhodium ($^{188}$Rh). Radioisotopes useful as labels, e.g., for use in diagnostics, include iodine ($^{131}$I or $^{125}$I), indium ($^{111}$In), technetium ($^{99}$mTc), phosphorus ($^{32}$P), carbon ($^{14}$C), and tritium ($^{3}$H), or one or more of the therapeutic isotopes listed above.

The present disclosure provides radiolabeled TCR molecules and methods of labeling the same. In an embodiment, a method of labeling a TCR molecule is disclosed. The method includes contacting a TCR molecule, with a chelating agent, to thereby produce a conjugated TCR. The conjugated antibody is radiolabeled with a radioisotope, e.g., $^{111}$Indium, $^{90}$Yttrium and $^{177}$Lutetium, to thereby produce a labeled TCR molecule.

In some aspects, this disclosure provides a method of making a TCR molecule disclosed herein. The method includes: providing an antigen, or a fragment thereof; obtaining a TCR molecule that specifically binds to the antigen; evaluating efficacy of the TCR molecule in modulating activity of the antigen and/or organism expressing the antigen. The method can further include administering the TCR molecule, including a derivative thereof (e.g., a humanized TCR molecule) to a subject, e.g., a human.

This disclosure provides an isolated nucleic acid molecule encoding the above TCR molecule, vectors and host cells thereof. The nucleic acid molecule includes, but is not limited to, RNA, genomic DNA and cDNA.

Animal Models

The polypeptides (e.g., binding polypeptides, e.g., antibody molecules or TCR molecules) described herein can be evaluated in vivo, e.g., using various animal models. For example, an animal model can be used to test the efficacy of a binding polypeptide (e.g., an antibody molecule or TCR molecule) described herein in modulating a biological function of a target molecule or cell. As another example, an animal model can also be used to test the efficacy of a binding polypeptide (e.g., an antibody molecule or TCR molecule) described herein in in treating, preventing, or diagnosing a disorder described herein. Animal models can also be used, e.g., to investigate for side effects, measure concentrations of binding polypeptides (e.g., antibody molecules or TCR molecules) in situ, demonstrate correlations between a function of a target molecule or cell and a disorder described herein.

Exemplary animal models for other disorders described herein are also known in the art. Exemplary types of animals that can be used to evaluate the binding polypeptides (e.g., antibody molecules or TCR molecules) described herein include, but are not limited to, mice, rats, rabbits, guinea pigs, and monkeys.

Pharmaceutical Compositions and Kits

In some aspects, this disclosure provides compositions, e.g., pharmaceutically acceptable compositions, which include a polypeptide (e.g., a binding polypeptide, e.g., an antibody molecule or a TCR molecule) described herein, formulated together with a pharmaceutically acceptable carrier.

As used herein, "pharmaceutically acceptable carrier" includes any and all solvents, dispersion media, isotonic and absorption delaying agents, and the like that are physiologically compatible. The carrier can be suitable for intravenous, intramuscular, subcutaneous, parenteral, rectal, spinal or epidermal administration (e.g., by injection or infusion). In certain embodiments, less than about 5%, e.g., less than about 4%, 3%, 2%, or 1% of the binding polypeptides in the pharmaceutical composition are present as aggregates. In other embodiments, at least about 95%, e.g., at least about 96%, 97%, 98%, 98.5%, 99%, 99.5%, 99.8%, or more of the binding polypeptides in the pharmaceutical composition are present as monomers. In some embodiments, the level of aggregates or monomers is determined by chromatography, e.g., high performance size exclusion chromatography (HPSEC).

The compositions set out herein may be in a variety of forms. These include, for example, liquid, semi-solid and solid dosage forms, such as liquid solutions (e.g., injectable and infusible solutions), dispersions or suspensions, liposomes, and suppositories. A suitable form depends on the intended mode of administration and therapeutic application. Typical suitable compositions are in the form of injectable or infusible solutions. One suitable mode of administration is parenteral (e.g., intravenous, subcutaneous, intraperitoneal, intramuscular). In an embodiment, the binding polypeptide is administered by intravenous infusion or injection. In another embodiment, the binding polypeptide is administered by intramuscular or subcutaneous injection.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Therapeutic compositions typically should be sterile and stable under the conditions of manufacture and storage. The composition can be formulated as a solution, microemulsion, dispersion, liposome, or other ordered structure suitable to high concentrations of binding polypeptides (e.g., antibody molecules or TCR molecules). Sterile injectable solutions can be prepared by incorporating the active compound (e.g., binding polypeptide) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The binding polypeptides (e.g., antibody molecules or TCR receptors) described herein can be administered by a variety of methods. Several are known in the art, and for many therapeutic, prophylactic, or diagnostic applications, an appropriate route/mode of administration is intravenous injection or infusion. For example, the binding polypeptides can be administered by intravenous infusion at a rate of less than 10 mg/min; preferably less than or equal to 5 mg/min to reach a dose of about 1 to 100 mg/m$^2$, preferably about 5 to 50 mg/m$^2$, about 7 to 25 mg/m$^2$ and more preferably, about 10 mg/m$^2$. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

In certain embodiments, the binding polypeptide (e.g., antibody molecule or TCR molecule) can be orally administered, for example, with an inert diluent or an assimilable edible carrier. The binding polypeptide (and other ingredients, if desired) may also be enclosed in a hard or soft shell gelatin capsule, compressed into tablets, or incorporated directly into the subject's diet. For oral therapeutic administration, the binding polypeptide may be incorporated with excipients and used in the form of ingestible tablets, buccal tablets, troches, capsules, elixirs, suspensions, syrups, wafers, and the like. To administer the binding polypeptide (e.g., antibody molecule) by other than parenteral administration, it may be necessary to coat the compound with, or co-administer the compound with, a material to prevent its inactivation. Therapeutic, prophylactic, or diagnostic compositions can also be administered with medical devices, and several are known in the art.

Dosage regimens are adjusted to provide the desired response (e.g., a therapeutic, prophylactic, or diagnostic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms are dictated by and directly dependent on (a) the unique characteristics of the antibody molecule and the particular therapeutic, prophylactic, or diagnostic effect to be achieved, and (b) the limitations inherent in the art of compounding such a binding polypeptide for the treatment of sensitivity in individuals.

An exemplary, non-limiting range for a therapeutically, prophylactically, or diagnostically effective amount of a binding polypeptide (e.g., an antibody molecule or TCR molecule) is about 0.1-50 mg/kg, e.g., about 0.1-30 mg/kg, e.g., about 1-30, 1-15, 1-10, 1-5, 5-10, or 1-3 mg/kg, e.g., about 1, 2, 3, 4, 5, 6, 7, 8, 9, 10, 15, 20, 30, 40, or 50 mg/kg. The binding polypeptide can be administered by intravenous infusion at a rate of less than 10 mg/min, e.g., less than or equal to 5 mg/min to reach a dose of about 1 to 100 mg/m$^2$, e.g., about 5 to 50 mg/m$^2$, about 7 to 25 mg/m$^2$, e.g., about 10 mg/m$^2$. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed compositions.

The pharmaceutical compositions herein may include a "therapeutically effective amount," "prophylactically effective amount," or "diagnostically effectively amount" of a binding polypeptide (e.g., an antibody molecule or TCR molecule) described herein.

A "therapeutically effective amount" refers to an amount effective, at dosages and for periods of time necessary, to achieve the desired therapeutic result. A therapeutically effective amount of the binding polypeptide (e.g., antibody molecule or TCR molecule) may vary according to factors such as the disease state, age, sex, and weight of the individual, and the ability of the antibody or antibody portion to elicit a desired response in the individual. A therapeutically effective amount is also one in which any toxic or detrimental effect of the antibody molecule is outweighed by the therapeutically beneficial effects.

A "therapeutically effective dosage" typically inhibits a measurable parameter by at least about 20%, e.g., by at least about 40%, by at least about 60%, or by at least about 80% relative to untreated subjects. The measurable parameter may be, e.g., hematuria, colored urine, foamy urine, pain, swelling (edema) in the hands and feet, or high blood pressure. The ability of a binding polypeptide (e.g., an antibody molecule) to inhibit a measurable parameter can be evaluated in an animal model system predictive of efficacy in treating or preventing a disorder described herein. Alternatively, this property of a composition can be evaluated by examining the ability of the binding polypeptide (e.g., antibody molecule or TCR molecule) to modulate a biological function of a target molecule or cell, e.g., by an in vitro assay.

A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

A "diagnostically effective amount" refers to an amount effective, at dosages and for periods of time necessary, to achieve the desired diagnostic result. Typically, a diagnostically effective amount is one in which a disorder, e.g., a disorder described herein, can be diagnosed in vitro, ex vivo, or in vivo.

Also within this disclosure is a kit that comprises a binding polypeptide (e.g., an antibody molecule or TCR molecule), described herein. The kit can include one or more other elements including: instructions for use; other reagents, e.g., a label, a therapeutic agent, or an agent useful for chelating, or otherwise coupling, an antibody molecule to a label or therapeutic agent, or a radioprotective composition; devices or other materials for preparing the binding polypeptide (e.g., antibody molecule or TCR molecule) for administration; pharmaceutically acceptable carriers; and devices or other materials for administration to a subject.

Nucleic Acids

The present disclosure also features nucleic acids comprising nucleotide sequences that encode polypeptides (e.g., binding polypeptides, e.g., antibody molecules or T cell receptor molecules), as described herein.

In an embodiment, the nucleic acid further comprises a nucleotide sequence encoding a heavy chain variable region of a polypeptide (e.g., an antibody molecule or TCR molecule) described herein, or having a nucleotide sequence substantially homologous thereto (e.g., a sequence at least about 85%, 90%, 95%, 99% or more identical thereto, and/or capable of hybridizing under the stringency conditions described herein). In another embodiment, the nucleic acid further comprises a nucleotide sequence encoding a light chain variable region of a polypeptide (e.g., an antibody molecule or TCR molecule) described herein, or a nucleotide sequence substantially homologous thereto (e.g., a sequence at least about 85%, 90%, 95%, 99% or more identical thereto, and/or capable of hybridizing under the stringency conditions described herein). In yet another embodiment, the nucleic acid further comprises a nucleotide sequence encoding a heavy chain variable region and a light chain variable region of a polypeptide (e.g., an antibody molecule or TCR molecule) described herein, or a nucleotide sequence substantially homologous thereto (e.g., a sequence at least about 85%, 90%, 95%, 99% or more identical thereto, and/or capable of hybridizing under the stringency conditions described herein).

In an embodiment, the nucleic acid further comprises a nucleotide sequence encoding at least one, two, or three CDRs from a heavy chain variable region of a polypeptide (e.g., an antibody molecule or TCR molecule) described herein, or a nucleotide sequence substantially homologous thereto (e.g., a sequence at least about 85%, 90%, 95%, 99% or more identical thereto, and/or capable of hybridizing under the stringency conditions described herein). In another embodiment, the nucleic acid further comprises a nucleotide sequence encoding at least one, two, or three CDRs from a light chain variable region of a polypeptide (e.g., an antibody molecule or TCR molecule) described herein, or a nucleotide sequence substantially homologous thereto (e.g., a sequence at least about 85%, 90%, 95%, 99% or more identical thereto, and/or capable of hybridizing under the stringency conditions described herein). In yet another embodiment, the nucleic acid comprises a nucleotide sequence encoding at least one, two, three, four, five, or six CDRs from heavy and light chain variable regions of a polypeptide (e.g., an antibody molecule or TCR molecule) described herein, or a nucleotide sequence substantially homologous thereto (e.g., a sequence at least about 85%, 90%, 95%, 99% or more identical thereto, and/or capable of hybridizing under the stringency conditions described herein).

In an embodiment, the nucleic acid comprises a portion of a nucleotide sequence described herein. The portion may encode, for example, a variable region (e.g., VH or VL); one, two, or three or more (e.g., four, five, or six) CDRs; or one, two, three, or four or more framework regions, optionally, a constant region or an Fc region.

The nucleic acids disclosed herein include deoxyribonucleotides or ribonucleotides, or analogs thereof. The polynucleotide may be either single-stranded or double-stranded, and if single-stranded may be the coding strand or non-coding (antisense) strand. A polynucleotide may comprise modified nucleotides, such as methylated nucleotides and nucleotide analogs. The sequence of nucleotides may be interrupted by non-nucleotide components. A polynucleotide may be further modified after polymerization, such as by conjugation with a labeling component. The nucleic acid may be a recombinant polynucleotide, or a polynucleotide of genomic, cDNA, semisynthetic, or synthetic origin which either does not occur in nature or is linked to another polynucleotide in a non-natural arrangement.

In some aspects, the application features host cells and vectors containing the nucleic acids described herein. The nucleic acids may be present in a single vector or separate vectors present in the same host cell or separate host cell, as described in more detail below.

Vectors

The present disclosure features vectors that comprise nucleotide sequences encoding polypeptides (e.g., binding polypeptides, e.g., antibody molecules or TCR molecules).

The vectors include, but are not limited to, a virus, plasmid, cosmid, lambda phage or a yeast artificial chromosome (YAC).

Numerous vector systems can be employed. For example, one class of vectors utilizes DNA elements which are derived from animal viruses such as, for example, bovine papilloma virus, polyoma virus, adenovirus, vaccinia virus, baculovirus, retroviruses (Rous Sarcoma Virus, MMTV or MOMLV) or SV40 virus. Another class of vectors utilizes RNA elements derived from RNA viruses such as Semliki Forest virus, Eastern Equine Encephalitis virus and Flaviviruses.

Additionally, cells which have stably integrated the DNA into their chromosomes may be selected by introducing one or more markers which allow for the selection of transfected host cells. The marker may provide, for example, prototropy to an auxotrophic host, biocide resistance (e.g., antibiotics), or resistance to heavy metals such as copper, or the like. The selectable marker gene can be either directly linked to the DNA sequences to be expressed, or introduced into the same cell by cotransformation. Additional elements may also be needed for optimal synthesis of mRNA. These elements may include splice signals, as well as transcriptional promoters, enhancers, and termination signals.

Once the expression vector or DNA sequence containing the constructs has been prepared for expression, the expression vectors may be transfected or introduced into an appropriate host cell. Various techniques may be employed to achieve this, such as, for example, protoplast fusion, calcium phosphate precipitation, electroporation, retroviral transduction, viral transfection, gene gun, lipid based transfection or other conventional techniques. In the case of protoplast fusion, the cells are grown in media and screened for the appropriate activity.

Methods and conditions for culturing the resulting transfected cells and for recovering the polypeptide (e.g., antibody molecule) produced are known to those skilled in the art, and may be varied or optimized depending upon the specific expression vector and mammalian host cell employed, based upon the present description.

Cells

The present disclosure also provides host cells comprising a nucleic acid encoding a polypeptide (e.g., an antibody molecule or TCR molecule) as described herein. The polypeptide (e.g., antibody molecule or TCR molecule) can be engineered in accordance with a method described herein. For example, the host cells may comprise a nucleic acid molecule having a nucleotide sequence of a polypeptide described herein (e.g., an antibody molecule or TCR molecule described herein), a sequence substantially homologous thereto (e.g., a sequence at least about 85%, 90%, 95%, 99% or more identical thereto, and/or capable of hybridizing under the stringency conditions described herein), or a portion of one of said nucleic acids.

In some embodiments, the host cells are genetically engineered to comprise nucleic acids encoding the polypeptide (e.g., antibody molecule or TCR molecule) described herein.

In certain embodiments, the host cells are genetically engineered by using an expression cassette. The phrase "expression cassette," refers to nucleotide sequences, which are capable of affecting expression of a gene in hosts compatible with such sequences. Such cassettes may include a promoter, an open reading frame with or without introns, and a termination signal. Additional factors necessary or helpful in effecting expression may also be used, such as, for example, an inducible promoter.

The disclosure also provides host cells comprising the vectors described herein.

The cell can be, but is not limited to, a eukaryotic cell, a bacterial cell, an insect cell, or a human cell. Suitable eukaryotic cells include, but are not limited to, Vero cells, HeLa cells, COS cells, CHO cells, HEK293 cells, BHK cells and MDCKII cells. Suitable insect cells include, but are not limited to, Sf9 cells.

Uses of Polypeptides

The polypeptides (e.g., binding polypeptides, e.g., antibody molecules or TCR molecule) disclosed herein, as well as the pharmaceutical compositions disclosed herein, have in vitro, ex vivo, and in vivo therapeutic, prophylactic, and/or diagnostic utilities.

In an embodiment, the polypeptide (e.g., antibody molecule or TCR molecule) modulates (e.g., reduces (e.g., inhibits, blocks, or neutralizes) or increases (e.g., activates, initiates, or enhances)) one or more biological activities of a target molecule (e.g., protein) or cell. For example, these polypeptides (e.g., antibody molecules or TCR molecules) can be administered to cells in culture, in vitro or ex vivo, or to a subject, e.g., a human subject, e.g., in vivo, to modulate one or more biological activities of the target molecule or cell. Accordingly, in an aspect, the disclosure provides a method of treating, preventing, or diagnosing a disorder, e.g., a disorder described herein, in a subject, comprising administering to the subject a polypeptide (e.g., an antibody molecule or TCR molecule) described herein, such that the disorder is treated, prevented, or diagnosed. For example, the disclosure provides a method comprising contacting the polypeptide (e.g., antibody molecule or TCR molecule) described herein with cells in culture, e.g. in vitro or ex vivo, or administering the polypeptide (e.g., antibody molecule or TCR molecule) described herein to a subject, e.g., in vivo, to treat, prevent, or diagnose a disorder, e.g., a disorder associated with a target molecule or cell (e.g., a disorder described herein).

As used herein, the term "subject" is intended to include human and non-human animals. In some embodiments, the subject is a human subject, e.g., a human patient having a disorder described herein, or at risk of having a disorder described herein. The term "non-human animals" includes mammals and non-mammals, such as non-human primates. In an embodiment, the subject is a human. The methods and compositions described herein are suitable for treating human patients for a disorder described herein. Patients having a disorder described herein include those who have developed a disorder described herein but are (at least temporarily) asymptomatic, patients who have exhibited a symptom of a disorder described herein, or patients having a disorder related to or associated with a disorder described herein.

Methods of Treating or Preventing Disorders

The polypeptides (e.g., antibody molecules or TCR molecules) described herein can be used to treat or prevent disorders or conditions. In an embodiment, the polypeptide has an optimal or improved half-life, which can be desirable for treating or preventing the disorder or condition. While not wishing to be bound by theory, it is believed that in an embodiment, the polypeptide described herein (e.g., the polypeptide having an optimal or improved half-life) can provide one or more benefits over another polypeptide having the same or similar binding affinity and/or specificity (e.g., a polypeptide that does not have, or has not been engineered to have, an optimal or improved half-life). These benefits can include, but are not limited to, an increased therapeutic or preventive efficacy, a reduced dosage regimen, or an improved pharmacokinetic property. In an embodiment, the polypeptide includes a mutated Fc region as described herein.

Exemplary disorders or conditions that can be treated or prevented by the polypeptides described herein include, but are not limited to, a cancer (e.g., a solid tumor or a hematologic cancer), an infectious disease (e.g., a bacterial infection or a viral infection), an immune disorder (e.g., an autoimmune disorder), an inflammatory disorder, a metabolic disorder (e.g., diabetes), a cardiovascular disorder, an organ transplant rejection.

Exemplary cancers that can be treated or prevented by the polypeptides described herein include, but are not limited to, acute lymphoblastic leukemia (ALL), acute myeloid leukemia (AML), adrenocortical carcinoma, Kaposi sarcoma, an AIDS-related lymphoma, primary central nervous system (CNS) lymphoma, anal cancer, appendix cancer, astrocytoma, atypical teratoid/rhabdoid tumor, basal cell carcinoma, bile duct cancer, bladder cancer, bone cancer (e.g., Ewing sarcoma or osteosarcoma and malignant fibrous histiocytoma), brain tumor (e.g., astrocytomas, brain stem glioma, central nervous system atypical teratoid/rhabdoid tumor, central nervous system embryonal tumor, central nervous system germ cell tumor, craniopharyngioma, or ependymoma), breast cancer, bronchial tumor, Burkitt lymphoma, carcinoid tumor (e.g., gastrointestinal carcinoid tumor), cardiac (heart) tumor, embryonal tumor, germ cell tumor, lymphoma, cervical cancer, cholangiocarcinoma, chordoma, chronic lymphocytic leukemia (CLL), chronic myelogenous leukemia (CML), chronic myeloproliferative neoplasm, colon cancer, colorectal cancer, craniopharyngioma, cutaneous T-cell lymphoma, ductal carcinoma in situ (DCIS), endometrial cancer, ependymoma, esophageal cancer, esthesioneuroblastoma, Ewing sarcoma, extracranial germ cell tumor, extragonadal germ cell tumor, eye cancer (e.g., intraocular melanoma or retinoblastoma), fallopian tube cancer, fibrous histiocytoma of bone, osteosarcoma, gallbladder cancer, gastric (stomach) cancer, gastrointestinal carcinoid tumor, gastrointestinal stromal tumors (GIST), germ cell tumor (e.g., central nervous system tumor, extracranial tumor, extragonadal tumor, ovarian cancer, or testicular cancer), gestational trophoblastic disease, glioma, hairy cell leukemia, head and neck cancer, hepatocellular (liver) cancer, Hodgkin lymphoma, hypopharyngeal cancer, intraocular melanoma, islet cell tumor, pancreatic neuroendocrine tumor, Kaposi sarcoma, kidney cancer (e.g., renal cell cancer or Wilms tumor), Langerhans cell histiocytosis (LCH), laryngeal cancer, leukemia (e.g., acute lymphoblastic leukemia (ALL), acute myeloid leukemia (AML), chronic lymphocytic leukemia (CLL), chronic myelogenous leukemia (CML), or hairy cell leukemia), lip and oral cavity cancer, liver cancer, lung cancer (e.g., non-small cell lung cancer (NSCLC) or small cell lung cancer), lymphoma (e.g., aids-related, Burkitt lymphoma, cutaneous T-cell lymphoma, Hodgkin lymphoma, non-Hodgkin lymphoma, or primary central nervous system (CNS) lymphoma), Waldenström macroglobulinemia, male breast cancer, malignant fibrous histiocytoma of bone and osteosarcoma, melanoma (e.g., intraocular (eye) melanoma), Merkel cell carcinoma, mesothelioma, metastatic squamous neck cancer, midline tract carcinoma, mouth cancer, multiple endocrine neoplasia syndrome, multiple myeloma/plasma cell neoplasm, mycosis fungoides, myelodysplastic syndrome, myelodysplastic/myeloproliferative neoplasm, chronic myeloproliferative neoplasm, nasal cavity and paranasal sinus cancer, nasopharyngeal cancer, neuroblastoma, oral cancer, lip and oral cavity cancer, oropharyngeal cancer, osteosarcoma and malignant fibrous histiocytoma of bone, ovarian cancer (e.g., epithelial ovarian cancer or germ cell ovarian tumor), pancreatic cancer, pancreatic neuroendocrine tumors (islet cell tumors), papillomatosis, paraganglioma, paranasal sinus and nasal cavity cancer, parathyroid cancer, penile cancer, pharyngeal cancer, pheochromocytoma, pituitary tumor, pleuropulmonary blastoma, peritoneal cancer, prostate cancer, rectal cancer, retinoblastoma, rhabdomyosarcoma, salivary gland cancer, sarcoma (e.g., Ewing sarcoma, Kaposi sarcoma, osteosarcoma, rhabdomyosarcoma, soft tissue sarcoma, or uterine sarcoma), Sézary syndrome, skin cancer (e.g., melanoma, Merkel cell carcinoma, or nonmelanoma skin cancer), small intestine cancer, squamous cell carcinoma, testicular cancer, throat cancer, thymoma and thymic carcinoma, thyroid cancer, transitional cell cancer of the renal pelvis and ureter, urethral cancer, endometrial uterine cancer, vaginal cancer, vulvar cancer, or a metastatic lesion thereof.

Exemplary infectious diseases that can be treated or prevented by the polypeptides described herein include, but are not limited to, *Acinetobacter* infections, actinomycosis, African sleeping sickness (African trypanosomiasis), AIDS (acquired immunodeficiency syndrome), amebiasis, anaplasmosis, angiostrongyliasis, anisakiasis, anthrax, *Arcanobacterium haemolyticum* infection, argentine hemorrhagic fever, ascariasis, aspergillosis, astrovirus infection, babesiosis, *Bacillus cereus* infection, bacterial pneumonia, bacterial vaginosis, *bacteroides* infection, balantidiasis, bartonellosis, *Baylisascaris* infection, bk virus infection, black *piedra*, blastocystosis, blastomycosis, bolivian hemorrhagic fever, botulism (and infant botulism), brazilian hemorrhagic fever, brucellosis, bubonic plague, *burkholderia* infection, buruli ulcer, calicivirus infection (norovirus and sapovirus), campylobacteriosis, candidiasis (moniliasis; thrush), capillariasis, carrion's disease, cat-scratch disease, cellulitis, chagas disease (american trypanosomiasis), chancroid, chickenpox, chikungunya, *chlamydia, chlamydophila pneumoniae* infection (taiwan acute respiratory agent or twar), cholera, chromoblastomycosis, chytridiomycosis, clonorchiasis, *Clostridium difficile* colitis, coccidioidomycosis, colorado tick fever (CTF), common cold (Acute viral rhinopharyngitis; Acute coryza), Creutzfeldt-Jakob disease (CJD), Crimean-Congo hemorrhagic fever (CCHF), cryptococcosis, cryptosporidiosis, cutaneous larva migrans (CLM), cyclosporiasis, cysticercosis, cytomegalovirus infection, dengue fever, desmodesmus infection, dientamoebiasis, diphtheria, diphyllobothriasis, dracunculiasis, ebola hemorrhagic fever, echinococcosis, ehrlichiosis, enterobiasis (pinworm infection), *enterococcus* infection, enterovirus infection, epidemic typhus, erythema infectiosum (fifth disease), exanthem subitum (sixth disease), fasciolasis, fasciolopsiasis, fatal familial insomnia (FFI), filariasis, food poisoning by *Clostridium perfringens*, free-living amebic infection, *fusobacterium* infection, gas gangrene (clostridial myonecrosis), geotrichosis, gerstmann-straussler-scheinker syndrome (GSS), giardiasis, glanders, gnathostomiasis, gonorrhea, granuloma inguinale (donovanosis), Group A streptococcal infection, Group B streptococcal infection, *Haemophilus influenzae* infection, hand, foot and mouth disease (HFMD), Hantavirus Pulmonary Syndrome (HPS), heartland virus disease, *Helicobacter pylori* infection, hemolytic-uremic syndrome (HUS), hemorrhagic fever with renal syndrome (HFRS), hepatitis A, hepatitis B, hepatitis C, hepatitis D, hepatitis E, herpes simplex, histoplasmosis, hookworm infection, human bocavirus infection, human *ewingii* ehrlichiosis, human granulocytic anaplasmosis (HGA), human metapneumovirus infection, Human monocytic ehrlichiosis, human papillomavirus (HPV) infection, Human parainfluenza virus infection, Hymenolepiasis, Epstein-Barr Virus Infectious Mononucleosis (Mono), influenza (flu), isosporiasis, kawasaki disease, keratitis, *kingella kingae* infection, kuru, lassa fever, legionellosis (legionnaires' disease), legionellosis (pontiac fever), leishmaniasis, leprosy, leptospirosis, listeriosis, lyme disease (lyme borreliosis), lymphatic filariasis (Elephantiasis), Lymphocytic choriomeningitis, Malaria, Marburg hemorrhagic fever (MHF), Measles, Middle East respiratory syndrome (MERS), melioidosis (Whitmore's disease), meningitis, meningococcal disease, metagonimiasis, microsporidiosis, molluscum contagiosum (MC), Monkeypox, Mumps, Murine typhus (Endemic typhus), *Mycoplasma pneumonia*, Mycetoma (disambiguation), Myiasis, Neonatal conjunctivitis (Ophthalmia neonatorum), (New) Variant Creutzfeldt-Jakob disease (vCJD, nvCJD), nocardiosis, onchocerciasis (River blindness), opisthorchiasis, paracoccidioidomycosis (South American blastomycosis), paragonimiasis, pasteurellosis, pediculosis capitis (head lice), pediculosis corporis (body lice), pediculosis pubis (pubic lice, crab lice), pelvic inflammatory disease (PID), pertussis (Whooping cough), plague, pneumococcal infection, *pneumocystis* pneumonia (PCP), pneumonia, poliomyelitis, *prevotella* infection, primary amoebic meningoencephalitis (PAM), progressive multifocal leukoencephalopathy, psittacosis, Q fever, rabies, relapsing fever, respiratory syncytial virus infection, rhinosporidiosis, rhinovirus infection, rickettsial infection, rickettsialpox, Rift Valley fever (RVF), Rocky Mountain spotted fever (RMSF), rotavirus infection, rubella, *salmonellosis*, SARS (Severe Acute Respiratory Syndrome), scabies, schistosomiasis, sepsis, shigellosis (Bacillary dysentery), shingles (Herpes zoster), smallpox (Variola), sporotrichosis, staphylococcal food poisoning, staphylococcal infection, strongyloidiasis, subacute sclerosing panencephalitis, syphilis, Taeniasis, Tetanus (Lockjaw), *Tinea barbae* (Barber's itch), *Tinea capitis* (Ringworm of the Scalp), *Tinea corporis* (Ringworm of the Body), *Tinea cruris* (Jock itch), *Tinea manum* (Ringworm of the Hand), *Tinea nigra, Tinea pedis* (Athlete's foot), *Tinea unguium* (Onychomycosis), *Tinea versicolor* (*Pityriasis versicolor*), Toxocariasis (Ocular Larva Migrans (OLM)), Toxocariasis (Visceral Larva Migrans (VLM)), Trachoma, Toxoplasmosis, Trichinosis, Trichomoniasis, Trichuriasis (Whipworm infection), Tuberculosis, Tularemia, Typhoid fever, Typhus fever, *Ureaplasma urealyticum* infection, Valley fever, Venezuelan equine encephalitis, Venezuelan hemorrhagic fever, *Vibrio vulnificus* infection, *Vibrio parahaemolyticus* enteritis, viral pneumonia, West Nile Fever, white *piedra* (*Tinea blanca*), *Yersinia pseudotuberculosis* infection, yersiniosis, yellow fever, Zika fever, or zygomycosis.

Exemplary immune disorders or conditions that can be treated or prevented by the polypeptides described herein include, but are not limited to, Addison's disease, agammaglobulinemia, alopecia areata, amyloidosis, ankylosing spondylitis, anti-GBM/anti-TBM nephritis, antiphospholipid syndrome (APS), autoimmune hepatitis, autoimmune inner ear disease (AIED), axonal & neuronal neuropathy (AMAN), Behcet's disease, Bullous pemphigoid, Castleman disease (CD), Celiac disease, Chagas disease, chronic inflammatory demyelinating polyneuropathy (CIDP), chronic recurrent multifocal osteomyelitis (CRMO), Churg-Strauss, Cicatricial pemphigoid/benign mucosal pemphigoid, Cogan's syndrome, Cold agglutinin disease, Congenital heart block, Coxsackie myocarditis, CREST syndrome, Crohn's disease, dermatitis herpetiformis, dermatomyositis, Devic's disease (neuromyelitis optica), Discoid lupus, Dressler's syndrome, endometriosis, eosinophilic esophagitis (EoE), eosinophilic fasciitis, erythema nodosum, essential mixed cryoglobulinemia, Evans syndrome, fibromyalgia, fibrosing alveolitis, giant cell arteritis (temporal arteritis), giant cell myocarditis, Glomerulonephritis, Goodpasture's syndrome, Granulomatosis with Polyangiitis, Graves' disease, Guillain-Barre syndrome, Hashimoto's thyroiditis, hemolytic anemia, Henoch-Schonlein purpura (HSP), herpes gestationis or pemphigoid gestationis (PG), hypogammalglobulinemia, IgA nephropathy, IgG4-related sclerosing disease, inclusion body myositis (IBM), interstitial cystitis (IC), juvenile arthritis, juvenile diabetes (Type 1 diabetes), juvenile myositis (JM), Kawasaki disease, Lambert-Eaton syndrome, leukocytoclastic vasculitis, Lichen planus, Lichen sclerosus, Ligneous conjunctivitis, linear IgA disease (LAD), lupus, Lyme disease chronic, Meniere's disease, microscopic polyangiitis (MPA), mixed connective tissue disease (MCTD), Mooren's ulcer, Mucha-Habermann disease, multiple sclerosis (MS), Myasthenia gravis, Myositis, Narcolepsy, Neuromyelitis optica, neutropenia, ocular cicatricial pemphigoid, optic neuritis, palindromic rheumatism (PR), PANDAS (Pediatric Autoimmune Neuropsychiatric Disorders Associated with *Streptococcus*), paraneoplastic cerebellar degeneration (PCD), Paroxysmal nocturnal hemoglobinuria (PNH), Parry Romberg syndrome, Pars planitis (peripheral uveitis), Parsonnage-Turner syndrome, Pemphigus, peripheral neuropathy, Perivenous encephalomyelitis, pernicious anemia (PA), POEMS syndrome (polyneuropathy, organomegaly, endocrinopathy, monoclonal gammopathy, skin changes), polyarteritis *nodosa*, polymyalgia rheumatica, polymyositis, postmyocardial infarction syndrome, postpericardiotomy syndrome, primary biliary cirrhosis, primary sclerosing cholangitis, progesterone dermatitis, psoriasis, psoriatic arthritis, pure red cell aplasia (PRCA), pyoderma gangrenosum, Raynaud's phenomenon, Reactive Arthritis, Reflex sympathetic dystrophy, Reiter's syndrome, relapsing polychondritis, restless legs syndrome (RLS), retroperitoneal fibrosis, rheumatic fever, rheumatoid arthritis (RA), sarcoidosis, Schmidt syndrome, scleritis, scleroderma, Sjogren's syndrome, sperm & testicular autoimmunity, Stiff person syndrome (SPS), subacute bacterial endocarditis (SBE), Susac's syndrome, sympathetic ophthalmia (SO), Takayasu's arteritis, temporal arteritis/Giant cell arteritis, thrombocytopenic purpura (TTP), Tolosa-Hunt syndrome (THS), transverse myelitis, type 1 diabetes, ulcerative colitis (UC), undifferentiated connective tissue disease (UCTD), uveitis, vasculitis, vitiligo, or Wegener's granulomatosis (Granulomatosis with Polyangiitis (GPA)).

The polypeptides (e.g., antibody molecules or TCR molecules) described herein are typically administered at a frequency that keeps a therapeutically effective level of polypeptides in the patient's system until the patient recovers. For example, the polypeptides may be administered at a frequency that achieves a serum concentration sufficient for at least about 1, 2, 5, 10, 20, 30, or 40 polypeptides to bind each target molecule or cell. In an embodiment, the polypeptides are administered every 1, 2, 3, 4, 5, 6, or 7 days, every 1, 2, 3, 4, 5, or 6 weeks, or every 1, 2, 3, 4, 5, or 6 months.

Methods of administering various polypeptides (e.g., antibody molecules or TCR molecules) are known in the art and are described below. Suitable dosages of the polypeptides used will depend on the age and weight of the subject and the particular drug used.

The polypeptides can be used by themselves or conjugated to a second agent, e.g., an bacterial agent, toxin, or protein, e.g., a second polypeptide. This method includes: administering the polypeptide, alone or conjugated to a second agent, to a subject requiring such treatment. The polypeptides can be used to deliver a variety of therapeutic agents, e.g., a toxin, or mixtures thereof.

Combination Therapies

The polypeptides (e.g., antibody molecules or TCR molecules) can be used in combination with other therapies. For example, the combination therapy can include a polypeptide co-formulated with, and/or co-administered with, one or more additional therapeutic agents, e.g., one or more additional therapeutic agents described herein. In other embodiments, the polypeptides are administered in combination with other therapeutic treatment modalities, e.g., other therapeutic treatment modalities described herein. Such combination therapies may advantageously utilize lower dosages of the administered therapeutic agents, thus avoiding possible toxicities or complications associated with the various monotherapies.

Administered "in combination", as used herein, means that two (or more) different treatments are delivered to the subject before, or during the course of the subject's affliction with a disorder. In an embodiment, two or more treatments are delivered prophylactically, e.g., before the subject has the disorder or is diagnosed with the disorder. In another embodiment, the two or more treatments are delivered after the subject has developed or diagnosed with the disorder. In some embodiments, the delivery of one treatment is still occurring when the delivery of the second begins, so that there is overlap. This is sometimes referred to herein as "simultaneous" or "concurrent delivery." In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

In an embodiment, the polypeptide is administered in combination with a second therapy (e.g., an additional agent) to treat or prevent a disorder described herein. In an embodiment, the additional agent is a second polypeptide (e.g., antibody molecule), e.g., a polypeptide (e.g., an antibody molecule) different from a first polypeptide (e.g., antibody molecule). Exemplary polypeptides (e.g., antibody molecules) that can be used in combination include, but are not limited to, any combination of the polypeptides (e.g., antibody molecules) described herein. In another embodiment, the additional agent is other than a polypeptide (e.g., antibody molecule). For example, the additional agent can be a small molecule or a nucleic acid molecule. In yet another embodiment, the second therapy is chosen from a surgery, a radiation therapy, a cell therapy (e.g., a stem cell therapy), or an organ or tissue transplantation.

In an embodiment, the second therapy comprises a therapy chosen from one or more of: an androgen replacement therapy, an antihormone therapy, an antiserum therapy, an autologous immune enhancement therapy, a biotherapy, a blood irradiation therapy, a brachytherapy, a cardiac resynchronization therapy, a cell therapy, a cell transfer therapy, a chelation therapy, a chemotherapy, a chrysotherapy, a cobalt therapy, a cold compression therapy, a cryotherapy, an electroconvulsive therapy, an electromagnetic therapy, an electron therapy, an electrotherapy, an enzyme replacement therapy, an epigenetic therapy, an estrogen replacement therapy, an extracorporeal shockwave therapy, a fast neutron therapy, a fluoride therapy, a gene therapy, a heat therapy, a helminthic therapy, a hormone therapy, a hormone replacement therapy, a host modulatory therapy, a hyperbaric oxygen therapy, a hyperthermia therapy, an immunosuppressive therapy, an immunotherapy, an intraoperative electron radiation therapy, an intraoperative radiation therapy, an inversion therapy, a laser therapy, a light therapy, a lithium therapy, a low level laser therapy, a magnet therapy, a magnetic resonance therapy, a medical gas therapy, a medical nutrition therapy, a molecular chaperone therapy, a molecular therapy, a monoclonal antibody therapy, a negative air ionization therapy, a neutron capture therapy, a neutron therapy, an oral rehydration therapy, an osmotherapy, an oxygen therapy, an ozone therapy, a palliative therapy, a particle therapy, a phage therapy, a phonemic neurological hypochromium therapy, a photodynamic therapy, a phototherapy, a photothermal therapy, a physical therapy, a prolotherapy, a protein therapy, a proton therapy, a pulsed electromagnetic field therapy, a PUVA therapy, a radiation therapy, a rehydration therapy, a respiratory therapy, salvage therapy, a serotherapy, a stem cell therapy, a stereotactic radiation therapy, a targeted therapy, a thermotherapy, a TK cell therapy, a tolerogenic therapy, a transdermal continuous oxygen therapy, an ultraviolet light therapy, or a virotherapy.

Exemplary therapies that can be used in combination with a polypeptide or composition described herein to treat or prevent other disorders are also described in the section of "Methods of Treating or Preventing Disorders" herein.

Methods of Diagnosis

In some aspects, the present disclosure provides a diagnostic method for detecting the presence of a target molecule (e.g., a protein) or cell in vitro (e.g., in a biological sample, such as a biopsy or body fluid (e.g., blood, urine, or cerebrospinal fluid) sample) or in vivo (e.g., in vivo imaging in a subject). The method includes: (i) contacting the sample with a polypeptide described herein (e.g., an antibody molecule described herein), or administering to the subject, the polypeptide (e.g., antibody molecule); (optionally) (ii) contacting a reference sample, e.g., a control sample (e.g., a control biological sample, such as a biopsy or body fluid (e.g., blood, urine, or cerebrospinal fluid) sample) or a control subject with a polypeptide described herein (e.g., an antibody molecule described herein); and (iii) detecting formation of a complex between the polypeptide (e.g., antibody molecule) and the target molecule or cell in the sample or subject, or the control sample or subject, wherein a change, e.g., a statistically significant change, in the formation of the complex in the sample or subject relative to the control sample or subject is indicative of the presence of the target molecule or cell in the sample. The polypeptide (e.g., antibody molecule) can be directly or indirectly labeled with a detectable substance to facilitate detection of the bound or unbound polypeptide (e.g., antibody molecule). Suitable detectable substances include various enzymes, prosthetic groups, fluorescent materials, luminescent materials and radioactive materials, as described herein.

The term "sample," as it refers to samples used for detecting bacteria includes, but is not limited to, cells, cell lysates, proteins or membrane extracts of cells, body fluids such as blood, urine, or CSF, or tissue samples such as biopsies.

Complex formation between the polypeptide (e.g., antibody molecule), and the target molecule or cell, can be detected by measuring or visualizing either the polypeptide (e.g., antibody molecule) bound to the target molecule or cell, or unbound polypeptide (e.g., antibody molecule). Any suitable detection assays can be used, and conventional detection assays include an enzyme-linked immunosorbent assay (ELISA), a radioimmunoassay (RIA), a FACS assay, a BIACORE assay, or tissue immunohistochemistry. Alternative to labeling the polypeptide, the presence of the target molecule or cell can be assayed in a sample by a competition immunoassay utilizing standards labeled with a detectable substance and an unlabeled polypeptide. In this assay, the biological sample, the labeled standards and the polypeptide are combined and the amount of labeled standard bound to the unlabeled binding molecule is determined. The amount of the target molecule or cell in the sample is inversely proportional to the amount of labeled standard bound to the polypeptide (e.g., antibody molecule).

The polypeptides (e.g., antibody molecules) described herein can be used to diagnose disorders that can be treated or prevented by the polypeptides described herein. The detection or diagnostic methods described herein can be used in combination with other methods described herein to treat or prevent disorders described herein.

Additional embodiments are described in the numbered paragraphs below.

1. A method of making a nucleic acid sequence comprising a sequence that encodes a heavy chain element (HC element) of an antibody heavy chain variable region (HCVR) and a light chain element (LC element) of an antibody light chain variable region (LCVR), and wherein the HCVR and LCVR are matched, the method comprising:
   a) acquiring an isolated production reaction site, e.g., a production micro-chamber, comprising:
      i) a heavy chain (HC) strand, wherein the HC strand is a strand of a heavy chain double-stranded cDNA (HC ds cDNA) comprising a segment that encodes an HC element of the HCVR from a cell, e.g., a heavy chain variable region sequence (HCVRS); and
      ii) a light chain (LC) strand, wherein the LC strand is a strand of a light chain double-stranded cDNA (LC ds cDNA) comprising a segment that encodes an LC element of the LCVR from the cell, e.g., a light chain variable region sequence (LCVRS), and
   b) covalent linking, e.g., ligation, of an HC strand to an LC strand,
   wherein the isolated production reaction site, e.g., a production micro-chamber, does not include a nucleic acid encoding an LCVR or an HCVR from a cell other than the cell,
   thereby making a nucleic acid sequence comprising a sequence that encodes an HC element of an HCVR and a LC element of an LCVR, wherein the HCVR and LCVR are matched.

2. The method of paragraph 1, wherein the HC element comprises, or consists of, an HCVRS, or a functional fragment thereof (e.g., an antigen binding fragment thereof).

3. The method of paragraph 1 or 2, wherein the LC element comprises, or consists of, an LCVRS, or a functional fragment thereof (e.g., an antigen binding fragment thereof).

4. The method of any of paragraphs 1-3, wherein the nucleic acid sequence is configured such that, when expressed, the HCVRS and the LCVRS form a functional antigen binding molecule, e.g., an scFv.

5. The method of paragraph 4, wherein the antigen binding molecule, e.g., an scFv, is functional in vitro, ex vivo, or in vivo, e.g., as determined by a method or assay described herein.

6. The method of any of paragraphs 1-5, wherein acquiring an isolated production reaction site, e.g., a production micro-chamber, comprises:
   a) acquiring a capture substrate bound to:
      (i) a first double-stranded cDNA (ds cDNA) comprising a strand that is complementary to a first mRNA that encodes an HCVR from a cell; and
      (ii) a second ds cDNA comprising a strand complementary to a second mRNA encoding an LCVR from the cell (the cDNA loaded capture substrate), and
   b) maintaining the isolated production reaction site, e.g., the production micro-chamber, under conditions that allow amplification of the first and second ds cDNAs, to produce:
   a plurality of HC ds cDNAs comprising a segment that encodes an HC element of the HCVR from the cell, e.g., an HCVRS; and
   a plurality of LC ds cDNAs comprising a segment that encodes an LC element of the LCVR from the cell, e.g., an LCVRS.

7. The method of paragraph 6, wherein the HC ds cDNA is identical, or substantially identical, to the first ds cDNA.

8. The method of paragraph 6 or 7, wherein the LC ds cDNA is identical, or substantially identical, to the second ds cDNA.

9. The method of any of paragraphs 6-8, wherein the capture substrate comprises a bead, e.g., a magnetic bead.

10. The method of any of paragraphs 6-9, wherein the capture substrate comprises a moiety (e.g., an oligonucleotide) which binds to cDNA, e.g., (i) a moiety which binds to the HC strand; (ii) a moiety which binds to the LC strand; or (iii) both (i) and (ii).

11. The method of any of paragraphs 6-10, wherein the first mRNA and the second mRNA are disposed on an mRNA loaded capture substrate.

12. The method of any of paragraphs 6-11, wherein the isolated production reaction site, e.g., the production micro-chamber, comprises:
   a reagent mixture suitable for producing, from the first and second mRNAs (e.g., after the first and second mRNAs are released from the mRNA loaded capture substrate into a solution), a first ds cDNA comprising a segment that encodes an HC element of the HCVR of the cell, e.g., an HCVRS, and a second ds cDNA comprising a segment that encodes an LC element of the LCVR of the cell, e.g., an LCVRS.

13. The method of any of paragraphs 6-12, wherein the isolated production reaction site, e.g., production micro-chamber, comprises primers that mediate the production of the first ds cDNA.

14. The method of any of paragraphs 6-13, wherein the isolated production reaction site, e.g., production micro-chamber, comprises primers that mediate the production of the second ds cDNA.

15. The method of any of paragraphs 6-14, wherein a cDNA strand that is complementary to a first mRNA that encodes an HCVR from a cell is made by reverse transcription of the first mRNA.

16. The method of any of paragraphs 6-15, wherein a cDNA strand that is complementary to a second mRNA that encodes an LCVR from a cell is made by reverse transcription of the second mRNA.

17. The method of paragraph 15 or 16, wherein the reverse transcription takes place in the isolated production reaction site, e.g., a production-micro chamber.

18. The method of paragraph 15 or 16, wherein the reverse transcription takes place in an isolated cell reaction site, e.g., a cell isolation micro-chamber.

19. The method of paragraph 15 or 16, wherein the reverse transcription takes place outside the isolated production reaction site, e.g., a production micro-chamber, or outside an isolated cell reaction site, e.g., a cell isolation micro-chamber.

20. The method of paragraph 15 or 16, wherein the reverse transcription takes place outside the isolated production reaction site, e.g., a production-micro chamber, and outside an isolated cell reaction site, e.g., a cell isolation micro-chamber.

21. The method of paragraph 15 or 16, wherein the reverse transcription takes place outside an isolated reaction site, e.g., outside a micro-chamber.

22. The method of any of paragraphs 6-21, wherein the amplification comprises 20 or fewer cycles, e.g., 15 or fewer, 14 or fewer, 13 or fewer, 12 or fewer, 11 or fewer, 10 or fewer, 9 or fewer, 8 or fewer, 7 or fewer, 6 or fewer, or 5 or fewer cycles.

23. The method of any of paragraphs 6-22, wherein the reverse transcription and/or amplification uses one or more primers, e.g., comprising a sequence specific for an HCVRS and/or an LCVRS.

24. The method of any of paragraphs 6-23, wherein the amplification comprises using two or more primers that mediate the production of the HC ds cDNA, wherein at least one primer comprises a nucleotide modification, and wherein at least one primer does not comprise a nucleotide modification.

25. The method of any of paragraphs 6-24, wherein the amplification comprises using two or more primers that mediate the production of the LC ds cDNA, wherein at least one primer comprises a nucleotide modification, and wherein at least one primer does not comprise a nucleotide modification.

26. The method of paragraph 25, wherein at least one primer comprises a nucleotide modification, e.g., which reduces, e.g., inhibits, DNA synthesis, e.g., by a DNA polymerase.

27. The method of paragraph 25 or 26, wherein at least one primer does not comprise a nucleotide modification, e.g., which reduces, e.g., inhibits, DNA synthesis, e.g., by a DNA polymerase.

28. The method of paragraph 26 or 27, wherein the nucleotide modification inhibits a DNA polymerase from extending the DNA.

29. The method of any of paragraphs 26-28, wherein the nucleotide modification is an insertion of a spacer to the primer, e.g., between two adjacent nucleotides in the primer.

30. The method of paragraph 29, wherein the spacer is a flexible spacer, a carbon spacer (e.g., —(CH2)n-, wherein n=3, 4, 5, or more), two or more (e.g., three, four, five, or more) abasic nucleotides or a PEG spacer.

31. The method of any of paragraphs 26-28, wherein the nucleotide modification is 2'-O-methyl, 2'-OH, 2'-NH$_2$, or uracil, e.g., to a ribose.

32. The method of any of paragraphs 26-31, wherein the nucleotide modification is located internally or at the 3' end of the primer.

33. The method of any of paragraphs 23-32, wherein at least one primer comprises (i) a first member; (ii) a second member; and optionally (iii) a nucleotide modification described herein, e.g., located between (i) and (ii).

34. The method of paragraph 33, wherein the first member is capable of annealing with the second member in the same primer or a different primer, e.g., forming a hairpin structure (via intramolecular hybridization) or a double-stranded structure (via intermolecular hybridization) comprising a duplex region of 4, 5, 6, 7, 8, 9, 10, 11, 12, 13, 14, 15, 16, 17, 18, 19, 20, more basepairs.

35. The method of paragraph 33 or 34, wherein the first member comprises a sequence that is complementary to the sequence of an oligonucleotide attached to the capture substrate.

36. The method of any of paragraphs 33-35, wherein the second member comprises (e.g., from 5' to 3') one, two, or all of: (i) a sequence that is complementary to at least a portion of the first member; (ii) a universal priming sequence (e.g., for PCR amplification or next-generation sequencing); and (iii) a sequence complementary to a target sequence, e.g., an HCVRS and/or a LCVRS, optionally, wherein the second member comprises a sequence for homologous recombination (e.g., in a yeast or mammalian cell).

37. The method of any of paragraphs 23-36, wherein at least one primer comprises a sequence encoding at least a portion of a linker sequence, or a complementary sequence thereof.

38. The method of paragraph 37, wherein the primer that comprises a sequence encoding at least a portion of a linker sequence, or a complementary sequence thereof, is phosphorylated, e.g., 5' phosphorylated.

39. The method of paragraph 37 or 38, wherein the linker sequence comprises, or consists of, (Gly-Gly-Gly-Gly-Ser)n, where n=1, 2, 3, 4, 5, or more (SEQ ID NO: 32).

40. The method of any of paragraphs 1-39, wherein the HC ds cDNA comprises a 5' overhang, e.g., a 5' overhang that is capable of hybridizing to an oligonucleotide attached to a capture substrate.

41. The method of any of paragraphs 1-40, wherein the HC ds cDNA comprises a blunt end, e.g., a blunt end comprising a 5' phosphate.

42. The method of any of paragraphs 1-41, wherein the LC ds cDNA comprises a 5' overhang, e.g., a 5' overhang that is capable of hybridizing to an oligonucleotide attached to a capture substrate.

43. The method of any of paragraphs 1-42, wherein the LC ds cDNA comprises a blunt end, e.g., a blunt end comprising a 5' phosphate.

44. The method of any of paragraphs 1-43, wherein the HC ds cDNA and the LC ds cDNA comprise sticky ends, e.g., both have 5' overhangs.

45. The method of any of paragraphs 1-44, wherein the HC strand and the LC strand are covalently linked, e.g., ligated, to produce a single stranded nucleic acid sequence, wherein the HC and LC strands are both sense strands or both antisense strands.

46. The method of any of paragraphs 1-44, wherein a denatured HC strand of the HC ds cDNA to a denatured LC strand of the LC ds cDNA are covalently linked, e.g., ligated, wherein the HC and LC strands are both sense strands or both antisense strands.

47. The method of any of paragraphs 1-44, wherein the HC strand is present in the HC ds cDNA and the LC strand is present in the LC ds cDNA, and wherein the HC ds cDNA and the LC ds cDNA are covalently linked, e.g., ligated, e.g., to produce a double stranded nucleic acid sequence.

48. The method of any of paragraphs 1-47, wherein the covalent linking, e.g., ligation, occurs in the isolated production reaction site.

49. The method of paragraph 48, wherein the isolated production reaction site, e.g., a production micro-chamber, comprises a reagent that is capable of covalently linking, e.g., ligating, the
HC and LC strands or the HC and LC ds cDNAs.

50. The method of paragraph 48 or 49, wherein the isolated production reaction site, e.g., a production micro-chamber comprises an enzyme that covalently couples the HC and LC strands or the HC and LC ds cDNAs.

51. The method of any of paragraphs 1-47, wherein the covalent linking, e.g., ligation, occurs in a site different from the isolated production reaction site, e.g., occurs in an isolated linkage reaction site, e.g., a linkage micro-chamber.

52. The method of paragraph 51, wherein the HC strand and the LC strand are transferred from the isolated production site to the isolated linkage reaction site, e.g., a linkage micro-chamber, and the covalent linking occurs in the isolated linkage reaction site, e.g., a linkage micro-chamber.

53. The method of paragraph 51 or 52, wherein the isolated linkage reaction site, e.g., a linkage micro-chamber, comprises a reagent that is capable of covalently linking, e.g., ligating, the HC and LC strands or the HC and LC ds cDNAs.

54. The method of any of paragraphs 51-53, wherein the isolated linkage reaction site, e.g., a linkage micro-chamber, comprises an enzyme that covalently couples the HC and LC strands or the
HC and LC ds cDNAs.

55. The method of paragraph 50 or 54, wherein the enzyme is a ligase, e.g., a thermal stable ligase.

56. The method of any of paragraphs 51-55, wherein the covalent linking, e.g., ligation, comprises:
(a) heating the isolated linkage reaction site, e.g., the linkage micro-chamber, under conditions (e.g., at 95° C.) that allow denaturation of the HC strand and the LC strand;
(b) cooling the isolated linkage reaction site, e.g., the linkage micro-chamber, under conditions (e.g., at 50-65° C.) that allow hybridization of the splint oligonucleotide to the HC strand and the LC strand;
(c) maintaining the isolated linkage reaction site, e.g., the linkage micro-chamber, under conditions (e.g., at 45-65° C.) that allow ligation of the HC strand and the LC strand (e.g., formation of phosphodiester bond between the HC strand and the LC strand); and
(d) repeating steps (a), (b), and (c) sequentially for 2, 5, 10, 15, 20, 25, 30, 35, 40, 45, 50, or more cycles.

57. The method of any of paragraphs 1-56, wherein the HC strand and the LC strand are covalently linked, e.g., ligated, in the presence of a splint oligonucleotide.

58. The method of paragraph 57, wherein the splint oligonucleotide is hybridized to a sequence comprising the junction of the HC strand and the LC strand, or a sequence complementary thereof, and forms a duplexed region at the site of ligation.

59. The method of paragraph 57 or 58, wherein the splint oligonucleotide comprises a modification (e.g., an $NH_2$ group) that inhibits DNA synthesis, e.g., by a DNA polymerase.

60. The method of paragraph 59, wherein the modification is at the 3' end of the splint oligonucleotide.

61. The method of any of paragraphs 1-60, wherein a strand complimentary to the covalently linked, e.g., ligated, HC and LC strands is produced by amplification.

62. The method of any of paragraphs 1-61, further comprising, prior to acquiring the isolated production reaction site, e.g., a production micro-chamber, acquiring an mRNA loaded capture substrate.

63. The method of paragraph 62, wherein acquiring the mRNA loaded capture substrate comprising:
a) acquiring an isolated cell reaction site, e.g., a cell isolation micro-chamber, comprising:
i) a cell; and
ii) a capture substrate capable of binding a first mRNA encoding an HCVR from the cell and a second mRNA encoding an LCVR from the cell; and
b) maintaining the isolated cell reaction site, e.g., the cell isolation micro-chamber, under conditions that allow lysis of the cell and binding of the capture substrate with the first mRNA and the second mRNA to form the mRNA loaded capture substrate,
wherein the isolated cell reaction site, e.g., cell isolation micro-chamber, does not include a nucleic acid encoding an HCVR or an LCVR from a cell other than the cell.

64. The method of paragraph 63, wherein the isolated cell reaction site, e.g., cell isolation micro-chamber, comprises a lysing reagent, e.g., a detergent.

65. The method of paragraph 63 or 64, wherein the cell is lysed by heat or an enzyme.

66. The method of any of paragraphs 63-65, wherein the capture substrate comprises a moiety (e.g., an oligonucleotide) which binds mRNA, e.g., an oligo(dT).

67. The method of any of paragraphs 62-66, further comprising releasing the mRNA loaded capture substrate from the isolated cell reaction site, e.g., the cell isolation micro-chamber.

68. The method of paragraph 67, wherein the releasing step is performed in the presence of a poly(dA) or poly(dT) oligonucleotide, e.g., to reduce cross-binding of non-captured mRNA.

69. The method of paragraph 62-68, wherein the mRNA loaded capture substrate is transferred from the isolated cell reaction site, e.g., the cell isolation micro-chamber, to the isolated production reaction site, e.g., the production micro-chamber.

70. The method of any of paragraphs 1-69, comprising releasing the nucleic acid sequence from the production micro-chamber.

71. The method of any of paragraphs 1-70, further comprising amplifying the nucleic acid sequence.

72. The method of any of paragraphs 1-71, comprising sequencing all or a portion of the nucleic acid sequence.

73. The method of any of paragraphs 1-72, comprising inserting all or a portion of nucleic acid sequence into a vector.

74. The method of paragraph 73, wherein the vector supplies an additional HC element or LC element not included in the nucleic acid sequence.

75. The method of paragraph 73 or 74, wherein the vector supplies an HC CDR1, an HC CDR2, or both.

76. The method of any of paragraphs 73-75, comprising expressing the vector.

77. The method of any of paragraphs 1-76, comprising expressing the nucleic acid sequence to produce a polypeptide comprising a segment that encodes an HC element of the HCVR, e.g., an HCVRS, and a segment that encodes an LC element of the LCVR, e.g., an LCVRS.

78. The method of paragraph 77, wherein the LC element is N-terminal to the HC element in the polypeptide.

79. The method of paragraph 77, wherein the HC element is C-terminal to the LC element in the polypeptide.

80. The method of any of paragraphs 77-79, further comprising contacting the polypeptide with an antigen.

81. The method of any of paragraphs 77-80, further comprising determining if the polypeptide binds the antigen.

82. The method of any of paragraphs 1-81, wherein the cell is an immune cell, e.g., a B cell or T cell, e.g., a human B cell or T cell.

83. The method of any of paragraphs 1-82, wherein the cell is a mammalian cell or an avian cell.

84. A method of making a nucleic acid sequence comprising a sequence that encodes a heavy chain element (HC element) of an antibody heavy chain variable region (HCVR) and a light chain element (LC element) of an antibody light chain variable region (LCVR), and wherein the HCVR and LCVR are matched, comprising:

a) acquiring an isolated cell reaction site, e.g., a cell isolation micro-chamber, comprising:
  i) a cell; and
  ii) a capture substrate capable of binding a first mRNA encoding an HCVR from the cell and a second mRNA encoding an LCVR from the cell;

b) maintaining isolated cell reaction site, e.g., the cell isolation micro-chamber, under conditions that allow lysis of the cell and binding of the capture substrate with the first mRNA and the second mRNA to form the mRNA loaded capture substrate, wherein the isolated cell reaction site, e.g., cell isolation micro-chamber, does not include a nucleic acid encoding an HCVR or an LCVR from a cell other than the cell;

c) contacting the mRNA loaded capture substrate with a reaction mixture, e.g., a reaction mixture comprising reverse transcriptase, that uses the loaded mRNA as a template to make cDNA (this can occur, e.g., in the isolated cell reaction site, in the isolated production reaction site, or in neither, e.g., not in an isolated reaction site);

d) acquiring an isolated production reaction site, e.g., a production micro-chamber, comprising:
  i) a heavy chain (HC) strand from step b), wherein the HC strand is a strand of a heavy chain double-stranded cDNA (HC ds cDNA) comprising a segment that encodes an HC element of the HCVR from the cell, e.g., a heavy chain variable region sequence (HCVRS); and
  ii) a light chain (LC) strand from step b), wherein the LC strand is a strand of a light chain double-stranded cDNA (LC ds cDNA) comprising a segment that encodes an LC element of the LCVR from the cell, e.g., a light chain variable region sequence (LCVRS); and e) covalent linking, e.g., ligation, of an HC strand to an LC strand, wherein the isolated production reaction site, e.g., a production micro-chamber, does not include a nucleic acid encoding an LCVR or an HCVR from a cell other than the cell.

85. A method of making a nucleic acid sequence comprising a sequence that encodes a heavy chain element (HC element) of an antibody heavy chain variable region (HCVR) and a light chain element (LC element) of an antibody light chain variable region (LCVR), and wherein the HCVR and LCVR are matched, comprising:

a) acquiring an isolated cell reaction site, e.g., a cell isolation micro-chamber, comprising:
  i) a cell; and
  ii) a capture substrate capable of binding a first mRNA encoding an HCVR from the cell and a second mRNA encoding an LCVR from the cell;

b) maintaining the isolated cell reaction site, e.g., the cell isolation micro-chamber, under conditions that allow lysis of the cell and binding of the capture substrate with the first mRNA and the second mRNA to form the mRNA loaded capture substrate, wherein the isolated cell reaction site, e.g., cell isolation micro-chamber, does not include a nucleic acid encoding an HCVR or an LCVR from a cell other than the cell;

c) acquiring an isolated production reaction site, e.g., a production micro-chamber, comprises: contacting the mRNA loaded capture substrate with a reaction mixture, e.g., a reaction mixture comprising reverse transcriptase, that uses the loaded mRNA as a template, to produce:
  a first double-stranded cDNA (ds cDNA) comprising a strand that is complementary to a first mRNA that encodes an HCVR from a cell; and
  a second ds cDNA comprising a strand complementary to a second mRNA encoding an LCVR from the cell (the cDNA loaded capture substrate);
  wherein the isolated production reaction site, e.g., a production micro-chamber, does not include a nucleic acid encoding an LCVR or an HCVR from a cell other than the cell.

d) maintaining the isolated production reaction site, e.g., the production micro-chamber, under conditions that allow amplification of the first and second ds cDNAs, to produce:
  a plurality of HC ds cDNAs comprising a segment that encodes an HC element of the HCVR from the cell, e.g., an HCVRS; and
  a plurality of LC ds cDNAs comprising a segment that encodes an LC element of the LCVR from the cell, e.g., an LCVRS;

e) acquiring an isolated linkage reaction site, e.g., a linkage micro-chamber, comprising: covalent linking, e.g., ligation, of a strand of the HC ds cDNA (HC strand) to a strand of the LC ds cDNA (LC strand), wherein the HC and LC strands are both sense strands or antisense strands; and f) amplifying the covalently linked, e.g., ligated, HC and LC strands.

86. A method of making a library comprising a plurality of unique members, the method comprising:

making the plurality of members, wherein each of the members comprises a sequence that encodes a heavy chain element (HC element) of a heavy chain variable region (HCVR) and a light chain element (LC element) of a light chain variable region (LCVR), and wherein the HCVR and LCVR are matched, made by a method of any of paragraphs 1-85, wherein each unique nucleic acid sequence of the plurality comprises an HC element and an LC element from a different unique cell, thereby making a library comprising a plurality of unique members.

87. The method of paragraph 86, wherein the plurality of unique members comprises at least $10^4$, $10^5$, $10^6$, $10^7$, $10^8$, or $10^9$ unique members.

88. The method of paragraph 86 or 87, wherein the plurality of unique members comprises $10^4$ to $10^9$, $10^4$ to $10^8$, $10^4$ to $10^7$, $10^4$ to $10^6$, $10^4$ to $10^5$, $10^8$ to $10^9$, $10^7$ to $10^9$, $10^6$ to $10^9$, $10^5$ to $10^9$, $10^5$ to $10^8$, $10^6$ to $10^7$, $10^4$ to $10^5$, $10^5$ to $10^6$, $10^6$ to $10^7$, $10^7$ to $10^8$, or $10^8$ to $10^9$ unique members.

89. The method of any of paragraphs 86-88, wherein at least 80%, 85%, 90%, 95%, 96%, 97%, 98%, 99%, or 100%, of the members in the library are unique members (which encode matched HC element and LC element sequences).

90. The method of any of paragraphs 86-89, wherein less than 20%, 15%, 10%, 5%, 4%, 3%, 2%, or 1%, of the members in the library are unique members (which encode matched HC element and LC element sequences).

91. A library comprising:
a plurality of unique members,
wherein,
i) each unique member of the plurality comprises a segment that encodes an HC element, e.g., an HCVRS, and a segment that encodes an LC element, e.g., an LCVRS, wherein the HC element and the LC element in each unique member is matched;
ii) each unique member of the plurality comprises a segment that encodes an HC element, e.g., an HCVRS, and a segment that encodes an LC element, e.g., an LCVRS, from a different unique cell; and
iii) the library comprises one or more (e.g., two, three, four, or all) of the following properties:
a) the library is made by a method of any of paragraphs 1-85;
b) the plurality of unique members comprises at least $10^4$, $10^5$, $10^6$, $10^7$, $10^8$, or $10^9$ unique nucleic acid sequences;
c) the plurality of unique members comprises $10^4$ to $10^9$, $10^4$ to $10^8$, $10^4$ to $10^7$, $10^4$ to $10^6$, $10^4$ to $10^5$, $10^8$ to $10^9$, $10^7$ to $10^9$, $10^6$ to $10^9$, $10^5$ to $10^9$, $10^5$ to $10^8$, $10^6$ to $10^7$, $10^4$ to $10^5$, $10^5$ to $10^6$, $10^6$ to $10^7$, $10^7$ to $10^8$, or $10^8$ to $10^9$ unique members;
d) at least 80%, 85%, 90%, 95%, 96%, 97%, 98%, 99%, or 100%, of the members in the library are unique members (which encode matched HC element and LC element sequences); or
e) less than 20%, 15%, 10%, 5%, 4%, 3%, 2%, or 1%, of the members in the library are unique members (which encode matched HC element and LC element sequences).

92. The library of paragraph 91, wherein each unique member of the plurality is configured such that, when expressed, the HC element, e.g., the HCVRS, and the LC element, e.g., the LCVRS, form a functional antigen binding molecule, e.g., an scFv.

93. The library of any of paragraphs 91-92, wherein the library is a display library.

94. The library of any of paragraphs 91-93, wherein each of the members of the plurality further encodes a polypeptide that results in display of the member on the surface of a display entity.

95. The library of any of paragraphs 91-94, wherein the library is a phage display library.

96. The library of any of paragraphs 91-94, wherein the library is a yeast display library.

97. The library of any of paragraphs 91-94, wherein the library is a mammalian display library.

98. A method of making a binding polypeptide, the method comprising:
a) acquiring a library of any of paragraphs 91-97; and
b) expressing a polypeptide encoded by a unique nucleic acid of the library.

99. The method of paragraph 98, further comprising contacting the polypeptide with an antigen.

100. The method of paragraph 98 or 99, further comprising retrieving the nucleic acid that encodes a polypeptide that binds the antigen.

101. A method of making a nucleic acid sequence comprising a sequence that encodes an α chain element (AC element) of a TCR α chain variable region (ACVR) and a β chain element (BC element) of a TCR β chain variable region (BCVR), and wherein the ACVR and BCVR are matched, the method comprising:
a) acquiring an isolated production reaction site, e.g., a production micro-chamber, comprising:
i) an α chain (AC) strand, wherein the AC strand is a strand of an α chain double-stranded cDNA (AC ds cDNA) comprising a segment that encodes an AC element of the ACVR from a cell, e.g., an α chain variable region sequence (ACVRS); and
ii) a β chain (BC) strand, wherein the BC strand is a strand of a β chain double-stranded cDNA (BC ds cDNA) comprising a segment that encodes a BC element of the BCVR from the cell, e.g., a β chain variable region sequence (BCVRS), and
b) covalent linking, e.g., ligation, of an AC strand to a BC strand,
wherein the isolated production reaction site, e.g., a production micro-chamber, does not include a nucleic acid encoding a BCVR or an ACVR from a cell other than the cell,
thereby making a nucleic acid sequence comprising a sequence that encodes an AC element of an ACVR and a BC element of a BCVR, wherein the ACVR and BCVR are matched.

102. The method of paragraph 101, wherein the AC element comprises, or consists of, an ACVRS, or a functional fragment thereof (e.g., an antigen binding fragment thereof).

103. The method of paragraph 101 or 102, wherein the BC element comprises, or consists of, a BCVRS, or a functional fragment thereof (e.g., an antigen binding fragment thereof).

104. The method of any of paragraphs 101-103, wherein the nucleic acid sequence is configured such that, when expressed, the ACVRS and the BCVRS form a functional antigen binding molecule, e.g., a single chain TCR molecule.

105. The method of paragraph 104, wherein the antigen binding molecule is functional in vitro, ex vivo, or in vivo, e.g., as determined by a method or assay described herein.

106. The method of any of paragraphs 101-105, wherein acquiring an isolated production reaction site, e.g., a production micro-chamber, comprises:
a) acquiring a capture substrate bound to:
(i) a first double-stranded cDNA (ds cDNA) comprising a strand that is complementary to a first mRNA that encodes an ACVR from a cell; and
(ii) a second ds cDNA comprising a strand complementary to a second mRNA encoding a BCVR from the cell (the cDNA loaded capture substrate), and b) maintaining the isolated production reaction site, e.g., the production micro-chamber, under conditions that allow amplification of the first and second ds cDNAs, to produce:

a plurality of AC ds cDNAs comprising a segment that encodes an AC element of the ACVR from the cell, e.g., an ACVRS; and a plurality of BC ds cDNAs comprising a segment that encodes a BC element of the BCVR from the cell, e.g., a BCVRS.

107. The method of paragraph 106, wherein the AC ds cDNA is identical, or substantially identical, to the first ds cDNA.

108. The method of paragraph 106 or 107, wherein the BC ds cDNA is identical, or substantially identical, to the second ds cDNA.

109. The method of any of paragraphs 106-108, wherein the capture substrate comprises a bead, e.g., a magnetic bead.

110. The method of any of paragraphs 106-109, wherein the capture substrate comprises a moiety (e.g., an oligonucleotide) which binds to cDNA, e.g., (i) a moiety which binds to the AC strand; (ii) a moiety which binds to the BC strand; or (iii) both (i) and (ii).

111. The method of any of paragraphs 106-110, wherein the first mRNA and the second mRNA are disposed on an mRNA loaded capture substrate.

112. The method of any of paragraphs 106-111, wherein the isolated production reaction site, e.g., the production micro-chamber, comprises:

a reagent mixture suitable for producing, from the first and second mRNAs (e.g., after the first and second mRNAs are released from the mRNA loaded capture substrate into a solution), a first ds cDNA comprising a segment that encodes an AC element of the ACVR of the cell, e.g., an ACVRS, and a second ds cDNA comprising a segment that encodes a BC element of the BCVR of the cell, e.g., a BCVRS.

113. The method of any of paragraphs 106-112, wherein the isolated production reaction site, e.g., production micro-chamber, comprises primers that mediate the production of the first ds cDNA.

114. The method of any of paragraphs 106-113, wherein the isolated production reaction site, e.g., production micro-chamber, comprises primers that mediate the production of the second ds cDNA.

115. The method of any of paragraphs 106-114, wherein a cDNA strand that is complementary to a first mRNA that encodes an ACVR from a cell is made by reverse transcription of the first mRNA.

116. The method of any of paragraphs 106-115, wherein a cDNA strand that is complementary to a second mRNA that encodes a BCVR from a cell is made by reverse transcription of the second mRNA.

117. The method of paragraph 115 or 116, wherein the reverse transcription takes place in the isolated production reaction site, e.g., a production-micro chamber.

118. The method of paragraph 115 or 116, wherein the reverse transcription takes place in an isolated cell reaction site, e.g., a cell isolation micro-chamber.

119. The method of paragraph 115 or 116, wherein the reverse transcription takes place outside the isolated production reaction site, e.g., a production micro-chamber, or outside an isolated cell reaction site, e.g., a cell isolation micro-chamber.

120. The method of paragraph 115 or 116, wherein the reverse transcription takes place outside the isolated production reaction site, e.g., a production-micro chamber, and outside an isolated cell reaction site, e.g., a cell isolation micro-chamber.

121. The method of paragraph 115 or 116, wherein the reverse transcription takes place outside an isolated reaction site, e.g., outside a micro-chamber.

122. The method of any of paragraphs 106-121, wherein the amplification comprises 20 or fewer cycles, e.g., 15 or fewer, 14 or fewer, 13 or fewer, 12 or fewer, 11 or fewer, 10 or fewer, 9 or fewer, 8 or fewer, 7 or fewer, 6 or fewer, or 5 or fewer cycles.

123. The method of any of paragraphs 106-122, wherein the reverse transcription and/or amplification uses one or more primers, e.g., comprising a sequence specific for an ACVRS and/or a BCVRS.

124. The method of any of paragraphs 106-123, wherein the amplification comprises using two or more primers that mediate the production of the AC ds cDNA, wherein at least one primer comprises a nucleotide modification, and wherein at least one primer does not comprise a nucleotide modification.

125. The method of any of paragraphs 106-124, wherein the amplification comprises using two or more primers that mediate the production of the BC ds cDNA, wherein at least one primer comprises a nucleotide modification, and wherein at least one primer does not comprise a nucleotide modification.

126. The method of paragraph 125, wherein at least one primer comprises a nucleotide modification, e.g., which reduces, e.g., inhibits, DNA synthesis, e.g., by a DNA polymerase.

127. The method of paragraph 125 or 126, wherein at least one primer does not comprise a nucleotide modification, e.g., which reduces, e.g., inhibits, DNA synthesis, e.g., by a DNA polymerase.

128. The method of paragraph 126 or 127, wherein the nucleotide modification inhibits a DNA polymerase from extending the DNA.

129. The method of any of paragraphs 126-128, wherein the nucleotide modification is an insertion of a spacer to the primer, e.g., between two adjacent nucleotides in the primer.

130. The method of paragraph 129, wherein the spacer is a flexible spacer, a carbon spacer (e.g., —(CH2)n-, wherein n=3, 4, 5, or more), two or more (e.g., three, four, five, or more) abasic nucleotides or a PEG spacer.

131. The method of any of paragraphs 126-128, wherein the nucleotide modification is 2'-O-methyl, 2'-OH, 2'-NH$_2$, or uracil, e.g., to a ribose.

132. The method of any of paragraphs 126-131, wherein the nucleotide modification is located internally or at the 3' end of the primer.

133. The method of any of paragraphs 123-132, wherein at least one primer comprises (i) a first member; (ii) a second member; and optionally (iii) a nucleotide modification described herein, e.g., located between (i) and (ii).

134. The method of paragraph 133, wherein the first member is capable of annealing with the second member in the same primer or a different primer, e.g., forming a hairpin structure (via intramolecular hybridization) or a double-stranded structure (via intermolecular hybridization) comprising a duplex region of 4, 5, 6, 7, 8, 9, 10, 11, 12, 13, 14, 15, 16, 17, 18, 19, 20, more basepairs.

135. The method of paragraph 133 or 134, wherein the first member comprises a sequence that is complementary to the sequence of an oligonucleotide attached to the capture substrate.

136. The method of any of paragraphs 133-135, wherein the second member comprises (e.g., from 5' to 3') one, two, or all of: (i) a sequence that is complementary to at least a portion of the first member; (ii) a universal priming sequence (e.g., for PCR amplification or next-generation sequencing); and (iii) a sequence complementary to a target sequence, e.g., an ACVRS and/or a BCVRS, optionally, wherein the second member comprises a sequence for homologous recombination (e.g., in a yeast or mammalian cell).

137. The method of any of paragraphs 123-136, wherein at least one primer comprises a sequence encoding at least a portion of a linker sequence, or a complementary sequence thereof.

138. The method of paragraph 137, wherein the primer that comprises a sequence encoding at least a portion of a linker sequence, or a complementary sequence thereof, is phosphorylated, e.g., 5' phosphorylated.

139. The method of paragraph 137 or 138, wherein the linker sequence comprises, or consists of, (Gly-Gly-Gly-Gly-Ser)n, where n=1, 2, 3, 4, 5, or more (SEQ ID NO: 32).

140. The method of any of paragraphs 101-139, wherein the AC ds cDNA comprises a 5' overhang, e.g., a 5' overhang that is capable of hybridizing to an oligonucleotide attached to a capture substrate.

141. The method of any of paragraphs 101-140, wherein the AC ds cDNA comprises a blunt end, e.g., a blunt end comprising a 5' phosphate.

142. The method of any of paragraphs 101-141, wherein the BC ds cDNA comprises a 5' overhang, e.g., a 5' overhang that is capable of hybridizing to an oligonucleotide attached to a capture substrate.

143. The method of any of paragraphs 101-142, wherein the BC ds cDNA comprises a blunt end, e.g., a blunt end comprising a 5' phosphate.

144. The method of any of paragraphs 101-143, wherein the AC ds cDNA and the BC ds cDNA comprise sticky ends, e.g., both have 5' overhangs.

145. The method of any of paragraphs 101-144, wherein the AC strand and the BC strand are covalently linked, e.g., ligated, to produce a single stranded nucleic acid sequence, wherein the AC and BC strands are both sense strands or both antisense strands.

146. The method of any of paragraphs 101-144, wherein a denatured AC strand of the AC ds cDNA to a denatured BC strand of the BC ds cDNA are covalently linked, e.g., ligated, wherein the AC and BC strands are both sense strands or both antisense strands.

147. The method of any of paragraphs 101-144, wherein the AC strand is present in the AC ds cDNA and the BC strand is present in the BC ds cDNA, and wherein the AC ds cDNA and the BC ds cDNA are covalently linked, e.g., ligated, e.g., to produce a double stranded nucleic acid sequence.

148. The method of any of paragraphs 101-147, wherein the covalent linking, e.g., ligation, occurs in the isolated production reaction site.

149. The method of paragraph 148, wherein the isolated production reaction site, e.g., a production micro-chamber, comprises a reagent that is capable of covalently linking, e.g., ligating, the AC and BC strands or the AC and BC ds cDNAs.

150. The method of paragraph 148 or 149, wherein the isolated production reaction site, e.g., a production micro-chamber comprises an enzyme that covalently couples the AC and BC strands or the AC and BC ds cDNAs.

151. The method of any of paragraphs 101-147, wherein the covalent linking, e.g., ligation, occurs in a site different from the isolated production reaction site, e.g., occurs in an isolated linkage reaction site, e.g., a linkage micro-chamber.

152. The method of paragraph 151, wherein the AC strand and the BC strand are transferred from the isolated production site to the isolated linkage reaction site, e.g., a linkage micro-chamber, and the covalent linking occurs in the isolated linkage reaction site, e.g., a linkage micro-chamber.

153. The method of paragraph 151 or 152, wherein the isolated linkage reaction site, e.g., a linkage micro-chamber, comprises a reagent that is capable of covalently linking, e.g., ligating, the AC and BC strands or the AC and BC ds cDNAs.

154. The method of any of paragraphs 151-153, wherein the isolated linkage reaction site, e.g., a linkage micro-chamber, comprises an enzyme that covalently couples the AC and BC strands or the AC and BC ds cDNAs.

155. The method of paragraph 150 or 154, wherein the enzyme is a ligase, e.g., a thermal stable ligase.

156. The method of any of paragraphs 151-155, wherein the covalent linking, e.g., ligation, comprises:
(a) heating the isolated linkage reaction site, e.g., the linkage micro-chamber, under conditions (e.g., at 95° C.) that allow denaturation of the AC strand and the BC strand;
(b) cooling the isolated linkage reaction site, e.g., the linkage micro-chamber, under conditions (e.g., at 50-65° C.) that allow hybridization of the splint oligonucleotide to the AC strand and the BC strand;
(c) maintaining the isolated linkage reaction site, e.g., the linkage micro-chamber, under conditions (e.g., at 45-65° C.) that allow ligation of the AC strand and the BC strand (e.g., formation of phosphodiester bond between the AC strand and the BC strand); and
(d) repeating steps (a), (b), and (c) sequentially for 2, 5, 10, 15, 20, 25, 30, 35, 40, 45, 50, or more cycles.

157. The method of any of paragraphs 101-156, wherein the AC strand and the BC strand are covalently linked, e.g., ligated, in the presence of a splint oligonucleotide.

158. The method of paragraph 157, wherein the splint oligonucleotide is hybridized to a sequence comprising the junction of the AC strand and the BC strand, or a sequence complementary thereof, and forms a duplexed region at the site of ligation.

159. The method of paragraph 157 or 158, wherein the splint oligonucleotide comprises a modification (e.g., an $NH_2$ group) that inhibits DNA synthesis, e.g., by a DNA polymerase.

160. The method of paragraph 159, wherein the modification is at the 3' end of the splint oligonucleotide.

161. The method of any of paragraphs 101-160, wherein a strand complimentary to the covalently linked, e.g., ligated, AC and BC strands is produced by amplification.

162. The method of any of paragraphs 101-161, further comprising, prior to acquiring the isolated production reaction site, e.g., a production micro-chamber, acquiring an mRNA loaded capture substrate.

163. The method of paragraph 162, wherein acquiring the mRNA loaded capture substrate comprising:
a) acquiring an isolated cell reaction site, e.g., a cell isolation micro-chamber, comprising:
i) a cell; and
ii) a capture substrate capable of binding a first mRNA encoding an ACVR from the cell and a second mRNA encoding a BCVR from the cell; and
b) maintaining the isolated cell reaction site, e.g., the cell isolation micro-chamber, under conditions that allow lysis of the cell and binding of the capture substrate with the first mRNA and the second mRNA to form the mRNA loaded capture substrate, wherein the isolated cell reaction site, e.g., cell isolation micro-chamber, does not include a nucleic acid encoding an ACVR or a BCVR from a cell other than the cell.

164. The method of paragraph 163, wherein the isolated cell reaction site, e.g., cell isolation micro-chamber, comprises a lysing reagent, e.g., a detergent.

165. The method of paragraph 163 or 164, wherein the cell is lysed by heat or an enzyme.

166. The method of any of paragraphs 163-165, wherein the capture substrate comprises a moiety (e.g., an oligonucleotide) which binds mRNA, e.g., an oligo(dT).

167. The method of any of paragraphs 162-166, further comprising releasing the mRNA loaded capture substrate from the isolated cell reaction site, e.g., the cell isolation micro-chamber.

168. The method of paragraph 167, wherein the releasing step is performed in the presence of a poly(dA) or poly(dT) oligonucleotide, e.g., to reduce cross-binding of non-captured mRNA.

169. The method of paragraph 162-168, wherein the mRNA loaded capture substrate is transferred from the isolated cell reaction site, e.g., the cell isolation micro-chamber, to the isolated production reaction site, e.g., the production micro-chamber.

170. The method of any of paragraphs 101-169, comprising releasing the nucleic acid sequence from the production micro-chamber.

171. The method of any of paragraphs 101-170, further comprising amplifying the nucleic acid sequence.

172. The method of any of paragraphs 101-171, comprising sequencing all or a portion of the nucleic acid sequence.

173. The method of any of paragraphs 101-72, comprising inserting all or a portion of nucleic acid sequence into a vector.

174. The method of paragraph 173, wherein the vector supplies an additional AC element or BC element not included in the nucleic acid sequence.

175. The method of paragraph 173 or 174, wherein the vector supplies an AC CDR1, an AC CDR2, or both.

176. The method of any of paragraphs 173-175, comprising expressing the vector.

177. The method of any of paragraphs 101-176, comprising expressing the nucleic acid sequence to produce a polypeptide comprising a segment that encodes an AC element of the ACVR, e.g., an ACVRS, and a segment that encodes a BC element of the BCVR, e.g., a BCVRS.

178. The method of paragraph 177, wherein the BC element is N-terminal to the AC element in the polypeptide.

179. The method of paragraph 177, wherein the AC element is C-terminal to the BC element in the polypeptide.

180. The method of any of paragraphs 177-179, further comprising contacting the polypeptide with an antigen.

181. The method of any of paragraphs 177-180, further comprising determining if the polypeptide binds the antigen.

182. The method of any of paragraphs 101-181, wherein the cell is an immune cell, e.g., a B cell or T cell, e.g., a human B cell or T cell.

183. The method of any of paragraphs 101-182, wherein the cell is a mammalian cell or an avian cell.

184. A method of making a nucleic acid sequence comprising a sequence that encodes an α chain element (AC element) of a TCR α chain variable region (ACVR) and a β chain element (BC element) of a TCR β chain variable region (BCVR), and wherein the ACVR and BCVR are matched, comprising:

a) acquiring an isolated cell reaction site, e.g., a cell isolation micro-chamber, comprising:
i) a cell; and
ii) a capture substrate capable of binding a first mRNA encoding an ACVR from the cell and a second mRNA encoding a BCVR from the cell;

b) maintaining isolated cell reaction site, e.g., the cell isolation micro-chamber, under conditions that allow lysis of the cell and binding of the capture substrate with the first mRNA and the second mRNA to form the mRNA loaded capture substrate, wherein the isolated cell reaction site, e.g., cell isolation micro-chamber, does not include a nucleic acid encoding an ACVR or a BCVR from a cell other than the cell;

c) contacting the mRNA loaded capture substrate with a reaction mixture, e.g., a reaction mixture comprising reverse transcriptase, that uses the loaded mRNA as a template to make cDNA (this can occur, e.g., in the isolated cell reaction site, in the isolated production reaction site, or in neither, e.g., not in an isolated reaction site);

d) acquiring an isolated production reaction site, e.g., a production micro-chamber, comprising:
i) an α chain (AC) strand from step b), wherein the AC strand is a strand of an α chain double-stranded cDNA (AC ds cDNA) comprising a segment that encodes an AC element of the ACVR from the cell, e.g., a α chain variable region sequence (ACVRS); and
ii) a β chain (BC) strand from step b), wherein the BC strand is a strand of a β chain double-stranded cDNA (BC ds cDNA) comprising a segment that encodes a BC element of the BCVR from the cell, e.g., a β chain variable region sequence (BCVRS); and e) covalent linking, e.g., ligation, of an AC strand to a BC strand, wherein the isolated production reaction site, e.g., a production micro-chamber, does not include a nucleic acid encoding a BCVR or an ACVR from a cell other than the cell.

185. A method of making a nucleic acid sequence comprising a sequence that encodes a α chain element (AC element) of an TCR α chain variable region (ACVR) and a β chain element (BC element) of an TCR β chain variable region (BCVR), and wherein the ACVR and BCVR are matched, comprising:

a) acquiring an isolated cell reaction site, e.g., a cell isolation micro-chamber, comprising:
i) a cell; and
ii) a capture substrate capable of binding a first mRNA encoding an ACVR from the cell and a second mRNA encoding a BCVR from the cell;

b) maintaining the isolated cell reaction site, e.g., the cell isolation micro-chamber, under conditions that allow lysis of the cell and binding of the capture substrate with the first mRNA and the second mRNA to form the mRNA loaded capture substrate, wherein the isolated cell reaction site, e.g., cell isolation micro-chamber, does not include a nucleic acid encoding an ACVR or a BCVR from a cell other than the cell;

c) acquiring an isolated production reaction site, e.g., a production micro-chamber, comprises: contacting the mRNA loaded capture substrate with a reaction mixture, e.g., a reaction mixture comprising reverse transcriptase, that uses the loaded mRNA as a template, to produce:

a first double-stranded cDNA (ds cDNA) comprising a strand that is complementary to a first mRNA that encodes an ACVR from a cell; and a second ds cDNA comprising a strand complementary to a second mRNA encoding a BCVR from the cell (the cDNA loaded capture substrate);

wherein the isolated production reaction site, e.g., a production micro-chamber, does not include a nucleic acid encoding a BCVR or an ACVR from a cell other than the cell.

d) maintaining the isolated production reaction site, e.g., the production micro-chamber, under conditions that allow amplification of the first and second ds cDNAs, to produce:

a plurality of AC ds cDNAs comprising a segment that encodes an AC element of the ACVR from the cell, e.g., an ACVRS; and a plurality of BC ds cDNAs comprising a segment that encodes a BC element of the BCVR from the cell, e.g., a BCVRS;

e) acquiring an isolated linkage reaction site, e.g., a linkage micro-chamber, comprising: covalent linking, e.g., ligation, of a strand of the AC ds cDNA (AC strand) to a strand of the BC ds cDNA (BC strand), wherein the AC and BC strands are both sense strands or antisense strands; and f) amplifying the covalently linked, e.g., ligated, AC and BC strands.

186. A method of making a library comprising a plurality of unique members, the method comprising:

making the plurality of members, wherein each of the members comprises a sequence that encodes a α chain element (AC element) of a α chain variable region (ACVR) and a β chain element (BC element) of a β chain variable region (BCVR), and wherein the ACVR and BCVR are matched, made by a method of any of paragraphs 101-185, wherein each unique nucleic acid sequence of the plurality comprises an AC element and a BC element from a different unique cell, thereby making a library comprising a plurality of unique members.

187. The method of paragraph 186, wherein the plurality of unique members comprises at least $10^4$, $10^5$, $10^6$, $10^7$, $10^8$, or $10^9$ unique members.

188. The method of paragraph 186 or 187, wherein the plurality of unique members comprises $10^4$ to $10^9$, $10^4$ to $10^8$, $10^4$ to $10^7$, $10^4$ to $10^6$, $10^4$ to $10^5$, $10^8$ to $10^9$, $10^7$ to $10^9$, $10^6$ to $10^9$, $10^5$ to $10^9$, $10^5$ to $10^8$, $10^6$ to $10^7$, $10^4$ to $10^5$, $10^5$ to $10^6$, $10^6$ to $10^7$, $10^7$ to $10^8$, or $10^8$ to $10^9$ unique members.

189. The method of any of paragraphs 186-188, wherein at least 80%, 85%, 90%, 95%, 96%, 97%, 98%, 99%, or 100%, of the members in the library are unique members (which encode matched AC element and BC elements sequences).

190. The method of any of paragraphs 186-189, wherein less than 20%, 15%, 10%, 5%, 4%, 3%, 2%, or 1%, of the members in the library are unique members (which encode matched AC element and BC elements sequences).

191. A library comprising:
a plurality of unique members,
wherein,
i) each unique member of the plurality comprises a segment that encodes an AC element, e.g., an ACVRS, and a segment that encodes a BC element, e.g., a BCVRS, wherein the AC element and the BC element in each unique member is matched;

ii) each unique member of the plurality comprises a segment that encodes an AC element, e.g., an ACVRS, and a segment that encodes a BC element, e.g., a BCVRS, from a different unique cell; and iii) the library comprises one or more (e.g., two, three, four, or all) of the following properties:

a) the library is made by a method of any of paragraphs 101-185;

b) the plurality of unique members comprises at least $10^4$, $10^5$, $10^6$, $10^7$, $10^8$, or $10^9$ unique nucleic acid sequences;

c) the plurality of unique members comprises $10^4$ to $10^9$, $10^4$ to $10^8$, $10^4$ to $10^7$, $10^4$ to $10^6$, $10^4$ to $10^5$, $10^8$ to $10^9$, $10^7$ to $10^9$, $10^6$ to $10^9$, $10^5$ to $10^9$, $10^5$ to $10^8$, $10^6$ to $10^7$, $10^4$ to $10^5$, $10^5$ to $10^6$, $10^6$ to $10^7$, $10^7$ to $10^8$, or $10^8$ to $10^9$ unique members;

d) at least 80%, 85%, 90%, 95%, 96%, 97%, 98%, 99%, or 100%, of the members in the library are unique members (which encode matched AC element and BC elements sequences); or e) less than 20%, 15%, 10%, 5%, 4%, 3%, 2%, or 1%, of the members in the library are unique members (which encode matched AC element and BC elements sequences).

192. The library of paragraph 191, wherein each unique member of the plurality is configured such that, when expressed, the AC element, e.g., the ACVRS, and the BC element, e.g., the BCVRS, form a functional antigen binding molecule, e.g., a single chain TCR.

193. The library of any of paragraphs 191-192, wherein the library is a display library.

194. The library of any of paragraphs 191-193, wherein each of the members of the plurality further encodes a polypeptide that results in display of the member on the surface of a display entity.

195. The library of any of paragraphs 191-194, wherein the library is a phage display library.

196. The library of any of paragraphs 191-194, wherein the library is a yeast display library.

197. The library of any of paragraphs 191-194, wherein the library is a mammalian display library.

198. A method of making a binding polypeptide, the method comprising:
a) acquiring a library of any of paragraphs 191-197; and
b) expressing a polypeptide encoded by a unique nucleic acid of the library.

199. The method of paragraph 198, further comprising contacting the polypeptide with an antigen.

200. The method of paragraph 198 or 199, further comprising retrieving the nucleic acid that encodes a polypeptide that binds the antigen.

201. A method of making a nucleic acid sequence comprising a sequence that encodes an γ chain element (GC element) of a TCR γ chain variable region (GCVR) and a δ chain element (DC element) of a TCR δ chain variable region (DCVR), and wherein the GCVR and DCVR are matched, the method comprising:

a) acquiring an isolated production reaction site, e.g., a production micro-chamber, comprising:
i) a γ chain (GC) strand, wherein the GC strand is a strand of a γ chain double-stranded cDNA (GC ds cDNA) comprising a segment that encodes a GC element of the GCVR from a cell, e.g., a γ chain variable region sequence (GCVRS); and
ii) a δ chain (DC) strand, wherein the DC strand is a strand of a δ chain double-stranded cDNA (DC ds cDNA)

comprising a segment that encodes a DC element of the DCVR from the cell, e.g., a δ chain variable region sequence (DCVRS), and b) covalent linking, e.g., ligation, of a GC strand to a DC strand, wherein the isolated production reaction site, e.g., a production micro-chamber, does not include a nucleic acid encoding a DCVR or a GCVR from a cell other than the cell, thereby making a nucleic acid sequence comprising a sequence that encodes a GC element of a GCVR and a DC element of a DCVR, wherein the GCVR and DCVR are matched.

202. The method of paragraph 201, wherein the GC element comprises, or consists of, a GCVRS, or a functional fragment thereof (e.g., an antigen binding fragment thereof).

203. The method of paragraph 201 or 202, wherein the DC element comprises, or consists of, a DCVRS, or a functional fragment thereof (e.g., an antigen binding fragment thereof).

204. The method of any of paragraphs 201-203, wherein the nucleic acid sequence is configured such that, when expressed, the GCVRS and the DCVRS form a functional antigen binding molecule, e.g., a single chain TCR molecule.

205. The method of paragraph 204, wherein the antigen binding molecule is functional in vitro, ex vivo, or in vivo, e.g., as determined by a method or assay described herein.

206. The method of any of paragraphs 201-205, wherein acquiring an isolated production reaction site, e.g., a production micro-chamber, comprises:

a) acquiring a capture substrate bound to:
(i) a first double-stranded cDNA (ds cDNA) comprising a strand that is complementary to a first mRNA that encodes a GCVR from a cell; and
(ii) a second ds cDNA comprising a strand complementary to a second mRNA encoding a DCVR from the cell (the cDNA loaded capture substrate), and b) maintaining the isolated production reaction site, e.g., the production micro-chamber, under conditions that allow amplification of the first and second ds cDNAs, to produce:

a plurality of GC ds cDNAs comprising a segment that encodes a GC element of the GCVR from the cell, e.g., a GCVRS; and a plurality of DC ds cDNAs comprising a segment that encodes a DC element of the DCVR from the cell, e.g., a DCVRS.

207. The method of paragraph 206, wherein the GC ds cDNA is identical, or substantially identical, to the first ds cDNA.

208. The method of paragraph 206 or 207, wherein the DC ds cDNA is identical, or substantially identical, to the second ds cDNA.

209. The method of any of paragraphs 206-208, wherein the capture substrate comprises a bead, e.g., a magnetic bead.

210. The method of any of paragraphs 206-209, wherein the capture substrate comprises a moiety (e.g., an oligonucleotide) which binds to cDNA, e.g., (i) a moiety which binds to the GC strand; (ii) a moiety which binds to the DC strand; or (iii) both (i) and (ii).

211. The method of any of paragraphs 206-220, wherein the first mRNA and the second mRNA are disposed on an mRNA loaded capture substrate.

212. The method of any of paragraphs 206-211, wherein the isolated production reaction site, e.g., the production micro-chamber, comprises:

a reagent mixture suitable for producing, from the first and second mRNAs (e.g., after the first and second mRNAs are released from the mRNA loaded capture substrate into a solution), a first ds cDNA comprising a segment that encodes a GC element of the GCVR of the cell, e.g., a GCVRS, and a second ds cDNA comprising a segment that encodes a DC element of the DCVR of the cell, e.g., a DCVRS.

213. The method of any of paragraphs 206-212, wherein the isolated production reaction site, e.g., production micro-chamber, comprises primers that mediate the production of the first ds cDNA.

214. The method of any of paragraphs 206-213, wherein the isolated production reaction site, e.g., production micro-chamber, comprises primers that mediate the production of the second ds cDNA.

215. The method of any of paragraphs 206-214, wherein a cDNA strand that is complementary to a first mRNA that encodes a GCVR from a cell is made by reverse transcription of the first mRNA.

216. The method of any of paragraphs 206-215, wherein a cDNA strand that is complementary to a second mRNA that encodes a DCVR from a cell is made by reverse transcription of the second mRNA.

217. The method of paragraph 215 or 216, wherein the reverse transcription takes place in the isolated production reaction site, e.g., a production-micro chamber.

218. The method of paragraph 215 or 216, wherein the reverse transcription takes place in an isolated cell reaction site, e.g., a cell isolation micro-chamber.

219. The method of paragraph 215 or 216, wherein the reverse transcription takes place outside the isolated production reaction site, e.g., a production micro-chamber, or outside an isolated cell reaction site, e.g., a cell isolation micro-chamber.

220. The method of paragraph 215 or 216, wherein the reverse transcription takes place outside the isolated production reaction site, e.g., a production-micro chamber, and outside an isolated cell reaction site, e.g., a cell isolation micro-chamber.

221. The method of paragraph 215 or 216, wherein the reverse transcription takes place outside an isolated reaction site, e.g., outside a micro-chamber.

222. The method of any of paragraphs 206-221, wherein the amplification comprises 20 or fewer cycles, e.g., 25 or fewer, 24 or fewer, 23 or fewer, 22 or fewer, 21 or fewer, 20 or fewer, 9 or fewer, 8 or fewer, 7 or fewer, 6 or fewer, or 5 or fewer cycles.

223. The method of any of paragraphs 206-222, wherein the reverse transcription and/or amplification uses one or more primers, e.g., comprising a sequence specific for a GCVRS and/or a DCVRS.

224. The method of any of paragraphs 206-223, wherein the amplification comprises using two or more primers that mediate the production of the GC ds cDNA, wherein at least one primer comprises a nucleotide modification, and wherein at least one primer does not comprise a nucleotide modification.

225. The method of any of paragraphs 206-224, wherein the amplification comprises using two or more primers that mediate the production of the DC ds cDNA, wherein at least one primer comprises a nucleotide modification, and wherein at least one primer does not comprise a nucleotide modification.

226. The method of paragraph 225, wherein at least one primer comprises a nucleotide modification, e.g., which reduces, e.g., inhibits, DNA synthesis, e.g., by a DNA polymerase.

227. The method of paragraph 225 or 226, wherein at least one primer does not comprise a nucleotide modification, e.g., which reduces, e.g., inhibits, DNA synthesis, e.g., by a DNA polymerase.

228. The method of paragraph 226 or 227, wherein the nucleotide modification inhibits a DNA polymerase from extending the DNA.

229. The method of any of paragraphs 226-228, wherein the nucleotide modification is an insertion of a spacer to the primer, e.g., between two adjacent nucleotides in the primer.

230. The method of paragraph 229, wherein the spacer is a flexible spacer, a carbon spacer (e.g., —(CH2)n-, wherein n=3, 4, 5, or more), two or more (e.g., three, four, five, or more) abasic nucleotides or a PEG spacer.

231. The method of any of paragraphs 226-228, wherein the nucleotide modification is 2'-O-methyl, 2'-OH, 2'-NH$_2$, or uracil, e.g., to a ribose.

232. The method of any of paragraphs 226-231, wherein the nucleotide modification is located internally or at the 3' end of the primer.

233. The method of any of paragraphs 223-232, wherein at least one primer comprises (i) a first member; (ii) a second member; and optionally (iii) a nucleotide modification described herein, e.g., located between (i) and (ii).

234. The method of paragraph 233, wherein the first member is capable of annealing with the second member in the same primer or a different primer, e.g., forming a hairpin structure (via intramolecular hybridization) or a double-stranded structure (via intermolecular hybridization) comprising a duplex region of 4, 5, 6, 7, 8, 9, 20, 21, 22, 23, 24, 25, 26, 27, 28, 29, 20, more basepairs.

235. The method of paragraph 233 or 234, wherein the first member comprises a sequence that is complementary to the sequence of an oligonucleotide attached to the capture substrate.

236. The method of any of paragraphs 233-235, wherein the second member comprises (e.g., from 5' to 3') one, two, or all of: (i) a sequence that is complementary to at least a portion of the first member; (ii) a universal priming sequence (e.g., for PCR amplification or next-generation sequencing); and (iii) a sequence complementary to a target sequence, e.g., a GCVRS and/or a DCVRS, optionally, wherein the second member comprises a sequence for homologous recombination (e.g., in a yeast or mammalian cell).

237. The method of any of paragraphs 223-236, wherein at least one primer comprises a sequence encoding at least a portion of a linker sequence, or a complementary sequence thereof.

238. The method of paragraph 237, wherein the primer that comprises a sequence encoding at least a portion of a linker sequence, or a complementary sequence thereof, is phosphorylated, e.g., 5' phosphorylated.

239. The method of paragraph 237 or 238, wherein the linker sequence comprises, or consists of, (Gly-Gly-Gly-Gly-Ser)n, where n=1, 2, 3, 4, 5, or more (SEQ ID NO: 32).

240. The method of any of paragraphs 201-239, wherein the GC ds cDNA comprises a 5' overhang, e.g., a 5' overhang that is capable of hybridizing to an oligonucleotide attached to a capture substrate.

241. The method of any of paragraphs 201-240, wherein the GC ds cDNA comprises a blunt end, e.g., a blunt end comprising a 5' phosphate.

242. The method of any of paragraphs 201-241, wherein the DC ds cDNA comprises a 5' overhang, e.g., a 5' overhang that is capable of hybridizing to an oligonucleotide attached to a capture substrate.

243. The method of any of paragraphs 201-242, wherein the DC ds cDNA comprises a blunt end, e.g., a blunt end comprising a 5' phosphate.

244. The method of any of paragraphs 201-243, wherein the GC ds cDNA and the DC ds cDNA comprise sticky ends, e.g., both have 5' overhangs.

245. The method of any of paragraphs 201-244, wherein the GC strand and the DC strand are covalently linked, e.g., ligated, to produce a single stranded nucleic acid sequence, wherein the GC and DC strands are both sense strands or both antisense strands.

246. The method of any of paragraphs 201-245, wherein a denatured GC strand of the GC ds cDNA to a denatured DC strand of the DC ds cDNA are covalently linked, e.g., ligated, wherein the GC and DC strands are both sense strands or both antisense strands.

247. The method of any of paragraphs 201-245, wherein the GC strand is present in the GC ds cDNA and the DC strand is present in the DC ds cDNA, and wherein the GC ds cDNA and the DC ds cDNA are covalently linked, e.g., ligated, e.g., to produce a double stranded nucleic acid sequence.

248. The method of any of paragraphs 201-247, wherein the covalent linking, e.g., ligation, occurs in the isolated production reaction site.

249. The method of paragraph 248, wherein the isolated production reaction site, e.g., a production micro-chamber, comprises a reagent that is capable of covalently linking, e.g., ligating, the GC and DC strands or the GC and DC ds cDNAs.

250. The method of paragraph 248 or 249, wherein the isolated production reaction site, e.g., a production micro-chamber comprises an enzyme that covalently couples the GC and DC strands or the GC and DC ds cDNAs.

251. The method of any of paragraphs 201-247, wherein the covalent linking, e.g., ligation, occurs in a site different from the isolated production reaction site, e.g., occurs in an isolated linkage reaction site, e.g., a linkage micro-chamber.

252. The method of paragraph 251, wherein the GC strand and the DC strand are transferred from the isolated production site to the isolated linkage reaction site, e.g., a linkage micro-chamber, and the covalent linking occurs in the isolated linkage reaction site, e.g., a linkage micro-chamber.

253. The method of paragraph 251 or 252, wherein the isolated linkage reaction site, e.g., a linkage micro-chamber, comprises a reagent that is capable of covalently linking, e.g., ligating, the GC and DC strands or the GC and DC ds cDNAs.

254. The method of any of paragraphs 251-253, wherein the isolated linkage reaction site, e.g., a linkage micro-chamber, comprises an enzyme that covalently couples the GC and DC strands or the GC and DC ds cDNAs.

255. The method of paragraph 250 or 254, wherein the enzyme is a ligase, e.g., a thermal stable ligase.

256. The method of any of paragraphs 251-255, wherein the covalent linking, e.g., ligation, comprises:
    (a) heating the isolated linkage reaction site, e.g., the linkage micro-chamber, under conditions (e.g., at 96° C.) that allow denaturation of the GC strand and the DC strand;
    (b) cooling the isolated linkage reaction site, e.g., the linkage micro-chamber, under conditions (e.g., at 60-66° C.) that allow hybridization of the splint oligonucleotide to the GC strand and the DC strand;

(c) maintaining the isolated linkage reaction site, e.g., the linkage micro-chamber, under conditions (e.g., at 46-66° C.) that allow ligation of the GC strand and the DC strand (e.g., formation of phosphodiester bond between the GC strand and the DC strand); and (d) repeating steps (a), (b), and (c) sequentially for 2, 6, 20, 26, 20, 26, 30, 36, 40, 46, 60, or more cycles.

257. The method of any of paragraphs 201-256, wherein the GC strand and the DC strand are covalently linked, e.g., ligated, in the presence of a splint oligonucleotide.

258. The method of paragraph 257, wherein the splint oligonucleotide is hybridized to a sequence comprising the junction of the GC strand and the DC strand, or a sequence complementary thereof, and forms a duplexed region at the site of ligation.

259. The method of paragraph 257 or 258, wherein the splint oligonucleotide comprises a modification (e.g., an $NH_2$ group) that inhibits DNA synthesis, e.g., by a DNA polymerase.

260. The method of paragraph 259, wherein the modification is at the 3' end of the splint oligonucleotide.

261. The method of any of paragraphs 201-260, wherein a strand complimentary to the covalently linked, e.g., ligated, GC and DC strands is produced by amplification.

262. The method of any of paragraphs 201-261, further comprising, prior to acquiring the isolated production reaction site, e.g., a production micro-chamber, acquiring an mRNA loaded capture substrate.

263. The method of paragraph 262, wherein acquiring the mRNA loaded capture substrate comprising:

a) acquiring an isolated cell reaction site, e.g., a cell isolation micro-chamber, comprising:
  i) a cell; and
  ii) a capture substrate capable of binding a first mRNA encoding a GCVR from the cell and a second mRNA encoding a DCVR from the cell; and
b) maintaining the isolated cell reaction site, e.g., the cell isolation micro-chamber, under conditions that allow lysis of the cell and binding of the capture substrate with the first mRNA and the second mRNA to form the mRNA loaded capture substrate,
wherein the isolated cell reaction site, e.g., cell isolation micro-chamber, does not include a nucleic acid encoding a GCVR or a DCVR from a cell other than the cell.

264. The method of paragraph 263, wherein the isolated cell reaction site, e.g., cell isolation micro-chamber, comprises a lysing reagent, e.g., a detergent.

265. The method of paragraph 263 or 264, wherein the cell is lysed by heat or an enzyme.

266. The method of any of paragraphs 263-265, wherein the capture substrate comprises a moiety (e.g., an oligonucleotide) which binds mRNA, e.g., an oligo(dT).

267. The method of any of paragraphs 262-266, further comprising releasing the mRNA loaded capture substrate from the isolated cell reaction site, e.g., the cell isolation micro-chamber.

268. The method of paragraph 267, wherein the releasing step is performed in the presence of a poly(dA) or poly(dT) oligonucleotide, e.g., to reduce cross-binding of non-captured mRNA.

269. The method of paragraph 262-268, wherein the mRNA loaded capture substrate is transferred from the isolated cell reaction site, e.g., the cell isolation micro-chamber, to the isolated production reaction site, e.g., the production micro-chamber.

270. The method of any of paragraphs 201-269, comprising releasing the nucleic acid sequence from the production micro-chamber.

271. The method of any of paragraphs 201-270, further comprising amplifying the nucleic acid sequence.

272. The method of any of paragraphs 201-271, comprising sequencing all or a portion of the nucleic acid sequence.

273. The method of any of paragraphs 201-272, comprising inserting all or a portion of nucleic acid sequence into a vector.

274. The method of paragraph 273, wherein the vector supplies an additional GC element or
DC element not included in the nucleic acid sequence.

275. The method of paragraph 273 or 274, wherein the vector supplies a GC CDR1, a GC CDR2, or both.

276. The method of any of paragraphs 273-275, comprising expressing the vector.

277. The method of any of paragraphs 201-276, comprising expressing the nucleic acid sequence to produce a polypeptide comprising a segment that encodes a GC element of the GCVR, e.g., a GCVRS, and a segment that encodes a DC element of the DCVR, e.g., a DCVRS.

278. The method of paragraph 277, wherein the DC element is N-terminal to the GC element in the polypeptide.

279. The method of paragraph 277, wherein the GC element is C-terminal to the DC element in the polypeptide.

280. The method of any of paragraphs 277-279, further comprising contacting the polypeptide with an antigen.

281. The method of any of paragraphs 277-280, further comprising determining if the polypeptide binds the antigen.

282. The method of any of paragraphs 201-281, wherein the cell is an immune cell, e.g., a B cell or T cell, e.g., a human B cell or T cell.

283. The method of any of paragraphs 201-282, wherein the cell is a mammalian cell or an avian cell.

284. A method of making a nucleic acid sequence comprising a sequence that encodes a γ chain element (GC element) of a TCR γ chain variable region (GCVR) and a δ chain element (DC element) of a TCR δ chain variable region (DCVR), and wherein the GCVR and DCVR are matched, comprising:

a) acquiring an isolated cell reaction site, e.g., a cell isolation micro-chamber, comprising:
  i) a cell; and
  ii) a capture substrate capable of binding a first mRNA encoding a GCVR from the cell and a second mRNA encoding a DCVR from the cell;
b) maintaining isolated cell reaction site, e.g., the cell isolation micro-chamber, under conditions that allow lysis of the cell and binding of the capture substrate with the first mRNA and the second mRNA to form the mRNA loaded capture substrate,
wherein the isolated cell reaction site, e.g., cell isolation micro-chamber, does not include a nucleic acid encoding a GCVR or a DCVR from a cell other than the cell;
c) contacting the mRNA loaded capture substrate with a reaction mixture, e.g., a reaction mixture comprising reverse transcriptase, that uses the loaded mRNA as a template to make cDNA (this can occur, e.g., in the isolated cell reaction site, in the isolated production reaction site, or in neither, e.g., not in an isolated reaction site);
d) acquiring an isolated production reaction site, e.g., a production micro-chamber, comprising:
  i) an γ chain (GC) strand from step b), wherein the GC strand is a strand of a γ chain double-stranded cDNA (GC ds cDNA) comprising a segment that encodes a GC element of the GCVR from the cell, e.g., a γ chain variable region sequence (GCVRS); and ii) a δ chain (DC) strand from step b), wherein the DC strand is a strand of a δ chain double-stranded cDNA (DC ds cDNA) comprising a segment that encodes a DC element of the DCVR from the cell, e.g., a δ chain variable region sequence (DCVRS); and e) covalent linking, e.g., ligation, of a GC strand to a DC strand, wherein the isolated production reaction site, e.g., a production micro-chamber, does not include a nucleic acid encoding a DCVR or a GCVR from a cell other than the cell.

285. A method of making a nucleic acid sequence comprising a sequence that encodes a γ chain element (GC element) of a TCR γ chain variable region (GCVR) and a δ chain element (DC element) of a TCR δ chain variable region (DCVR), and wherein the GCVR and DCVR are matched, comprising:

a) acquiring an isolated cell reaction site, e.g., a cell isolation micro-chamber, comprising:
  i) a cell; and
  ii) a capture substrate capable of binding a first mRNA encoding a GCVR from the cell and a second mRNA encoding a DCVR from the cell;

b) maintaining the isolated cell reaction site, e.g., the cell isolation micro-chamber, under conditions that allow lysis of the cell and binding of the capture substrate with the first mRNA and the second mRNA to form the mRNA loaded capture substrate, wherein the isolated cell reaction site, e.g., cell isolation micro-chamber, does not include a nucleic acid encoding a GCVR or a DCVR from a cell other than the cell;

c) acquiring an isolated production reaction site, e.g., a production micro-chamber, comprises: contacting the mRNA loaded capture substrate with a reaction mixture, e.g., a reaction mixture comprising reverse transcriptase, that uses the loaded mRNA as a template, to produce:

a first double-stranded cDNA (ds cDNA) comprising a strand that is complementary to a first mRNA that encodes a GCVR from a cell; and a second ds cDNA comprising a strand complementary to a second mRNA encoding a DCVR from the cell (the cDNA loaded capture substrate);

wherein the isolated production reaction site, e.g., a production micro-chamber, does not include a nucleic acid encoding a DCVR or a GCVR from a cell other than the cell.

d) maintaining the isolated production reaction site, e.g., the production micro-chamber, under conditions that allow amplification of the first and second ds cDNAs, to produce:

a plurality of GC ds cDNAs comprising a segment that encodes a GC element of the GCVR from the cell, e.g., a GCVRS; and a plurality of DC ds cDNAs comprising a segment that encodes a DC element of the DCVR from the cell, e.g., a DCVRS;

e) acquiring an isolated linkage reaction site, e.g., a linkage micro-chamber, comprising: covalent linking, e.g., ligation, of a strand of the GC ds cDNA (GC strand) to a strand of the DC ds cDNA (DC strand), wherein the GC and DC strands are both sense strands or antisense strands; and f) amplifying the covalently linked, e.g., ligated, GC and DC strands.

286. A method of making a library comprising a plurality of unique members, the method comprising:

making the plurality of members, wherein each of the members comprises a sequence that encodes a γ chain element (GC element) of a γ chain variable region (GCVR) and a δ chain element (DC element) of a δ chain variable region (DCVR), and wherein the GCVR and DCVR are matched, made by a method of any of paragraphs 201-285, wherein each unique nucleic acid sequence of the plurality comprises a GC element and a DC element from a different unique cell, thereby making a library comprising a plurality of unique members.

287. The method of paragraph 86, wherein the plurality of unique members comprises at least $20^4$, $20^5$, $20^6$, $20^7$, $20^8$, or $20^9$ unique members.

288. The method of paragraph 286 or 287, wherein the plurality of unique members comprises $20^4$ to $20^9$, $20^4$ to $20^8$, $20^4$ to $20^7$, $20^4$ to $20^6$, $20^4$ to $20^5$, $20^8$ to $20^9$, $20^7$ to $20^9$, $20^6$ to $20^9$, $20^5$ to $20^9$, $20^5$ to $20^8$, $20^6$ to $20^7$, $20^4$ to $20^5$, $20^5$ to $20^6$, $20^6$ to $20^7$, $20^7$ to $20^8$, or $20^8$ to $20^9$ unique members.

289. The method of any of paragraphs 286-288, wherein at least 80%, 85%, 90%, 95%, 96%, 97%, 98%, 99%, or 200%, of the members in the library are unique members (which encode matched GC element and DC elements sequences).

290. The method of any of paragraphs 286-289, wherein less than 20%, 25%, 20%, 5%, 4%, 3%, 2%, or 1%, of the members in the library are unique members (which encode matched GC element and DC elements sequences).

291. A library comprising:
a plurality of unique members,
wherein,
i) each unique member of the plurality comprises a segment that encodes a GC element, e.g., a GCVRS, and a segment that encodes a DC element, e.g., a DCVRS, wherein the GC element and the DC element in each unique member is matched;
ii) each unique member of the plurality comprises a segment that encodes a GC element, e.g., a GCVRS, and a segment that encodes a DC element, e.g., a DCVRS, from a different unique cell; and
iii) the library comprises one or more (e.g., two, three, four, or all) of the following properties:
  a) the library is made by a method of any of paragraphs 201-285;
  b) the plurality of unique members comprises at least $20^4$, $20^5$, $20^6$, $20^7$, $20^8$, or $20^9$ unique nucleic acid sequences;
  c) the plurality of unique members comprises $20^4$ to $20^9$, $20^4$ to $20^8$, $20^4$ to $20^7$, $20^4$ to $20^6$, $20^4$ to $20^5$, $20^8$ to $20^9$, $20^7$ to $20^9$, $20^6$ to $20^9$, $20^5$ to $20^9$, $20^5$ to $20^8$, $20^6$ to $20^7$, $20^4$ to $20^5$, $20^5$ to $20^6$, $20^6$ to $20^7$, $20^7$ to $20^8$, or $20^8$ to $20^9$ unique members;
  d) at least 80%, 85%, 90%, 95%, 96%, 97%, 98%, 99%, or 200%, of the members in the library are unique members (which encode matched GC element and DC elements sequences); or
  e) less than 20%, 25%, 20%, 5%, 4%, 3%, 2%, or 1%, of the members in the library are unique members (which encode matched GC element and DC elements sequences).

292. The library of paragraph 291, wherein each unique member of the plurality is configured such that, when expressed, the GC element, e.g., the GCVRS, and the DC element, e.g., the DCVRS, form a functional antigen binding molecule, e.g., a single chain TCR.

293. The library of any of paragraphs 291-292, wherein the library is a display library.

294. The library of any of paragraphs 291-293, wherein each of the members of the plurality further encodes a polypeptide that results in display of the member on the surface of a display entity.

295. The library of any of paragraphs 291-294, wherein the library is a phage display library.

296. The library of any of paragraphs 291-294, wherein the library is a yeast display library.

297. The library of any of paragraphs 291-294, wherein the library is a mammalian display library.

298. A method of making a binding polypeptide, the method comprising:
a) acquiring a library of any of paragraphs 291-297; and
b) expressing a polypeptide encoded by a unique nucleic acid of the library.

299. The method of paragraph 298, further comprising contacting the polypeptide with an antigen.

300. The method of paragraph 298 or 299, further comprising retrieving the nucleic acid that encodes a polypeptide that binds the antigen.

301. An isolated production reaction site, e.g., a production micro-chamber, which is an isolated production reaction site described in any of paragraphs 1-85, 101-185, or 201-285.

302. The isolated production reaction site, e.g., a production micro-chamber, of paragraph 401, which does not include a nucleic acid encoding (i) an HCVR or an LCVR, (ii) an ACVR or a BCVR, or (iii) a GCVR or a DCVR, from a cell other than the cell, 303. The isolated production reaction site, e.g., a production micro-chamber, of paragraph 301 or 302, which comprises one, two, or all of:
(i) one or more primers specific to V gene sequences of the (a) HC and LC, (b) α chain and β chain, or (c) γ chain and δ chain;
(ii) one or more primers specific to overhangs introduced onto the (a) HC and LC, (b) α chain and β chain, or (c) γ chain and δ chain, cDNAs;
(iii) one or more primers comprising a first member, a second member, and a nucleotide modification (e.g., a spacer) located between the first and second members, wherein the first member is capable of annealing with the second member in the same primer or a different primer, e.g., forming a hairpin structure (via intramolecular hybridization) or a double-stranded structure (via intermolecular hybridization) comprising a duplex region of 4, 5, 6, 7, 8, 9, 10, 11, 12, 13, 14, 15, 16, 17, 18, 19, 20, more basepairs.

304. The isolated production reaction site, e.g., a production micro-chamber, of any of paragraphs 301-103, which does not comprise a reagent that can covalently link nucleic acids, e.g., a ligase, e.g., a thermostable ligase.

305. The isolated production reaction site, e.g., a production micro-chamber, of any of paragraphs 301-303, which comprises a reagent that can covalently link nucleic acids, e.g., a ligase, e.g., a thermostable ligase.

306. A self-annealing oligonucleotide comprising a first member, a second member, and a nucleotide modification (e.g., a spacer) located between the first and second members, wherein the first member is capable of annealing with the second member in the same oligonucleotide or a different oligonucleotide, e.g., forming a hairpin structure (via intramolecular hybridization) or a double-stranded structure (via intermolecular hybridization) comprising a duplex region of 4, 5, 6, 7, 8, 9, 10, 11, 12, 13, 14, 15, 16, 17, 18, 19, 20, more basepairs.

307. The oligonucleotide of paragraph 306, wherein the first and second members are capable of forming a hairpin structure comprising a duplex region of 4, 5, 6, 7, 8, 9, 10, 11, 12, 13, 14, 15, 16, 17, 18, 19, 20, more basepairs.

308. The oligonucleotide of paragraph 306 or 307, wherein the first member is 5-40 nucleotides, e.g., 5-10, 5-20, 5-30, 30-40, 20-40, 10-30, 10-30, or 15-25 nucleotides, in length.

309. The oligonucleotide of any of paragraphs 306-308, wherein the second member is 5-40 nucleotides, e.g., 5-10, 5-20, 5-30, 30-40, 20-40, 10-30, 10-30, or 15-25 nucleotides, in length.

310. The oligonucleotide of any of paragraphs 306-309, wherein the spacer is a flexible spacer or a PEG spacer.

311. The oligonucleotide of any of paragraphs 306-310, wherein the first member comprises a sequence that is complementary to the sequence of an oligonucleotide attached to a capture substrate.

312. The oligonucleotide of any of paragraphs 306-311, wherein the second member comprises (e.g., from 5' to 3') one, two, or all of: (i) a sequence that is complementary to at least a portion of the first member; (ii) a universal priming sequence (e.g., for PCR amplification or next-generation sequencing); and (iii) a sequence complementary to a target sequence, e.g., a GCVRS and/or a DCVRS, optionally, wherein the second member comprises a sequence for homologous recombination (e.g., in a yeast or mammalian cell).

313. An isolated linkage reaction site, e.g., a linkage micro-chamber, which is an isolated linkage reaction site described in any of paragraphs 51-83, 85, 151-183, 185, 251-283, or 285.

314. The isolated linkage reaction site, e.g., a linkage micro-chamber, of paragraph 313, which does not include a nucleic acid encoding (i) an HCVR or an LCVR, (ii) an ACVR or a BCVR, or (iii) a GCVR or a DCVR, from a cell other than the cell, 315. The isolated linkage reaction site, e.g., a linkage micro-chamber, of paragraph 313 or 314, which comprises a splint oligonucleotide that is capable of hybridizing to a sequence comprising the junction of (i) the HC strand and the LC strand, (ii) the AC strand and the BC strand, or (iii) the GC strand and the DC strand, or a sequence complementary thereof, to form a duplexed region at the site of ligation.

316. The isolated linkage reaction site, e.g., a linkage micro-chamber, of any of paragraphs 313-315, which comprises a reagent that can covalently link nucleic acids, e.g., a ligase, e.g., a thermostable ligase.

317. The method of any of paragraphs 1-300, which does not include a step of overlap extension polymerase chain reaction (OE-PCR), also known as splicing by overlap extension or splicing by overhang extension (SOE) PCR (Higuchi et al., *Nucleic Acids Res.* 1988; 16(15):7351-67), e.g., in the linking step.

EXAMPLES

Example 1: Cohesive-End PCR-Ligation in Drops

B cells were encapsulated in droplets. B cells were encapsulated into droplets, with droplet volume ranging from 10 pL to 100 nL, typically ~100-1000 pL. Sources of B cells can include, for example, mice, human, rat, rabbit, or chicken. The carrier (oil) phase was composed of 3M HFE-7500 with ~1% fluorosurfactant (RAN Biotechnologies). Droplets were formed by a microfluidic chip (e.g., 2R 100 μm from Dolomite) with flow of fluid phases controlled by a syringe or pressure pump. The aqueous phase of droplets was composed of a buffer (e.g., Tris, pH 7.5), a detergent to aid cell lysis, and magnetic beads which contain oligonucleotides (primers) to anneal to heavy and light chain mRNAs. Occupancy of drops should be not more than 1 cell per droplet, and at least one bead per droplet.

The droplets were incubated to facilitate cell lysis. The emulsion was heated to improved lysis efficiency in the presence of certain detergents (e.g., Tween 20). For example, the emulsion can be heated to a temperature of 40° C., 50° C., 60° C., 70° C., or 80° C., for approximately 5-60 minutes. After the cells were lysed, mRNA was released and captured on beads by annealing to oligonucleotides on the beads.

The emulsion was broken and the beads were recovered. Emulsions (or coalesce different solution phases) were broken using drop destabilizing reagent, such as PFO (perfluorooctanol). The aqueous phase containing the beads was recovered. The beads were isolated using magnet. The beads were washed and resuspended in a buffer (e.g., Tris, pH 7.5).

Reverse transcription (RT) was performed to create cDNA-beads (in a non-emulsion reaction). The beads were resuspended in a buffer-enzyme mix to facilitate RT (e.g., Superscript II RT). The reaction was incubated at 40° C. for 15 minutes to facilitate RT. The beads were washed once with a buffer (e.g., Tris, pH 7.5).

The recovered beads can be encapsulated for PCR-Ligation reaction. Droplets ranging in volume from about 5 pL-500 pL, most commonly about 10-50 pL, can be used. The carrier (oil) phase can be composed of 3M HFE-7500 containing ~2% fluorosurfactant (RAN Biotechnologies). Drops can be encapsulated with: beads which have cDNA; PCR reagents (including, e.g., a DNA polymerase, e.g., Phusion® High-Fidelity DNA Polymerase (NEB), Q5® High-Fidelity DNA Polymerase (NEB), Pfu DNA polymerase, KAPA DNA polymerase, Vent® DNA polymerase, or Taq DNA polymerase); oligonucleotides that allow for amplification of VH and VL sequences; a thermostable ligase (e.g., Taq DNA ligase, Pfu DNA ligase, Ampligase® thermostable DNA ligase, Tsc DNA ligase, Rma DNA ligase, Tfi DNA ligase, or Tth DNA ligase); and optimized buffer conditions (compatibility to support both DNA polymerase and ligase enzymatic activities).

The scFv cassette was constructed as VL-Linker-VH, as tested in tubes. The order can be switched (VH-Linker-VL) with no significant impact on function or performance. The reverse primers of the VL sequence can contain an overhang sequence encoding a Linker sequence and with at least 1 modified nucleotide (e.g., 3 consecutive nucleotides with 2'-O-methyl modification). The VL reverse primers can also contain 5'-phosphate (required to be substrate of ligase). The forward primers of the VH sequence can contain an overhang sequence encoding a Linker sequence and with at least 1 modified nucleotide (e.g., 3 consecutive nucleotides with 2'-O-methyl modification). The VH forward primers can also contain 5'-phosphate (required to be substrate of ligase). The occupancy of drops should be not more than 1 bead per drop.

Thermocycling can be performed with emulsion. The generated emulsion can be transferred to PCR tubes. Thermocycling can be performed using the following conditions: initial denaturation at 95-98° C. for 30 seconds to 2 minutes; 10-30 cycles of: denaturation at 95-98° C. for 10-30 seconds, primer annealing at 50-60° C. for 10-30 seconds, polymerase extension at 72° C. for 30 seconds, and cohesive product annealing and ligation at 45-55° C. for 3 minutes. The reaction can be hold at 4° C.

The emulsion was broken and the portion which contains linked (and non-linked) product was recovered. Emulsions can be broken using drop destabilizing reagent, such as PFO (perfluorooctanol). The aqueous phase can be recovered and the beads can be discarded.

The linked product (representing natively linked VL-linker-VH), as tested in tubes, was purified from non-linked VH and VL products. Ligated product was separated from non-ligated products by size separation. For example, denaturing PAGE (polyacrylamide gel electrophoresis) or denaturing HPLC-SEC can be used Linked product (about 800-900 bp) was isolated from non-linked product (about 350-500 bp). For denaturing PAGE purification, the ligated band was cut out from the gel and electroelution was performed to extract DNA from the gel slice (Bio-Rad Electro-Elutor).

The purified linked product can be amplified by PCR. Polymerase/conditions which can moderately read through DNA containing modified nucleotides, e.g., Taq polymerase, can be used.

Final PCR product can be introduced to yeast using standard methods (e.g., electroporation with expression vector) to create a natively paired library derived from biological sources.

Example 2: Ligase Cycling Approach

B cells were encapsulated in droplets. B cells were encapsulated into droplets, with droplet volume ranging from 10 pL to 100 nL, typically ~100-1000 pL. Sources of B cells can include, for example, mice, human, rat, rabbit, or chicken. The carrier (oil) phase was composed of 3M HFE-7500 with ~1% fluorosurfactant (RAN Biotechnologies). Droplets were formed by a microfluidic chip (e.g., 2R 100 μm from Dolomite) with flow of fluid phases controlled by a syringe or pressure pump. The aqueous phase of droplets was composed of a buffer (e.g., Tris, pH 7.5), a detergent to aid cell lysis, and magnetic beads which contain oligonucleotides (primers) to anneal to heavy and light chain mRNAs. Occupancy of drops should be not more than 1 cell per droplet, and at least one bead per droplet.

The droplets were incubated to facilitate cell lysis. The emulsion was heated to improved lysis efficiency in the presence of certain detergents (e.g., Tween 20). For example, the emulsion can be heated to a temperature of 40° C., 50° C., 60° C., 70° C., or 80° C., for approximately 5-60 minutes. After the cells were lysed, mRNA was released and captured on beads by annealing to oligonucleotides on the beads.

The emulsion was broken and the beads were recovered. Emulsions (or coalesce different solution phases) were broken using drop destabilizing reagent, such as PFO (perfluorooctanol). The aqueous phase containing the beads was recovered. The beads were isolated using magnet. The beads were washed and resuspended in a buffer (e.g., Tris, pH 7.5).

Reverse transcription (RT) can be performed to create cDNA-beads (in a non-emulsion reaction). The beads can be resuspended in a buffer-enzyme mix to facilitate RT (e.g., Superscript II RT). The reaction can be incubated at 40° C. for 15 minutes to facilitate RT. The beads can be washed once with a buffer (e.g., Tris, pH 7.5).

Recovered beads were encapsulated for PCR reaction. Droplets ranging in volume from about 5 pL-500 pL, most commonly about 10-50 pL, can be used. The carrier (oil) phase can be composed of 3M HFE-7500 containing ~2% fluorosurfactant (RAN Biotechnologies). Drops can be encapsulated with: beads which contain cDNA (some beads can be 'empty', which is not problematic); PCR reagents (including, e.g., a DNA polymerase, e.g., Phusion® High-Fidelity DNA Polymerase (NEB), Q5® High-Fidelity DNA Polymerase (NEB), Pfu DNA polymerase, KAPA DNA polymerase, Vent® DNA polymerase, or Taq DNA polymerase); oligonucleotides that allow for amplification of VH and VL sequences.

The scFv cassette can be constructed as VL-Linker-VH. The order can be switched (VH-Linker-VL) with no significant impact on function or performance. The VL reverse and VH forward primers can contain an overhang sequence encoding Linker. The VH reverse primer can have a 5'-phosphate. The occupancy of drops should be not more than 1 bead per drop.

Thermocycling can be performed with emulsion. The generated emulsion can be transferred to PCR tubes. The thermocycling can be performed using standard PCR conditions: initial denaturation: 95-98° C. for 30 seconds to 2 minutes; 10-30 cycles of: denaturation at 95-98° C. for 10-30 seconds, primer annealing at 50-60° C. for 10-30 seconds, polymerase extension at 72° C. for 30 seconds. The reaction can be hold at 4° C.

The emulsion can be broken and the beads can be recovered. Emulsions (or coalesce different solution phases) can be broken using drop destabilizing reagent, such as PFO (perfluorooctanol). The aqueous phase that contains beads can be recovered. The beads can be isolated using magnet. The beads can be washed to remove PCR product not captured on beads. The beads can be resuspended in a buffer (e.g., Tris, pH 7.5).

The recovered beads can be encapsulated for ligase cycling reaction. Droplets ranging in volume from about 5 pL-500 pL, most commonly about 10-50 pL, can be used. The carrier (oil) phase can be composed of 3M HFE-7500 containing ~2% fluorosurfactant (RAN Biotechnologies). The drops can be encapsulated with a Stint oligonucleotide which is complementary and anneals to 3' terminus of 'top' VL strain and 5' terminus of 'top' VH strand; a thermostable ligase (e.g., Taq DNA ligase, Pfu DNA ligase, Ampligase® thermostable DNA ligase, Tsc DNA ligase, Rma DNA ligase, Tfi DNA ligase, or Tth DNA ligase); reaction components required to support ligase enzymatic activity (e.g., NAD). The occupancy should be not more than 1 bead per drop.

Thermocycling can be performed with emulsion. The generated emulsion can be transferred to PCR tubes. Thermocycling can be performed using standard conditions: 3-15 cycles of: denaturation: 90-95° C. for 30 seconds, annealing and ligation at 50-60° C. for 1-3 minutes. The reaction can be hold at 4° C.

The emulsion can be broken and the aqueous portion which contains the linked product can be recovered. Emulsions (or coalesce different solution phases) can be broken using drop destabilizing reagent, such as PFO (perfluorooctanol). The aqueous phase can be recovered and the beads can be discarded.

The purified linked product can be amplified by PCR. Standard conditions can be used with oligonucleotides that anneal the outer termini of the linked VL-Linker-VH ligated fragment.

Final PCR product can be introduced to yeast to create a natively paired library derived from biological sources.

Example 3: Ligase Cycling Reaction

In this example, VH and VL PCR products were covalently linked using a thermostable ligase and a splint oligo. RNA from a hybridoma clone (ATCC, HB-112, "4G2") was isolated using an RNeasy Kit (Qiagen). cDNA was generated using SuperScript IV Reverse Transcriptase (Thermo Fisher) and the isolated RNA following manufacturer recommended conditions. Primers used were directed to constant regions of the heavy and light chains: mouse IgG_CH1_rev (5'-CHGATGGGGSTGTYGTTKTRGC (SEQ ID NO: 1)) and mouse Kappa_Rev (5'-GTGCAGCATCAGCCC (SEQ ID NO: 2)). As used herein, the nucleotides are defined by IUPAC nucleotide code, e.g., R=A or G; Y=C or T; S=G or C; K=G or T; H=A or C or T.

| Component | Volume (ul) |
| --- | --- |
| Water | 10 |
| 10 mM dNTP mix | 1 |
| 2 uM primer | 1 |
| RNA template | 1 |

The components were mixed, heated to 65° C. for 5 min, and then incubated on ice for at least 1 min. The following components were then added:

| Component | Volume (ul) |
| --- | --- |
| 5X SSIV buffer | 4 |
| 100 mM DTT | 1 |
| RNaseOUT RNase Inhibitor (40 U/ul) | 1 |
| Superscript IV Reverse Transcriptase | 1 |

The components were mixed and then incubated at 55° C. for 10 minutes. The reaction was then inactivated by incubating at 80° C. for 10 minutes. cDNA products were used as templates for PCR to separately generate VH and VL products. The primers used included:

```
4G2 VL_Fwd
                                            (SEQ ID NO: 3)
5'-GACATCAAGATGACCCAGTCTC

Mouse Kappa_Rev-Phos
                                            (SEQ ID NO: 4)
5'-/5Phos/ACCAGCAGAGCTCTCACCTGGTGCAGCATCAGCCC 4G2 VH_Fwd-Phos
                                            (SEQ ID NO: 5)
5'-/5Phos/GGAACTACCGAAGGCACAGGTGAGGTCCAGCTGCAACAG
TC Mouse IgG_CH1_rev
                                            (SEQ ID NO: 1)
5'-CHGATGGGGSTGTYGTTKTRGC
```

The PCR reactions each included:

| Component | Volume (ul) |
| --- | --- |
| Q5 Hot Start 2X Master Mix (NEB) | 50 |
| Fwd primer (10 uM) | 5 |
| Rev primer (10 uM) | 5 |
| 4G2 cDNA | 1 |
| Water | 39 |

Thermocycling was then performed as follows:

| Initial Denaturation | Denature | Anneal | Extend | Hold |
|---|---|---|---|---|
| 1 cycle | 35 cycles | | | — |
| 95° C. | 95° C. | 60° C. | 72° C. | 4° C. |
| 2 min | 30 sec | 30 sec | 30 sec | Forever |

PCR products were purified using AMPure beads. Purified PCR products were quantified by Nanodrop. Ligase cycling reactions were set up in 25 ul reactions to achieve a 1:1:1 molar ratio of VH product, VL product, and splint oligo. The splint oligo used had the following sequence:

```
                                         (SEQ ID NO: 6)
5'-
ACCTGTGCCTTCGGTAGTTCCACCAGCAGAGCTCTCACCTG/3AmMO/.
```

Each ligase cycling reaction included:

| Component | Amount |
|---|---|
| 4G2 VH PCR product | 38 ng |
| 4G2 VL PCR product | 35 ng |
| Splint oligo (0.1 mM) | 3.3 ul |
| Taq ligase buffer (NEB) | 2.5 ul |
| Taq ligase (NEB) | 1 ul |
| Water | Up to 25 ul |

The ligase cycling reactions were analyzed by denaturing PAGE (polyacrylamide gel electrophoresis). In addition to Taq Ligase, an additional thermostable ligase (Ampligase (Amp), Lucigen) was evaluated.

Figure 3:
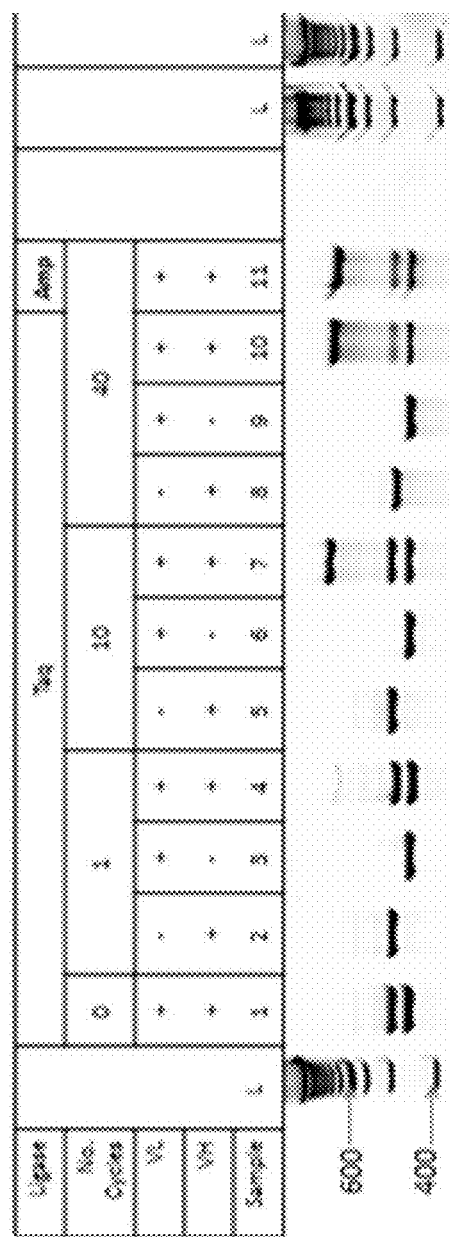
FIG. 3 is a polyacrylamide gel electrophoresis (PAGE) image showing that Taq ligase and Ampligase thermostable ligase (Amp; Lucigen) were capable of efficiently linking VH and VL product.

As shown in FIG. 3, efficient linking of VH and VL product was observed using both Taq ligase and Ampligase thermostable ligase.

Example 4: Retention of Native Pairing During Bulk Re-Amplification of Linked Products An emulsion OE-PCR workflow creates VH and VL products which necessarily share sequences to facilitate splicing by overlap extension. In such a workflow, any retained VH/VL product which is not spliced together within a drop can become spliced during bulk (non-emulsion) PCR amplification of products. Since such splicing occurs during the bulk phase when all cell products (e.g., many clones/unique sequences) are mixed, random (non-native) pairing could occur (see *Eur J Immunol.* 2013; 43(9):2507-15). The workflow would benefit from a strategy that not only reduces this occurrence, but completely prevents it. Described herein is a method in which VH and VL products do not share any common sequence, and thus the workflow is not susceptible to incidental splicing by OE-PCR during bulk re-amplification steps.

To demonstrate this, linked VH-VL products were generated from two hybridoma clones which differ from each other by size. Native versus non-native pairing could therefore be assessed by size of products. VH and VL products from hybridoma 4G2 were generated as described in Example 3. Hybridoma 9E10 (ATCC, CRL-1729) "mini" VH and VL products were similarly produced using the same RT primers and the following PCR primers:

```
9E10 Mini_VL_Fwd
                                         (SEQ ID NO: 7)
5'-GGCAGTGGGTCTGGGACAG mouse Kappa_Rev-Phos
                                         (SEQ ID NO: 4)
5'-/5Phos/ACCAGCAGAGCTCTCACCTGGTGCAGCATCAGCCC 9E10_VH_Fwd
                                         (SEQ ID NO: 8)
5'-/5Phos/GGAACTACCGAAGGCACAGGTGAGGTGCACCTGGTGGAG
TCTGGGGG 9E10 Mini_VH_Rev
                                         (SEQ ID NO: 9)
5'-GGATAGTGGGTGTAAGTACCACGACTACCAATG
```

The 4G2 VH and VL products produced were of size 400 bp and 378 bp, respectively. The mini 9E10 VH and VL products produced were of size 203 bp and 168 bp, respectively. The PCR products were purified using AMPure beads.

Figure 4A:
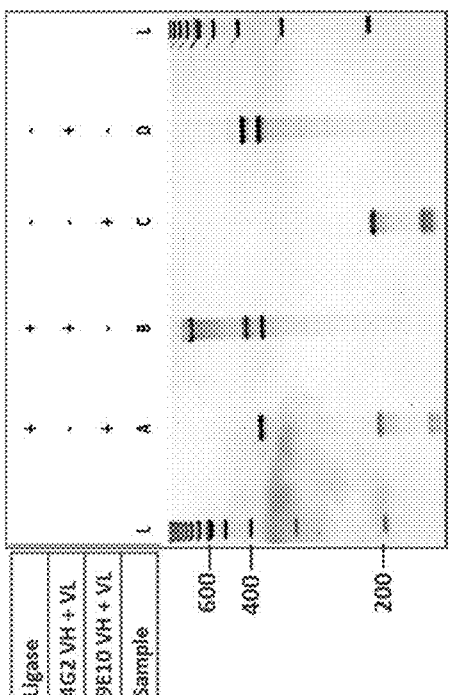
FIGS. 4A-4B are gel electrophoresis images showing that natively paired, linked VH+VL products for each of antibodies 4G2 and 9E10 were successfully produced by ligase cycling.

The products were then subjected to ligase cycling reactions as described in Example 3, using 20 cycles of thermocycling. 4G2 and 9E10 VH-VL products were ligated in separate tubes, simulating generation of natively linked products in droplets (in individual compartments). The products were analyzed by denaturing PAGE. Natively linked products of 4G2 VH-VL and of 9E10 VH-VL corresponded to sizes of 778 bp and 371 bp, respectively. Twenty cycles of ligase cycling were used to create products containing both ligated products as well as non-ligated VH and VL DNA. As shown in FIG. 4A, natively linked VH-VL products were generated for both 6G2 and 9E10.

The ligation products were purified by AMPure beads and then combined and used as template for PCR re-amplification of linked products. This step simulated recovery of products after performing linking of VH-VL in drops, followed by PCR re-amplification of linked VH-VL. By having non-ligated VH and VL DNA as template in the PCR, this provided an opportunity for DNA to become linked together during bulk re-amplification by PCR. Since the DNA was not compartmentalized by individual clones, any linking that occurred in bulk phase would lead to non-native pairing.

PCR re-amplification was performed as described below. "Outer" primers used to amplify linked products are as follows:

```
9E10 Mini_VL_Fwd
                                         (SEQ ID NO: 7)
5'-GGCAGTGGGTCTGGGACAG 4G2 VL_Fwd
                                         (SEQ ID NO: 3)
5'-GACATCAAGATGACCCAGTCTC 9E10 Mini_VH_Rev
                                         (SEQ ID NO: 9)
5'-GGATAGTGGGTGTAAGTACCACGACTACCAATG Mouse IgG_CH1_rev
                                         (SEQ ID NO: 1)
5'-CHGATGGGGSTGTYGTTKTRGC
```

The PCR reactions each included:

| Component | Volume (ul) |
|---|---|
| Q5 Hot Start 2X Master Mix | 12.5 |
| Fwd primers (10 uM) | 0.9 (each) |

| Component | Volume (ul) |
| --- | --- |
| Rev primers (10 uM) | 0.9 (each) |
| Purified ligation products | 4.5 (each) |
| Water | Up to 25 |

Thermocycling was then performed as follows:

| Initial Denaturation | Denature | Anneal | Extend | Hold |
| --- | --- | --- | --- | --- |
| 1 cycle | 20 cycles | | | — |
| 95° C. | 95° C. | 60° C. | 72° C. | 4° C. |
| 2 min | 30 sec | 30 sec | 30 sec | Forever |

Figure 4B:
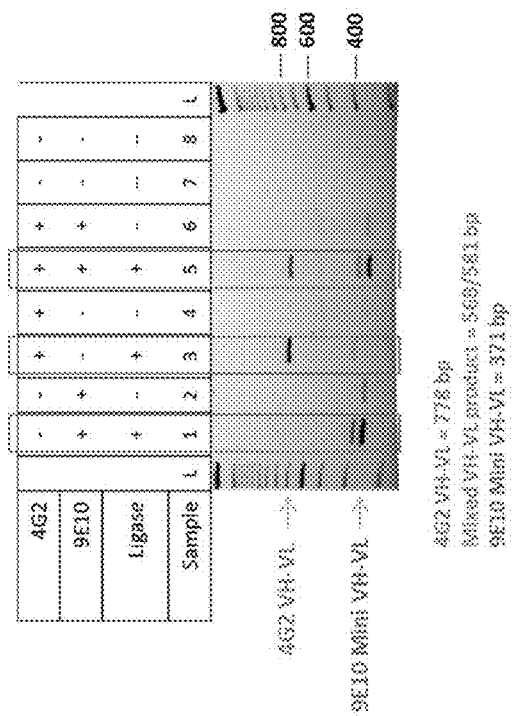

Finally, products were analyzed by agarose gel electrophoresis. Non-natively linked products could be readily identified by their intermediate size. Specifically, 4G2-VL/9E10-mini-VH and 9E10-mini-VL/4G2 VH linked products would correspond to sizes of 581 bp and 568 bp, respectively. As shown in FIG. 4B, retention of native pairing was observed when mixed during bulk re-amplification (lane 5).

Example 5: Oligo Design to Facilitate Capture of PCR Product onto Beads

After RT-PCR in droplets (e.g., as described above), the PCR product can be captured onto beads within the drop to retain native matching of the VH and VL products. To facilitate efficient capture of dsDNA PCR products onto beads, a strategy was devised to generate products which have defined ssDNA at their ends. The sequence of this ssDNA is complementary to sequence of an oligo conjugated to the beads. The complementarity of these sequences thus facilitates specific and efficient capture of dsDNA PCR products.

PCR products from 4G2 cDNA were produced using PCR with the following primers and Q5 DNA polymerase. The reverse primer contains a 5'-biotin moiety to facilitate specific detection of PCR product on beads. The PCR strategy was as follows:

| Sample/Product | Fwd Primer | Rev Primer |
| --- | --- | --- |
| (1) (VL) | 4G2 VL Fwd +PEG | Mus Kap Rev biotin |
| (2) (VL) | 4G2 VL Fwd −PEG | Mus Kap Rev biotin |
| (3) (VL) | 4G2 VL Fwd No_5' | Mus Kap Rev biotin |
| (3) (VH) | 4G2 VH Fwd Biotin | Mus IgG-HC Rev +PEG |

The following primers were used:

4G2 VL Fwd + PEG
(SEQ ID NOS 10 and 27)
5'-TGGATCGTTACTAATATTCGC/iSp18/GGACTCAGACACTTCCGTGCGACATCAAGATGACCCAGTCTC 4G2 VL Fwd − PEG
(SEQ ID NO: 11)
5'-TGGATCGTTACTAATATTCGCGGACTCAGACACTTCCGTGCGACATCAAGATGACCCAGTCTC 4G2 VL Fwd No_5'
(SEQ ID NO: 12)
5'-GGACTCAGACACTTCCGTGCGACATCAAGATGACCCAGTCTC Mus Kap Rev biotin
(SEQ ID NO: 13)
5'-/5BiotinTEG/ACCAGCAGAGCTCTCACCTGGTGCAGCATCAGCCC Mus IgG-HC Rev + PEG
(SEQ ID NOS 14 and 28)
5'-GCAATCCATCAACGTC/iSp18/CGTGACACATGTGGTTCAAGTACGGCHGATGGGGSTGTYGTTKTRGC 4G2 VH Fwd Biotin
(SEQ ID NO: 15)
5'-/5BiotinTEG/GGAACTACCGAAGGCACAGGTGAGGTCCAGCTGCAACAGTC PCR products were analyzed by agarose gel electrophoresis, purified by AMPure beads and quantified by Nanodrop.

Amine-labeled capture oligos were conjugated to carboxylated beads (COMPEL, Bangs Laboratories) using standard methods. The following oligos having sequence complementary to sequence 5' of the PEG spacers in the above PCR primers were used for conjugation to beads. Beads were conjugated to VL oligo only, to VH oligo only, or to both oligos.

VL Capture
(SEQ ID NO: 16)
5'-GCGAATATTAGTAACGATCCAAAAAAAAAAAAAAAAAAAAA/iSp18//iSp18//iSp18//3AmMO/

VH Capture
(SEQ ID NO: 17)
5'-GACGTTGATGGATTGCAAAAAAAAAAAAAAAAAAAA/iSp18//iSp18//iSp18//3AmMO/

To capture PCR product, the following reactions were set up. Purified PCR products were diluted in 0.5×SSC buffer to achieve 250 ng DNA in 25 ul final volume. Oligo-conjugated beads were washed with 0.5×SSC, and 400,000 beads were then mixed with each diluted PCR product. The bead-PCR product mix was mixed by pipet to suspend the beads, and the tubes were then placed in a thermocycler and the following program was run:

| Step | Temp | Time |
| --- | --- | --- |
| 1 | 70° C. | 30 sec |
| 2 | 55° C. | 30 sec |
| 3 | 50° C. | 30 sec |
| 4 | 45° C. | 4 min |
| 5 | 40° C. | 4 min |
| 6 | 35° C. | 4 min |
| 7 | 4° C. | hold |

The samples were as follows:

| Sample # | Bead | PCR Product |
| --- | --- | --- |
| 1 | Blank (no capture oligo) | (1) (VL) |
| 2 | Blank (no capture oligo) | (2) (VL) |
| 3 | Blank (no capture oligo) | (3) (VL) |
| 4 | Blank (no capture oligo) | (4) (VH) |
| 5 | VL capture | (1) (VL) |
| 6 | VL capture | (2) (VL) |
| 7 | VL capture | (3) (VL) |
| 8 | VL capture | (4) (VH) |
| 9 | VH capture | (1) (VL) |
| 10 | VH capture | (4) (VH) |
| 11 | VH and VL capture | (1) (VL) |
| 12 | VH and VL capture | (4) (VH) |

After temperature incubation, the samples were applied to a magnet to collect beads on the side of the tube. Supernatants were removed, and the beads were washed with 0.5×SSC buffer. Each sample was probed for captured PCR product with 50 µl of AlexaFluor 647 IgG Fraction Monoclonal Mouse Anti-Biotin antibody (Jackson) diluted 1:1000 in PBS containing 1% BSA. After incubation with mixing for 25 minutes at room temperature, the tubes were applied to a magnet, the supernatants were removed, and the beads were washed with PBS buffer. The beads were resuspended in 50 µl PBS and then analyzed by flow cytometry.

Figure 5A:
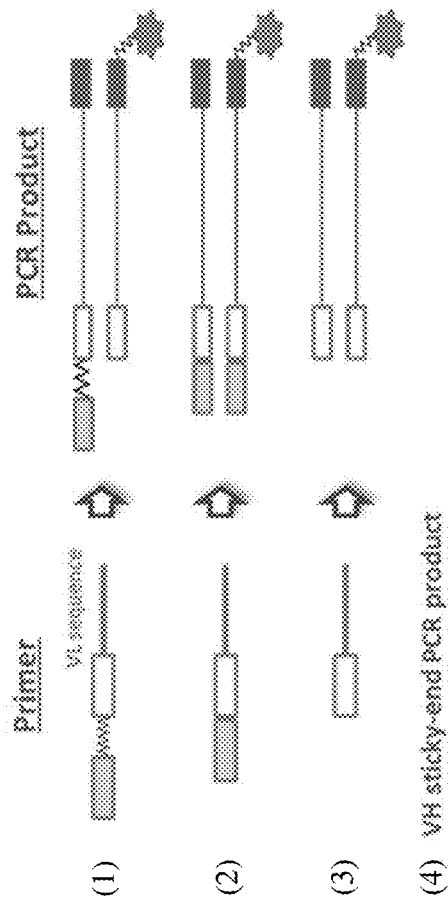
FIGS. 5A-5B are a graph and diagram showing efficient and specific PCR product capture using a self-annealing primer.
Figure 5B:
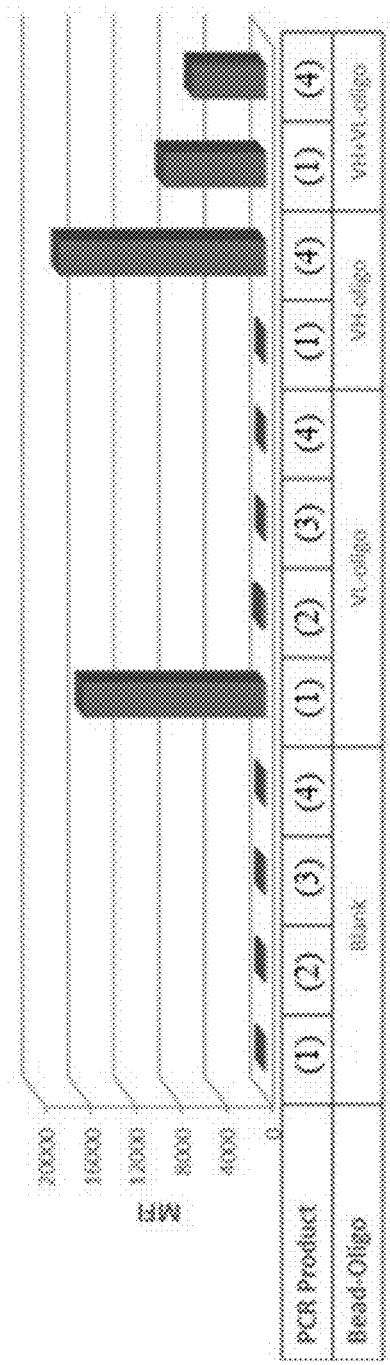

As shown in FIGS. 5A-5B, the results demonstrate efficient and specific PCR product capture by this method, with a requirement for a PEG spacer in the PCR primers and an appropriate complementary oligo conjugated to the beads (e.g., as in sample (1)).

Example 6: Generation of Natively Paired VH-VL Product in Drops by Ligase Cycling In this example, cells expressing VH and VL sequences of antibody 4G2 were lysed and mRNAs from the lysate were used to generate natively paired VH-VL products by ligase cycling. Cell lysis buffer was prepared as follows:

| | |
|---|---|
| 300 ul | 20% Ficoll PM400 |
| 10 ul | 20% Sarkosyl |
| 40 ul | 5 mM EDTA |
| 100 ul | 2M Tris pH 7.5 |
| 350 ul | Water |
| 200 ul | 100% Optiprep |

Carboxylated COMPEL magnetic beads (Bangs Labs) were conjugated with the following amine-modified oligos:

```
VL Capture
                              (SEQ ID NO: 16)
5'-GCGAATATTAGTAACGATCCAAAAAAAAAAAAAAAAAAAA/
iSp18//iSp18//iSp18//3AmMO/

VH Capture
                              (SEQ ID NO: 17)
5'-GACGTTGATGGATTGCAAAAAAAAAAAAAAAAAAAA/iSp18//
iSp18//iSp18//3AmMO/

Mus_IgG_CH1_mRNA capture
                              (SEQ ID NO: 18)
5'-CTGGACAGGGATCCAKAGTTCCAAAAAAAAAAAAAAAAAAAA/
iSp18//iSp18//iSp18//3AmMO/

Mus_Kap_mRNA capture
                              (SEQ ID NO: 19)
5'-GTGCAGCATCAGCCCGAAAAAAAAAAAAAAAAAAAA/iSp18//
iSp18//iSp18//3AmMO/
```

Oligo(dT) may also be used for mRNA capture (e.g., for capture of mRNAs encoding a VH and/or VL).

Beads were suspended in lysis buffer at a density of $2 \times 10^7$ beads/ml, which facilitates encapsulation of about 2.5 beads per drop with drop sizes used.

4G2 mouse hybridoma cells were washed with PBS and resuspended in PBS containing 0.1% BSA and 24% Optiprep at a density of $2 \times 10^6$ cells/ml. This density facilitates encapsulation into drops at approximately one cell per two drops. For co-encapsulation of cells and beads in drops, a 2-reagent, 100 µm diameter fluorophilic microfluidic chip (Dolomite) was used with solution flow controlled by three Mitos P-Pump pressure pumps (Dolomite). The microfluidic chip contained two input channels for aqueous solutions and two input channels for fluorocarbon oil. Cells and beads were flowed at a rate of 10 µl/min each, and fluorinated oil (HFE-7500 containing 1% fluorosurfactant (RAN Biotechnologies)) was flowed at 55 µl/min. These flow rates resulted in droplets of approximately 500 pl in volume. Emulsions were collected for an hour.

The emulsions (cells and no-cell control) were applied to a heat block at 45° C. for 20 mM to facilitate mRNA capture onto beads. The emulsions and beads were subsequently kept and handled at 4° C. to reduce dissociation of mRNA from beads. Excess oil was removed by syringe, and 5 ml of ice-cold 6×SSC buffer containing RNAse inhibitor (1:100) was added to the emulsion. PFO (1H,1H,2H,2H-Perfluoro-1-octanol) was added (100 µL) to the emulsion to induce drop coalescence. The sample was mixed thoroughly by inversion followed by centrifugation at 500×g for 5 min at 4° C. The aqueous phase was mixed by pipet, collected and then transferred to a new tube. After applying the tube to the magnet, the beads (having hybridized mRNA) were washed twice with 500 ul of ice-cold buffer (100 mM Tris HCl pH 8, 500 mM KCl, 15 mM MgCl$_2$) containing RNase inhibitor (1:100). The beads were then suspended in 500 ul of ice-cold buffer (100 mM Tris HCl pH 8, 500 mM KCl, 15 mM MgCl$_2$) containing RNase inhibitor (1:100).

A second emulsion was prepared with the mRNA beads and RT-PCR mix. The mRNA beads were suspended in the RT-PCR bead buffer (100 ul 2×RT-PCR buffer (OneTaq One-Step RT-PCR, NEB), 70 ul of Optiprep, 4 ul of RNase inhibitor, 6.4 ul of premixed 25 uM primers, and 32 ul of water). Primers used were:

```
4G2 VL Fwd + PEG
                         (SEQ ID NOS 10 and 27)
5'-TGGATCGTTACTAATATTCGC/iSp18/GGACTCAGACACTTCCGT
GCGACATCAAGATGACCCAGTCTC Mus IgG-HC Rev + PEG
                         (SEQ ID NOS 14 and 28)
5'-GCAATCCATCAACGTC/iSp18/CGTGACACATGTGGTTCAAGTAC
GGCHGATGGGGSTGTYGTTKTRGC mouse Kappa_Rev-Phos
                              (SEQ ID NO: 4)
5'-/5Phos/ACCAGCAGAGCTCTCACCTGGTGCAGCATCAGCCC 4G2 VH Fwd-Phos
                              (SEQ ID NO: 5)
5'-/5Phos/GGAACTACCGAAGGCACAGGTGAGGTCCAGCTGCAACAG
TC
```

Separately, enzyme mix was prepared (400 ul 2×RT-PCR buffer, 43 ul of enzyme diluted to 1.33× in RT-PCR buffer, 16 ul RNase inhibitor, and 341 ul water).

Emulsions for RT-PCR were generated by co-flowing beads and enzyme mix at 2.5 µl/min and 7.5 µl/min, respectively, and oil (HFE7500 containing 2% fluorosurfactant) at 35 µl/min. A two-reagent 30 µm diameter fluorophilic microfluidic chip (Dolomite) was used with pressure pumps to generate droplets. Under these conditions, droplets of approximately 15-35 µl in volume were formed, with bead occupancy of less than one bead per 5 drops. Drops were generated until all beads were encapsulated (about 30-60 minutes). The emulsions were then aliquoted into PCR tubes for thermocyling in a thermocycler with the following program:

| RT | Denature | Denature | Anneal | Extend | Extend | Gradually Cool | | | Hold |
|---|---|---|---|---|---|---|---|---|---|
| 1 Cycle | 1 Cycle | 40 Cycles | | | 1 Cycle | 1 Cycle | 1 Cycle | 1 Cycle | 1 Cycle | — |
| 55° C. | 94° C. | 94° C. | 58° C. | 68° C. | 70° C. | 55° C. | 50° C. | 45° C. | 40° C. | 12° C. |
| 30 min | 2 min | 15 sec | 30 sec | 30 sec | 2 min | 30 sec | 30 sec | 4 min | 30 min | Forever |

The thermocycled emulsions were combined into one tube. Excess oil was removed from the bottom using a syringe. To break the drops, 100 ul of PFO was added followed by mixing and centrifugation at 2000×g for two minutes. The aqueous phase was then mixed by pipet (to suspend beads) and transferred to a new tube. The beads contained captured PCR product. The tube was applied to a magnet and supernatant removed. The beads were gently washed with 500 µl of ice-cold 0.5×SSC buffer. The beads were again applied to a magnet, supernatant removed and then resuspended in 100 µl ice-cold 0.5×SSC buffer.

Samples were then prepared for ligase cycling emulsion to covalently link VH and VL products. The beads were suspended in bead solution (20 µl 10×Taq Ligase buffer (NEB), 117 µl 60% sucrose, and 63 µl water). Taq ligase mixture was prepared (80 µl 10×Taq Ligase buffer, 42 µl Taq Ligase, 13 µl of splint oligo (at 0.1 µM), and 665 µl water). The splint oligo used was (SEQ ID NO: 6)
5'-ACCTGTGCCTTCGGTAGTTCCACCAGCAGAGCTCTCACCTG/
3AmMO/.

Emulsions were generated by flowing the bead solution at 2 µl/min, enzyme mix at 6 µl/min, and oil (HFE7500 containing 2% fluorosurfactant) at 35 µl/min. A two-reagent 30 µm diameter fluorophilic microfluidic chip (Dolomite) was used with pressure pumps to generate droplets. Under these conditions, droplets of approximately 15-35 µl in volume were formed, with bead occupancy of less than one bead per 5 drops. Drops were generated until all beads were encapsulated (about 30-60 minutes). The emulsion was then aliquoted into PCR tubes for thermocyling in a thermocycler using the following program:

| Initial Denaturation | Denature | Anneal | Ligate | Hold |
|---|---|---|---|---|
| 1 cycle | 40 cycles | | | — |
| 95° C. | 95° C. | 55° C. | 45° C. | 4° C. |
| 2 minutes | 20 seconds | 30 seconds | 1 minute | Forever |

The thermocycled emulsions were combined into one tube. Excess oil was removed from the bottom using a syringe. To break drops, 100 µl of PFO was added followed by mixing and centrifugation at 2000×g for two minutes. The aqueous phase was then mixed by pipet (to suspend beads) and transferred to PCR tubes (50 µl per tube). The samples were then applied to a thermocyler preheated to 80° C. to facilitate dissociation of ligated PCR products hybridized to beads. After allowing beads to settle, the supernatant was removed and transferred to a new tube. The products were then purified using AMPure beads.

The ligated products were then reamplified in tubes by PCR using the following primers:

(SEQ ID NO: 23)
4G2-VL-Fwd-Reamp  5'-TGACCCAGTCTCCATCTTCA (SEQ ID NO: 24)
4G2-VH-Rev-Reamp  5'-TGTTGTTTTGGCTGAGGAGA

| Component | Volume (ul) |
|---|---|
| Q5 Hot Start 2X Master Mix | 12.5 |
| Fwd and Rev primers (10 uM each) | 1.25 |
| Purified ligation products | 2 |
| Water | 9.25 |

Thermocycling was performed as follows:

| Initial Denaturation | Denature | Anneal | Extend | Hold |
|---|---|---|---|---|
| 1 cycle | 25 cycles | | | — |
| 95° C. | 95° C. | 60° C. | 72° C. | 4° C. |
| 2 min | 30 sec | 30 sec | 30 sec | Forever |

Figure 6:
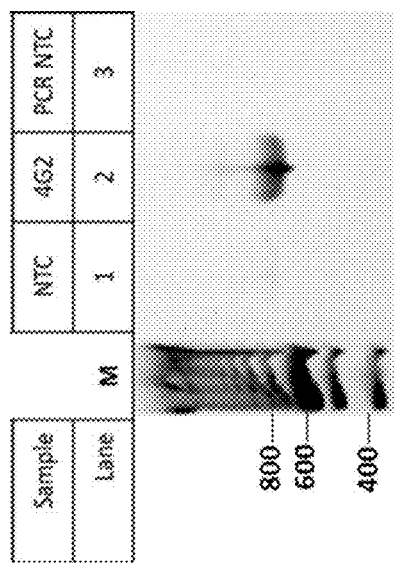
FIG. 6 is an agarose gel electrophoresis image showing that natively paired VH-VL products could be produced in drops from nucleic acids obtained from cells expressing the 4G2 antibody. NTC=sample in which the entire droplet workflow was performed but no cells were included; PCR NTC=no-template control.

The reamplification products were analyzed by agarose gel electrophoresis. As shown in FIG. 6, the 4G2 cell sample yielded the intended product of linked VH-VL DNA, whereas negative control samples did not yield any product.

It is contemplated that the final PCR product, containing, e.g., natively paired VL and VH with a flexible linker sequence between in an intact open reading frame, can be cloned into a yeast surface expression vector and transformed into yeast using standard methods, resulting in a natively paired yeast display library. For example, an additional 50 bp on each terminus can be incorporated by PCR. These 50 bp match appropriate sequences in a yeast expression vector to facilitate cloning by homologous recombination in yeast, following yeast co-transformation of insert PCR product (e.g., containing natively linked VL-VH) and a linearized yeast expression vector.

Example 7: Self-Annealing Primers to Prevent PCR Product Capture Competition from Primers PCR product capture onto beads was facilitated by generation of sticky ends (ssDNA) on a terminus of PCR products through incorporation of a spacer, such as PEG. These ssDNA portions had sequence complementarity to oligos conjugated to beads, thereby facilitating specific hybridization. The sequences in the PCR products were incorporated by their inclusion in amplification primers. Since the PCR primers had the same sequences as the PCR product ssDNA termini, they too can be captured onto beads through specific hybridization. Such primer capture would necessarily compete with PCR product capture.

Amplification of antibody repertoires by PCR typically requires a multitude of PCR primers to amplify the varied antibody gene sequences. For example, primer sets recognizing V and J regions of human and mouse repertoires are often composed of about 15-20 primers directed to the V regions of the heavy and light chains. The requirement for a multitude of primers leads to circumstances that exacerbate the competing effect of primers on capturing PCR product onto beads. For multiplex PCR scenarios, in a given drop (compartment), a single primer (or limited number) can have complementarity to the target antibody sequence within in the drop. The remaining repertoire primers will not match the target sequence. These non-matching primers would not be incorporated into amplicons during PCR, and as such, are poised to effectively compete for PCR product capture. To address this limitation, a design was generated that mitigates the ability of the unused PCR primers within a drop to compete with PCR product for capture. PCR product capture can be attainable, for example, under conditions of 15:1 molar ratio of unused primer to primer that generates amplicon.

Carboxylated magnetic beads were conjugated with the following amine-modified oligos, as described above.

```
VL_Capture
                                        (SEQ ID NO: 16)
GCGAATATTAGTAACGATCCAAAAAAAAAAAAAAAAAAAA/iSp18//
iSp18//iSp18//3AmMO/

VH_Capture
                                        (SEQ ID NO: 17)
GACGTTGATGGATTGCAAAAAAAAAAAAAAAAAAAA/iSp18//
iSp18//iSp18//3AmMO/

Mus_IgG_CH1_mRNA_capt
                                        (SEQ ID NO: 18)
CTGGACAGGGATCCAKAGTTCCAAAAAAAAAAAAAAAAAAAA/
iSp18//iSp18//iSp18//3AmMO/

Mus_Kap_mRNA_capt
                                        (SEQ ID NO: 19)
GTGCAGCATCAGCCCGAAAAAAAAAAAAAAAAAAAA/iSp18//
iSp18//iSp18//3AmMO/
```

RT-PCR reactions were set up to amplify VL sequence corresponding to 4G2 hybridoma using the following oligos. These oligos represent a design without a self-annealing sequence (Non-SA) and a design with a self-annealing sequence (SA). Additionally, an oligo that has a self-annealing sequence on its 5'-end but has a 3'-end sequence that does not match the 4G2 VL or VH mRNA sequences (Mismatch) was included as an exemplary PCR primer that would not be consumed during PCR, akin to multiplex repertoire primers. The reverse primer was biotinylated to facilitate detection of captured PCR product on the bead.

```
4G2_VL_Fwd_Non-SA
                                 (SEQ ID NOS 10 and 27)
5'-TGGATCGTTACTAATATTCGC/iSp18/GGACTCAGACACTTCCGTG
CGACATCAAGATGACCCAGTCTC Mismatch_VL_Fwd_Non-SA
                                 (SEQ ID NOS 20 and 29)
5'-TGGATCGTTACTAATATTCGC/iSp18/GGACTCAGACACTTCCGTG
CATTGTGCTGACGCAAACTGTTA 4G2_VL_Fwd_SA
                                 (SEQ ID NOS 21 and 30)
5'-TGGATCGTTACTAATATTCGC/iSp18/GAATATTAGTAACGATCCA
GGACTCGGACCGACATCAAGATGACCCAGTCTC Mismatch_VL_Fwd_SA
                                 (SEQ ID NOS 22 and 31)
5'-TGGATCGTTACTAATATTCGC/iSp18/GAATATTAGTAACGATCCA
GGACTCGGACCATTGTGCTGACGCAAACTGTTA Mus_Kappa_Rev_Biotin
                                        (SEQ ID NO: 13)
5'-/5BiotinTEG/ACCAGCAGAGCTCTCACCTGGTGCAGCATCAGCCC
```

The underline designates the self-annealing (complementary) sequences.

| Component | Volume (ul) for 25 ul reaction |
|---|---|
| 4G2 VL amplification primers (10 uM each) | 0.5 |
| 4G2 RNA | 0.1 (20 ng) |
| 2X OneTaq One-Step RT-PCR Buffer (NEB) | 12.5 |
| OneTaq One-Step RT-PCR enzyme (NEB) | 1 |
| Oligo-conjugated beads | 2 |
| Mismatch_VL_Fwd oligo (varying concentrations, as listed below) | 2.5 |
| Water | 4 |
| Optiprep | 2 |
| RNase inhibitor | 0.5 |

| 4G2 VL Amplification Primer Mix | Fwd Primer | Rev Primer |
|---|---|---|
| #1 | 4G2_VL_Fwd_Non-SA | Mus_Kappa_Rev_Biotin |
| #2 | 4G2_VL_Fwd_SA | Mus_Kappa_Rev_Biotin |

For competing mismatch oligo concentration used with the forward self-annealing primer (4G2_VL_Fwd_SA), the following conditions were used:

| Molar Ratio of Fwd Oligos (Mismatch_VL_Fwd_SA:4G2_VL_Fwd_SA) | Mismatch_VL_Fwd_SA concentration (μM) |
|---|---|
| 15:1 | 30 |
| 5:1 | 10 |
| 2.5:1 | 5 |
| 1.25:1 | 2.5 |
| 0.625:1 | 1.25 |
| 0:1 | 0 |

For competing mismatch oligo concentration used with the Fwd non-self-annealing primer (4G2_VL_Fwd_Non-SA), the following conditions were used:

| Molar Ratio of Fwd Oligos (Mismatch_VL_Fwd_Non-SA:4G2_VL_Fwd_Non-SA) | Mismatch_VL_Fwd_Non-SA concentration (μM) |
|---|---|
| 5:1 | 10 |
| 1:1 | 2 |
| 0.1:1 | 0.2 |
| 0.01:1 | 0.02 |
| 0:1 | 0 |

The samples were thermocycled with the following program:

| RT | Denature | Denature | Anneal | Extend | Extend | Hold |
|---|---|---|---|---|---|---|
| 1 cycle | 1 cycle | | 35 cycles | | 1 cycle | — |
| 55° C. | 94° C. | 94° C. | 58° C. | 68° C. | 68° C. | 4° C. |
| 30 min | 2 min | 15 sec | 30 sec | 30 sec | 2 min | Forever |

After thermocycling, the samples were gently mixed by pipetting to suspend the beads. The samples were then placed in a thermocycler with the following program to facilitate PCR product capture onto beads:

| Step | Temp | Time |
|---|---|---|
| 1 | 70° C. | 30 sec |
| 2 | 55° C. | 4 min |
| 3 | 50° C. | 4 min |
| 4 | 45° C. | 4 min |
| 5 | 40° C. | 3 min |
| 7 | 4° C. | hold |

After the capturing procedure, the tubes were applied to magnets and the supernatants were recovered. The supernatants were analyzed by agarose gel electrophoresis to confirm successful generation of PCR product. The beads, having captured PCR product, were washed three times with 100 µl ice-cold PBSA (1×PBS containing 1% BSA) using a magnet to sequester beads. Each sample was then incubated with 100 µl of 1:500 AlexaFluor 647 IgG Fraction Monoclonal Mouse Anti-Biotin (Jackson) in PBSA with rotation at 4° C. and away from light for 45 minutes. After incubation, the beads were washed three times with 100 µl ice-cold PBSA. After a final wash, beads were resuspended with 100 µl ice-cold PBSA and analyzed with a flow cytometer for AlexaGluo647 fluorescence signal.

Figures 7A, 7B:
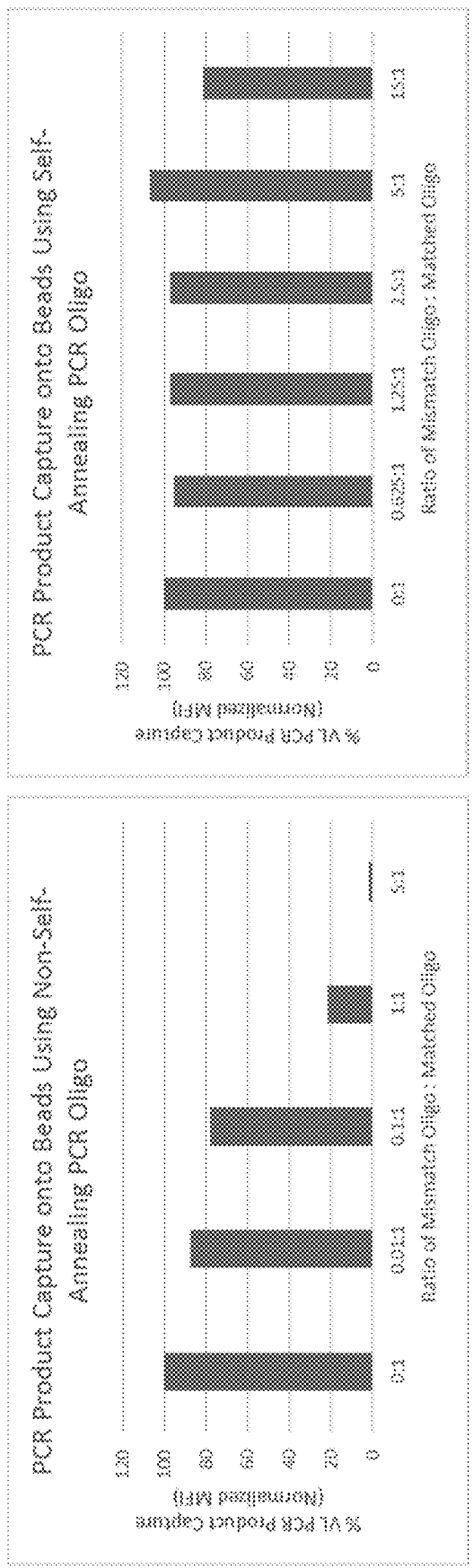
FIGS. 7A-7B are a series of graphs showing that self-annealing primers (in FIG. 7A) can prevent PCR product capture competition at high levels of unused primer, whereas non-self-annealing primers (in FIG. 7B) can only do so at low levels of unused primer.

Mean fluorescence intensity (MFI) was determined for each sample. The sample data were plotted as a percentage of MFI relative to MFI corresponding to absence of mismatch oligo. As shown in FIGS. 7A-7B, only the self-annealing primers were capable of preventing PCR product capture competition at high ratios of mismatched primer oligo to matched primer oligo. These results show that, specifically with the self-annealing primer design, the PCR product can be efficiently captured under conditions of 15-fold more unused primer-conditions that, for example, simulate multiple antibody repertoire conditions.

INCORPORATION BY REFERENCE

All publications, patents, and Accession numbers mentioned herein are hereby incorporated by reference in their entirety as if each individual publication or patent was specifically and individually indicated to be incorporated by reference.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

What is claimed is:

1. A method of making a nucleic acid sequence comprising a sequence that encodes a heavy chain element (HC element) of an antibody heavy chain variable region (HCVR) and a light chain element (LC element) of an antibody light chain variable region (LCVR), and wherein the HCVR and LCVR are matched, the method comprising:
   a) acquiring an isolated production reaction site, comprising:
      i) a heavy chain (HC) strand, wherein the HC strand is a strand of a heavy chain double-stranded cDNA (HC ds cDNA) comprising a segment that encodes the HC element of the HCVR from a cell; and
      ii) a light chain (LC) strand, wherein the LC strand is a strand of a light chain double-stranded cDNA (LC ds cDNA) comprising a segment that encodes the LC element of the LCVR from the cell,
      wherein the HC strand is single stranded, and the LC strand is single stranded; and
   b) covalently linking the single stranded HC strand to the single stranded LC strand, wherein the single stranded HC strand and the single stranded LC strand are covalently linked to produce a single stranded nucleic acid sequence,
   wherein the isolated production reaction site does not comprise a nucleic acid encoding an HCVR or an LCVR from a cell other than the cell,
   thereby making the nucleic acid sequence.

2. The method of claim 1, wherein the HC element comprises, or consists of, a heavy chain variable region sequence (HCVRS), or an antigen binding fragment thereof.

3. The method of claim 1, wherein the LC element comprises, or consists of, a light chain variable region sequence (LCVRS), or an antigen binding fragment thereof.

4. The method of claim 1, wherein the nucleic acid sequence is configured such that, when expressed, the HC element and the LC element form a functional antigen binding molecule in vitro, ex vivo, or in vivo.

5. The method of claim 1, wherein acquiring the isolated production reaction site comprises:
   a) acquiring a capture substrate bound to:
      (i) a first double-stranded cDNA (ds cDNA) comprising a strand that is complementary to a first mRNA that encodes the HCVR from the cell; and
      (ii) a second ds cDNA comprising a strand complementary to a second mRNA encoding the LCVR from the cell, to produce a loaded capture substrate, and
   b) maintaining the isolated production reaction site under conditions that allow amplification of the first and second ds cDNAs, to produce:
      a plurality of HC ds cDNAs comprising the segment that encodes the HC element of the HCVR from the cell; and
      a plurality of LC ds cDNAs comprising the segment that encodes the LC element of the LCVR from the cell.

6. The method of claim 1, wherein the capture substrate comprises a bead and a moiety which binds to cDNA.

7. The method of claim 1, wherein the isolated production reaction site comprises a reagent mixture suitable for producing, from the first and second mRNAs, a first ds cDNA comprising the segment that encodes the HC element of the HCVR of the cell, and a second ds cDNA comprising a segment that encodes the LC element of the LCVR of the cell.

8. The method of claim 5, wherein the first and second ds cDNAs are amplified in the presence of primers, wherein at least one of the primers comprises a first member, a second member, and a nucleotide modification between the first and second members, wherein the nucleotide modification reduces DNA synthesis.

9. The method of claim 8, wherein the nucleotide modification comprises an insertion of a spacer between two adjacent nucleotides or a modification to a ribose.

10. The method of claim 8, wherein the first member is capable of annealing with the second member in the same primer or a different primer, forming a double-stranded structure comprising a duplex region of 4, 5, 6, 7, 8, 9, 10, 11, 12, 13, 14, 15, 16, 17, 18, 19, 20, more basepairs.

11. The method of claim 8, wherein at least one of the primers is phosphorylated and comprises a sequence encoding at least a portion of a linker sequence, or a complementary sequence thereof.

12. The method of claim 1, wherein the HC ds cDNA comprises a 5' overhang and a blunt end and the LC ds cDNA comprises a 5' overhang and a blunt end.

13. The method of claim 1, wherein the HC and LC strands are both sense strands or both antisense strands.

14. The method of claim 1, wherein the covalent linking occurs in an isolated linkage reaction site comprising a ligase.

15. The method of claim 1, wherein the HC strand and the LC strand are covalently linked in the presence of a splint oligonucleotide, wherein the splint oligonucleotide is hybridized to a sequence comprising the junction of the HC strand and the LC strand to form a duplexed region at the site of linkage.

16. The method of claim 15, wherein the splint oligonucleotide comprises a modification that inhibits DNA synthesis.

17. The method of claim 1, further comprising, prior to acquiring the isolated production reaction site, acquiring an mRNA loaded capture substrate comprising:
   a) acquiring an isolated cell reaction site, comprising:
      i) a cell; and
      ii) a capture substrate capable of binding a first mRNA encoding an HCVR from the cell and a second mRNA encoding an LCVR from the cell; and
   b) maintaining the isolated cell reaction site under conditions that allow lysis of the cell and binding of the capture substrate with the first mRNA and the second mRNA to form the mRNA loaded capture substrate,
   wherein the isolated cell reaction site does not include a nucleic acid encoding an HCVR or an LCVR from a cell other than the cell.

18. The method of claim 17, further comprising releasing the mRNA loaded capture substrate from the isolated cell reaction site in the presence of a poly(dA) or poly(dT) oligonucleotide.

19. The method of claim 1, further comprising amplifying the nucleic acid sequence.

20. The method of claim 1, further comprising sequencing all or a portion of the nucleic acid sequence.

21. The method of claim 1, further comprising inserting all or a portion of nucleic acid sequence into a vector.

22. The method of claim 1, comprising expressing the nucleic acid sequence to produce a polypeptide comprising the segment that encodes the HC element of the HCVR, and the segment that encodes the LC element of the LCVR.

23. The method of claim 22, further comprising contacting the polypeptide with an antigen and determining if the polypeptide binds the antigen.

24. A method of making a library comprising a plurality of unique members, the method comprising:
  making the plurality of members by the method of claim 1,
  wherein each of the members comprises a sequence that encodes a heavy chain element (HC element) of a heavy chain variable region (HCVR) and a light chain element (LC element) of a light chain variable region (LCVR), wherein the HCVR and the LCVR are matched, and wherein each unique nucleic acid sequence of the plurality comprises an HC element and an LC element from a different unique cell,
  thereby making the library.

25. The method of claim 24, wherein the library comprises one, two,
  three, or all of the following properties:
  a) the plurality of unique members comprises at least $10^4$, $10^5$, $10^6$, $10^7$, $10^8$, or $10^9$ unique members;
  b) the plurality of unique members comprises $10^4$ to $10^9$, $10^4$ to $10^1$, $10^4$ to $10^7$, $10^4$ to $10^6$, $10^4$ to $10^5$, $10^8$ to $10^9$, $10^7$ to $10^9$, $10^6$ to $10^9$, $10^5$ to $10^9$, $10^5$ to $10^8$, $10^6$ to $10^7$, $10^4$ to $10^5$, $10^5$ to $10^6$, $10^6$ to $10^7$, $10^7$ to $10^8$, or $10^8$ to $10^9$ unique members;
  c) at least 80%, 85%, 90%, 95%, 96%, 97%, 98%, 99%, or 100%, of the members in the library are unique members; or
  d) less than 20%, 15%, 10%, 5%, 4%, 3%, 2%, or 1%, of the members in the library are unique members.

26. A library made by the method of claim 25.

27. The library of claim 26, wherein the library is a display library.

28. A method of making a binding polypeptide, the method comprising:
  a) acquiring a library of claim 26; and
  b) expressing a polypeptide encoded by a unique nucleic acid of the library.

29. The method of claim 28, further comprising contacting the polypeptide with an antigen and obtaining a nucleic acid that encodes a polypeptide that binds the antigen.

30. The method of claim 14, wherein the ligase is a thermostable ligase.

31. The method of claim 14, wherein the ligase retains at least 95% activity at 95° C. or more.

32. The method of claim 14, wherein the ligase is selected from the group consisting of: Taq DNA ligase, Pfu DNA ligase, Ampligase® thermostable DNA ligase, Tsc DNA ligase, Rma DNA ligase, Tfi DNA ligase, and Tth DNA ligase.

* * * * *

UNITED STATES PATENT AND TRADEMARK OFFICE
CERTIFICATE OF CORRECTION

PATENT NO. : 11,820,979 B2
APPLICATION NO. : 15/852718
DATED : November 21, 2023
INVENTOR(S) : Zachary Shriver et al.

It is certified that error appears in the above-identified patent and that said Letters Patent is hereby corrected as shown below:

In the Claims

At Column 149, Claim number 25, Line number 19, delete "$10^1$" and insert -- $10^8$ --.

Signed and Sealed this
Sixteenth Day of April, 2024

Katherine Kelly Vidal
*Director of the United States Patent and Trademark Office*